(12) United States Patent  (10) Patent No.: US 7,826,728 B2
Konno et al.  (45) Date of Patent: Nov. 2, 2010

(54) IMAGE PROCESSING SYSTEM AND CAMERA

(75) Inventors: Osamu Konno, Iruma (JP); Yasuhiro Komiya, Hino (JP); Toru Wada, Niiza (JP); Nobumasa Sato, Ageo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/486,455

(22) Filed: Jul. 13, 2006

(65) Prior Publication Data

US 2006/0251408 A1  Nov. 9, 2006

Related U.S. Application Data

(63) Continuation of application No. pct/jp05/00783, filed on Jan. 21, 2005.

(30) Foreign Application Priority Data

Jan. 23, 2004  (JP) ............................. 2004-016264

(51) Int. Cl.
  *G03B 15/03* (2006.01)
  *G03B 29/00* (2006.01)
  *A61B 1/04* (2006.01)
(52) U.S. Cl. .................. 396/16; 396/182; 396/201; 396/322
(58) Field of Classification Search ............... 396/16, 396/155, 182, 322, 201; 348/66, 77, 269, 348/333.02, 370, 371
  See application file for complete search history.

(56) References Cited

U.S. PATENT DOCUMENTS 4,011,571 A    3/1977  Okuzawa 4,300,823 A    11/1981 Yamanaka et al.
4,845,553 A    7/1989  Konomura et al.

(Continued)

FOREIGN PATENT DOCUMENTS

DE    199 62 779 A1    6/2001

(Continued)

OTHER PUBLICATIONS

Occupational Health Services—Dictionary Page: www.occupational-health-services.co.uk.html, pp. 1-7.

(Continued)

*Primary Examiner*—W. B. Perkey
(74) *Attorney, Agent, or Firm*—Holtz, Holtz, Goodman & Chick, P.C.

(57) ABSTRACT

The image processing system is applied to dentistry, for example, and performs photography of the teeth of a patient while causing a plurality of illumination light LEDs of different wavelengths to emit light by means of a photography device when producing a crown repair or denture of the patient, whereby image data are acquired. The image data are transmitted to a dental filing system constituting a processing device where color reproduction data are determined through computation. In addition, color reproduction data are transmitted to the dental technician's office via a public switched network. Therefore, a repair material compound ratio calculation database is searched and the compound data for a material that matches the hue of the patient's teeth are found, whereby a crown repair or denture or the like that very closely matches the color of the patient's teeth is produced.

35 Claims, 76 Drawing Sheets

U.S. PATENT DOCUMENTS

| | | | |
|---|---|---|---|
| 4,953,355 A | 9/1990 | Poulain et al. | |
| 4,959,679 A | 9/1990 | Yamamoto et al. | |
| 5,051,823 A | 9/1991 | Cooper et al. | |
| 5,381,207 A | 1/1995 | Kazumi | |
| 5,408,268 A * | 4/1995 | Shipp | 348/269 |
| 5,503,559 A | 4/1996 | Vari | |
| 5,523,786 A | 6/1996 | Parulski | |
| 5,654,756 A * | 8/1997 | Takahashi et al. | 348/268 |
| 5,690,486 A | 11/1997 | Zigelbaum | |
| 5,766,006 A | 6/1998 | Murljacic | |
| 5,995,763 A | 11/1999 | Posa et al. | |
| 6,006,041 A | 12/1999 | Mizumaki et al. | |
| 6,038,024 A | 3/2000 | Berner | |
| 6,055,325 A | 4/2000 | Garini et al. | |
| 6,111,650 A | 8/2000 | Rawicz et al. | |
| 6,144,805 A | 11/2000 | Ogino | |
| 6,201,880 B1 | 3/2001 | Elbaum et al. | |
| 6,264,470 B1 | 7/2001 | Jung et al. | |
| 6,276,933 B1 | 8/2001 | Melnyk et al. | |
| 6,306,421 B1 | 10/2001 | Kunz et al. | |
| 6,307,629 B1 | 10/2001 | Jung et al. | |
| 6,341,957 B1 | 1/2002 | Momot et al. | |
| 6,358,047 B2 | 3/2002 | Lehmann | |
| 6,359,680 B1 | 3/2002 | Rubbert | |
| 6,362,888 B1 | 3/2002 | Jung et al. | |
| 6,381,017 B2 | 4/2002 | Jung et al. | |
| 6,396,873 B1 | 5/2002 | Goldstein et al. | |
| 6,413,207 B1 | 7/2002 | Minami | |
| 6,414,750 B2 | 7/2002 | Jung et al. | |
| 6,417,917 B1 | 7/2002 | Jung et al. | |
| 6,431,870 B1 | 8/2002 | Sachdeva | |
| 6,454,437 B1 | 9/2002 | Kelly | |
| 6,540,513 B2 | 4/2003 | Berner et al. | |
| 6,570,654 B2 | 5/2003 | Jung et al. | |
| 6,600,832 B1 | 7/2003 | Nakayama et al. | |
| 6,606,514 B2 | 8/2003 | Grass et al. | |
| 6,650,834 B2 | 11/2003 | Ume | |
| 6,672,868 B1 | 1/2004 | Momot et al. | |
| 6,714,657 B1 | 3/2004 | Jacobs et al. | |
| 6,721,009 B1 | 4/2004 | Iizuka | |
| 6,721,099 B2 * | 4/2004 | Hatano et al. | 359/578 |
| 6,749,310 B2 * | 6/2004 | Pohlert et al. | 362/11 |
| 6,750,971 B2 | 6/2004 | Overbeck et al. | |
| 6,776,614 B2 | 8/2004 | Wiechmann et al. | |
| 6,807,297 B1 | 10/2004 | Tankovich et al. | |
| 6,832,913 B2 | 12/2004 | Lehmann | |
| 6,856,354 B1 | 2/2005 | Ohsawa | |
| 6,870,616 B2 | 3/2005 | Jung et al. | |
| 6,917,429 B2 | 7/2005 | Imura et al. | |
| 6,940,545 B1 | 9/2005 | Ray et al. | |
| 6,954,227 B2 | 10/2005 | Yoda | |
| 6,964,567 B2 | 11/2005 | Kerschbaumer et al. | |
| 6,967,644 B1 | 11/2005 | Kobayashi | |
| 7,006,126 B2 | 2/2006 | Kerschbaumer et al. | |
| 7,030,986 B2 | 4/2006 | Overbeck et al. | |
| 7,033,172 B2 | 4/2006 | Hansen et al. | |
| 7,058,213 B2 | 6/2006 | Rubbert et al. | |
| 7,097,450 B2 | 8/2006 | Jung et al. | |
| 7,106,511 B2 | 9/2006 | Grot et al. | |
| 7,106,958 B2 | 9/2006 | Kerschbaumer et al. | |
| 7,118,374 B2 | 10/2006 | Culp | |
| 7,133,154 B2 | 11/2006 | Sugiyama | |
| 7,136,093 B1 | 11/2006 | Itoh et al. | |
| 7,142,312 B2 | 11/2006 | Quadling et al. | |
| 7,144,248 B2 | 12/2006 | Irwin | |
| 7,184,150 B2 | 2/2007 | Quadling et al. | |
| 7,215,803 B2 | 5/2007 | Marshall | |
| 7,255,558 B2 | 8/2007 | Babayoff et al. | |
| 7,341,450 B2 | 3/2008 | Pye et al. | |
| 7,342,668 B2 | 3/2008 | Quadling et al. | |
| 7,355,633 B2 | 4/2008 | Kurosawa et al. | |
| 7,355,721 B2 | 4/2008 | Quadling et al. | |
| 7,490,294 B2 | 2/2009 | Okada | |
| 7,538,878 B2 | 5/2009 | Jung et al. | |
| 7,576,845 B2 | 8/2009 | Asakura et al. | |
| 7,596,253 B2 | 9/2009 | Wong et al. | |
| 7,682,150 B2 | 3/2010 | Jung et al. | |
| 2002/0015933 A1 | 2/2002 | Berner et al. | |
| 2002/0054208 A1 | 5/2002 | Goldstein et al. | |
| 2002/0071124 A1 | 6/2002 | Schwarz | |
| 2002/0080276 A1 | 6/2002 | Mori et al. | |
| 2002/0099295 A1 | 7/2002 | Gil et al. | |
| 2002/0102009 A1 | 8/2002 | Jones et al. | |
| 2002/0114505 A1 | 8/2002 | Mahon et al. | |
| 2002/0168784 A1 | 11/2002 | Sundrehagen et al. | |
| 2002/0177751 A1 | 11/2002 | Ueno et al. | |
| 2002/0191102 A1 * | 12/2002 | Yuyama et al. | 348/370 |
| 2003/0011767 A1 | 1/2003 | Imura et al. | |
| 2003/0107652 A1 | 6/2003 | Williams | |
| 2003/0206279 A1 | 11/2003 | Kimura et al. | |
| 2004/0076921 A1 | 4/2004 | Gofman et al. | |
| 2004/0125996 A1 * | 7/2004 | Eddowes et al. | 382/128 |
| 2005/0026703 A1 | 2/2005 | Fukawa | |
| 2005/0084144 A1 | 4/2005 | Feldman | |
| 2005/0231592 A1 | 10/2005 | Cable et al. | |
| 2005/0254704 A1 * | 11/2005 | Komiya et al. | 382/162 |
| 2005/0256383 A1 | 11/2005 | Gandjbakhche et al. | |
| 2006/0152586 A1 * | 7/2006 | Komiya et al. | 348/207.99 |
| 2006/0251408 A1 | 11/2006 | Konno et al. | |
| 2006/0280360 A1 | 12/2006 | Holub | |
| 2007/0064119 A1 | 3/2007 | Komiya et al. | |
| 2008/0192235 A1 | 8/2008 | Komiya et al. | |
| 2008/0259336 A1 | 10/2008 | Konno et al. | |
| 2008/0284902 A1 | 11/2008 | Konno et al. | |
| 2008/0292295 A1 | 11/2008 | Konno et al. | |
| 2009/0067695 A1 | 3/2009 | Komiya et al. | |
| 2009/0102964 A1 | 4/2009 | Yuyama et al. | |

FOREIGN PATENT DOCUMENTS

| | | | |
|---|---|---|---|
| EP | 0660616 A2 | 6/1995 | |
| EP | 1 072 884 A2 | 1/2001 | |
| JP | 03-090123 A | 4/1991 | |
| JP | 03-090128 A | 4/1991 | |
| JP | 7-120324 A | 5/1995 | |
| JP | 7-322103 A | 12/1995 | |
| JP | 08-065690 A | 3/1996 | |
| JP | 08-079770 A | 3/1996 | |
| JP | 8-149352 A | 6/1996 | |
| JP | 9-172649 A | 6/1997 | |
| JP | 9-178564 A | 7/1997 | |
| JP | 10-042302 A | 2/1998 | |
| JP | 10-051796 A | 2/1998 | |
| JP | 11-055444 A | 2/1999 | |
| JP | 11-104061 A | 4/1999 | |
| JP | 11-146265 A | 5/1999 | |
| JP | 11-196301 A | 7/1999 | |
| JP | 11-225953 A | 8/1999 | |
| JP | 11-331493 A | 11/1999 | |
| JP | 2000-152264 A | 5/2000 | |
| JP | 2000-152269 A | 5/2000 | |
| JP | 2000-296114 A | 10/2000 | |
| JP | 2000-338950 A | 12/2000 | |
| JP | 2000-341499 A | 12/2000 | |
| JP | 2000-341681 A | 12/2000 | |
| JP | 2001-024971 A | 1/2001 | |
| JP | 2001-083009 A | 3/2001 | |
| JP | 2002-009879 A | 1/2002 | |
| JP | 2002-112960 A | 4/2002 | |
| JP | 2002-158948 A | 5/2002 | |
| JP | 2002-232769 A | 8/2002 | |
| JP | 2003-021859 A | 1/2003 | |
| JP | 2003-023643 A | 1/2003 | |
| JP | 2003-039856 A | 2/2003 | |

| | | | |
|---|---|---|---|
| JP | 2003-043559 A | 2/2003 |
| JP | 2003-087806 A | 3/2003 |
| JP | 2003-189068 A | 7/2003 |
| JP | 2003-309856 A | 10/2003 |
| JP | 2003-333608 A | 11/2003 |
| WO | 00/50927 A2 | 8/2000 |
| WO | 01/29542 A1 | 4/2001 |
| WO | 01/55956 A1 | 8/2001 |
| WO | 02/12847 A1 | 2/2002 |
| WO | WO 2004/012461 A1 * | 2/2004 |
| WO | WO 2004/036162 A1 * | 4/2004 |

OTHER PUBLICATIONS

Related U.S. Appl. No. 12/264,056, filed Nov. 3, 2008.

Japanese Office Action dated Sep. 29, 2009 and English translation thereof issued in Japanese Application No. 2007-268275, which is a counterpart of related U.S. Appl. No. 11/486,455.

Karremann, R., "Farbmessung und Farbregelung in der Papierproduktion", Technisches Messen TM, R. Oldenbourg Verlag. Munchen, DE, vol. 59, No. 5, May 1, 1992, pp. 209-213.

Supplementary European Search Report dated Nov. 5, 2009 (6 pages), issued in European Application Serial No. 03808856.3, which is a counterpart of related U.S. Appl. No. 12/062,399.

Japanese Office Action dated Dec. 22, 2009 and English translation thereof issued in a counterpart Japanese Application No. 2007-268275.

Japanese Office Action dated Apr. 13, 2010 and English translation thereof in counterpart Japanese Application No. 2007-268274.

* cited by examiner

FIG.10

LIGHT EMISSION MODE (EXAMPLE)

| LED No. | PRIMARY COLOR No. | 1 LIGHTING OF ALL LEDS | 2 LIGHTING OF SINGLE LED | 3 LIGHTING OF SINGLE PRIMARY COLOR | 4 GROUP LIGHTING | 5 GROUP LIGHTING B | 6 GROUP LIGHTING G | 7 GROUP LIGHTING R | 8 LIGHTING OF SINGLE B LED | 9 LIGHTING OF SINGLE G LED | 10 LIGHTING OF SINGLE R LED |
|---|---|---|---|---|---|---|---|---|---|---|---|
| 1 | 1 | O | O (EXAMPLE) | O | | | | | | | |
| 2 | 2 | O | | (EXAMPLE) | O | O | | | | | |
| 3 | 3 | O | | | O | | | | | | |
| 4 | 4 | O | | | O | | | | | | |
| 5 | 5 | O | | | O | | | | | | O |
| 6 | 6 | O | | | (EXAMPLE) | | | | | | |
| 7 | 1 | O | | O | | O | | | | | |
| 8 | 2 | O | | | | O | | | O | | |
| 9 | 3 | O | | | | | O | | | O | |
| 10 | 4 | O | | | | | O | O | | | |
| 11 | 5 | O | | | | | | O | | | O |
| 12 | 6 | O | | | | | | O | O | | |
| 13 | 1 | O | | O | | O | | | | | |
| 14 | 2 | O | | | | O | | | O | | |
| 15 | 3 | O | | | | | O | | | O | |
| 16 | 4 | O | | | | | O | O | | | |
| 17 | 5 | O | | | | | | O | | | O |
| 18 | 6 | O | | | | | | O | | | |

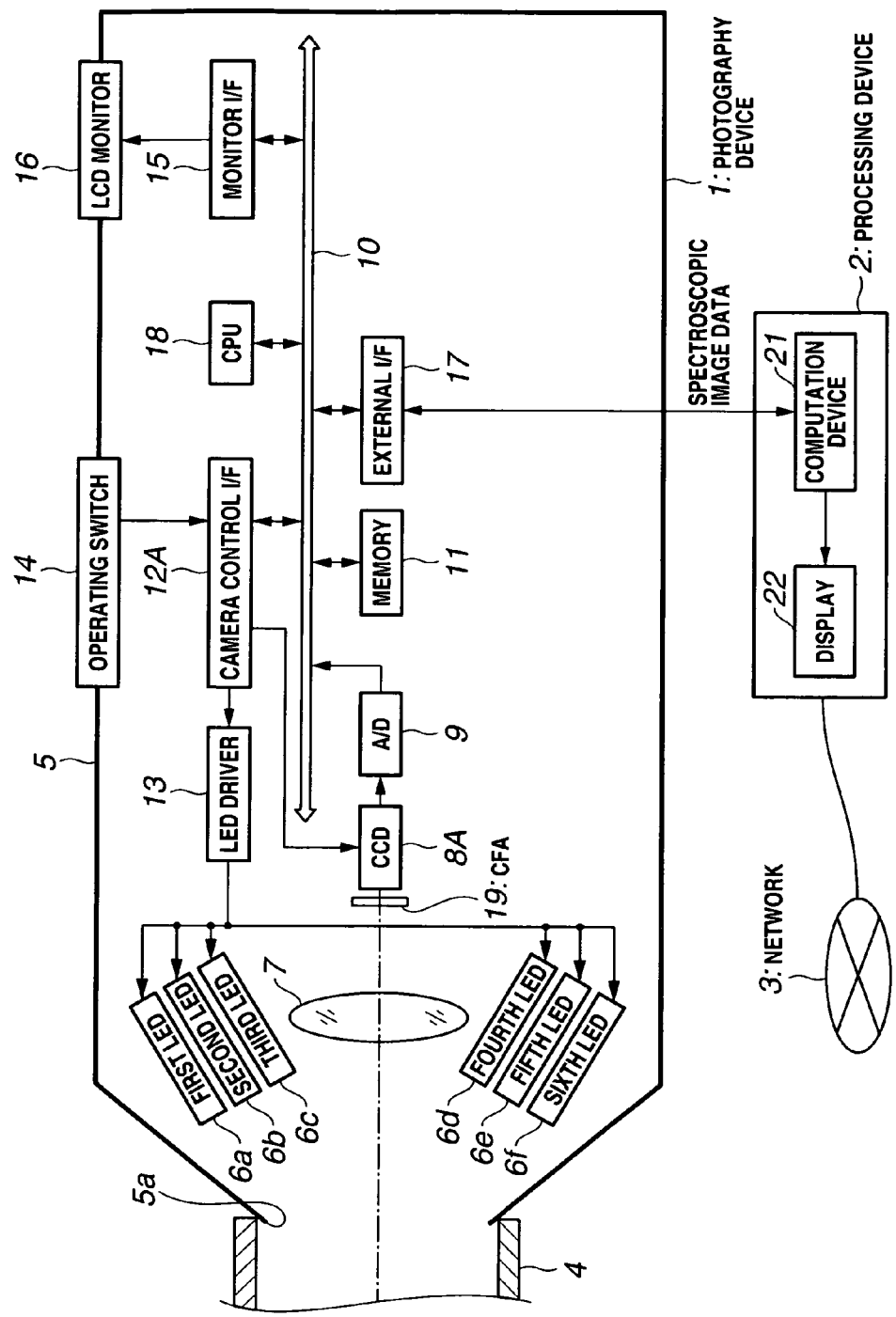

TOTAL NUMBER OF LINES: S

TOTAL NUMBER OF LINES: S

FRAME N
(2-BAND GENERATION)

FRAME N+1
(3-BAND GENERATION)

FRAME N+2
(3-BAND GENERATION)

OBJECT SURFACE

OBJECT SURFACE

$G_1$ $G_2$ $G_3$ $G_4$

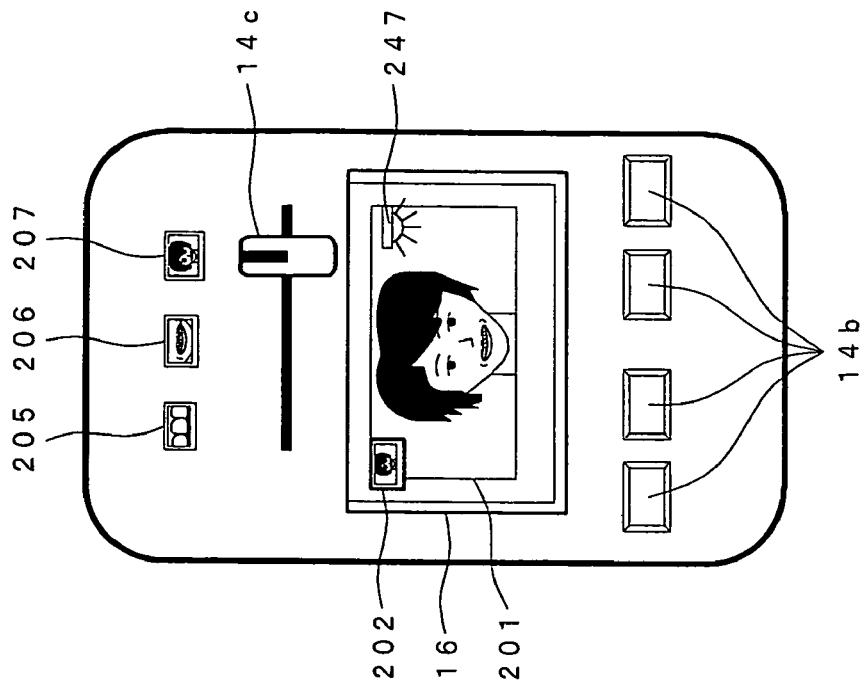
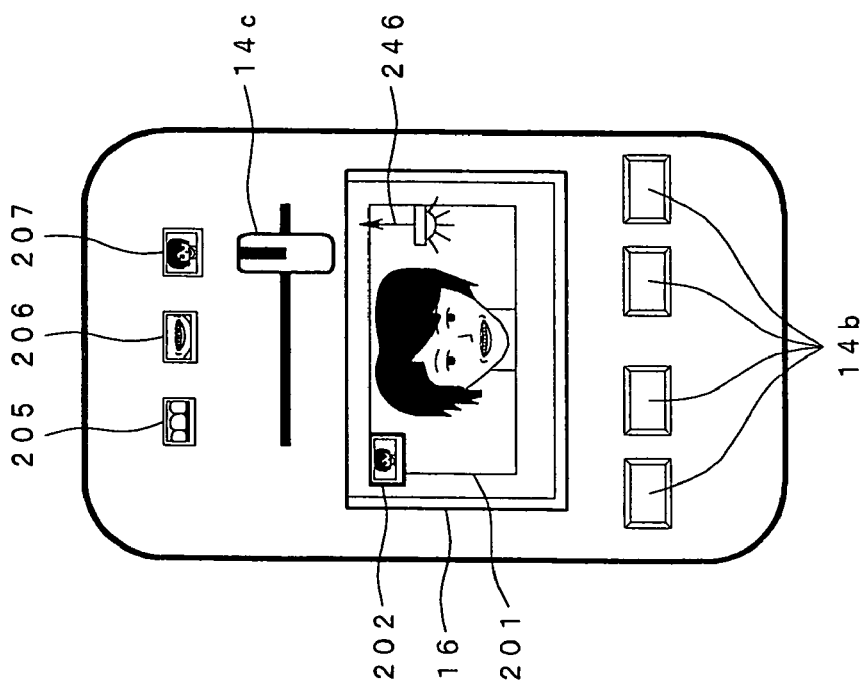

IMAGE PROCESSING SYSTEM AND CAMERA

CROSS REFERENCE TO RELATED APPLICATION

This application is a continuation application of PCT/JP2005/000783 filed on Jan. 21, 2005 and claims benefit of Japanese Application No. 2004-016264 filed in Japan on Jan. 23, 2004, the entire contents of which are incorporated herein by this reference.

BACKGROUND OF THE INVENTION

1. Field of the Invention

The present invention relates to an image processing system and camera that acquire a spectroscopic spectral image information on an object, and perform highly accurate color reproduction, examination, and judgment and so forth on an image of the object from the acquired image information.

2. Description of the Related Art

In recent years, there has been a growing interest in health and an increased need for whitening due to the pursuit of beauty. Conventionally, diagnoses using skin diagnosis cameras have been provided in dermatology, esthetic salons, and beauty counseling and so forth. In the case of dermatology in particular, counseling that grasps characteristics from an image of skin grooves and hills and so forth is performed as diagnosis of the skin surface. Further, the abovementioned skin diagnosis camera has been proposed by Japanese Patent Application Laid Open No. H8-149352, Japanese Patent Application Laid Open No. H7-322103 and the like.

On the other hand, with respect to restoration of a dental crown in a dental treatment, conventionally a color grade judgment is performed by means of a comparison with the color of the patient's teeth by means of a shade guide when determining the color of the tooth that is to be restored.

Although accurate color reproduction is determined in each field including dermatology and dentistry as mentioned earlier, the system disclosed by Japanese Patent Application No. 2000-152269 as a conventional highly accurate color reproduction system applies a camera that captures an image of an externally illuminated object by means of a multispretral. In this system, a multiplicity of rotatable spectroscopic filters are used for a highly accurate estimate of the object spectroscopic spectral and multiple band data are acquired as a result of the rotation of the filters to allow high color reproduction to be implemented.

A variety of other techniques have been proposed as techniques for acquiring spectroscopic images.

A device for capturing a multiband image through time division by using a rotating filter that is constituted of a plurality of optical bandpass filters placed in a row on the circumference appears in Japanese Patent Application No. H9-172649, for example.

Furthermore, a device that easily performs multiband photography by using a filter (comb-shaped filter) that multiply divides a spectroscopic wavelength band appears in Japanese Patent Application Laid Open No. 2002-296114.

In addition, Japanese Patent Application Laid Open No. 2003-087806 mentions a constitution of a multispectral camera that is capable of photographing images of a multiplicity of bands at the same time by integrating a color filter array of six bands or more with a single-panel CCD.

Further, Japanese Patent Application Laid Open No. 2003-023643 mentions a constitution of a multispectral camera that is capable of photographing images of six bands by means of 3-panel CCDs by using a half mirror and a dichroic mirror.

For the abovementioned dermatology, dentistry and other fields in which accurate color reproduction is sought, a contribution to examination, confirmation and discrimination and the like is required through strict color reproduction of the paint color of an automobile, the paint color of a building, the spectroscopic characterization of a foodstuff, and the dye of a garment, and so forth, for example. Further, these devices are also required to be small and lightweight and handy for the sake of examination operability.

SUMMARY OF THE INVENTION

In order to achieve the above object, the image processing system of a first aspect of the invention is an image processing system that comprises an image photography section including a photography optical system for forming an object image, an image pickup element section for outputting an image signal by picking up the object image formed by the photography optical system, and a photography operation section for performing an image photography-related operation, the image photography section being constituted capable of acquiring a spectroscopic image, the system further comprising: mode display means for displaying mode-related information each corresponding to a plurality of modes that the image processing system can adopt.

Further, the image processing system of a second invention is the image processing system according to the first aspect of the invention, wherein the plurality of modes that the image processing system can adopt include a monitor mode for monitoring the object image and a capture mode for capturing the object image.

In addition, the image processing system of a third aspect of the invention is the image processing system according to the second aspect of the invention, wherein the capture mode is a spectroscopic image capture mode for capturing the object image as a spectroscopic image.

The image processing system of a fourth aspect of the invention is the image processing system according to the second aspect of the invention, wherein the capture mode is an RGB capture mode for capturing the object image as an RGB image.

The image processing system of a fifth aspect of the invention is the image processing system according to the first aspect of the invention, further comprising: an illumination light source for illuminating an object, wherein the plurality of modes that the image processing system can adopt include an illumination light lit mode that illuminates the object by turning on the illumination light source and an illumination light unlit mode in which the illumination light source is not lit.

The image processing system of a sixth aspect of the invention is the image processing system according to the third aspect of the invention, wherein the spectroscopic image capture mode further comprises a high-speed reading mode that reads a spectroscopic image more rapidly than normal reading.

The image processing system of a seventh aspect of the invention is the image processing system according to the first aspect of the invention, further comprising: an illumination light source for illuminating an object that comprises a plurality of light-emitting elements that perform light emission of a plurality of different spectroscopic distribution characteristics that are mutually independent in at least the range of visible light, and mode selection means for selecting a desired mode from among a plurality of modes that the image processing system can adopt, wherein the plurality of modes include a plurality of LED light emission modes that cause the plurality of light-emitting elements to emit light in a plurality of different aspects, and a plurality of capture modes that capture a spectroscopic image in a plurality of different aspects each corresponding to the plurality of LED light emission modes; and when any of the plurality of LED light emission modes is selected by the mode selection means, the capture mode that corresponds to the selected LED light emission mode is automatically selected.

The image processing system of an eighth aspect of the invention is the image processing system according to the first aspect of the invention, wherein the plurality of modes that the image processing system can adopt include a full capture mode that captures the whole of the object and a partial capture mode that captures a portion of the object.

The image processing system of a ninth aspect of the invention is the image processing system according to the first aspect of the invention, further comprising: an illumination unit that can be attached to and detached from the image photography section, wherein the mode display means is capable of displaying the attached/detached state of the illumination unit.

The image processing system of a tenth aspect of the invention is the image processing system according to the first aspect of the invention, further comprising: an illumination unit that can be attached to and detached from the image photography section, wherein the mode display means is able to display the type of the illumination unit when the illumination unit is mounted.

The image processing system of an eleventh aspect of the invention is the image processing system according to the first aspect of the invention, further comprising: an external operation section that can be connected to the image photography section constituted to allow an operation related to the image photography section to be performed from outside the image photography section, wherein the mode display means is capable of displaying a state to indicate whether the external operation section is connected and operable.

The image processing system of a twelfth aspect of the invention is the image processing system according to the eleventh aspect of the invention, wherein the external operation section is a foot switch constituted to be able to be operated by foot.

The image processing system of a thirteenth aspect of the invention is the image processing system according to the eleventh aspect of the invention, wherein the external operation section is connected via a network.

The image processing system of a fourteenth aspect of the invention is the image processing system according to the first aspect of the invention, wherein the plurality of modes that the image processing system can adopt include a measurement mode that performs temperature detection, a measurement mode that performs pulse detection, a measurement mode that performs auscultation, and a measurement mode that performs ranging; and the mode display means is constituted capable of displaying, by means of icons that correspond to the respective measurement modes, whether the respective measurement modes for temperature detection, pulse detection, auscultation, and ranging are effective.

The image processing system of a fifteenth aspect of the invention is the image processing system according to the first aspect of the invention, further comprising: an illumination light source for illuminating an object that comprises a plurality of light-emitting elements that perform light emission of a plurality of different spectroscopic distribution characteristics that are mutually independent, wherein the plurality of modes that the image processing system can adopt include LED light emission modes of a plurality of types that cause the plurality of light-emitting elements to emit light in a plurality of different aspects; and the mode display means is constituted capable of displaying the types of selectable LED light emission mode and wavelength information for each of the LED light emission mode types.

The image processing system of a sixteenth aspect of the invention is the image processing system according to the fifteenth aspect of the invention, wherein the selectable LED light emission modes include at least one of an infrared mode in which infrared light is emitted and an ultraviolet mode in which ultraviolet light is emitted.

The image processing system of a seventeenth aspect of the invention is the image processing system according to the first aspect of the invention, further comprising: an illumination light source for illuminating an object; a first polarizing plate that can be inserted in the light path from the illumination light source to the object; and a second polarizing plate that can be inserted in the light path from the object to the image pickup element section, wherein the mode display means is constituted capable of displaying whether the first polarizing plate and second polarizing plate are inserted in the respective light paths.

The image processing system of an eighteenth aspect of the invention is the image processing system according to the seventeenth aspect of the invention, wherein the first polarizing plate and second polarizing plate are constituted capable of relative rotation; and the mode display means is constituted capable of displaying the relative rotation angle between the first polarizing plate and the second polarizing plate.

The image processing system of a nineteenth aspect of the invention is the image processing system according to the first invention, wherein the mode display means is constituted capable of displaying the next operating procedure of a serial operation of the image processing system.

The image processing system of a twentieth aspect of the invention is the image processing system according to the first aspect of the invention, further comprising: operation instruction means for instructing the next operating procedure of the serial operation of the image processing system.

The image processing system of a twenty-first aspect of the invention is the image processing system according to the twentieth aspect of the invention, wherein the operation instruction means instructs the next operating procedure by causing the mode display means to display the next operating procedure.

The image processing system of a twenty-second aspect of the invention is the image processing system according to the twentieth aspect of the invention, wherein the operation instruction means is constituted comprising progress status display means for displaying which operation of which stage in the serial operation of the image processing system is being performed.

The image processing system of a twenty-third aspect of the invention is the image processing system according to the first aspect of the invention, wherein the mode display means is constituted capable of displaying the progress status with respect to which operation of which stage in the serial operation of the image processing system is being performed.

The image processing system of a twenty-fourth aspect of the invention is the image processing system according to the first aspect of the invention, further comprising: set state display means for displaying the set state of the image processing system.

The image processing system of a twenty-fifth aspect of the invention is the image processing system according to the twenty-fourth aspect of the invention, wherein the mode display means also serve as the set state display means.

The image processing system of a twenty-sixth aspect of the invention is the image processing system according to the twenty-fourth or twenty-fifth aspect of the invention, wherein at least a portion of the information displayed on the mode display means and the information displayed on the set state display means can be transferred to an external device as image-data additional data.

The image processing system of a twenty-seventh aspect of the invention is the image processing system according to the first or twenty-fourth aspect of the invention, further comprising: warning reporting means for issuing a warning with respect to the image processing system.

The image processing system of a twenty-eighth aspect of the invention is the image processing system according to the twenty-seventh aspect of the invention, wherein the warning reporting means issues at least one of a warning report when leaked light is detected, a warning report when there is a positional shift during photography, and a warning report when the photography optical system is dim.

The image processing system of a twenty-ninth aspect of the invention is the image processing system according to the twenty-seventh aspect of the invention, wherein the warning reporting means issues the warning report by displaying a warning on the mode display means.

The image processing system of a thirtieth aspect of the invention is the image processing system according to the twenty-seventh aspect of the invention, wherein the warning reporting means issues the warning report by displaying a warning on the set state display means.

A camera according to a thirty-first aspect of the invention that comprises an image photography section comprising a photography optical system for forming an object image, an image pickup element section for outputting an image signal by picking up the object image formed by the photography optical system, and a photography operation section for performing an image photography-related operation, the image photography section being constituted capable of acquiring a spectroscopic image; wherein the camera is constituted capable of adopting a plurality of capture modes for capturing an object image in a plurality of aspects; and the photography operation section is constituted comprising photographic range setting means for setting the photographic range of the object.

The camera according to a thirty-second aspect of the invention is the camera according to the thirty-first aspect of the invention, wherein the plurality of capture modes include at least one of a spectroscopic image capture mode for capturing an object image as a spectroscopic image, and an RGB capture mode for capturing the object image as an RGB image.

The camera according to a thirty-third aspect of the invention is the camera according to the thirty-first aspect of the invention, wherein the photographic range setting means is constituted comprising manual setting means for manually setting the photographic range.

The camera according to a thirty-fourth aspect of the invention is the camera according to the thirty-first aspect of the invention, wherein the photographic range setting means is constituted comprising automatic setting means for automatically setting the photographic range.

The camera according to a thirty-fifth aspect of the invention is the camera according to the thirty-first aspect of the invention, further comprising: remote instruction means which is constituted capable of issuing an instruction with respect to the image photography section from outside the image photography section and which can be mounted on the image photography section, wherein the photographic range setting means sets the photographic range on the basis of instruction information relating to the photographic range from the remote instruction means.

The camera according to a thirty-sixth aspect of the invention is the camera according to the thirty-fourth aspect of the invention, further comprising: measurement procedure instruction means for instructing a measurement procedure employing the camera, wherein the automatic setting means automatically sets the photographic range in accordance with the measurement procedure instructed by the measurement procedure instruction means.

The camera according to a thirty-seventh aspect of the invention is the camera according to the thirty-fourth aspect of the invention, further comprising: autofocus means for measuring the distance to the object and outputting AF information, wherein the automatic setting means automatically set the photographic range in accordance with the AF information that is output by the autofocus means.

The camera according to a thirty-eighth aspect of the invention is the camera according to the thirty-first aspect of the invention, wherein one capture mode is set from the plurality of capture modes with relation to the photographic range set by the photographic range setting means.

The camera according to a thirty-ninth aspect of the invention is the camera according to the thirty-first aspect of the invention, wherein the photographic range setting means is constituted capable of setting, as the photographic range, two or more of dental enlargement photography, full jaw photography, complexion photography, and full body photography.

The camera according to a fortieth aspect of the invention is the camera according to the thirty-ninth aspect of the invention, wherein the image photography section is constituted to acquire a spectroscopic image when the photographic range set by the photographic range setting means is dental enlargement photography and to acquire a normal photographic image when the photographic range set by the photographic range setting means is a photographic range other than dental enlargement photography.

The camera according to a forty-first aspect of the invention is the camera according to the thirty-first aspect of the invention, wherein the photography operation section is constituted comprising guide means for positioning the photographic range.

The camera according to a forty-second aspect of the invention is the camera according to the forty-first aspect of the invention, wherein the guide means is constituted comprising guide display means for clearly displaying the position of the photographic range by using text or marks.

The camera according to a forty-third aspect of the invention is the camera according to the thirty-first aspect of the invention, further comprising: photographic range display means for displaying the photographic range set by the photographic range setting means.

The camera according to a forty-fourth aspect of the invention is the camera according to the forty-third aspect of the invention, wherein the photographic range display means is constituted capable of displaying the photographic ranges that can be set by the photographic range setting means.

The camera according to a forty-fifth aspect of the invention is the camera according to the forty-third aspect of the invention, wherein the photographic range display means is constituted capable of clearly displaying the photographic range set by the photographic range setting means by using text or marks.

The camera according to a forty-sixth aspect of the invention is the camera according to the thirty-first aspect of the invention, further comprising: an illumination light source for illuminating the object, wherein the ON/OFF operation of the illumination light source is constituted to be performed with relation to the photographic range set by the photographic range setting means.

The camera according to a forty-seventh aspect of the invention is a camera that comprises an image photography section comprising an illumination light source for illuminating an object, a photography optical system for forming an object image, an image pickup element section for outputting an image signal by picking up the object image formed by the photography optical system, and a photography operation section for performing an image photography-related operation, the image photography section being constituted capable of acquiring a spectroscopic image, wherein the photography operation performed by the image photography section is constituted capable of performing an ON/OFF operation of the illumination light source in the event of a photography operation in which a spectroscopic image is not acquired.

The camera according to a forty-eighth aspect of the invention is the camera according to the forty-seventh aspect of the invention, wherein the photography operation section is constituted comprising photographic range setting means for setting the photographic range of the object; and the ON/OFF operation of the illumination light source is constituted to be performed with relation to the photographic range set by the photographic range setting means.

The camera according to a forty-ninth aspect of the invention is the camera according to the forty-seventh aspect of the invention, further comprising: a external light source, for illuminating an object, that can be detachably mounted on the image photography section, wherein the ON/OFF operation of the illumination light source is constituted to be performed upon the attachment/detachment of the external light source.

The camera according to a fiftieth aspect of the invention is a camera that comprises an image photography section comprising an illumination light source for illuminating an object, a photography optical system for forming an object image, an image pickup element section for outputting an image signal by picking up the object image formed by the photography optical system, and a photography operation section for performing an image photography-related operation, the image photography section being constituted capable of acquiring a spectroscopic image, wherein at least one of the illumination light source, the photography optical system, the image pickup element section, and the photography operation section is constituted as a detachable unit.

The camera according to a fifty-first aspect of the invention is the camera according to the fiftieth aspect of the invention, wherein the detachable unit is constituted comprising at least one of at least a portion of the illumination light source, at least a portion of the photography optical system, and at least a portion of the image pickup element section.

The camera according to a fifty-second aspect of the invention is the camera according to the fiftieth aspect of the invention, further comprising: temperature detection means for detecting the temperature of the illumination light source.

The camera according to a fifty-third aspect of the invention is the camera according to the fifty-first aspect of the invention, further comprising: an attachment adapter one end of which is attached to the object and which is constituted to be able to be mounted on the detachable unit.

The camera according to a fifty-fourth aspect of the invention is the camera according to the fifty-third aspect of the invention, wherein the attachment adapter is constituted comprising a light-shielding function that prevents external light from being irradiated onto the object.

The camera according to a fifty-fifth aspect of the invention is the camera according to the fifty-first aspect of the invention, wherein the detachable unit is constituted further comprising spectroscopic detection means.

The camera according to a fifty-sixth aspect of the invention is a camera that comprises: an image photography section comprising an illumination light source for illuminating an object, a photography optical system for forming an object image, an image pickup element section for outputting an image signal by picking up the object image formed by the photography optical system, and a photography operation section for performing an image photography-related operation, the image photography section being constituted capable of acquiring a spectroscopic image; and an external operation section, for performing a photography-related operation from outside the image photography section, that can be connected to the image photography section.

The camera according to a fifty-seventh aspect of the invention is the camera according to the fifty-sixth aspect of the invention, wherein the external operation section is a foot switch constituted to be able to be operated by foot.

The camera according to a fifty-eighth aspect of the invention is the camera according to the fifty-sixth aspect of the invention, wherein the external operation section is speech instruction means for issuing an instruction to perform an operation by means of speech.

The camera according to a fifty-ninth aspect of the invention is the camera according to the fifty-sixth aspect of the invention, wherein the external operation section is connected via a network.

The camera according to a sixtieth aspect of the invention is the camera according to the fifty-sixth aspect of the invention, wherein the external operation section is constituted comprising operation confirmation means for confirming the operation of the camera.

The camera according to a sixty-first aspect of the invention is the camera according to the fifty-sixth aspect of the invention, wherein the external operation section is constituted comprising photographic data confirmation means for confirming photographic data of the camera.

BRIEF DESCRIPTION OF THE DRAWINGS

FIG. 10 shows an example of a method of turning on the LEDs when three each of LEDs of six primary colors are provided in the first embodiment;

FIG. 17 is a block diagram showing the constitution of the image processing system in a second embodiment of the present invention;

FIG. 50A shows the disposition of the regular reflection object, the LEDs of each color and the CCD during image formation and FIG. 50B shows an image with a regular reflection part;

FIG. 58A and FIG. 58B show an aspect before correction of the state of a shading performed by an LED light source of the photography device of the image processing system in FIG. 57, wherein FIGS. 58A and 58B show the shading states of different LEDs;

FIG. 59A and FIG. 59B show an aspect following correction of the state of a shading performed by an LED light source of the photography device of the image processing system in FIG. 57, wherein FIGS. 59A and 59B show the shading correction states of each of the different LEDs;

FIG. 90A and FIG. 90B show an example of a display related to the mounting of an illumination unit in the sixth embodiment;

DETAILED DESCRIPTION OF THE PREFERRED EMBODIMENT(S)

Embodiments of the present invention will be described hereinbelow with reference to the drawings.

First Embodiment

Figure 1:
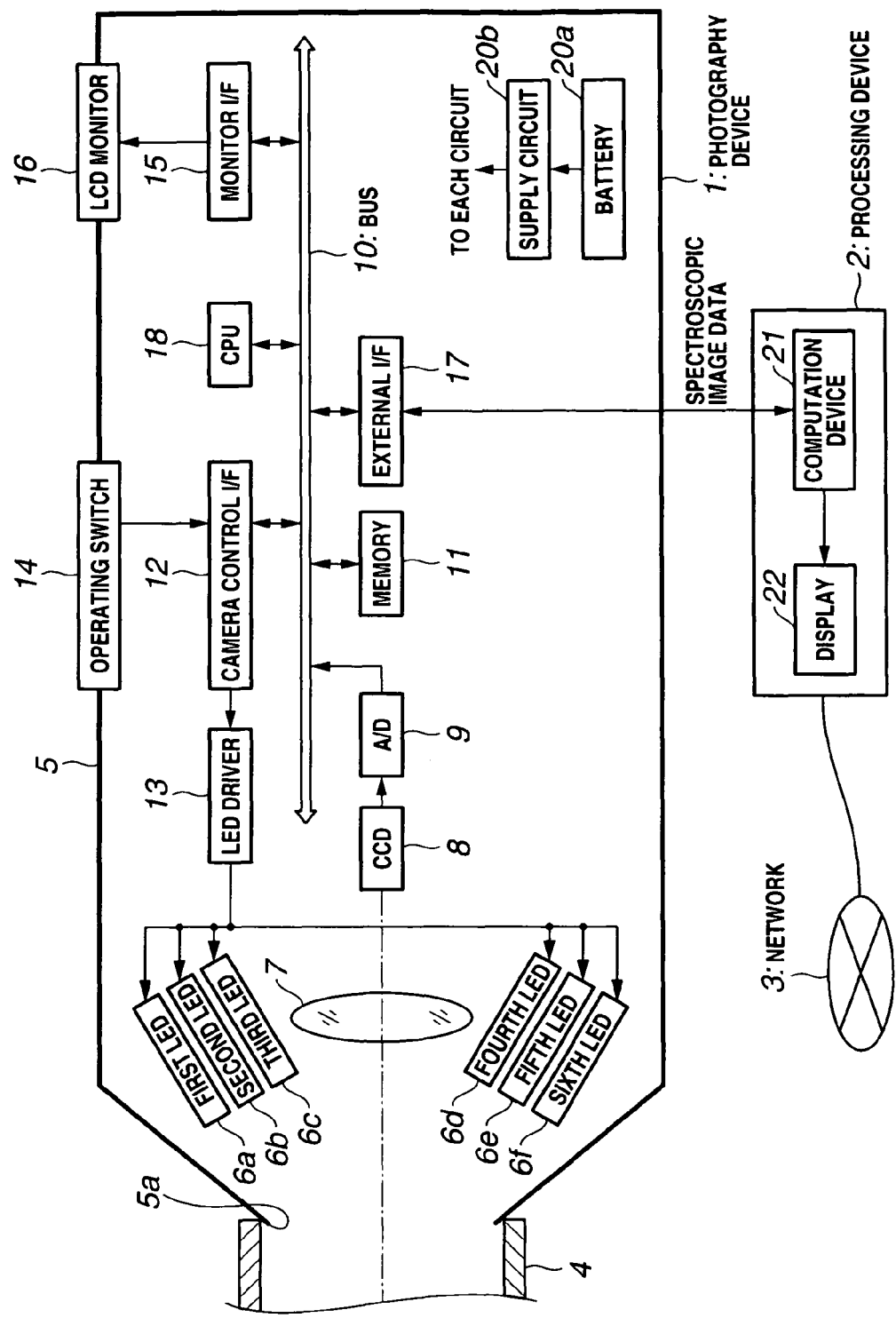
FIG. 1 is a block diagram showing the constitution of the image processing system of a first embodiment of the present invention.

FIGS. 1 to 16, 70 to 88, and 99 show a first embodiment of the present invention and FIG. 1 is a block diagram showing the constitution of an image processing system.

This image processing system is constituted comprising a photography device 1 that is capable of photographing an object spectroscopic image by illuminating the object with illumination light of a plurality of different wavelength bands that are mutually independent in the range of visible light, and a processing device 2 that is connected to the photography device 1 and which processes an object spectroscopic image that is output by the photography device 1, wherein the processing device 2 is constituted such that the same can be connected to a network 3 if required.

In this embodiment, the photography device 1 is capable of performing: image pickup in which an installed light source is put in an illumination light lighting mode in order to use the same in the spectroscopic image acquisition, illumination light (illumination light of six primary colors) of wavelength bands of six types is sequentially irradiated onto an object, and six object spectroscopic images are captured as still images; and image pickup in which the object is captured as a moving image of the frame sequential method by selecting one or more illumination lights each from the illumination light of six primary colors to produce RGB illumination light of three colors and this RGB light is sequentially irradiated.

Further, the illumination lighting mode is not limited to the modes detailed above. There exist a variety of modes, such as a full color continuous lighting mode, a selectively sequential lighting mode, and a one-color continuous lighting mode. The image processing system can be set in these modes.

The photography device 1 is constituted comprising an enclosure 5 that comprises a projection opening 5a applying illumination light (described subsequently) to an object and for introducing reflected light reflected from the object; an attachment section 4 that is detachably attached to the projection opening 5a side of the enclosure 5 and which is formed in a substantially cylindrical shape by a flexible element that serves to block light so that external light does not mix with the illumination light that is projected onto the object via the projection opening 5a; first to sixth LEDs 6a to 6f which are light-emitting elements that are built into the enclosure 5 and which emit illumination light to illuminate the object as a result of being turned on; a photography optical system 7 for forming an object image that is irradiated by the first to sixth LEDs 6a to 6f built into the enclosure 5, a CCD 8 constituting image pickup elements that are contained in an image pickup element section that outputs an image signal by picking up the object image that is formed by the photography optical system 7; an A/D converter 9 that converts the analog signal output from the CCD 8 into a digital signal; a memory 11 that temporarily stores an object spectroscopic image that is output from the A/D converter 9 and transferred via a bus 10 (described subsequently), and which is also used as a work area by a CPU 18 (described subsequently); an operating switch 14 constituting mode selection means which is a photography operating section comprising a variety of operating switches and operating buttons and so forth that allow the user to make inputs to indicate the start of a spectroscopic image photography operation and to make inputs to indicate the start and end of a moving image photography operation; a camera control I/F 12 that transmits instruction inputs from the operating switch 14 to the CPU 18 (described subsequently) and which issues commands or the like related to controlling the light emission of the first to sixth LEDs 6a to 6f according to the instructions from the CPU 18 and performs control related to the image pickup operation of the photography device 1; an LED driver 13 that performs control related to a light emission operation such as light emission start timing and light emission end timing of the first to sixth LEDs 6a to 6f on the basis of an instruction from the camera control I/F 12; a monitor I/F 15 that performs control to display moving images picked up by the CCD 8 and object spectroscopic images (still images) stored in the memory 11 to an LCD monitor 16 (described subsequently); the LCD monitor 16 which is provided as display means, is constituted to allow images output from the monitor I/F 15 to be displayed and to allow operating instructions and displaying of states, the LCD monitor combining mode displaying means and set state display means; an external I/F 17 for outputting to the processing device 2 object spectroscopic images stored in the memory 11 and control data and so forth from the CPU 18 (described subsequently) or for inputting communication data from the processing device 2; a bus 10 that mutually connects the A/D converter 9, memory 11, camera control I/F 12, monitor I/F 15, external I/F 17, and CPU 18 (described subsequently) and so forth; a battery 20a that is constituted in a detachable form, for example; a supply circuit 20b that converts power supplied from the battery 20a to a suitable voltage or the like before supplies this voltage or the like to each circuit described earlier; and a CPU 18 constituting a control section that centrally controls the photography device 1 comprising each of the circuits described earlier.

Further, the photography operation section is provided attached to the photography device 1 and is generally operated by being pushed down by the finger of one's hand. In such an operation, so-called 'camera shake' sometimes occurs and a vivid image cannot be obtained. Hence, when a more accurate image is to be obtained, camera shake must be suppressed as far as possible.

As one means of suppressing camera shake, the following may be considered: camera shake of photography device 1 or blurring of a photographed image is detected and a warning is issued when camera shake/blurring is detected, whereupon the user is urged to take the required measures. That is, the following may be considered: camera shake detection means for detecting camera shake or the like, for example, is provided, and, when it is judged by the camera shake detection means that camera shake that is not suited to image processing has occurred, the display means of the photography device 1 is used as warning reporting means, and a camera shake alarm display 211 shown by way of example in FIG. 70 is executed.

Figure 70:
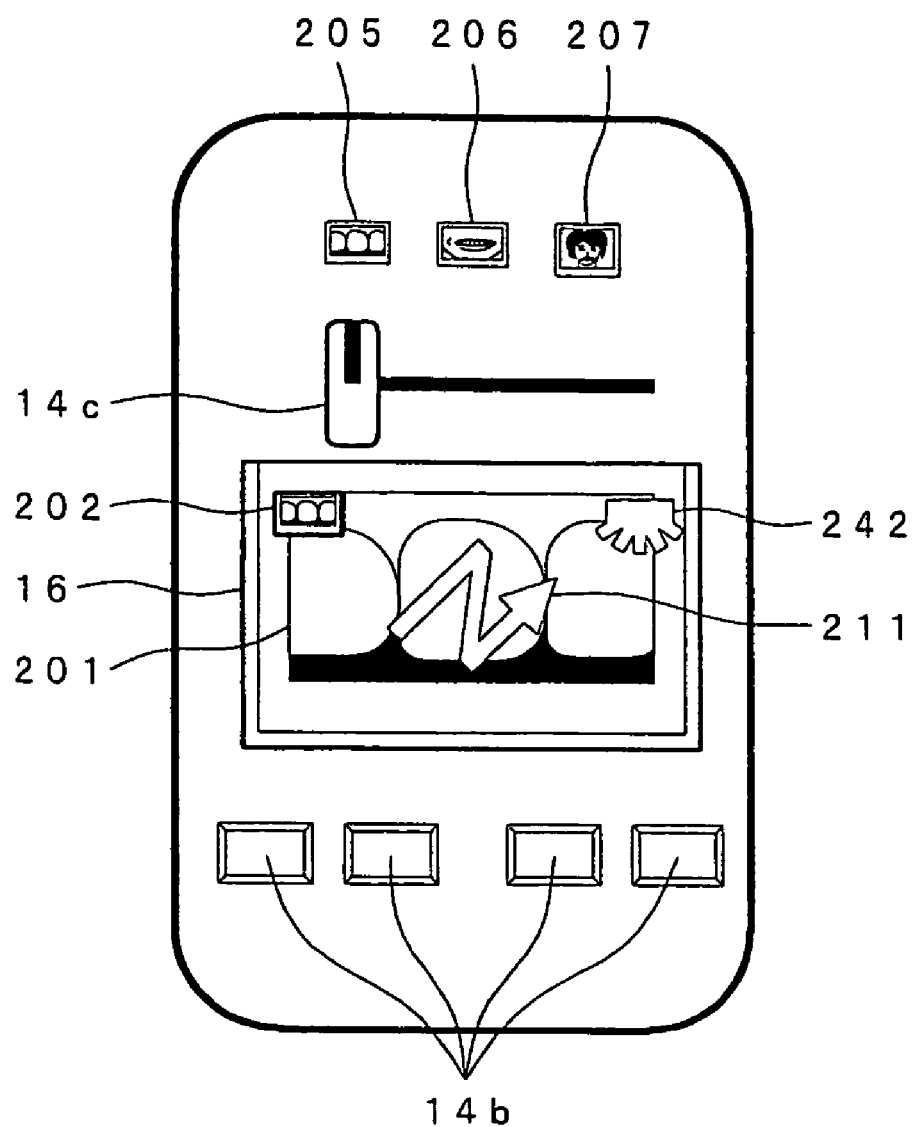
FIG. 70 shows an example of a camera shake alarm display of the first embodiment.

FIG. 70 shows a camera shake alarm display example.

The operating switch 14 and LCD monitor 16 are disposed in an operating panel such as the one shown in FIG. 70, for example. The operating switch 14 comprises a plurality of switches 14b and a photographic range setting lever 14c (described subsequently). Marks 205, 206, and 207 showing a capture mode (described subsequently) that is changed in accordance with the operation of the photographic range setting lever 14c are provided above the photographic range setting lever 14c.

Furthermore, a display area 201 that displays an image of the object is provided on the LCD monitor 16 and a capture mode that is provided by the photographic range setting lever 14c is displayed as a mark 202 on the top left, for example, of the display area 201. In addition, an illumination light source lighting mark 242 (described subsequently) is displayed if required on the top right, for example, of the display area 201. Further, the camera shake alarm display 211 is displayed if required in the center, for example, of the display area 201.

As a result, the photographer is able to photograph again or take camera shake countermeasures that employ an external operation section such as a foot switch 213 as will be described subsequently, whereby image processing can be performed by acquiring unblurred images.

Figure 71:
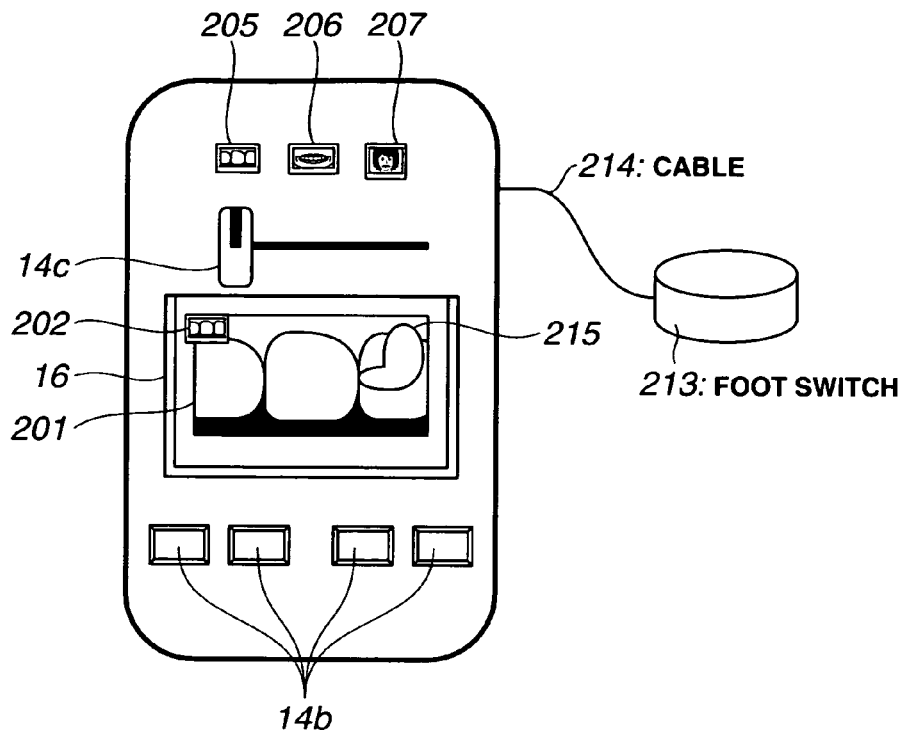
FIG. 71 shows a display example of a foot switch connection mark of the first embodiment.

That is, as one means of solving camera shake, means that eliminate camera shake of the photography device 1 by performing a photography instruction operation or the like by means of a remote operation from an external operation section that is remote instruction means disposed in a location other than that of the photography device 1. More specifically, as shown in FIG. 71, drawing an operating switch function via a cable 214 from the photography device 1 to use the function on the foot switch 213 may be considered. In this case, by displaying a mark 215 or the like that indicates that a foot switch has been connected on the LCD monitor 16 constituting the display means of the photography device 1, it may be made clear that the foot switch 213 is available. FIG. 71 shows a display example of a foot switch connection mark. As a result, the operation can be performed stably without worry of producing camera shake.

Figure 72:
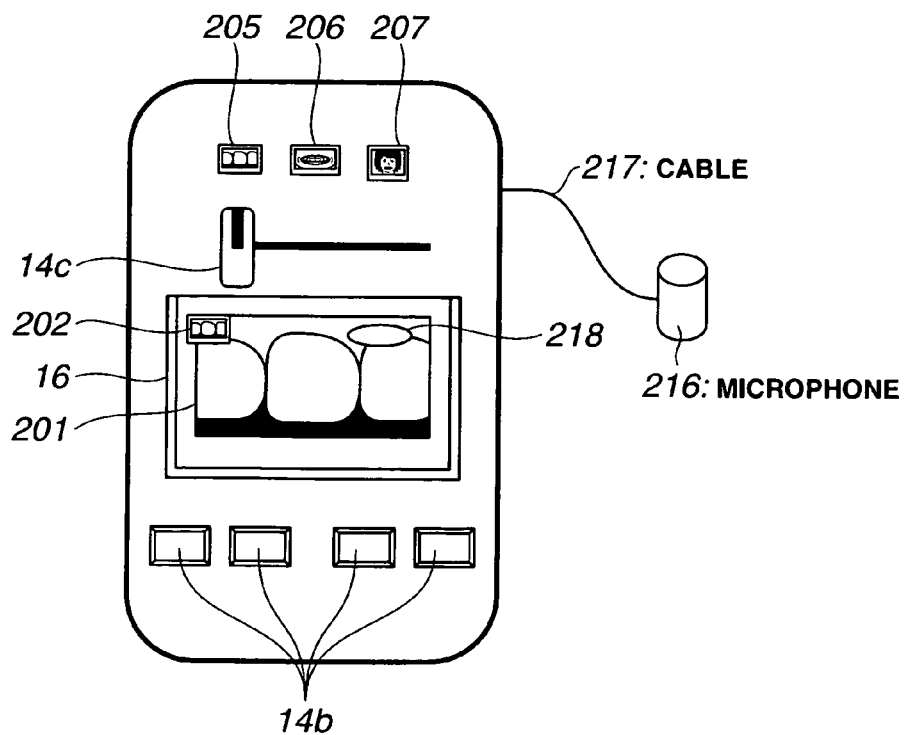
FIG. 72 shows a display example of a mike connection mark of the first embodiment.

Furthermore, a remote operation input is not limited to being made by the foot switch 213 and may also be made by a speech input, for example. That is, the following may be considered: As shown in FIG. 72, the constitution may be such that a microphone 216 constituting speech instruction means which is an external operation section is connected via a cable 217 to the photography device 1 and speech is input from the microphone 216. In addition, a speech recognition circuit or the like is provided in the photography device 1, an operation that is indicated by recognizing the speech thus input is interpreted, and the operation is performed. In this case, by displaying a mark 218 or the like indicating that the microphone 216 has been connected on the LCD monitor 16 constituting the display means of the photography device 1, it may be made clear that the microphone 216 is available. Here, FIG. 72 shows a display example of a microphone connection mark.

Figure 73:
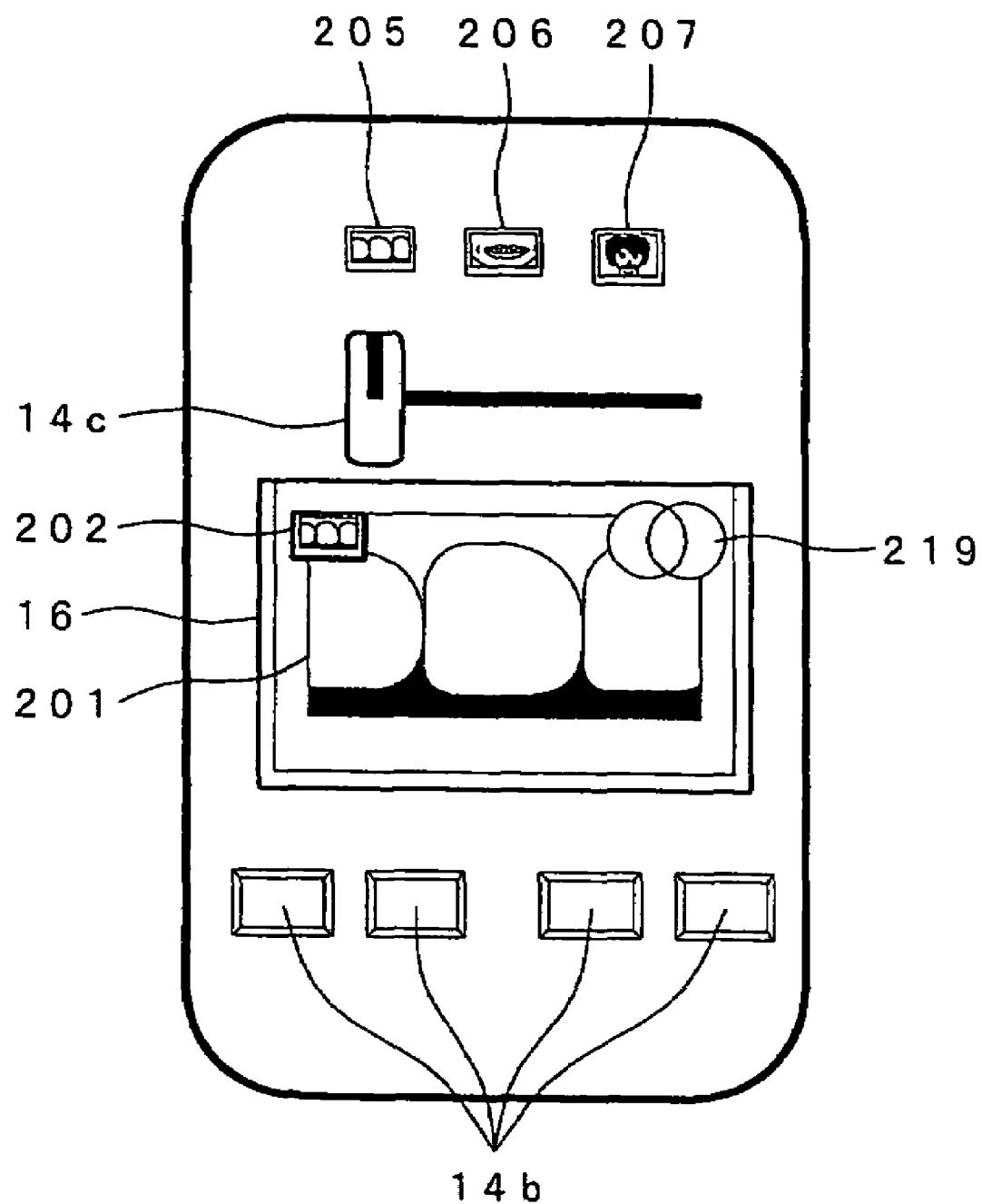
FIG. 73 shows a display example of a LAN connection mark of the first embodiment.

In addition, when the location in which the photography device 1 is used is subject to unfavorable conditions for humankind such as altitude and so forth, the location can also be switched for control via a network from an external operation section constituting remote instruction means disposed in a remote location. So too in this case, in order to make it clear that a remote operation is available, a mark 219 to that effect may be displayed on the LCD monitor 16 constituting the display means of the photography device 1. The mark or the like that is displayed at such time may more explicit state that such a remote operation is via a network, as shown by way of example in FIG. 73. FIG. 73 shows a display example of the LAN connection mark. That is, the example shown in FIG. 73 is one in which the mark 219 indicates that the network is a so-called local area network (LAN). Further, here, operation confirmation means for confirming the operation of the photography device 1 is desirably provided in the external operation section. As means for confirming the operation, confirmation via a display on a monitor or the like may be considered but such means is not limited to this means of confirmation. Confirmation via a lit lamp or speech or the like can also be adopted. In addition, photographic data confirmation means for confirming the photographic data of the photography device 1 may be provided in the external operation section. Display means such as a monitor is basically adopted as the photographic data confirmation means in this case.

In addition, the photography device 1 is constituted to be able to transfer all or a portion of the information displayed on the LCD monitor 16 constituting the display means, that is, the mode related displaying information and state related displaying information, for example, to the processing device 2 and other external device as additional data of the image data.

The processing device 2 is a personal computer or the like, for example, and is constituted comprising a computation device 21 that receives an object spectroscopic image that is output from the external I/F 17, calculates XYZ tristimulus values by using an input profile that will be described subsequently, and generates a display signal from which a display 22 (described subsequently) may obtain substantially the same XYZ tristimulus values as the XYZ tristimulus values that are estimated when the object is supplied by using a display profile from the XYZ tristimulus values; a display 22 that displays highly accurate color-reproduced images by means of the display signal that is output by the computation device 21; and, although not particularly illustrated, a network interface or the like for a connection to the network 3.

Figure 74:
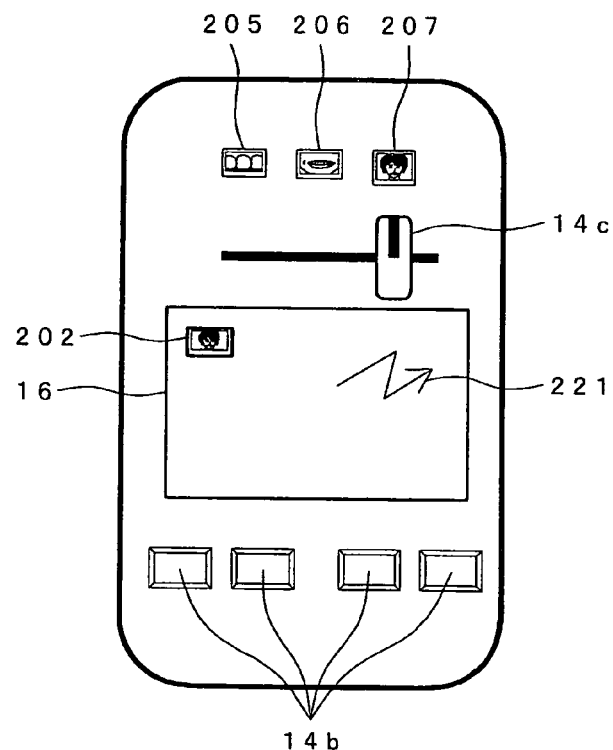
FIG. 74 shows a display example of data transfer in progress mark of the first embodiment.

Further, during data transfer, a data transfer in progress mark 221 as shown in FIG. 74, for example, is displayed on the LCD monitor 16 constituting the display means in order to make data transfer state clear. FIG. 74 shows a display example of the data transfer in progress mark. Naturally, the display indicating that data transfer is in progress is not limited to the display shown in FIG. 74.

Further, the photography device 1 and processing device 2 may be connected through wire or may be connected wirelessly via Bluetooth or a wireless LAN or the like, for example, or may be integrated with one another.

Figure 75:
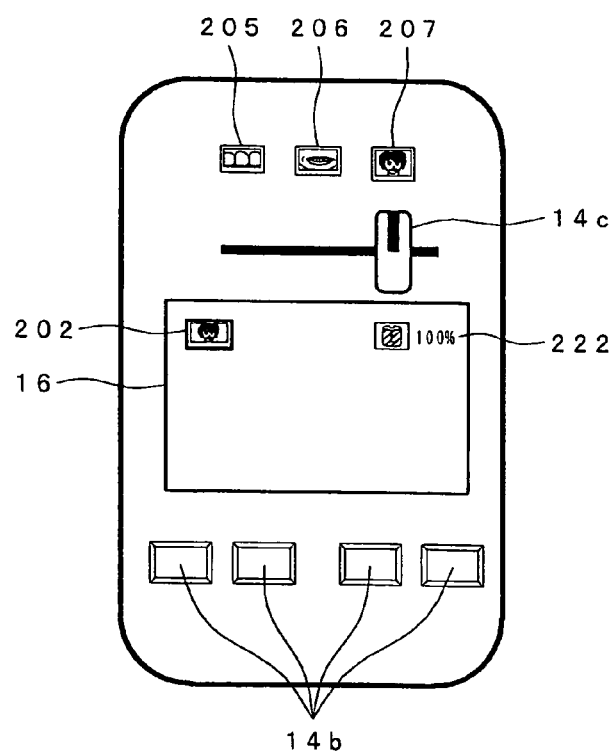
FIG. 75 shows a display example of battery remaining mark of the first embodiment.

The photography device 1 is constituted to comprise the battery 20*a* as shown in FIG. 1. The battery 20*a* is not necessarily required because it is possible to receive a supply of power when the photography device 1 is connected by fixed wire, but may be said to be more or less essential when the photography device 1 is connected wirelessly (however, the extent to which the battery 20*a* is essential would be somewhat alleviated should technology to supply power wirelessly that is being developed be put to practical use). Hence, it is important to know to the extent of the current battery remaining amount of the battery 20*a* with respect to the battery remaining amount (that is, the battery capacity) when the battery is fully charged. A mark 222 that indicates the battery remaining amount is displayed on the LCD monitor 16 constituting the display means as shown in FIG. 75, for example, for this purpose. FIG. 75 shows a display example of the battery remaining amount mark. In this example, the fact that the battery is 100% charged is indicated by a picture of the battery or text. Here also, the display of the battery remaining amount is not limited to the display shown in FIG. 75. Furthermore, the information relating to the battery 20*a* is not limited to the battery remaining amount. Other information may also be displayed.

Figure 3A:
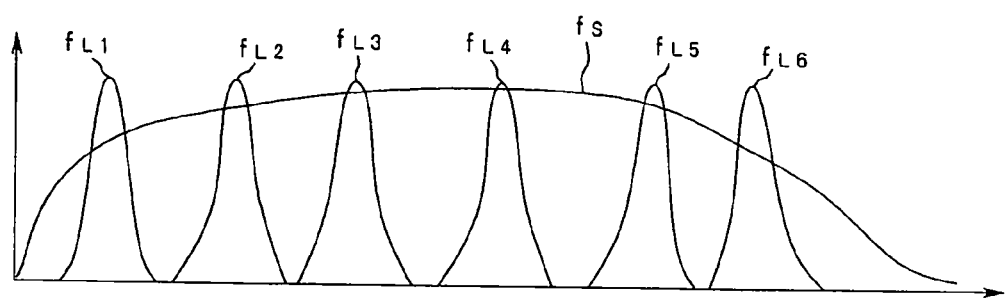
FIG. 3A and FIG. 3B are a line diagram showing a CCD spectroscopic sensitivity characteristic and an LED light-emission spectral, as well as the spectroscopic characteristic of the CCD spectroscopic sensitivity characteristic and LED light-emission spectral, of the first embodiment.
Figure 3B:
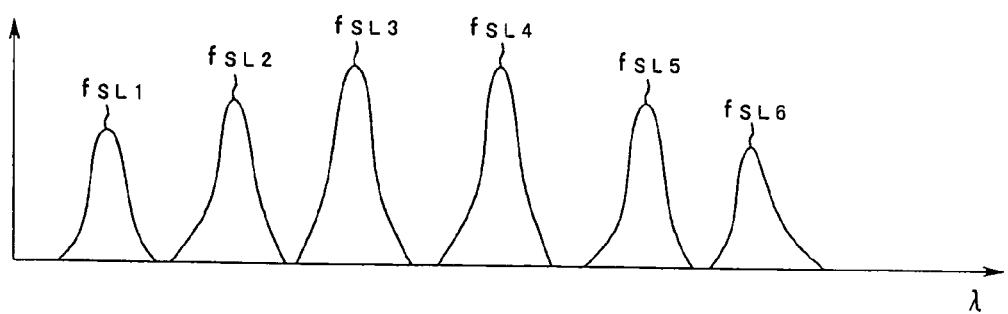

FIG. 3A and FIG. 3B are a line diagram showing the spectroscopic sensitivity characteristic of the CCD 8 and the light emission spectral of the LEDs 6*a* to 6*f* and the spectroscopic characteristic of both the spectroscopic sensitivity characteristic and the light emission spectral.

The first to sixth LEDs 6*a* to 6*f*, which are light-emitting elements, have different independent light emission spectrals as shown in FIG. 3A in such a manner that the light of the first LED 6*a* indicated by the curve fL1 is blue with a tinge of violet, for example, the light of the second LED 6*b* indicated by the curve fL2 is blue with a tinge of green, for example, the light of the third LED 6*c* indicated by the curve fL3 is green with a tinge of blue, for example, the light of the fourth LED 6*d* indicated by the curve fL4 is green with a tinge of yellow, for example, the light of the fifth LED 6*e* indicated by the curve fL5 is orange, for example, and the light of the sixth LED 6*f* indicated by the curve fL6 is red, for example.

Further, in the illustrated example, the respective light emission spectrals of the first to sixth LEDs 6*a* to 6*f* are completely separated without overlapping one another. However, light emission spectrals a portion of which overlaps are acceptable. Naturally, the types of LED are not limited to six types. A combination of LEDs of a suitable number of types can be adopted.

Here, it is possible to adopt, as the spectral arrangement of the illumination light emitted by the respective LEDs, any of an equal wavelength interval (peaks, for example, stand in a line at equal intervals in the wavelength direction), an equal wavelength ratio interval (peaks or the like stand in a line at fixed ratio intervals in the wavelength direction), a specific arrangement for a specific purpose (peaks or the like stand in a line in a specific arrangement in the wavelength direction in keeping with the specific purpose), a specific wavelength color multiplication setting (peaks or the like stand in a line in the wavelength multiplication position with a specific wavelength serving as the fundamental wavelength), a specified polarized color arrangement (the respective light components represented by the peaks that stand in a line in the wavelength direction are polarized in a specific direction), and light disposition outside the visible range (light that is represented by peaks that stand in a line in the wavelength direction reaches areas outside the visible range). The illumination light spectral arrangement best suited to the intended use may be selected.

Furthermore, here, although LEDs, which are semiconductor light-emitting elements of high brightness that are small and lightweight, relatively inexpensive, and easily obtained, are used as the light-emitting elements. However, the light-emitting elements are not limited to LEDs. Other light-emitting elements such as LDs (laser diodes) or other semiconductor lasers, for example, and other light-emitting elements can also be used.

Meanwhile, in this embodiment, the CCD 8 uses a monochrome-type CCD and the sensor sensitivity substantially covers the visible light range as indicated by the curve fS in FIG. 3A. Further, although a monochrome CCD is used as the image pickup element here, the image pickup element is not limited to a monochrome CCD. As will be mentioned in subsequently described embodiments, a color-type CCD may be used but the image pickup element is not limited to a CCD. A CMOS-type image pickup element or image pickup elements of a variety of other types can be widely used.

Further, the spectroscopic sensitivity characteristics when an image of an object illuminated by the first to sixth LEDs 6*a* to 6*f* is received by the CCD 8 are as per the curves fSL1 to fSL6 shown in FIG. 3B, for example. The wavelength-induced difference in the total spectroscopic sensitivity characteristic is electrically processed downstream or corrected as an input profile related to the photography device 1.

Figure 2A:
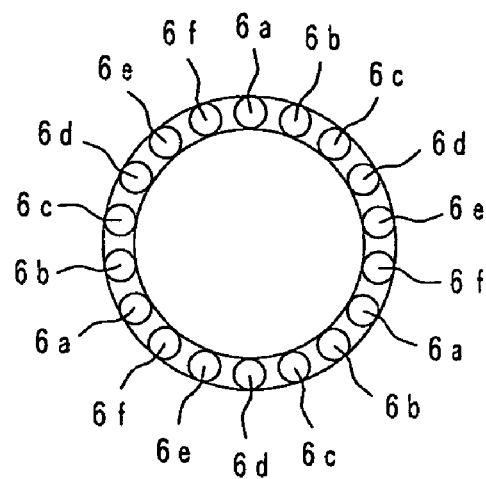
FIG. 2A to FIG. 2C show LED disposition examples and constitutional examples of the first embodiment.
Figure 2B:
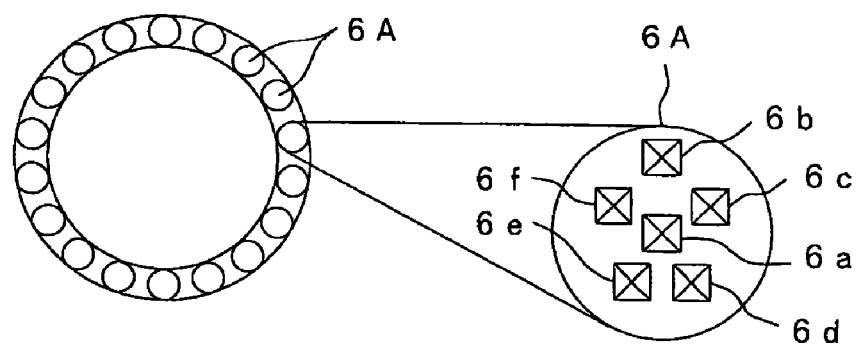
Figure 2C:
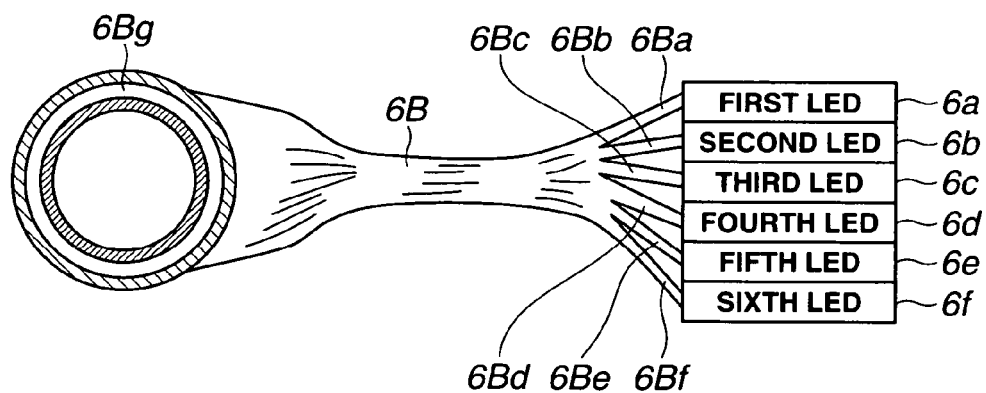

Furthermore, FIG. 2A to FIG. 2C show LED disposition examples and constitution examples, and so forth.

FIG. 2A shows an example in which the first to sixth LEDs 6*a* to 6*f* constituted of primary colors of six types are sequentially arranged in three sets (three of each color) in a ring shape. Further, the illustrated arrangement order is only represents one example. The arrangement order is not limited to this arrangement order. An optional arrangement such as reverse order or a random arrangement is widely applicable.

Subsequently, FIG. 2B shows an example in which a plurality of light-emitting sections 6A are arranged in a ring shape and the first to sixth LEDs 6*a* to 6*f* are arranged such that primary colors of six types are included in the respective light-emitting sections 6A. Although all six primary colors are arranged in one light-emitting section 6A in the illustrated example, the arrangement is not limited to this arrangement. Six primary colors may be divided among a plurality of light-emitting sections 6A such as an arrangement with three primary colors in each light-emitting section 6A.

In addition, FIG. 2C shows an arrangement in which first ends 6Ba to 6Bf of a fiber bundle 6B are connected to the first to sixth LEDs 6*a* to 6*f* respectively and the other ends 6Bg are formed in a ring shape. As a result, the illumination light that is emitted from the LEDs 6*a* to 6*f* enters the bundle fiber ends 6Ba to 6Bf. The bundle fiber ends are further constituted of a plurality of narrower fibers and the narrow fibers from the respective LEDs are mixed with one another in the bundle fiber exit section 6Bg such that a ring-shaped uniform light source is produced and irradiated onto the object, whereby the effect of total reflection caused by the object can be reduced.

Further, the LED arrangement is not limited to the example shown in FIG. 2A to FIG. 2C and, as long as a given arrangement supports the image pickup by the CCD 8, any suitable arrangement can be adopted such as a ring-shaped arrangement, a cross-shaped arrangement, a rectangular-shaped arrangement, a random arrangement, a lateral (or vertical or opposite) arrangement, a parallel arrangement, and a multiple point arrangement.

The two types of image acquisition mode that the photography device 1 has will be described next.

The image acquisition modes that can be adopted by the photography device 1 are monitor mode and capture mode.

The monitor mode displays images on display means such as the LCD monitor 16 in order to determine the photographic range with respect to the object and so forth.

Further, the capture mode is a mode that acquires required object image data. In this capture mode, not only is it possible to acquire a spectroscopic image (spectroscopic image capture mode), moving images, normal RGB images (RGB capture mode) and frame photographic images and so forth can also be acquired.

As mentioned earlier, the photography device 1 can pick up images such as moving images which are normal RGB images and still images which are object spectroscopic images of six primary colors permitting highly accurate color reproduction. Moving images are picked up in monitor mode, which acquires images for monitor use and still images are picked up in spectroscopic image capture mode within capture mode that captures image data.

These two modes, that is, monitor mode and capture mode are constituted such that these modes are switched by pressing a photography button 14a (See FIG. 16) which is a push-type button switch contained in the operating switch 14.

That is, the monitor mode is automatically set by first turning on the power supply switch or similar and the object image is displayed on the LCD monitor 16 as a moving image. In this state, the part of the object for which a spectroscopic image is to be shot is sought and the photography device 1 is positioned. Thus, by pushing the photography button 14a (See FIG. 16) at the moment when the object part to be photographed is introduced to the image pickup range and positioning is performed, the monitor mode is switched to the spectroscopic image capture mode and an object spectroscopic image is acquired as a still image.

The photography device 1 is constituted such that, after the object spectroscopic image has been acquired, the photography device 1 reverts to the monitor mode and is then able to seek an object part of which a spectroscopic image is to be acquired next.

Figure 76A:
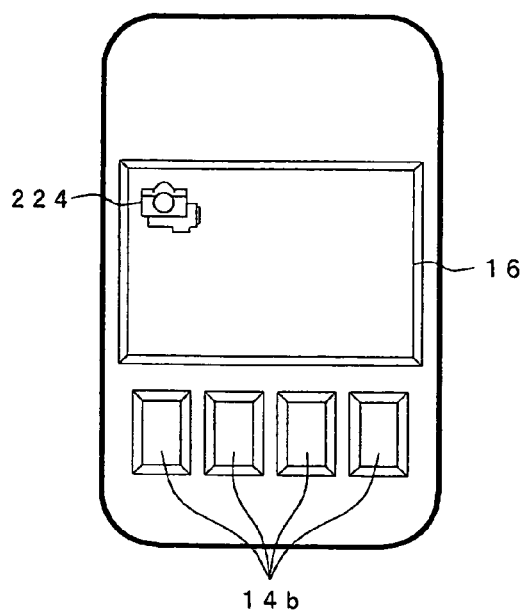
FIG. 76A and FIG. 76B show a first display example of a capture mode and monitor mode of the first embodiment.
Figure 76B:
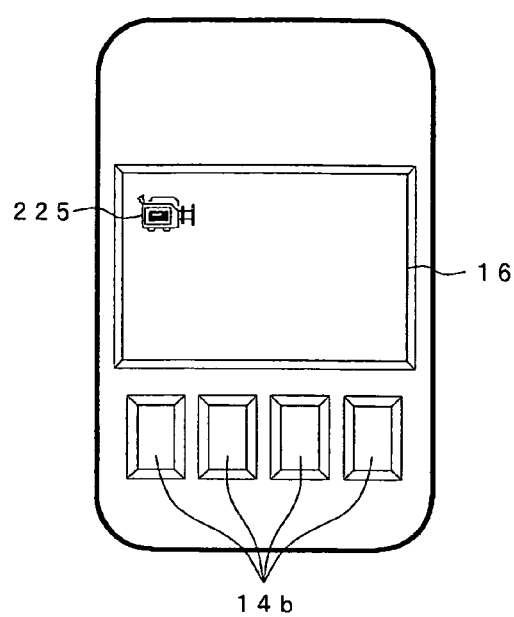

Further, the states of the respective modes are displayed on the LCD monitor 16 constituting the display means as shown in FIG. 76A and FIG. 76B. FIG. 76A and FIG. 76B show a first display example of the capture mode and monitor mode. That is, in monitor mode, a mark 225 of a so-called movie camera as shown in FIG. 76B is displayed on the LCD monitor 16 and, in spectroscopic image capture mode, a mark 224 of a so-called still camera as shown in FIG. 76A is displayed on the LCD monitor 16.

Further, the LCD monitor 16 for executing such a display is desirably a color monitor but may also be a monochrome monitor.

Furthermore, the display means is not limited to an LCD and, although not illustrated, display means capable of displaying image-related information such as an LED panel or EL panel, for example, are widely applicable.

The LCD monitor 16 is not limited to such a display and is also capable of executing other displays.

Figure 77A:
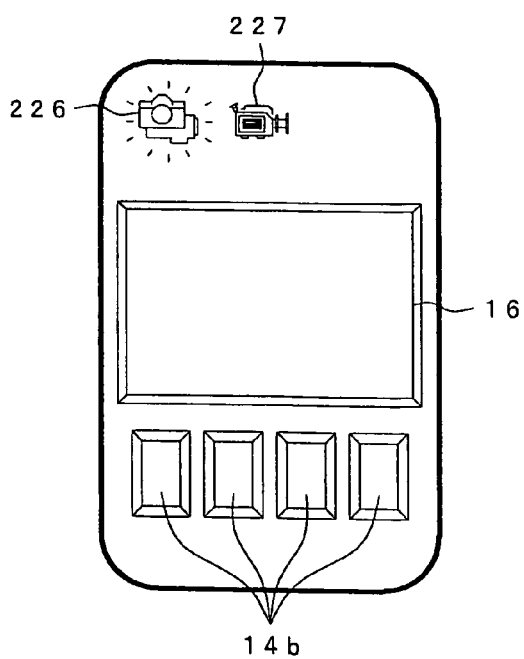
FIG. 77A and FIG. 77B show a second display example of the capture mode and monitor mode of the first embodiment.
Figure 77B:
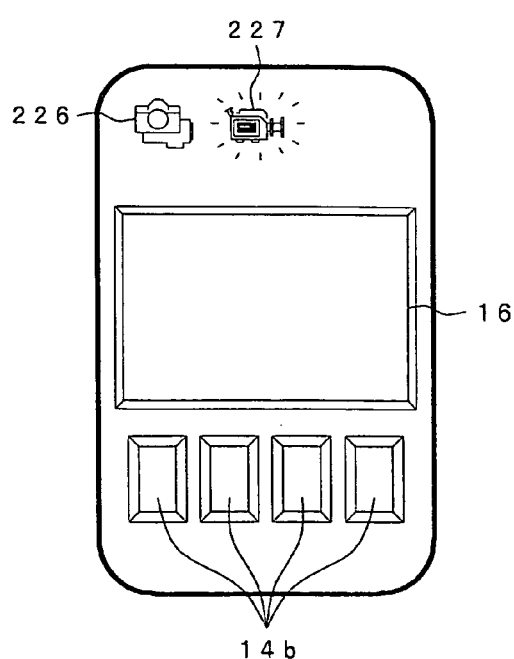

First, FIG. 77A and FIG. 77B show a second display example of capture mode and monitor mode. The example shown in FIG. 77A and FIG. 77B are an example in which a picture of the still camera is shown, capably lit or unlit, as a mark 226 indicating capture mode and a picture of the movie camera is shown, capably lit or unlit, as a mark 227 that indicates monitor mode. FIG. 77A shows a display example for when capture mode is adopted and FIG. 77B shows a display example for when monitor mode is adopted.

Figure 78A:
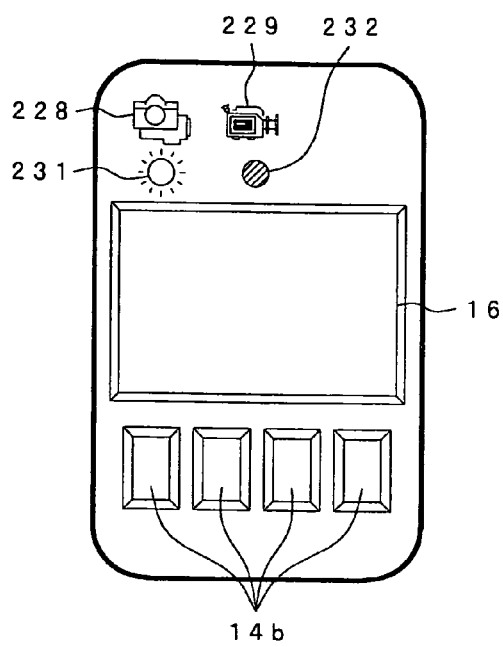
FIG. 78A and FIG. 78B show a third display example of the capture mode and monitor mode of the first embodiment.
Figure 78B:
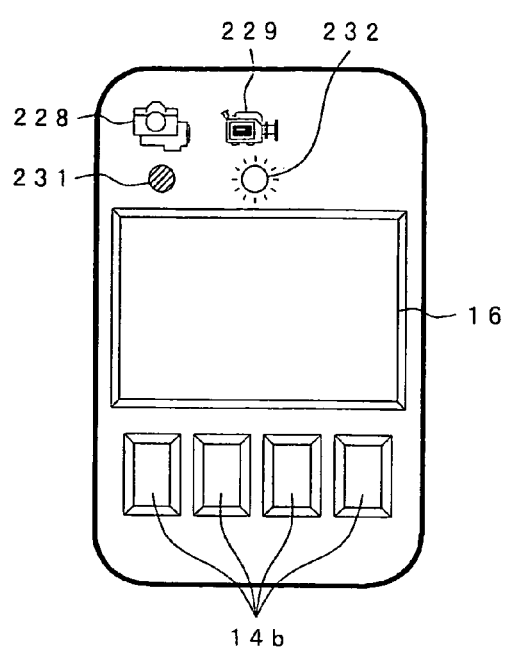

Thereafter, FIG. 78A and FIG. 78B show a third display example of capture mode and monitor mode. The example shown in FIG. 78A and FIG. 78B are an example in which a picture of the still camera is displayed as a mark 228 that indicates capture mode and a picture of the movie camera is displayed as a mark 229 that indicates monitor mode and in which LEDs 231 and 232 that indicate which mode has been selected are disposed such that the same can be lit and unlit below the marks 228 and 229. FIG. 78A shows a display example for when capture mode has been adopted and FIG. 78B shows a display example for when monitor mode has been adopted.

Figure 79A:
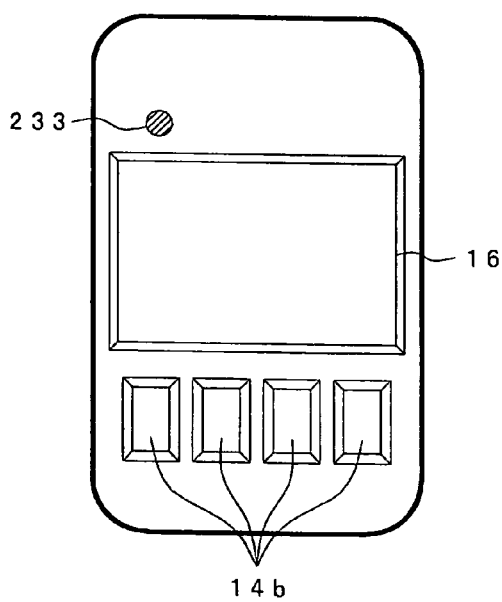
FIG. 79A and FIG. 79B show a fourth display example of the capture mode and monitor mode of the first embodiment.
Figure 79B:
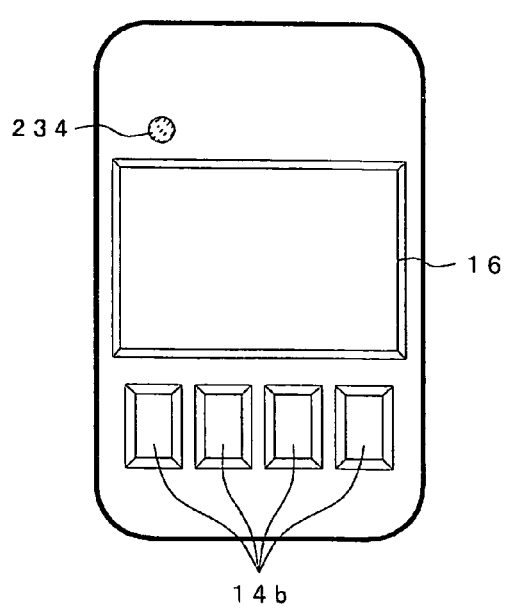

In addition, FIG. 79A and FIG. 79B show a fourth display example of capture mode and monitor mode. FIG. 79A and FIG. 79B are a type of display in which lamps of different colors are disposed and which displays modes by means of the colors of lit lamps. FIG. 79A shows that capture mode has been adopted by turning on a yellow lamp 233, for example. Further, FIG. 79B shows that monitor mode has been adopted by turning on an orange lamp 234, for example.

Additionally, the display is not limited to being executed by means of marks. For example, the display may also be executed by displaying text such as 'monitor' and 'capture', for example.

Figure 80:
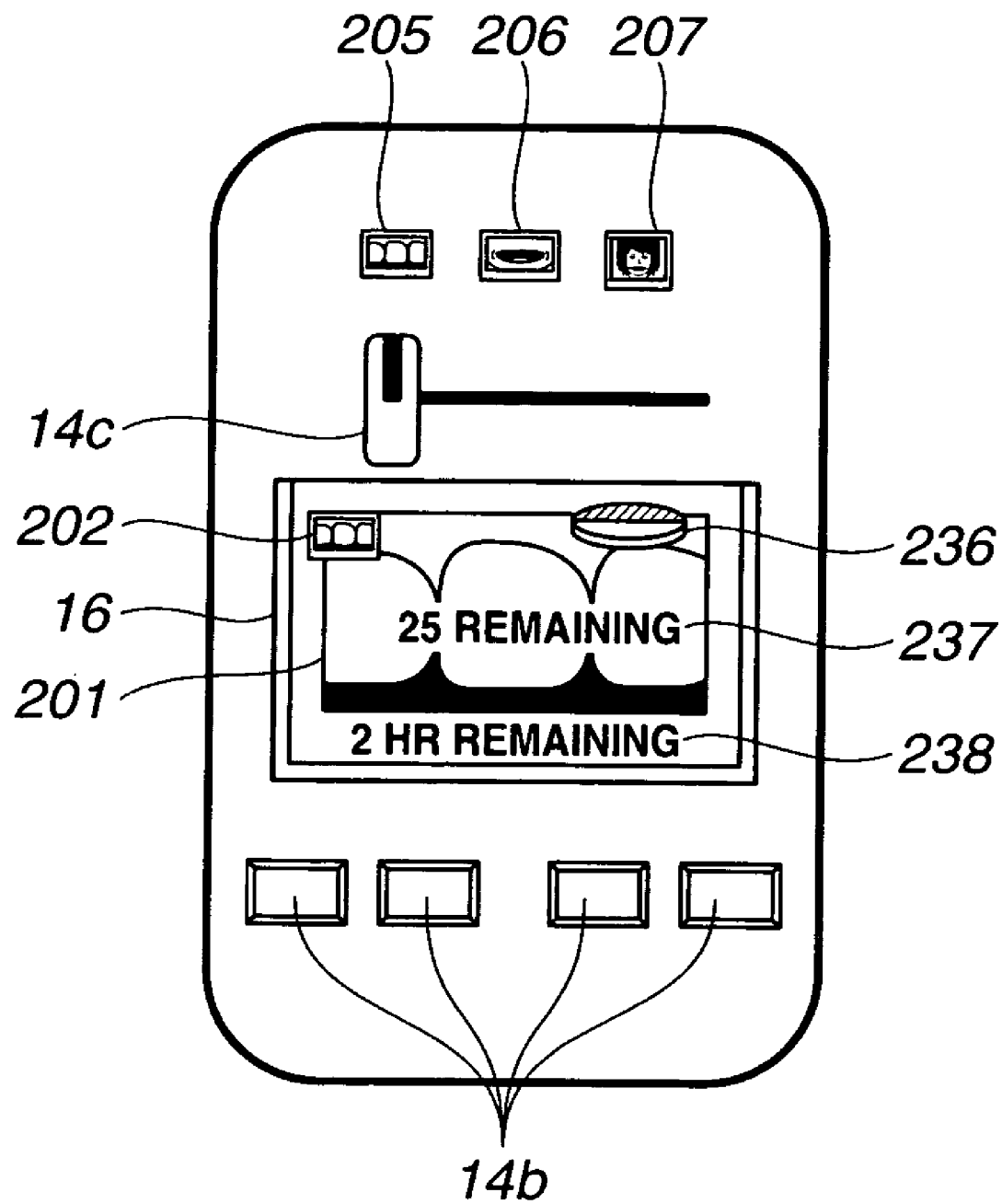
FIG. 80 shows an example in which various states are displayed in the first embodiment.

Further, in addition to the abovementioned modes, the remaining memory amount can be displayed as a mark 236, the number of possible photographs remaining can be displayed as text 237, and the remaining usage time can be displayed as text 238, as shown in FIG. 80 by way of example, as items that are displayed on the LCD monitor 16 constituting the display means. Here, FIG. 80 shows an example that displays a variety of states. Further, such displays are similarly not limited to the examples shown in FIG. 80.

Further, although not illustrated, by making additional settings, a color reproduction display that uses the acquired spectroscopic image and a display that results from an interpretation of the spectroscopic image, and so forth, can be displayed on the LCD monitor 16 or the display 22 immediately following the acquisition of the spectroscopic image.

Figure 4:
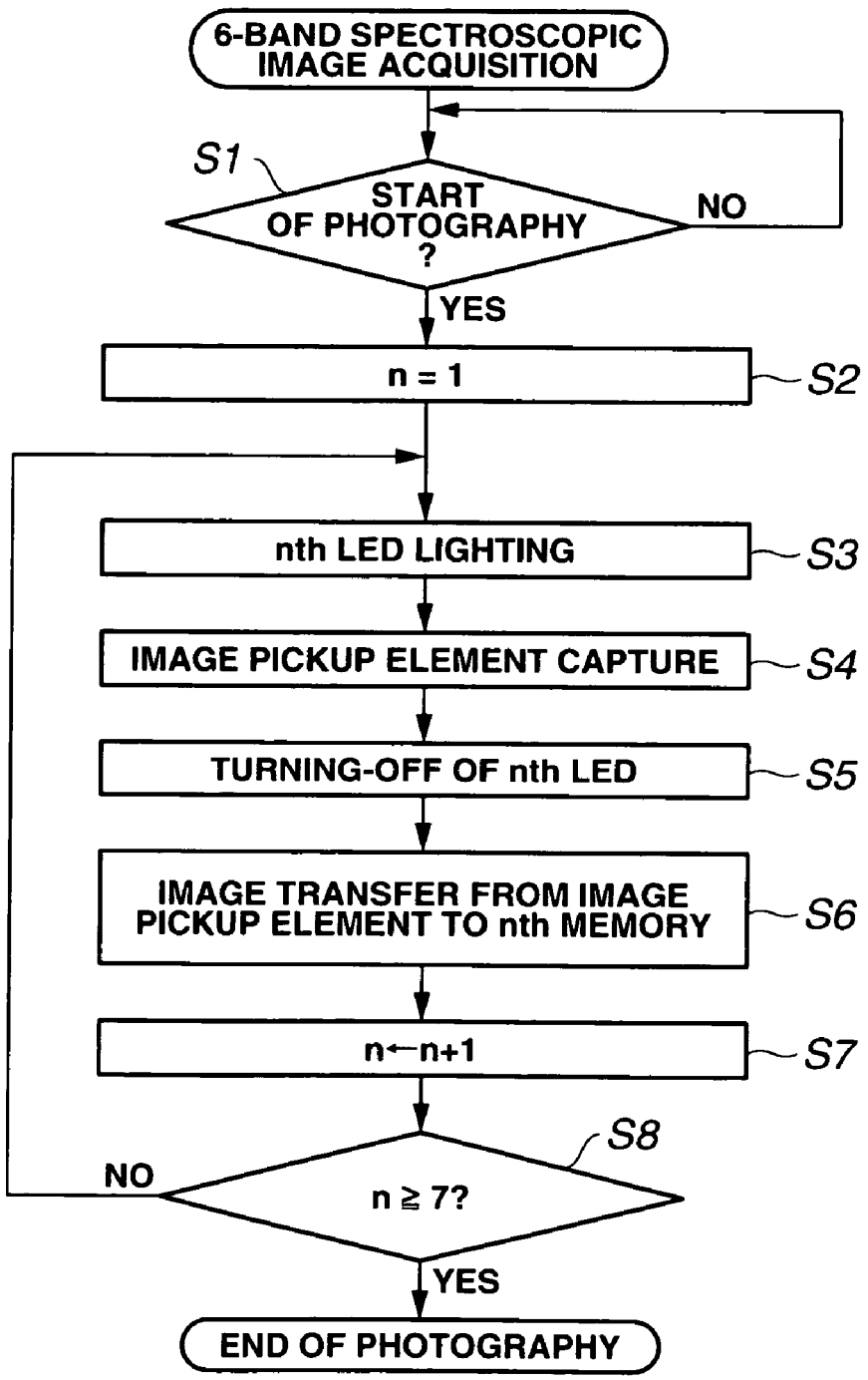
FIG. 4 is a flowchart showing the operation of the light emission of each LED in 6-band spectroscopic image acquisition and the image acquisition of the image pickup element of the first embodiment.
Figure 5:
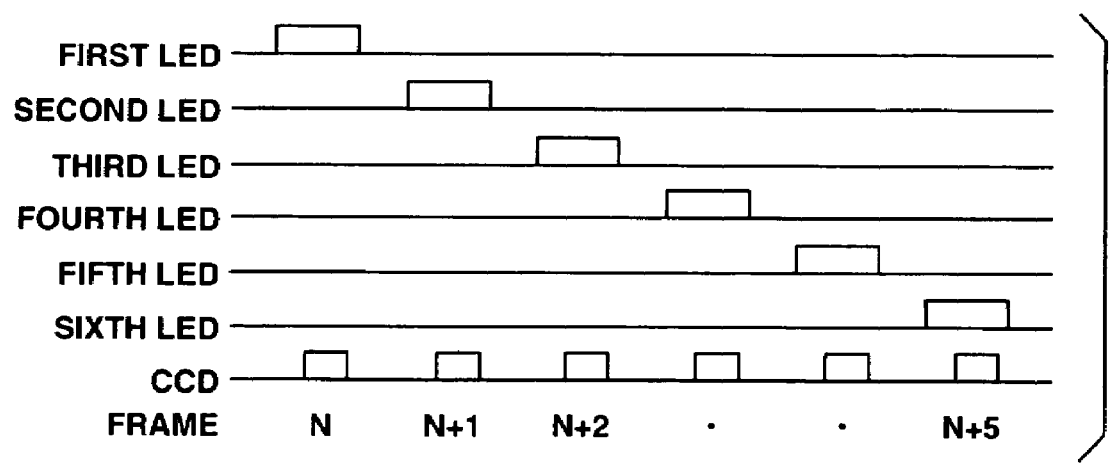
FIG. 5 is a timing chart showing an aspect of the operation of the light emission of each LED in the 6-band spectroscopic image acquisition and the image acquisition of the image pickup element of the first embodiment.
Figure 6:
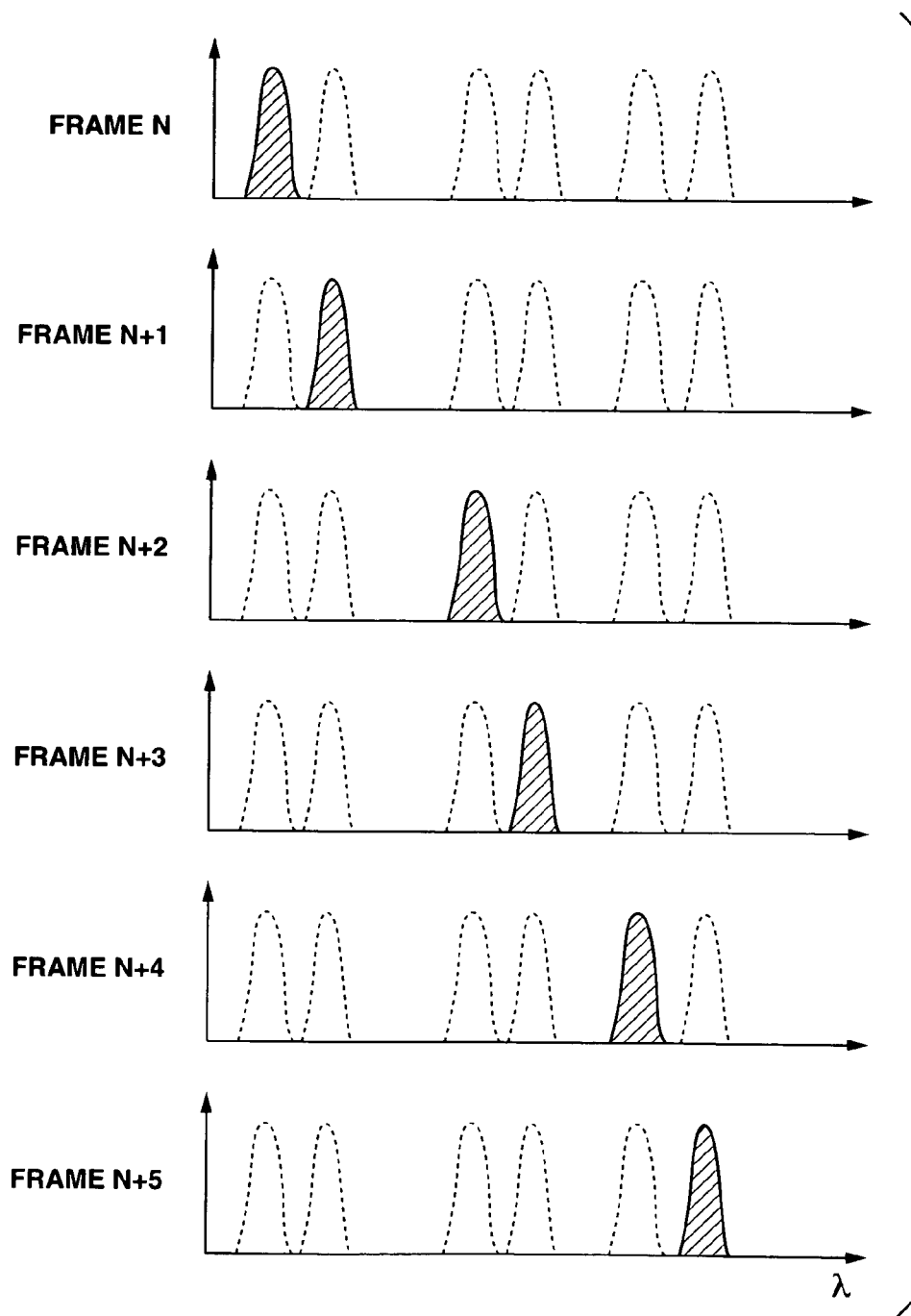
FIG. 6 is a line diagram showing the band characteristic of each frame in the 6-band spectroscopic image acquisition of the first embodiment.

The operation of the spectroscopic image capture mode in the image processing system will be described next with reference to FIGS. 4 to 6. FIG. 4 is a flowchart showing the operation of the light emission of each LED in 6-band spectroscopic image acquisition and the image acquisition of the image pickup element; FIG. 5 is a timing chart showing an aspect of the operation of the light emission of each LED in the 6-band spectroscopic image acquisition and the image acquisition of the image pickup element; FIG. 6 is a line diagram showing the band characteristic of each frame in the 6-band spectroscopic image acquisition.

When the photography device 1 is switched from monitor mode to spectroscopic image capture mode by pressing the photography button 14a (See FIG. 16), it is judged whether to start spectroscopic-image image pickup (step S1). The judgment operation need not be performed when spectroscopic-image image pickup is started immediately by pressing the photography button 14a. However, when the photography button 14a is constituted of a two-stage-type push button, for example, and focal adjustment and exposure amount adjustment are performed in a first half-pressed state and exposure is started in a second fully pressed state, it is judged whether the photography button 14a has been pressed in the second stage in step S1.

Thereafter, 1 is set as the variable n (step S2) and the nth LED is turned on (step S3). Here, the first LED 6a is turned on in order to make the setting n=1. The illumination light of the first LED 6a is irradiated onto the object via the projection opening 5a of the enclosure 5. Here, the attachment 4 is flexibly attached to the surface of the object and, in order to prevent the invasion of external light, only the illumination light from the first LED 6a is cast onto the object. The reflected light from the object is made to form an image on the surface of the CCD 8 by the photographic optical system 7.

After the lighting of the first LED 6a is started, the image pickup by the CCD 8 or, more precisely, the accumulation of electrical charge, is started (See FIG. 5) (step S4).

The first LED 6a is then turned off once the image pickup by the CCD 8 has ended (step S5). Image data are read from the CCD 8, converted into digital data by the A/D converter 9, and then stored in a predetermined storage area (nth memory: first memory here) in memory 11 via the bus 10 (step S6). When a 6-band spectroscopic image is picked up, the storage areas from the first memory to the sixth memory are provided in memory 11 and the respective spectroscopic images are sequentially held in these storage areas.

Thereafter, n is incremented (step S7). Here, n is incremented from 1 to 2.

It is judged whether n is 7 or more (step S8) and, because n is still 2 here, the processing returns to step S3 and the second LED 6b is turned on, whereupon the operations from step S3 to step S7 mentioned above are performed.

Thus, when the operations up to step S6 is ended by turning on the sixth LED 6f when n=6, a 6-band spectroscopic image with the band characteristic shown in FIG. 6 is acquired and saved in the memory 11. Further, n has reached 7 in the judgment of step S8 because of the increment to n=7 in step S7, and the 6-band spectroscopic image acquisition operation is ended.

Further, although not illustrated, the timing of the image acquisition by the light-emitting elements (LED) and image pickup element (CCD) is not limited to the timing mentioned earlier. The same results are obtained when the light-emitting elements are turned on after the start of image acquisition by the image pickup element and when the image acquisition by the image pickup element is ended after the light-emitting elements are turned off, or similar.

Figure 7:
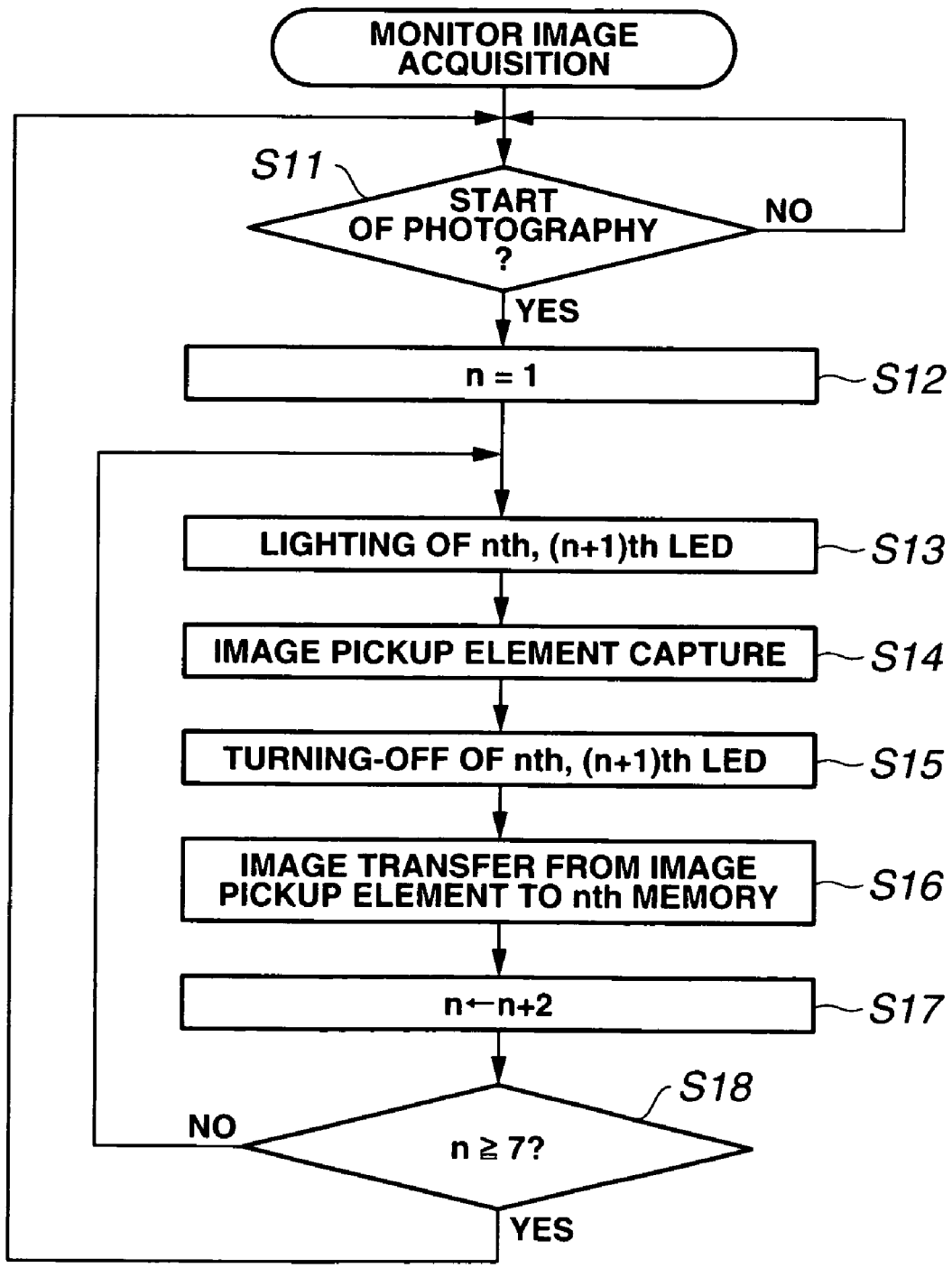
FIG. 7 is a flowchart showing the operation of the light emission of each LED and the image acquisition of the image pickup element in monitor image acquisition of the first embodiment.
Figure 8:
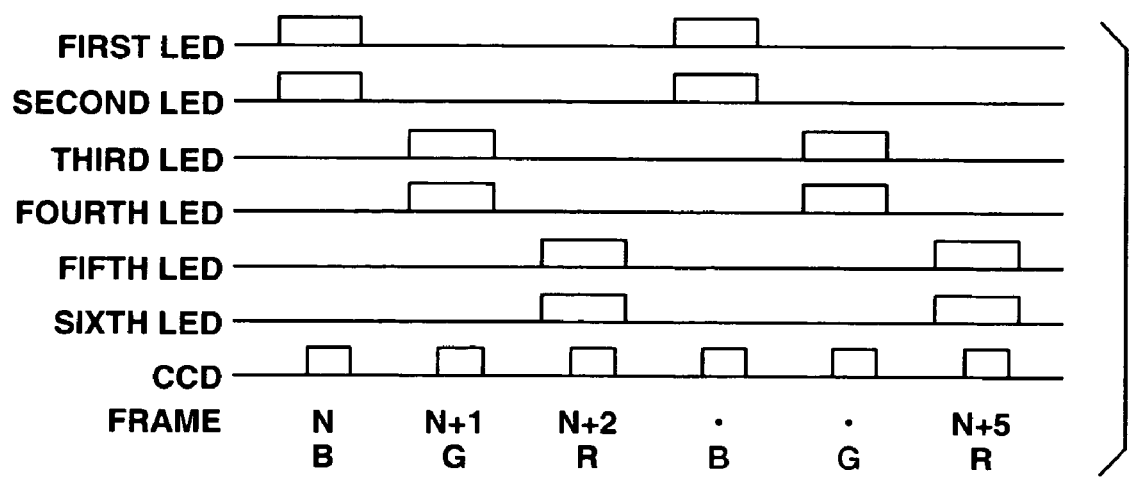
FIG. 8 is a timing chart showing an aspect of the operation of the light emission of each LED and the image acquisition of the image pickup element in monitor image acquisition of the first embodiment.
Figure 9:
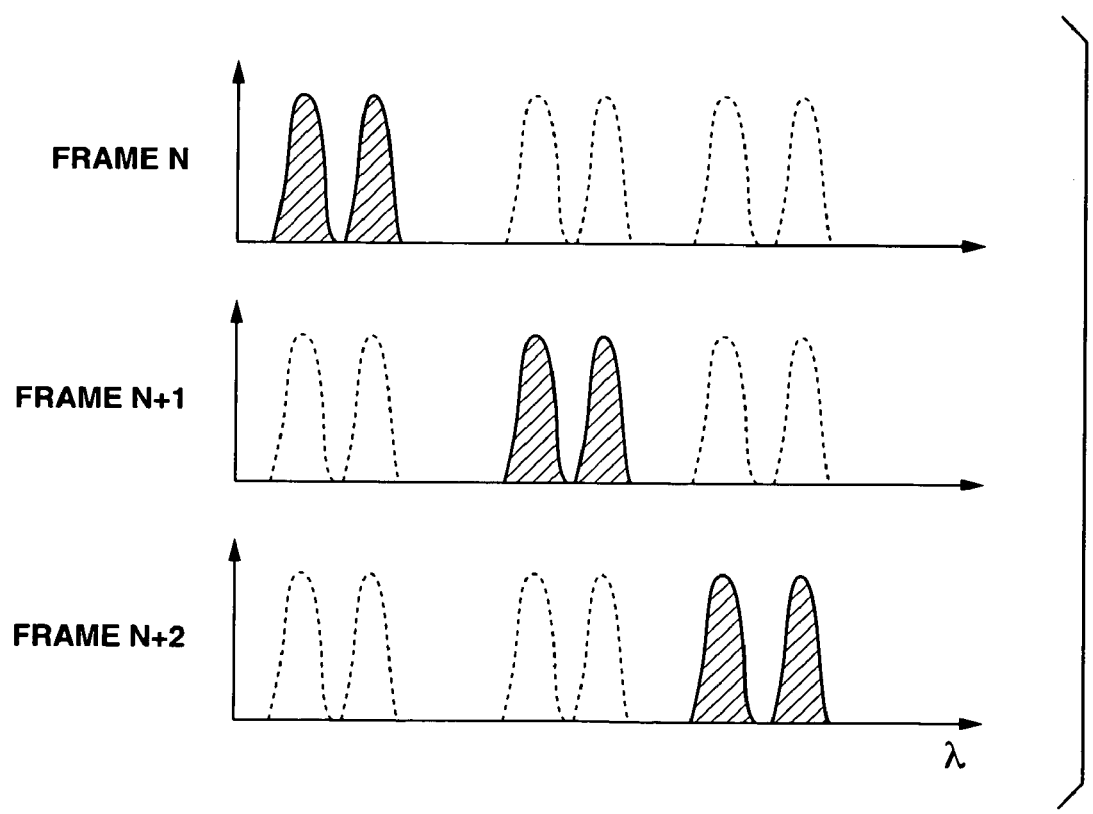
FIG. 9 is a line diagram showing the band characteristic of each frame in the monitor image acquisition of the first embodiment.

The operation of the monitor mode of the image processing system will be described next with reference to FIGS. 7 to 9. FIG. 7 is a flowchart showing the operation of the light emission of each LED and the image acquisition of the image pickup element in monitor image acquisition, FIG. 8 is a timing chart showing an aspect of the operation of the light emission of each LED and the image acquisition of the image pickup element in monitor image acquisition, and FIG. 9 is a line diagram showing the band characteristic of each frame in the monitor image acquisition.

This monitor mode is a mode that acquires an RGB image as a moving image by means of the frame sequential method by sequentially obtaining: from the illumination light of six primary colors of the first to sixth LEDs 6a to 6f, a state in which the first LED 6a and second LED 6b that correspond to a blue (B) category are turned on, a state in which the third LED 6c and fourth LED 6d that correspond to a green (G) category are turned on, and a state where a fifth LED 6e and sixth LED 6f that correspond to a red (R) category are turned on.

Further, although light emission primary colors are selected by assuming general RGB image usage here, the selection is not limited to that detailed above. Other light emission primary colors suited to a special application or the like can also be selected.

When the monitor mode is set by turning the power supply switch on or monitor mode is restored by ending the spectroscopic image capture mode, the start of monitor-image image pickup is awaited (step S11).

Here, image pickup is immediately started and 1 is set as the variable n (step S12). The nth LED and n+1 th LED are turned on (step S13). Here, the first LED 6a and second LED 6b are turned on in order to make the setting n=1.

After the lighting of the first LED 6a and second LED 6b has started, image pickup by the CCD 8 is started (see FIG. 8) (step S14).

The first LED 6a and second LED 6b are turned off once image pickup by the CCD 8 has ended (step S15), whereupon image data are read from the CCD 8, converted into digital data by the A/D converter 9, and stored in a predetermined storage area (nth memory: first memory here) in the memory 11 via the bus 10 (step S16).

Thereafter, n is incremented by 2 (step S17). Here, n is increased from 1 to 3.

It is judged whether n is 7 or more (step S18) and, because n is still 3 here, the processing returns to step S13, whereupon the third LED 6c and fourth LED 6d are turned on and the operations from step S13 to step S17 are performed.

As a result, n=5 and the processing returns to step S13, whereupon the fifth LED 6e and sixth LED 6f are turned on. When the operations up to step S16 are complete, RGB images of the band characteristics shown in FIG. 9 are acquired in the order B, G, R and saved in the first memory, third memory, and fifth memory respectively of the memory 11. It is then judged that n is 7 in the judgment of step S18 because n has been incremented to n=7 in step S17.

Thus, after the RGB image has been acquired, the processing returns to step S11 and it is judged whether the next RGB image has been acquired. When monitor mode is subsequently set, the next RGB image is acquired and, by successively repeating this process, an RGB moving image can be obtained.

Further, although not illustrated, the timing of image acquisition by the light-emitting elements (LED) and image pickup element (CCD) is not limited to the timing mentioned earlier. The same results are obtained when the light-emitting elements are turned on after the start of image acquisition by the image pickup element and when the image acquisition by the image pickup element is ended after the light-emitting elements are turned off, or similar.

Thus, the image data that is stored in the memory 11 is subsequently read and converted into an image signal for a monitor display is output to the LCD monitor 16 via the monitor I/F 15 and is displayed on the LCD monitor 16. Further, a display can also be executed on the display 22 of the processing device 2 by changing the settings of the image processing system.

Further, in order to secure the intensity of illumination here, LEDs of six primary colors are divided into twos to form groups which are three element clusters, that is, an R element cluster, a G element cluster, and a B element cluster. However, the LED light emission is not limited to such clusters. Light emission may be executed for each single color in which the first LED 6a is made to emit light for B (blue), the third LED 6c is made to emit light for G (green) and the fifth LED 6e is made to emit light for R (red), for example. Here, the spectroscopic characteristics of the LEDs may be selected to suit the RGB light emission.

In addition, a monitor display can be performed at high speed by acquiring a monochrome monitor image by turning on only one or a plurality of LEDs of a specific primary color.

FIG. 10 shows an example of a method of turning on the LEDs when three each of LEDs of six primary colors are provided.

Light-emitting modes (LED light-emitting modes) include, by way of example, a case where all LEDs are turned on, a case where only one LED of one primary color is turned on individually, a single primary color lighting case where three LEDs are turned on for one primary color, a case where LEDs of six primary colors are turned on individually, a case where six LEDs belonging to blue (B), for example, among eighteen LEDs of six primary colors are turned on, a case where six LEDs belonging to green (G), for example, among eighteen LEDs of six primary colors are turned on, a case where six LEDs belonging to red (R), for example, among eighteen LEDs of six primary colors are turned on, a case where three LEDS belonging to blue (B), for example, among eighteen LEDs of six primary colors are turned on, a case where three LEDs belonging to green (G), for example, among eighteen LEDS of six primary colors are turned on, a case where three LEDs belonging to red (R), for example, among eighteen LEDs of six primary colors are turned on. Thus, element clusters grouped by color can be made to emit light at the same time and element clusters grouped by position can be made to emit light at the same time.

Further, when an image of an object is picked up, the photography device 1 of this embodiment can be used with contact or contactlessly. However, in order to perform accurate color reproduction on the image, it is necessary to ensure that the image does not suffer the effects of light other than that produced by the photography device 1.

Therefore, when an image of the object is picked up contactlessly, external light illumination must be switched off.

Here, the photography areas when the object is photographed are varied depending on the application field. However, when the photographic areas of capture modes are classified from a general standpoint, a broad classification into a full capture mode in which the whole of the object is photographed and a partial capture mode in which a relevant point is photographed may be considered.

When dentistry is taken as an example of one application field, examples of images found in the field of dentistry include three types of image, namely, an image of one to three teeth, a full jaw image, and a complexion image. The requirement for such images is to confirm the nature of the treatment and the treatment result or for the purpose of being effectively used for the informed consent of the patient. Therefore, this photography device 1 is constituted so that capture modes that correspond with these images can be set. That is, the capture modes that can be set for the photography device 1 are as shown in (1) to (4) below.

(1) One to Three Teeth Image Mode (Partial Capture Mode)

Figure 81A:
FIG. 81A and FIG. 81B show an aspect of a close-up photography mode in the first embodiment.
Figure 81B:
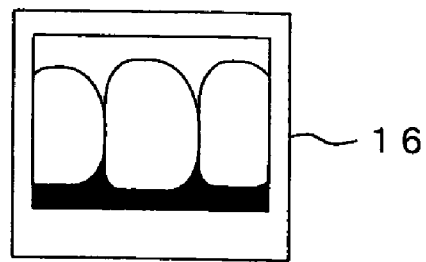

This mode is a mode (close-up photography mode) that takes an enlarged photograph of a tooth for observation of the status of an affected area or the status before and after treatment, as shown in FIG. 81A and FIG. 81B. FIG. 81A and FIG. 81B show an aspect of the close-up photography mode. Here, because a color evaluation is also important, this is a mode that performs color reproduction by acquiring an image by means of the above method in order to perform color reproduction highly accurately. Here, as shown in FIG. 81A, the photographer takes photographs as close as possible to the object and the results are displayed on the display 22 of the processing device 2 and also displayed as shown in FIG. 81B on the LCD monitor 16.

(2) Full Jaw Image Mode (Full Capture Mode)

Figure 82A:
FIG. 82A and FIG. 82B show an aspect of a nearby photography mode in the first embodiment.
Figure 82B:
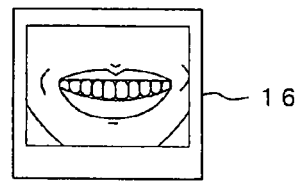

As shown by way of example in FIG. 82A and FIG. 82B, this mode is a mode that takes a full jaw photograph in order to confirm the balance between the treated tooth and the other teeth (nearby photography mode). FIG. 82A and FIG. 82B show an aspect of the nearby photography mode. The illumination system is constituted to be off in this mode. In this case, although there is not necessarily a need for high color reproduction, if required, such photography is made possible by connecting a high color reproduction light source unit shown in FIG. 60, for example. Here, as shown in FIG. 82A, the photographer performs photography pretty close to the object and the results are displayed on the display 22 of the processing device 2 and also displayed as shown in FIG. 82B on the LCD monitor 16.

(3) Complexion Image Mode (Full Capture Mode)

Figure 83A:
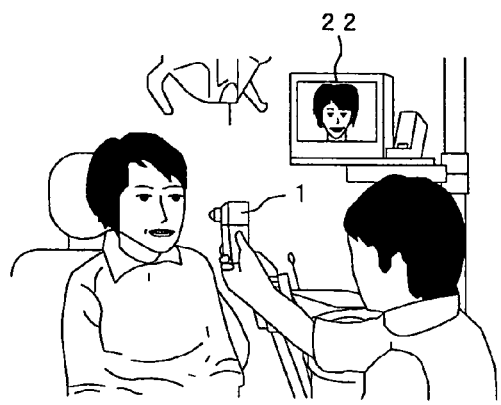
FIG. 83A and FIG. 83B show an aspect of a face photography mode in the first embodiment.
Figure 83B:
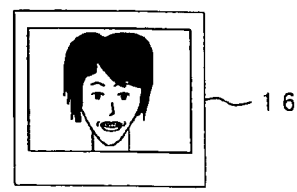

As shown in FIG. 83A and FIG. 83B, this mode is a mode (complexion photography mode) that takes a complexion photograph for observation of the balance of the whole face. FIG. 83A and FIG. 83B show an aspect of the facial photography mode. The illumination system is constituted to be off in this mode. Here, as shown in FIG. 83A, the photographer photographs the object from a suitable distance and the results are displayed on the display 22 of the processing device 2 and also displayed as shown in FIG. 83B on the LCD monitor 16.

(4) Whole Body Image Mode (Full Capture Mode)

Although not illustrated, this mode is a mode that takes a photograph of the whole body for observation of the balance of the whole body. Here, the photographer takes a photograph a fair distance apart from the object and the results are displayed on the display 22 of the processing device 2 and also displayed on the LCD monitor 16.

The image obtained by the partial capture mode (that is, mode (1)) among the modes above is a spectroscopic image and the image obtained by the full capture modes above (that is, modes (2) to (4)) is a normal photographic image. With regard to the illumination light when the normal photographic image is acquired, the illumination light source may be unlit because the general indoor light can be used. That is, in this example, the illumination light source is turned on only in the partial capture mode and the illumination light source is turned off in full capture mode.

Further, the photography device 1 need not deal with the setting of all the modes (1) to (4). The setting of two or more modes is acceptable.

The constitution and operation and so forth for setting three modes (1) to (3) among modes (1) to (4) above will be described next (that is, a constitution that allows three modes (1) to (3) to be set will be described by way of example here).

Figure 84:
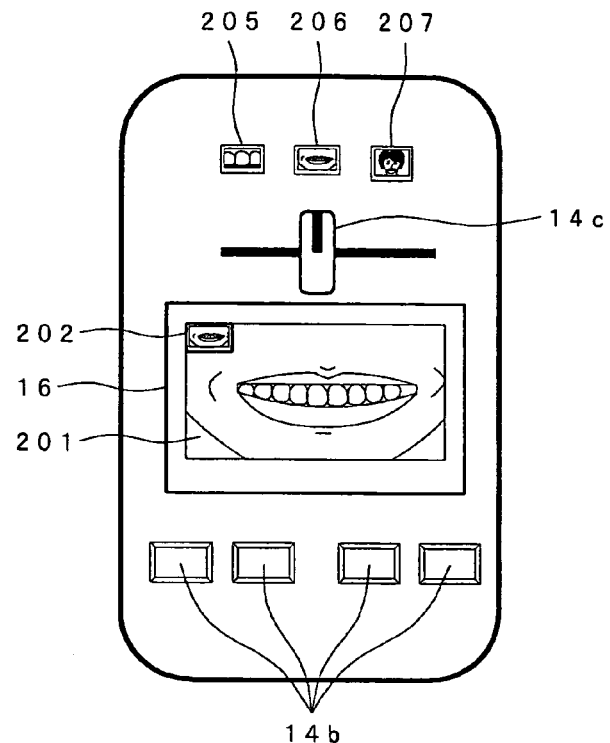
FIG. 84 shows an aspect in which a capture mode is provided in the first embodiment.

FIG. 84 shows an aspect in which a capture mode is set.

In the example shown in FIG. 84, the photographic range setting lever 14*c* that constitutes the photographic range setting means is provided as means for setting one capture mode among a plurality of capture modes.

This photographic range setting lever 14*c* is constituted to perform setting through the operation of the lever that is made to slide manually in a lateral direction, for example. Further, the photographic range setting lever 14*c* is constituted directly linked to the focus adjustment lever for adjusting the focus lens of the photography optical system 7 or work with relation to the focus adjustment lever.

The photographic range setting lever 14*c* maybe constituted to be positioned in a predetermined position by means of a notch mechanism or the like when operated manually. Further, the photographic range setting lever 14*c* may be constituted directly being linked to a focusing lens without the intervention of the focus adjustment lever or to work with a focusing lens.

In addition, focus adjustment and a zoom operation or the like may be performed manually (manual setting means) or may be performed automatically (automatic setting means).

Examples of automatic operations include remote adjustment/operation as represented by remote medical care or the like. Here, in an application assuming a certain fixed procedure, the following may be considered: the measurement area is changed automatically in accordance with the progress of the procedure, or focus adjustment is performed automatically so that the focal position is in a predetermined position, the focal position is automatically detected by an automatic focus adjustment mechanism, and the focal position is moved to this position, or similar.

Marks 205, 206, and 207 indicating the corresponding capture modes are added to the top side, for example, of the photographic range setting lever 14c. Here, mark 205, which corresponds to the one to three teeth image mode of (1) above is displayed on the left side of the photographic range setting lever 14c. Mark 206, which corresponds to the full jaw image mode of (2) above is displayed in the center of the photographic range setting lever 14c. Mark 207, which corresponds to the complexion image mode of (3) above is displayed on the right side of the photographic range setting lever 14c. Further, although marks are displayed as setting markers, such markers are not limited to marks. Text may be displayed, for example.

In addition, the capture mode that is set by the photographic range setting lever 14c is displayed as mark 202 on the top left, for example, of the display area 201. In this example, a mark of the same design as that of any of marks 205, 206, and 207 is displayed as mark 202.

Figure 85:
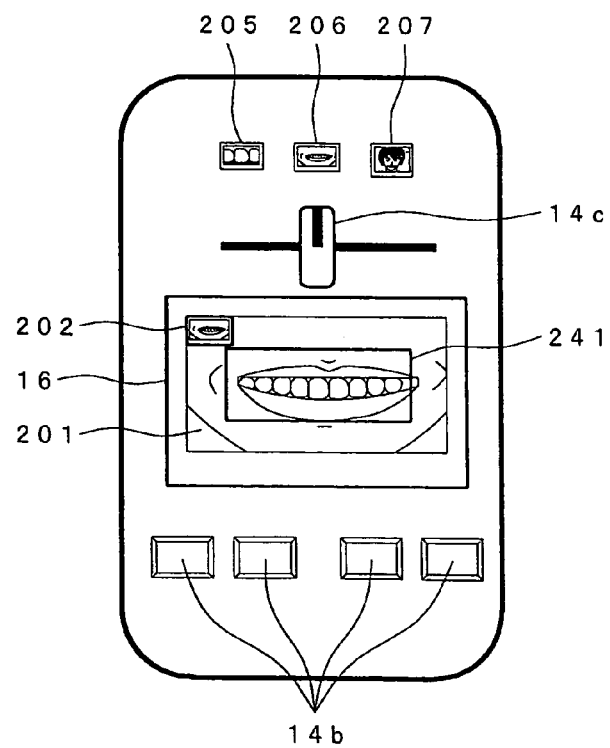
FIG. 85 shows a display example of a positioning guide in the first embodiment.

Furthermore, in dentistry, a comparison before and after treatment is essential. Hence, a photograph must be taken before treatment and after treatment, for example. However, the photographed size and position and so forth of the treated part to be photographed are sometimes changed each time a photograph is taken. Therefore, without further measures, reliability on an effective evaluation or on a confirmation of the results of treatment drops because of the substantial difficulties involved in comparing images. In order to avoid this, accurate positioning is important each time a photograph is taken. In this embodiment, as shown in FIG. 85, a positioning guide 241 constituting guide display means is displayed on the monitor (LCD monitor 16 or the like) constituting photographic range display means and provides assistance when performing positioning. FIG. 85 shows a display example of the positioning guide. Further, in the example shown in FIG. 85, the positioning guide 241 constituting guide means is rectangular but is not limited to being rectangular. The guide means may be a full jaw-shaped line, or means that accurately display the position of the photographic range by using text or marks can be widely applied, for example. In a more highly accurate case, a positioning judgment may be performed by executing image processing or the like that compares the monitor image with the previous image constituting the comparison target and then issuing an instruction such as 'left', 'right', 'up', 'down', 'forward', 'backward' to the photographer on the basis of the judgment result.

In addition, although not illustrated, distance information resulting from determining the range by means of an AF (autofocus) mechanism constituting autofocus means is recorded as image additional data. Distance information on the distance to the object may be acquired from additional data for the previous image and the photographer may be instructed to equalize the distance to the object currently being photographed with the previous distance.

Furthermore, automatic settings to perform photography in any of modes (1) to (4) above, that is, to perform automatic settings for the photographic range may be performed on the basis of the distance information acquired from the AF mechanism.

A capture mode that corresponds to photographic ranges of three types has been described by taking the field of dentistry as an example here, but capture modes are not limited to dentistry. Rather, capture modes that correspond to a plurality of photographic ranges can be similarly set in other fields. The photographic ranges here may naturally be considered to be photographic ranges of different types with those of the field of dentistry, depending on the field. The same mechanisms and operations and so forth as those described earlier can also be applied to such photographic ranges of different types.

Figure 86:
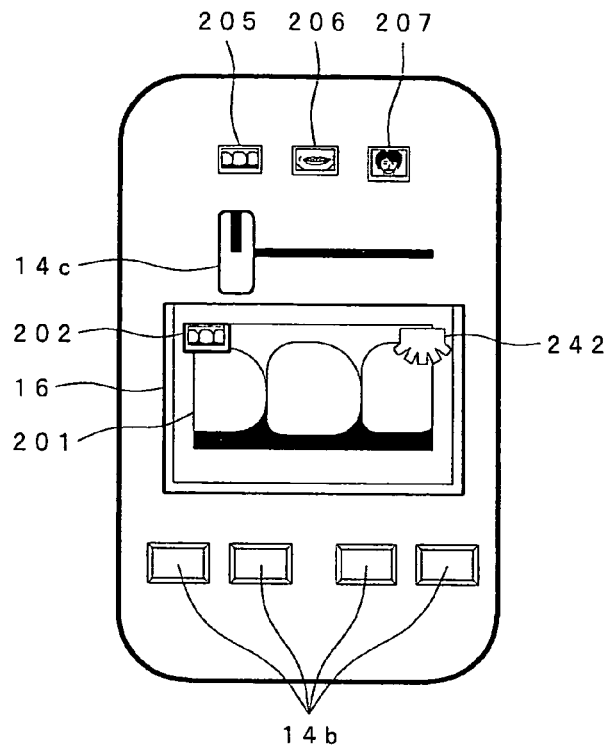
FIG. 86 shows a display example of an illumination light source lighting mark in the first embodiment.

As mentioned earlier, the illumination light source of this system is constituted to adopt the states lit/unlit upon a mode change. The states lit/unlit of the illumination light source are displayed as the illumination light source lighting mark 242 on the LCD monitor 16 constituting the display means as shown in FIG. 86 and the display can be visually confirmed. FIG. 86 shows a display example of the illumination light lighting mark. Further, as mentioned earlier, the lit/unlit states of the illumination light source are not limited to being displayed by the LCD monitor 16. Other means can also be used.

Furthermore, the built-in illumination light source is generally constituted to be unlit when an external light source is connected (that is, the illumination light source operates upon the attachment and detachment of an external light source). However, when necessary depending on the status of the object, the built-in illumination light source may be lit instead of the external light source or together with the external light source.

Further, the illumination light source is constituted such that, when the photography operation that is performed by the image photography section is a photography operation in which a spectroscopic image is to be acquired, the on/off operation of the illumination light source can be desirably switched.

Furthermore, a light-shielding characteristic can be secured because the attachment section 4 formed in a substantially cylindrical shape can be flexibly attached to the object as described earlier when an object that can be photographed with contact such as a coated surface, skin surface, or neighboring image (See FIG. 1). The shape of the attachment section 4 may differ depending on each of the applications for securing the light-shielding characteristic and on each object.

Figure 11:
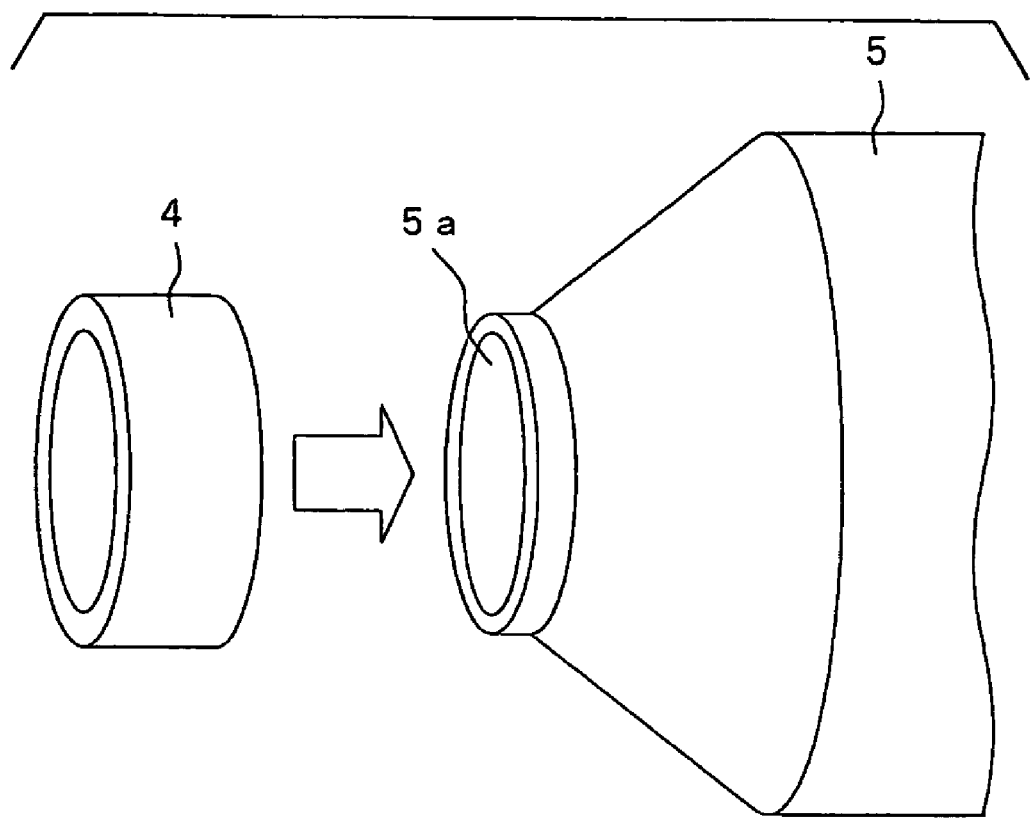
FIG. 11 is a perspective view of an attachment portion that is constituted so that the same can be attached to and detached from the projection opening of the enclosure of the first embodiment.

For use in a contact-type application, the attachment section 4 is a detachable and disposable member as shown in FIG. 11 for the sake of preventing the transfer of dirt when the object is a coated plate or the like, for example. FIG. 11 is a perspective view of the attachment portion 4 that is constituted such that the same can be attached to and detached from the projection opening 5a of the enclosure 5.

The attachment section 4 can be constituted of a heat-insulating material in cases where the object is a high-temperature or low-temperature object, can be constituted of an insulating material in cases where the object is of a material that bears static electricity or is an electrically conductive electrical object, can be constituted of an insoluble material when the object is immersed in a solution, and a glass window or the like for receiving the reflected light produced by casting the illumination light can be formed. Because the attachment section 4 is a single detachable part, the attachment section 4 can be easily constituted in a variety of shapes by a variety of materials. In addition, an observation window or similar that can be opened and closed can also be easily provided in the attachment section 4 in order to observe the surface of the object with the naked eye.

Further, this embodiment can also be used in the examination and discrimination of specific applications by using a specific one or plurality of primary colors among the plurality of primary colors emitted by the LEDs.

The color reproduction of the processing device 2 will be described next.

The object spectroscopic image recorded in the memory 11 by the image pickup operation of the photography device 1 mentioned above is transmitted to the processing device 2 via the external I/F 17, recorded in the image memory section 32 (See FIG. 12) built into the processing device 2, and color reproduction and image processing and so forth are performed by the computation device 21 that operates by means of predetermined software. The processing results are displayed on the display 22 of the processing device 2 or transferred to and displayed on the LCD monitor 16.

Figure 12:
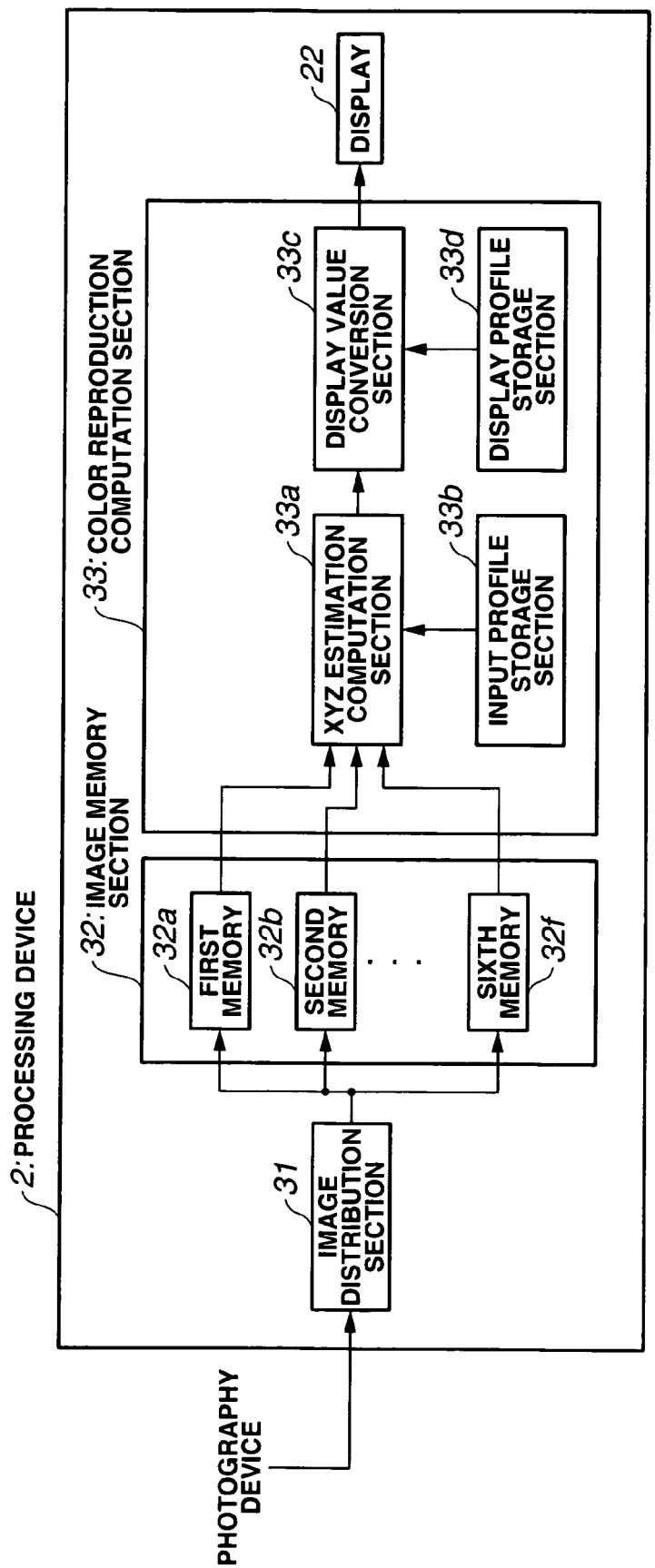
FIG. 12 is a block diagram showing a constitution in which color reproduction is performed for a display on a display of the processing device of the first embodiment.

FIG. 12 is a block diagram showing a constitution in which color reproduction is performed for displaying on the display 22 of the processing device 2.

The processing device 2 is constituted comprising an image distribution section 31 that distributes the storage area in the image memory section 32 depending on whether the object spectroscopic image that is input from the photography device 1 is illuminated by any of the first to sixth LEDs 6a to 6f; an image memory section 32 that comprises first to sixth memories 32a to 32f which are storage areas that respectively store object spectroscopic images distributed by the image distribution section 31; and a color reproduction processor section 33 that reads the object spectroscopic images stored in the image memory section 32 and calculates and outputs display image data for displaying an image that has undergone highly accurate color reproduction on the display 22, the foregoing image distribution section 31, image memory section 32, and color reproduction computation section 33 being contained in the computation device 21 shown in FIG. 1, for example, and further comprising the abovementioned display 22, which displays the image that has undergone highly accurate color reproduction on the basis of the display image data output by the color reproduction computation section 33.

The color reproduction computation section 33 is constituted comprising an input profile storage section 33b that stores a profile related to the photography device 1; an XYZ estimation computation section 33a that reads the object spectroscopic images respectively stored in the first to sixth memories 32a to 32f of the image memory section 32 and generates image data of XYZ tristimulus values by performing estimation computation by using the input profile that is stored in the input profile storage section 33b and an internally set predetermined color-matching function; a display profile storage section 33d that stores a profile related to the display 22, and a display value conversion section 33c that generates display image data that is to be output to the display 22 by performing computation by using the image data of the XYZ tristimulus values estimated by the XYZ estimation computation section 33a and the display profile stored in the display profile storage section 33d.

The input profile stored in the input profile storage section 33b appears in Japanese Patent Application Laid Open No. 2000-341499, for example, and is calculated on the basis of: the characteristics and settings and so forth (image input device) of the photography device 1 that include the spectroscopic sensitivity of the CCD 8 used in the image pickup; spectral data on the illumination light when the object is photographed (photographic illumination light information); spectral data for the illumination light at the point where the display 22 for observing the generated object spectroscopic image is installed (observation illumination light information); information such as the statistic profile of the spectroscopic reflectance of the photographed object (object characteristic information), and the like.

Figure 14:
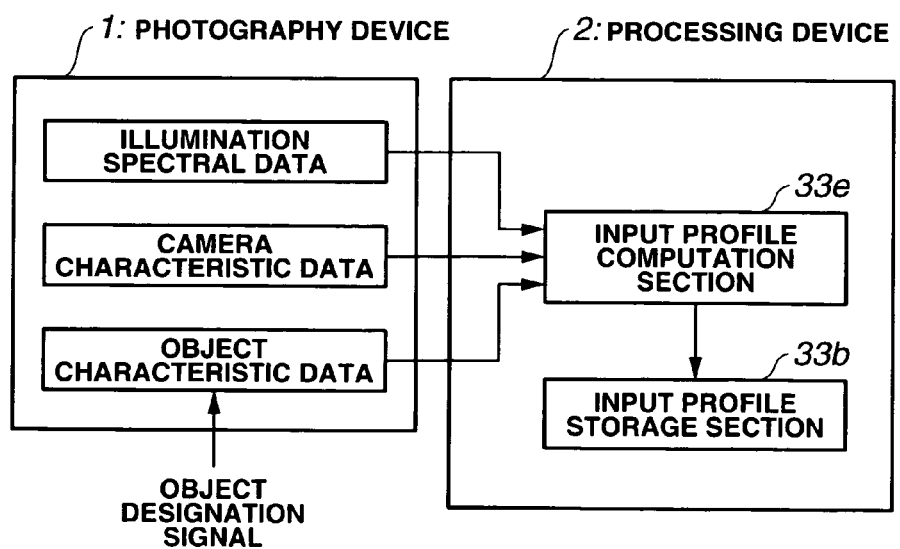
FIG. 14 is a block diagram showing a constitutional example in which an input profile is generated by the processing device in the first embodiment.

FIG. 14 is a block diagram showing a constitutional example in which an input profile is generated by the processing device 2.

The input profile may be generated by the processing device 2 on the basis of respective data acquired by the photography device 1 as shown in FIG. 14.

Data acquired by the photography device 1 includes, by way of example, illumination light spectral data, camera characteristic data, object characteristic data, and so forth.

The illumination spectral data is spectral data related to illumination when an object undergoes image pickup, for example, and is spectral data of the respective LEDs 6a to 6f that are contained in the photography device 1 in the case of a contact-type application. In the case of a contactless application, spectral data for external illumination necessary when an object is photographed is also included.

The camera characteristic data is constituted comprising various characteristics such as characteristics of the photographic optical system 7 including focus values and so forth, the image pickup characteristic of the CCD 8, the shutter speed, and the iris value.

The object characteristics are constituted of spectroscopic statistical data and so forth when the object is a tooth, skin, or a coating material, for example, and, in order to create a highly accurate input profile, an object designation signal for designating the object may be input by providing the operating switch 14 or the like to an object designation operation section.

The processing device 2 for creating an input profile on the basis of the data is constituted comprising an input profile computation section 33e, which generates an input profile by performing computation by reading the illumination spectral data, camera characteristic data, and object characteristic data, and an input profile storage section 33b, which stores the input profile generated by the input profile computation section 33e, as shown in FIG. 14.

As a result of such a constitution, highly accurate color reproduction can be performed adaptively by changing the photography device 1 connected to the processing device to a photography device of a different individual or model and so forth (change in the photographic optical system 7), by changing the ambient lighting for performing the photography, or by making various changes to the object constituting the photographic target.

Furthermore, the display profile stored in the display profile storage section 33d is calculated on the basis of information such as the color values of the display primary color values of the display 22 (RGB primary color values when the display 22 is an RGB monitor, for example) and the tone curve of the display 22, and so forth. Further, the display may use a color reproduction system of a multiplicity of primary colors as described in Japanese Patent Application Laid Open No. 2000-338950.

Figure 13:
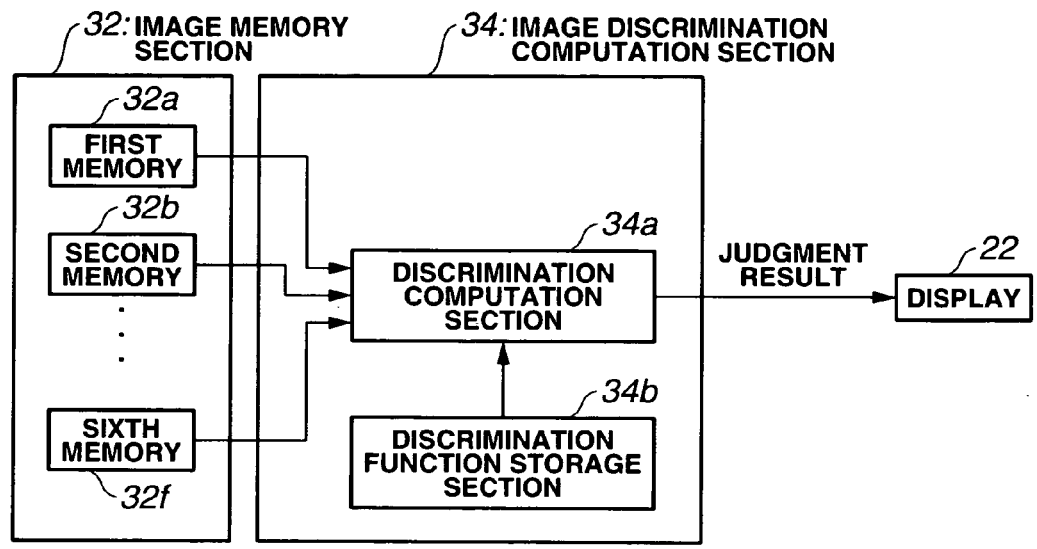
FIG. 13 is a block diagram showing a constitutional example for performing object-related image discrimination on the basis of an acquired object spectroscopic image of the first embodiment.

Further, FIG. 13 is a block diagram showing a constitutional example for performing object-related image discrimination on the basis of an acquired object spectroscopic image.

The object spectroscopic images respectively stored in the first to sixth memories 32a to 32f of the image memory 32 are displayed on the display 22 as a result of being read by the image discrimination computation section 34, object-related image discrimination being performed, and the judgment results being output. The constitution may also be such that image discrimination computation may be performed via a network and the results displayed on the LCD monitor 16.

The image discrimination computation section 34 is constituted comprising a discrimination function storage section 34b that stores a discrimination function for performing a variety of object-related classifications/judgments and so forth, and a discrimination computation section 34a that calculates the discrimination results by using the discrimination function to compute all six object spectroscopic images that are respectively stored in the first to sixth memories 32a to 32f of the image memory 32 or one or more object spectroscopic images selected from among the six object spectroscopic images, and which generates discrimination result display image data for displaying the judgment results on the display 22.

Further, various substitutions can be made for the discrimination function depending on the application of the image processing system. Hence, the discrimination function storage section 34b is constituted of a rewriteable storage medium or recordable storage medium and the discrimination function used in accordance with the application may be written or rewritten. Specific examples of the discrimination function can include, byway of example, a function for performing processing as appears in Japanese Patent Application Laid Open H7-120324.

The image discrimination computation section 34 shown in FIG. 13 may be provided in the processing device 2 instead of the color reproduction computation section 33 shown in FIG. 12. Alternatively, the processing may be executed simultaneously in parallel by providing the image discrimination computation section 34 in the processing device 2 together with the color reproduction computation section 33 shown in FIG. 12, or processing may be performed by selectively switching only the required section 33 or 34.

Figures 15A, 15B, 15C:
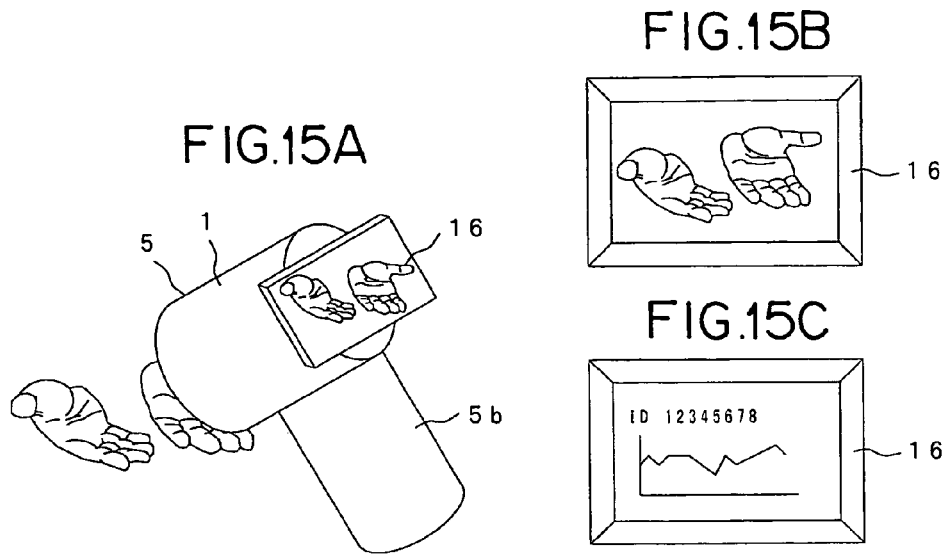
FIG. 15A to FIG. 15C show a display example of the LCD monitor of the photography device of the first embodiment.

Thereafter, FIG. 15A to FIG. 15C show a display example of the LCD monitor 16 of the photography device 1. The LCD monitor 16, for example, can be used as the display monitor, but the display monitor is not limited to the LCD monitor 16. An EL panel or LED panel or the like may also be used. In addition, the display monitor may be either a monochrome display or a color display.

The LCD monitor 16, for example, constituting the display means is installed at the top of a grasp section 5b on the rear face side of the enclosure 5 of the photography device 1 and displays the images displayed in FIGS. 15B and 15C and so forth, as shown in FIG. 15A, for example. Further, here, an example in which an image of hands is picked up as the object is shown.

First, FIG. 15B shows an aspect where a moving image that is picked up by means of the monitor mode is displayed and, as a result, the LCD monitor 16 functions as a finder.

Thereafter, FIG. 15C shows an aspect that displays the discrimination result of the object image by the image discrimination computation section 34, for example. Here, the ID number of the object (patient number and so forth of the diagnostic support system in the field of dentistry, for example) and a graph (diagnostic process, for example) of the results of numerical analysis obtained by the image discrimination are displayed. The LCD monitor 16 is not limited to such a display and can display various information such as color reproduction images, patient clinical records, various data, and charts.

Thus, the LCD monitor 16 functions as a finder when photographed parts are selected and functions as a monitor when the color reproduction results and the results of classification/judgment are displayed.

Further, various information for supporting the operations of the operator can be displayed on a display monitor such as the LCD monitor 16. Here, the variety of displayed information includes, for example, 'on state of the power supply', 'state of switching of monitor mode/capture mode', and the 'switching state of each capture mode of one tooth/full jaw (upper and lower jaw)/face/full body'. The display of various information displays icons and letters and so forth that correspond to the mode selected on the screen of the display monitor such as the LCD monitor 16 when each mode is selected.

With regard to the capture mode in particular, as mentioned earlier, the capture mode works in tandem with the focus operation and, in the case of autofocus, a constitution such that a mode is displayed from range data may be considered. Further, in the case of manual focus, a constitution may be considered such that a capture mode operates in accordance with the operating position of the focus adjustment lever (focus ring). Marks and letters and so forth indicating capture mode may also be displayed in the operating position corresponding to the focus adjustment lever (focus ring) when manual focus is being used.

In addition, the lit/unlit states of the built-in illumination light source can be displayed on the display monitor such as the LCD monitor 16 as various information for supporting the operations of the operator. The lit/unlit states of the built-in illumination light source are switched with relation to the image angle (photographic range set by the photographic range setting means) and, as mentioned earlier, switched depending on whether an external light source is connected (that is, the built-in illumination light source is generally unlit when an external light source is connected).

Meanwhile, because the display of the processing device 2 has, in most cases, a larger and highly resoluted area than the LCD monitor 16 provided in the handy-type photography device 1, the display 22 of the processing device 2 may perform a startup display, a condition setting display, a GUI display for inputting information such as object IDs and so forth, a patient history display, an object information display of previous information or the like, and a processing result display, with respect to software that is executed depending on the purpose by the processing device 2.

An external database, for example, is connected to the network 3 and object information is acquired by the processing device 2 from the external database or the results of processing executed by the processing device 2 may be stored in the external database. Here, in order to ensure security, the constitution can be such that mutual authentication to connect the processing device 2 and an external system via the network 3 is performed and level-dependent authentication can be performed by providing the object data with a security level.

Figure 16:
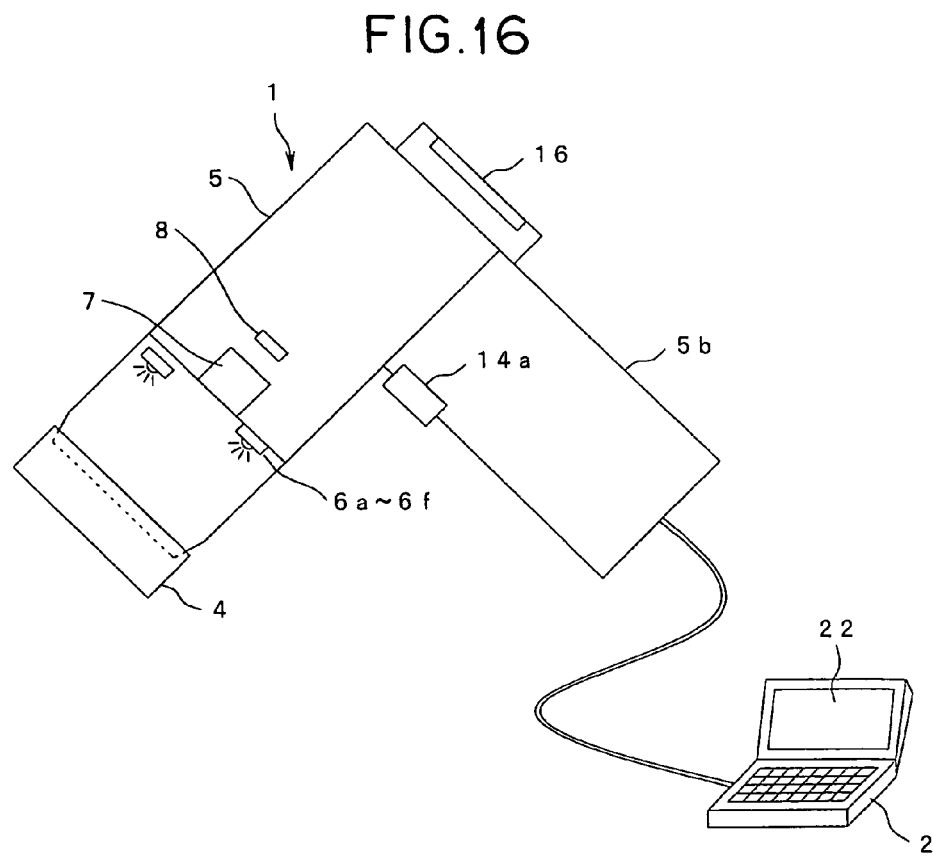
FIG. 16 shows an example of an aspect when the image processing system of the first embodiment is used.

Thereafter, FIG. 16 shows an example of an aspect when an image processing system is employed.

The photography device 1 is constituted to be lightweight and small and allows image pickup to be performed by grasping the grasp section 5b with one hand and applying the leading end of the enclosure 5 in which the image pickup system is provided to the photographic target part of the object via the attachment section 4, for example.

As mentioned earlier, the attachment section 4 is a detachable and disposable member that shields light from the outside from striking the photographic target part of the object.

The photography button 14a contained in the operating switch 14 is provided at the top of the grasp section 5b, for example, in a position that permits operation by means of an index finger. By pressing the photography button 14a after specifying the part that is to be photographed by the LCD monitor 16, the transition is made from the monitor mode to the spectroscopic image capture mode as mentioned earlier and image pickup of the spectroscopic image is performed.

The acquired spectroscopic image is subjected to data processing by the processing device 2 and displayed on the display 22. However, by making settings or the like if required, the processing results of the processing device 2 may be displayed on the LCD monitor 16 of the photography device 1 as mentioned earlier.

Further, in the example shown in FIG. 16, the processing device 2 is illustrated as a notebook-type personal computer with a display. In this case, the processing device 2 may be connected to the network 3 via an RS-232C, USB, IEEE1394 or other interface (I/F) that is provided in the notebook-type personal computer.

The first embodiment allows an object spectroscopic image to be picked up by providing LEDs of six types of different spectroscopic distributions in visible light bandwidths in the photography device of the image processing system and causing the LEDs to emit light while blocking external light. Here, because a compact and lightweight semiconductor light-emitting element such as an LED is used as the light source, the photography device can be miniaturized and a handy-type photography device can also be created.

Further, by performing processing by means of the processing device, a highly accurately color-reproduced image can be displayed on the display.

In addition, by designating the LED light emission order and the LEDs that are made to emit light, images that are used for a variety of different purposes such as a normal RGB moving image can be picked up.

In addition, because a monochrome CCD is used, costs can be somewhat reduced and interpolation processing can be omitted in order to acquire one screen at a time without the respective color image data producing missing pixels.

Further, as the image photography section that allows spectroscopic images to be obtained, other constitutions can be used in addition to a constitution that uses multiband illumination and image pickup elements as illustrated in each of the embodiments including this embodiment. Technology that can be applied to the image photography section includes, for example, the technology that appears in the earlier described Japanese Patent Application Laid Open No. H9-172649, Japanese Patent Application Laid Open No. 2002-296114, Japanese Patent Application Laid Open No. 2003-023643, and Japanese Patent Application Laid Open No. 2003-087806.

Furthermore, when an image is acquired by actually using the photography device, this image acquisition is implemented in keeping with the operating steps (operating procedure) of a plurality of stages. In the case of this image processing system, with the objective of facilitating the operation, the next operating step and progress status and so forth can also be made explicit by the display means of the photography device by using a progress bar or the like as will be described subsequently, for example. As a result, smooth operation progress is made possible, for example. The operating steps are varied depending on the application field but coping is possible by storing operating steps suited to the field in the built-in memory. Alternatively, a constitution is possible in which operating steps corresponding to a plurality of fields can be pre-stored in the built-in memory and operating steps are selected from among the stored operating steps and set.

Figure 87:
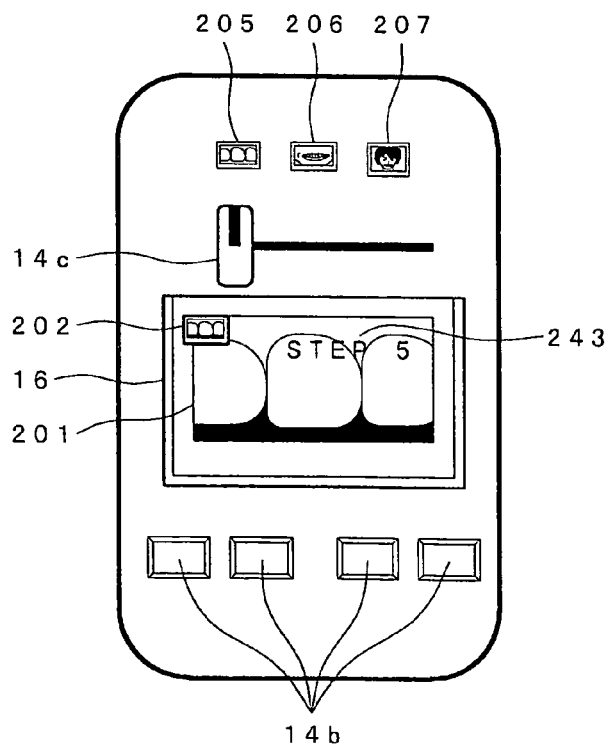
FIG. 87 shows an aspect in which an operating step is displayed in the first embodiment.

FIG. 87 shows an aspect in which operating steps are displayed.

In this example, the current operating steps are displayed as text 243 constituting the progress status display means on a display monitor such as the LCD monitor 16 and the fact that this is fifth step 'STEP 5' is displayed here.

Figure 88:
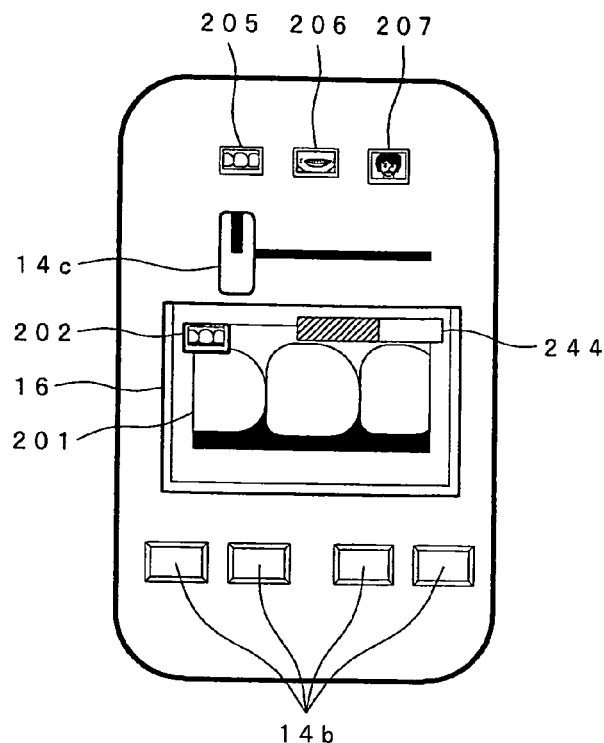
FIG. 88 shows an aspect in which the progress status of the operation is displayed in the first embodiment.

Further, FIG. 88 shows an aspect in which the progress status of the operation is displayed.

In this example, the progress status of the current work is displayed as a progress bar 244 constituting the progress status display means on a display monitor such as the LCD monitor 16.

Further, the display of the operating steps and progress status is not limited to being implemented by such text or such bar. The LCD monitor 16 may be used as operation indicator means or measurement procedure indicator means, for example, or a speaker or the like is provided as the operation indicator means or measurement procedure indicator means, and the next operation procedure may be displayed or indicated by means of sound.

Figure 99:
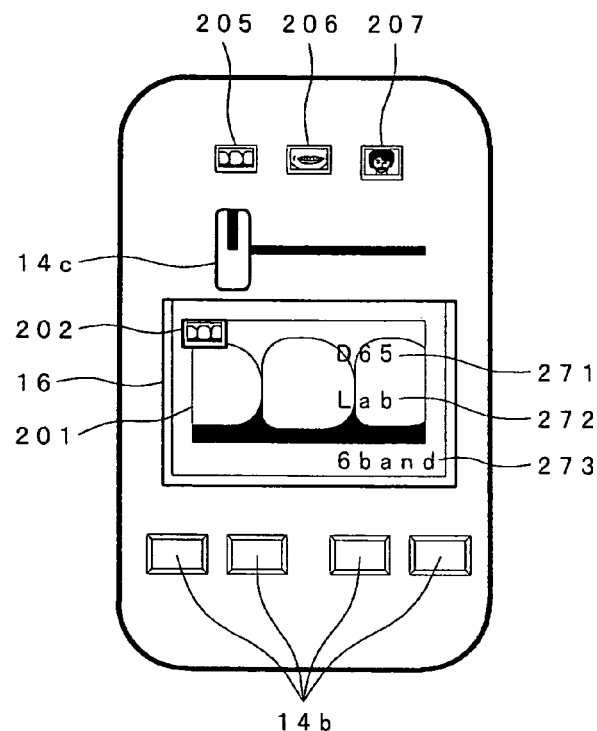
FIG. 99 shows a display example of a measurement mode in the first embodiment.

In addition, the setting state of the image processing system may be displayed on a display monitor such as the LCD monitor 16. FIG. 99 shows a display example of the setting state.

In the example shown in FIG. 99, the fact that the type of light source is 'D65' is displayed by text 271, the fact that the color space is 'Lab' is displayed by text 272, and the fact that the number of primary colors is '6' is displayed by text 273 (6 band).

Such displays of setting states include the following examples.

First, a display of the number of primary colors (six, for example) and the lighting (on, for example) as the illumination settings may be considered.

Further, a display of the shutter speed, F value, zoom position, and so forth may be considered as the photography settings.

Further, as the color reproduction settings, a display of the light source (D65, A, B, C, and so forth, for example), the viewing angle (2 degrees, for example), color space (XYZ, Lab, for example), measurement target (object color, for example), color difference threshold value (0.1, for example), tooth color reference (Std01, for example), and so forth, may be considered.

By displaying the setting state in this manner, the photographer is able to grasp the state of the system easily.

Second Embodiment

Figure 18A:
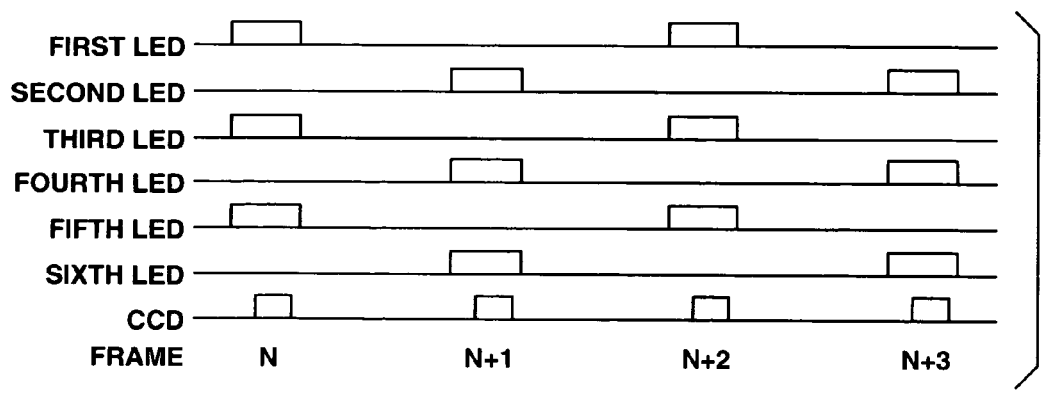
FIG. 18A and FIG. 18B show timing charts that show reading aspects in full mode and reading two-speed mode in the second embodiment.
Figure 18B:
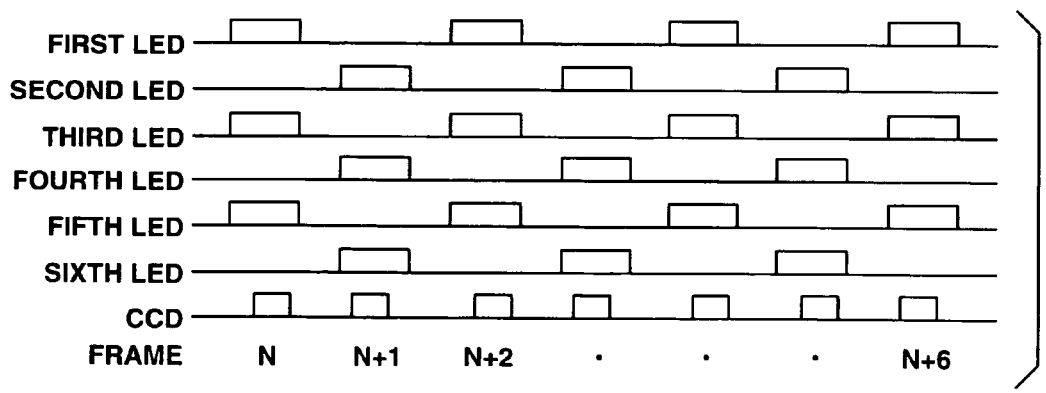
Figure 19A:
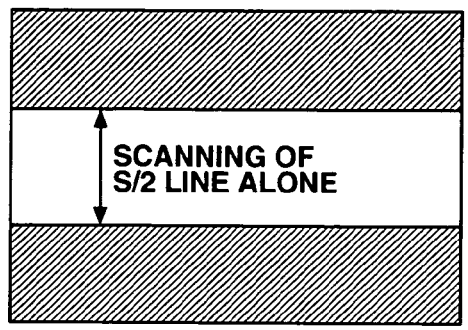
FIG. 19A and FIG. 19B show aspects of lines read in 2/4 line two-speed mode and 2/8 line four-speed mode in the second embodiment.
Figure 19B:
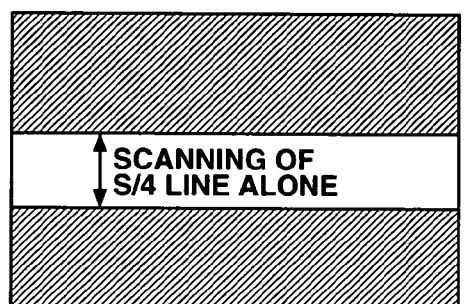
Figure 20:
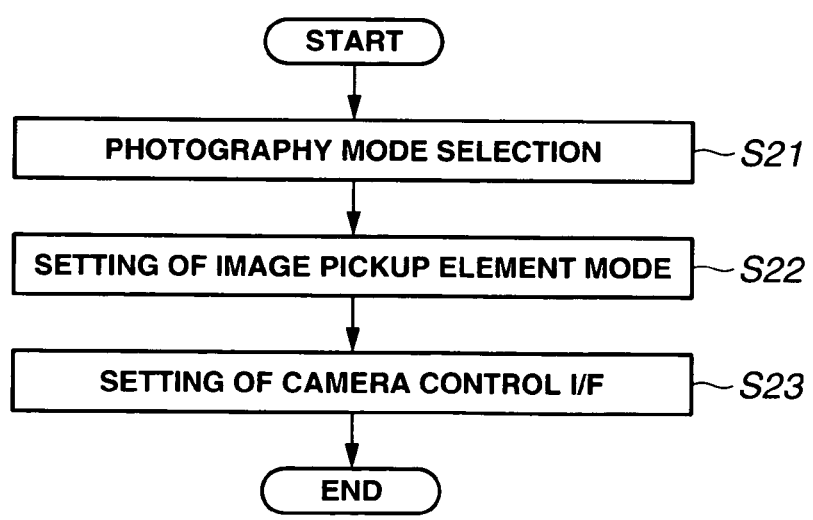
FIG. 20 is a flowchart that shows an operation when a photography mode is set in the second embodiment.

FIGS. 17 to 20 and FIG. 100 show a second embodiment of the present invention. FIG. 17 is a block diagram showing the constitution of the image processing system, FIG. 18A and FIG. 18B are timing charts that show reading aspects in full mode and reading two-speed mode in the second embodiment, FIG. 19A and FIG. 19B show aspects of lines read in 2/4 line two-speed mode and 2/8 line four-speed mode, and FIG. 20 is a flowchart showing the operation when the photography mode is set.

In this second embodiment, the same numerals are assigned to the parts that are the same as those of the first embodiment above and a description thereof will be omitted only the differences are mainly described.

The second embodiment has the basic constitution of the first embodiment described earlier and is constituted to permit the adjustment of the image reading speed from a color CCD that comprises a color filter array (CFA) 19 at the front face thereof.

The image reading speed is related to the display speed and the display speed cannot be as fast as or faster than the reading speed.

Generally, when images are monitored, a display interval equal to or more than about 30 images/second is desirable. However, as the number of primary colors N increases, the display interval undergoes a relative increase, and a flicker state is sometimes produced or a large image positional shift caused by the respective primary color image acquisition time difference is sometimes produced.

Therefore, this embodiment is a high-speed reading mode that avoids an increase in the display interval and, in order to fix the display interval without dependence on the number of reading primary colors N, adjusts the image reading speed from a CCD 8A by the color control I/F 12A as shown in FIG. 17.

The operation when the photography mode is set will now be described with reference to FIG. 20.

When there is an operating input to select the photography mode from the operating switch 14 (step S21), the CPU 18 detects the operating input, records the photography mode to be set and information or the like related to the photography mode in a portion of the recording area in the memory 11 (step S22), and issues a command to cause the camera control I/F 12A to implement control to change the photography mode (step S23).

The camera control I/F 12A receives the command and controls the drive of the CCD 8A to change the photography mode. Here, the camera control I/F 12A performs adjustment so that the light emission amount of the respective LEDs 6a to 6f match by controlling the LED driver 13 in interlocking with the operation of the CCD 8A.

The photography modes that can be set for the photography device 1 are as follows, for example.

(1) Full mode
(2) Reading two-speed mode
(3) 2/4 line two-speed mode
(4) 2/8 line four-speed mode
(5) 2/16 line eight-speed mode
(6) First center scan mode
(7) Second center scan mode
(8) Third center scan mode
(9) Fourth center scan mode
(10) First center speed scan mode
(11) Second center speed scan mode 'Full mode' is a normal mode that sequentially reads at normal speed all the pixels of all the scan lines of the CCD 8A as shown in FIG. 18A. Here, the respective frames are constituted of the frames in which the first LED 6a, third LED 6c, and fifth LED 6e are simultaneously made to emit light and the frames in which the second LED 6b, fourth LED 6d, and sixth LED 6f are simultaneously made to emit light. The means for capturing an image of six primary colors through such light emission will be described in the third embodiment that follows.

The 'reading speed two-speed mode' is a mode in which all the pixels of all the scan lines of the CCD 8A are sequentially read at two times the normal reading speed as shown in FIG. 18B with respect to the normal mode shown in FIG. 18A. Further, here, two speed reading is cited by way of example but reading is not limited thereto. Any suitable speed factor is acceptable and variable speeds are also possible.

The '2/4 line two-speed mode' halves the time required to read one frame by scanning only two lines for every four lines and, although the resolution in a vertical direction is halved, an image of all effective areas can be acquired.

The '2/8 line four-speed mode' also renders the time required to read one frame 1/4 of that of normal mode by scanning only two lines for every eight lines.

The '2/16 line eight-speed mode' similarly renders the time required to read one frame 1/8 that of normal mode by examination only two lines for every sixteen lines.

The 'first center scan mode' halves the time required to read one frame by scanning only a part of S/2 lines in the center within the effective area when the number of lines of all the scan lines is S, as shown in FIG. 19A.

The 'second center scan mode' renders the time required to read one frame 1/4 by scanning only a part of S/4 lines of the center within the effective area when the number of lines of all the scan lines is S, as shown in FIG. 19B.

The 'third center scan mode' likewise renders the time required to read one frame 1/8 by scanning only a part of S/8 lines of the center within the effective area.

The 'fourth center scan mode' likewise renders the time required to read one frame 1/16 by scanning only a part of S/16 lines of the center within the effective area.

The 'first center high-speed scanning mode' renders the time required to read one frame 1/4 by scanning at two times the normal speed only a part of S/2 lines of the center within the effective area as shown in FIG. 19A.

The 'second center high-speed scanning mode' renders the time required to read one frame 1/8 by scanning at two times the normal speed only a part of S/4 lines of the center within the effective area as shown in FIG. 19B.

The modes are not limited to the above modes. High-speed scanning can also be performed by other means and can be summarized as following including the above.

First is a simple increase in the scan speed. This makes it possible by adjusting the timing of a trigger signal that indicates the start of reading, for example. For example, in an example in which the display time of one frame is 1/30 seconds, this is achieved by setting the timing of the trigger signal so that the read time of each primary color (N primary colors) is 1/30/N.

Second is a speed increase by means of thinning scanning. With the first speed increase means, a limit to the speed increase is produced by the image pickup elements. Although, on the other hand, the image quality drops when thinning is performed, because the speed can be increased by performing stable scanning, the frame rate does not drop and flicker is not produced in the display. As examples of thinning, thinning can be performed in pixel units in addition to the thinning procedure mentioned earlier in which thinning is performed at fixed intervals in line units or in a fixed range and, when the image pickup element is an XY address-type image pickup element, only the desired pixel can be read.

Third is a speed increase that changes the frame rate in accordance with the primary color. So too in the case of a CCD having a normal RGB color filter or the like, green (G) pixels close to a brightness signal are often installed in a quantity that is two times the number of red (R) and blue (B) pixels. In consideration of this point, reading frames close to green (G) among the six primary colors in a number that is two times the frames of the other colors may be considered. Naturally, reading is not limited to such reading and, in accordance with the intended usage, a large number of frames of specified primary colors may be read and the rate of reading may be changed stepwise in accordance with necessity.

Figure 100:
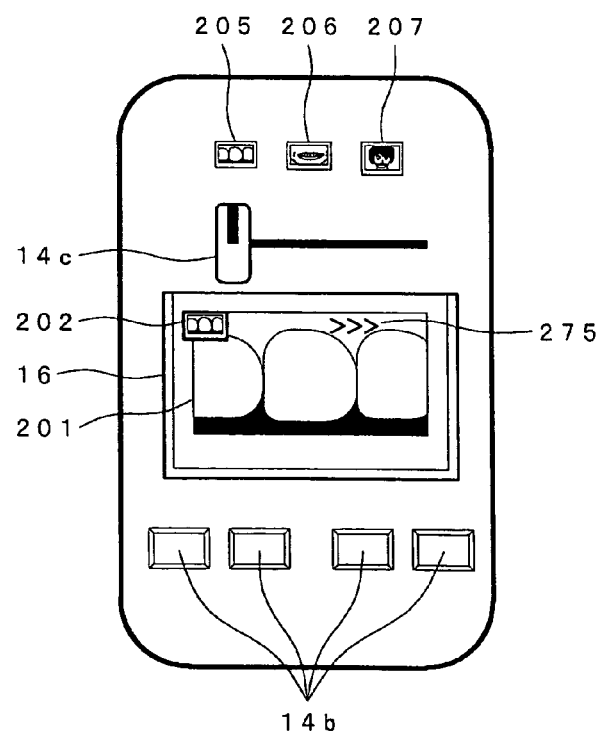
FIG. 100 shows a display example of a high speed reading mark in the second embodiment.

Whether or not the abovementioned high-speed reading mode has been set is displayed as a high-speed reading mark 275 on the LCD monitor 16 constituting the display means as shown in FIG. 100 and can be confirmed by viewing the display. FIG. 100 shows a display example of the high-speed reading mark. Further, the display of the high-speed reading mode is naturally not limited to that shown in FIG. 100 and is not limited to the LCD monitor 16. The high-speed reading mode can also be displayed by other means. For example, each display may be different in order to be able to distinguish which mode has been set among a plurality of high-speed reading modes.

The second embodiment exhibits substantially the same effects as those of the first embodiment and, by changing the reading speed, a fixed display speed can be secured and a natural moving image can be displayed even when there is movement during highly accurate color reproduction.

Third Embodiment

Figure 21:
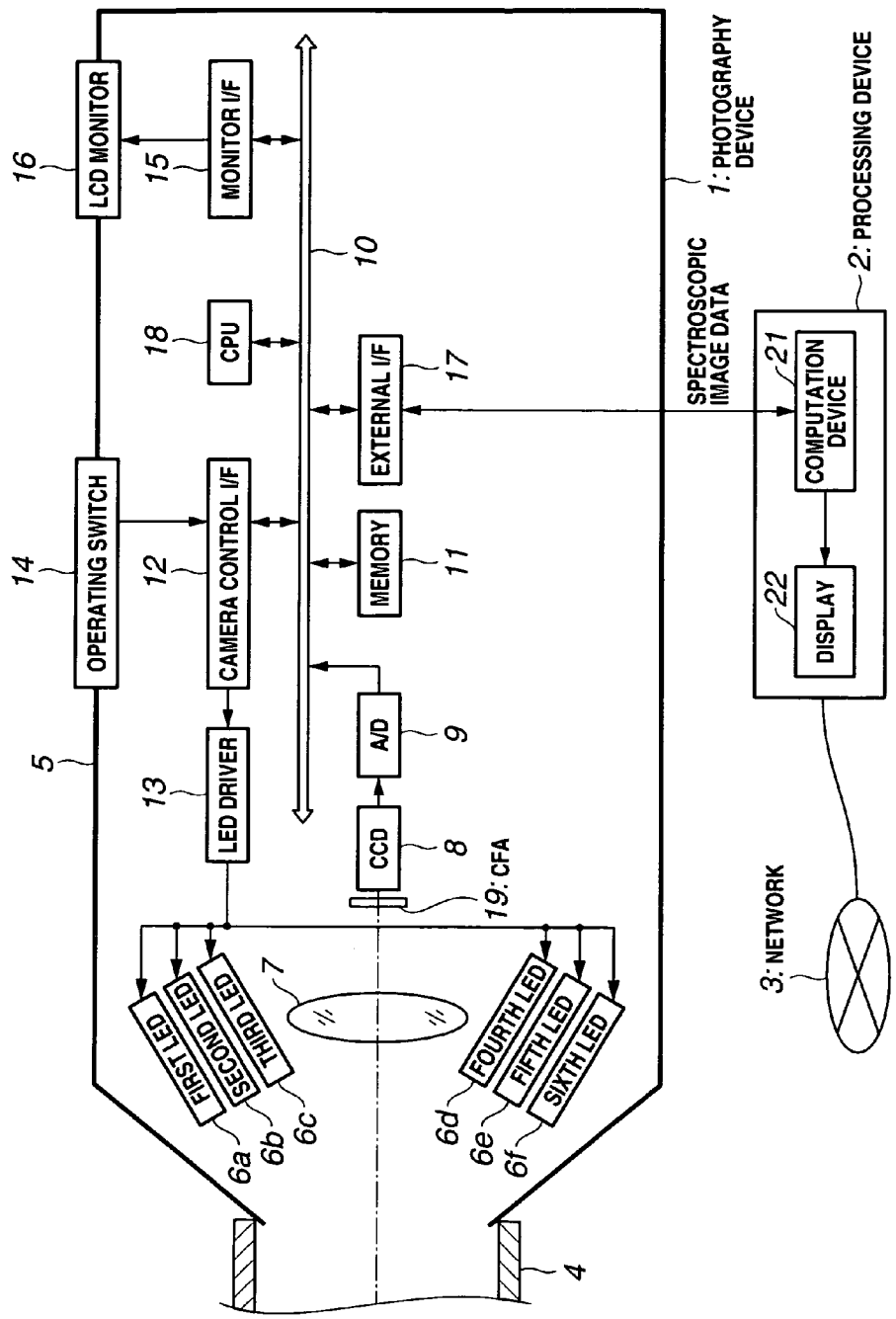
FIG. 21 is a block diagram showing the constitution of an image processing system of a third embodiment of the present invention.
Figure 22:
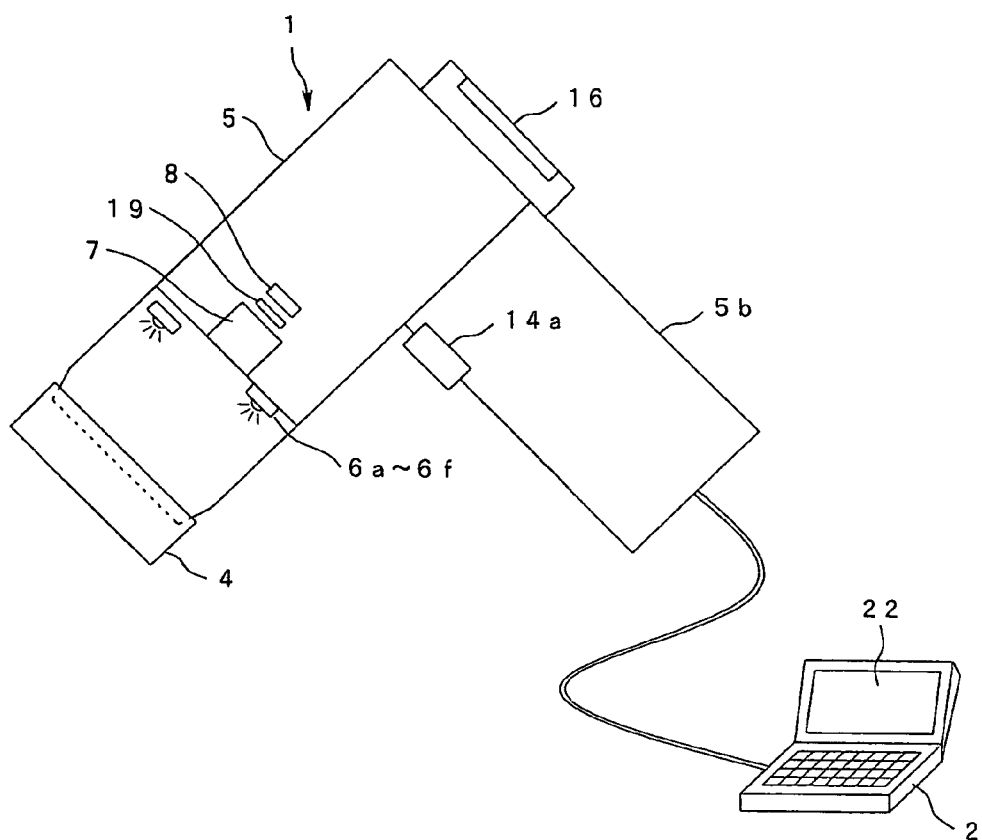
FIG. 22 shows an example of an aspect when the image processing system of the third embodiment is used.

FIGS. 21 to 36 show a third embodiment of the present invention. FIG. 21 is a block diagram showing the constitution of an image processing system and FIG. 22 shows an example of an aspect when the image processing system is used. In the third embodiment, the same numerals are assigned to the parts that are the same as those of the first and second embodiments above and a description of these parts will be omitted. Only the differences are mainly described.

The third embodiment has the basic constitution of the first embodiment described earlier and is constituted such that a three-band color filter array is installed on the photographic face of the CCD.

That is, as shown in FIGS. 21 and 22, the photography device 1 has an RBG 3-band color filter array (abbreviated as CFA in FIG. 21) 19 installed in the vicinity of the CCD 8 in the light path in which the object image is formed by the photography optical system 7 and a so-called single-panel-type color image pickup element is constituted as the image pickup element section.

Therefore, although not illustrated, a normal RGB image can also be acquired in capture mode in the same way as by a normal camera. The illumination of the object at such time may turn the illumination light source off by setting the photography device 1 in the illumination light off mode and ambient light such as general indoor light and solar light and so forth may be used. Alternatively, by combining a plurality of LEDs that are built into the photography device 1, a light source of a spectral regarded as a white light source may be constituted and continuously lit and irradiated onto the object.

Figure 23:
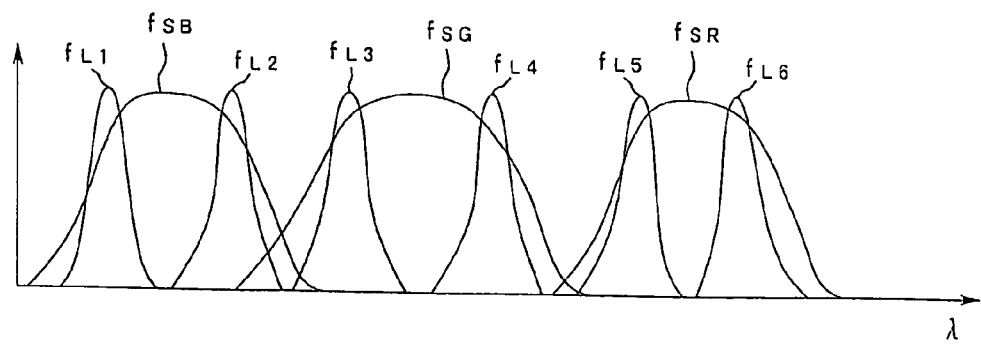
FIG. 23 is a line diagram showing an LED light emission spectral and a CCD spectroscopic sensitivity characteristic after being passed through a color filter array of the third embodiment.

FIG. 23 is a line diagram showing the light emission spectrals of the LEDs 6a to 6f and the spectroscopic sensitivity characteristic of the CCD 8 after being passed through the color filter array 19.

With respect to the light emission spectrals of the LEDs of six primary colors indicated by the curves fL1 to fL6 shown in the first embodiment, the total spectroscopic sensitivity characteristics obtained by means of the transmittance distribution of the color filter array 19 and the light reception sensitivity distribution of the CCD 8 are the illustrated curves fSB, fSG, and fSR.

The constitution is such that the curve fSB that indicates the spectroscopic bandwidth that corresponds to the blue color filter among these curves contains the two curves fL1 and fL2 and can sense the light that is emitted by the first LED 6a and second LED 6b, the curve fSG that indicates the spectroscopic bandwidth that corresponds to the green color filter contains the two curves fL3 and fL4 and can sense the light that is emitted by the third LED 6c and fourth LED 6d, the curve fSR that indicates the spectroscopic bandwidth that corresponds to the red color filter contains the two curves fL5 and fL6 and can sense the light that is emitted by the fifth LED 6e and sixth LED 6f.

However, there is no need to individually separate the total spectroscopic sensitivity characteristics from each other. There may be a portion of mutual overlap in the peripheral part. In addition, as per the first embodiment, the respective light emission spectrals of the first to sixth LEDs 6a to 6f may be light emission spectrals a portion of which overlap. Naturally, the types of LEDs are not limited to six types and combinations of LEDs of a suitable number of types can similarly be adopted.

The operation when an image is acquired will be described next.

In the case of the image processing system, as per the first embodiment above, the monitor mode and spectroscopic image capture mode are switched when an image is acquired.

Figure 24A:
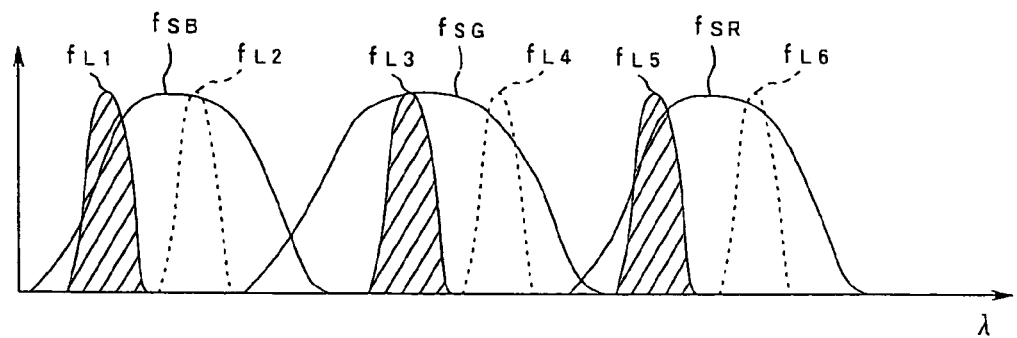
FIG. 24A and FIG. 24B are a line diagram showing a spectroscopic characteristic of a spectroscopic image for each frame when a 6-band spectroscopic image is generated in the third embodiment.
Figure 24B:
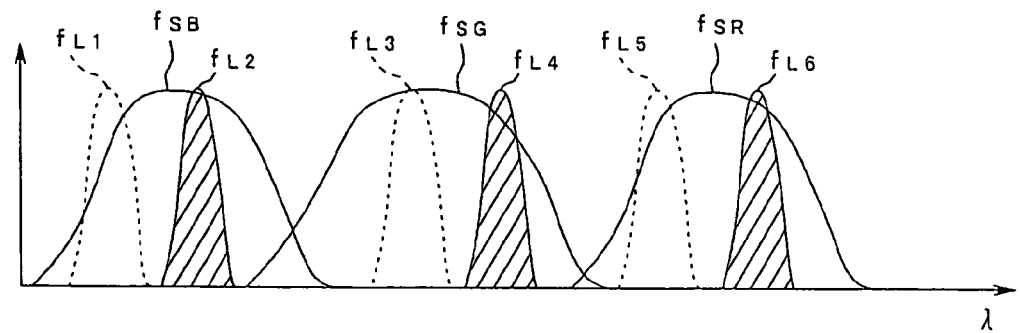
Figure 26:
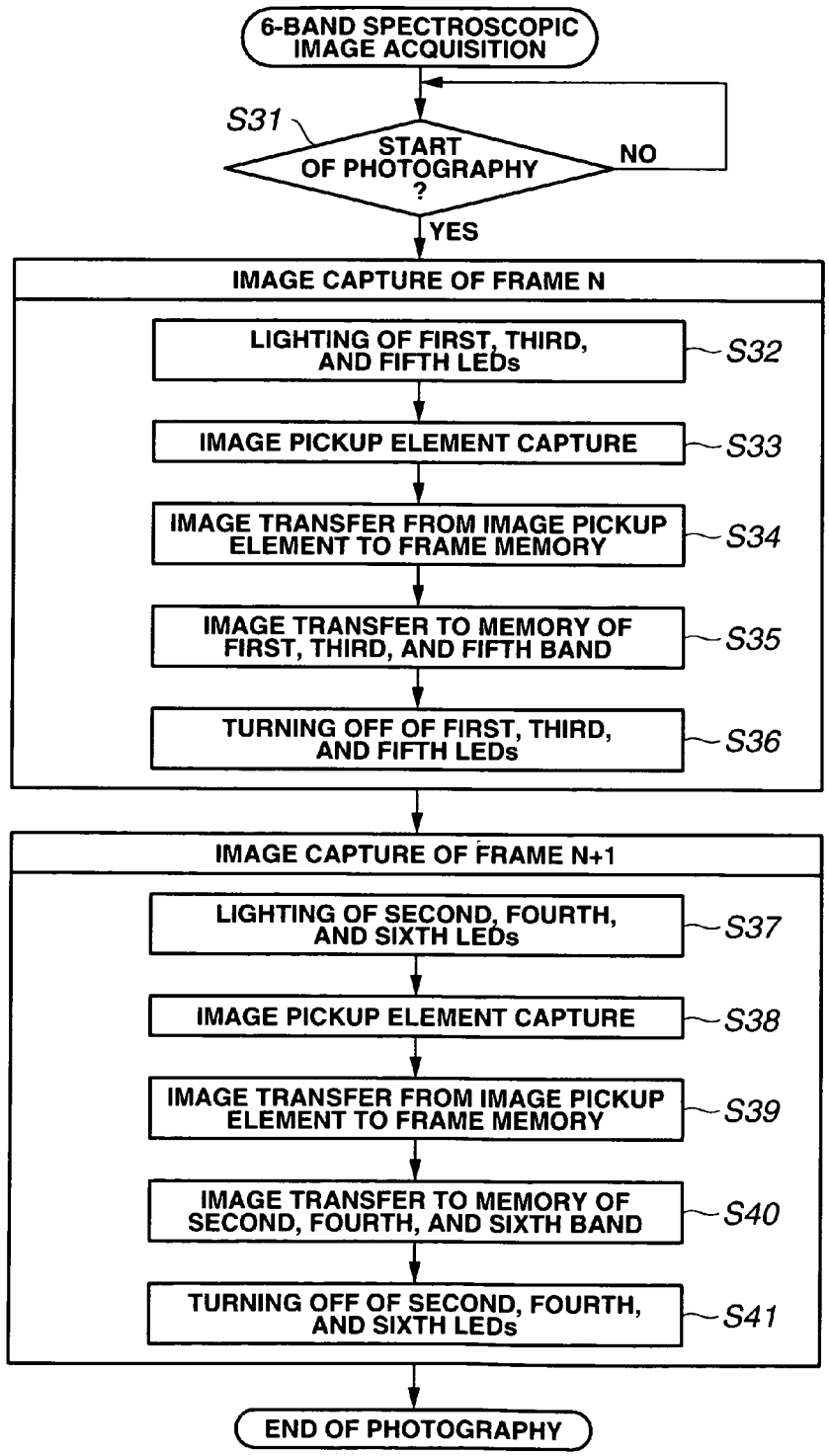
FIG. 26 is a flowchart showing the operation of the light emission of each LED and image acquisition of an image pickup element in the 6-band spectroscopic image acquisition of the third embodiment.
Figure 27:
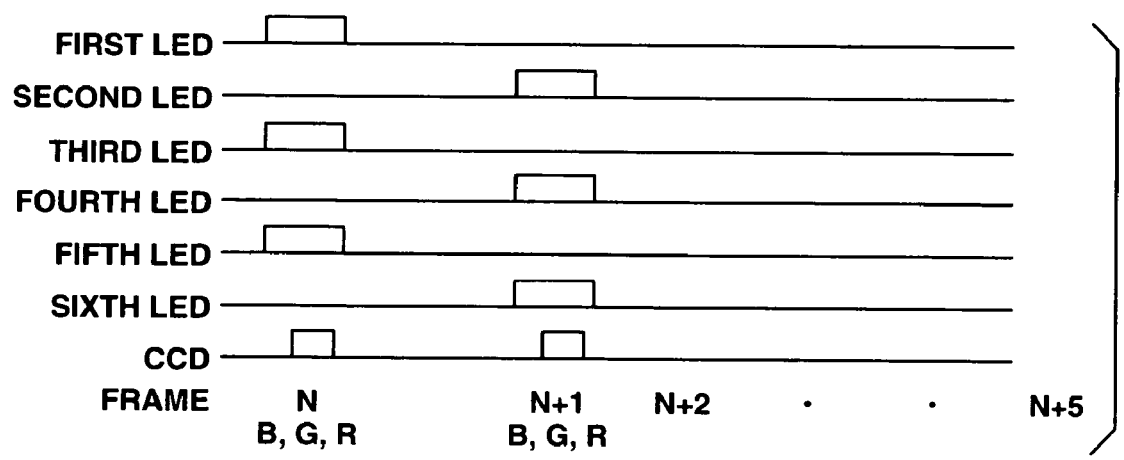
FIG. 27 is a timing chart showing an aspect of the operation of the light emission of each LED and image acquisition of an image pickup element in the 6-band spectroscopic image acquisition of the third embodiment.

An operation of the spectroscopic image capture mode will now be described with reference to FIG. 24A, FIG. 24B, FIG. 26, and FIG. 27. FIG. 24A and FIG. 24B are a line diagram showing the spectroscopic characteristic of a spectroscopic image for each frame when a 6-band spectroscopic image is generated. FIG. 26 is a flowchart showing the operation of the light emission of each LED and image acquisition of an image pickup element in the 6-band spectroscopic image acquisition. FIG. 27 is a timing chart showing an aspect of the operation of the light emission of each LED and image acquisition of an image pickup element in the 6-band spectroscopic image acquisition.

As described in the first embodiment, when the photography button 14a is pressed and the spectroscopic image capture mode is established by switching, a judgment that starts image pickup of a spectroscopic image is performed (step S31).

Here, when image pickup of the spectroscopic image is performed, an image of a frame N is captured and then an image of a frame N+1 is performed.

First, when the capture of an image of frame N is started, the first LED 6a, third LED 6c, and fifth LED 6e are lit at the same time (See FIG. 24A) (step S32) and, after the lighting has started, image pickup using a CCD 8 is started (See FIG. 27) (step S33).

Once the image pickup by the CCD 8 has ended, image data are read from the CCD 8, converted into digital data by the A/D converter 9, and then stored in a predetermined storage area (frame memory) in the memory 11 via the bus 10 (step S34).

Further, the respective image data stored in the frame memory are classified for each primary color and then stored in predetermined storage areas (first, third, and fifth memories) in the memory 11 (step S35).

Thereafter, by turning off each of the LEDs 6a, 6c, and 6e (step S36), the image capture of frame N ends.

The capture of the image of the next frame N+1 is basically the same as the capture of the image of frame N except the lit LEDs and the memory areas to which the picked up image data are transferred.

That is, the second LED 6b, fourth LED 6d, and sixth LED 6f are lit at the same time (See FIG. 24B) (step S37) and, after the lighting has started, the image pickup by the CCD 8 is started (See FIG. 27) (step S38).

Once the image pickup by the CCD 8 has ended, image data are read from the CCD 8, converted into digital data by the A/D converter 9, and then stored in a predetermined storage area (frame memory) in the memory 11 via the bus 10 (step S39).

Further, the respective image data stored in the frame memory are classified for each primary color and then stored in predetermined storage areas (second, fourth, and sixth memories) in the memory 11 (step S40).

Thereafter, by turning off each of the LEDs 6b, 6d, and 6f (step S41), the image capture of frame N+1 ends.

Further, although not illustrated, the image acquisition timing by the light-emitting elements (LED) and image pickup element (CCD) is not limited to that described above. The same results are obtained even if the light-emitting elements are turned on after the start of image acquisition of the image pickup elements and even if the image acquisition by the image pickup elements is ended after the light-emitting elements are turned off, and so forth.

Further, the images of each primary color stored in the first to sixth memories in step S35 and step S40 undergo interpolation processing in the photography device 1 or processing device 2 if required because of the generation of missing pixels in correspondence with the arrangement of primary colors of the color filter array 19.

Thus, the 6-band object spectroscopic image stored in the memory 11 is sent to the processing device 2 and undergoes color reproduction and image processing and so forth by means of a processing program. The processing result is displayed on the display 22 by another processing program or transferred to the photography device 1 and displayed on the LCD monitor 16.

Figure 25:
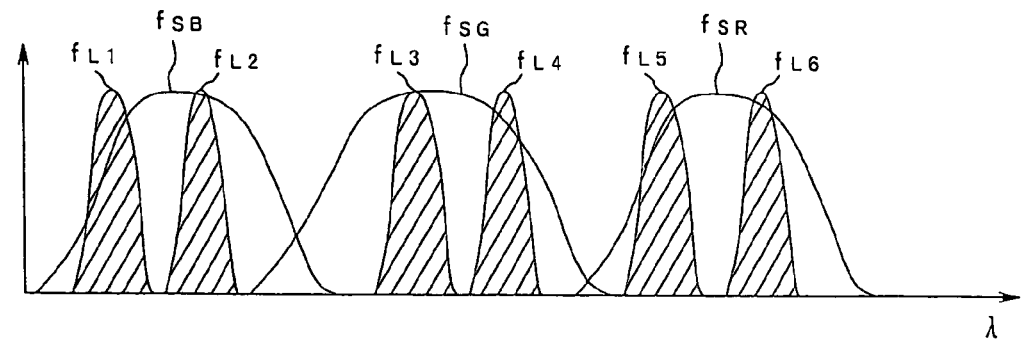
FIG. 25 is a line diagram showing a spectroscopic characteristic of a spectroscopic image for each frame when a monitor image is generated in the third embodiment.
Figure 28:
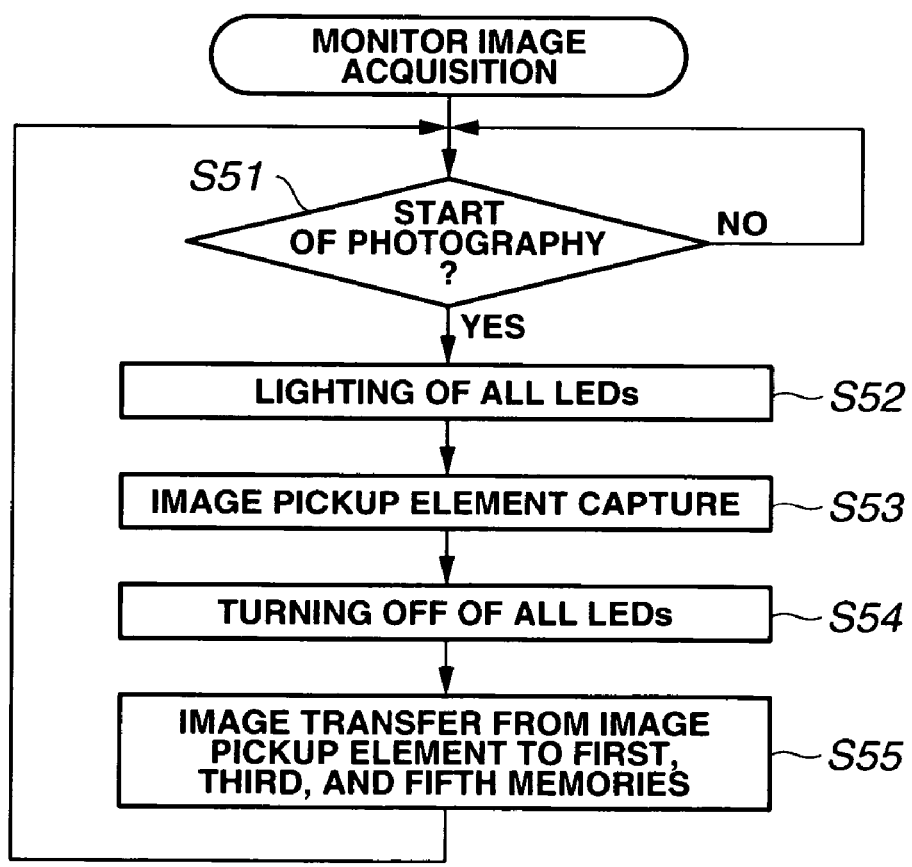
FIG. 28 is a flowchart showing the operation of the light emission of each LED and image acquisition of an image pickup element in the monitor image acquisition of the third embodiment.
Figure 29:
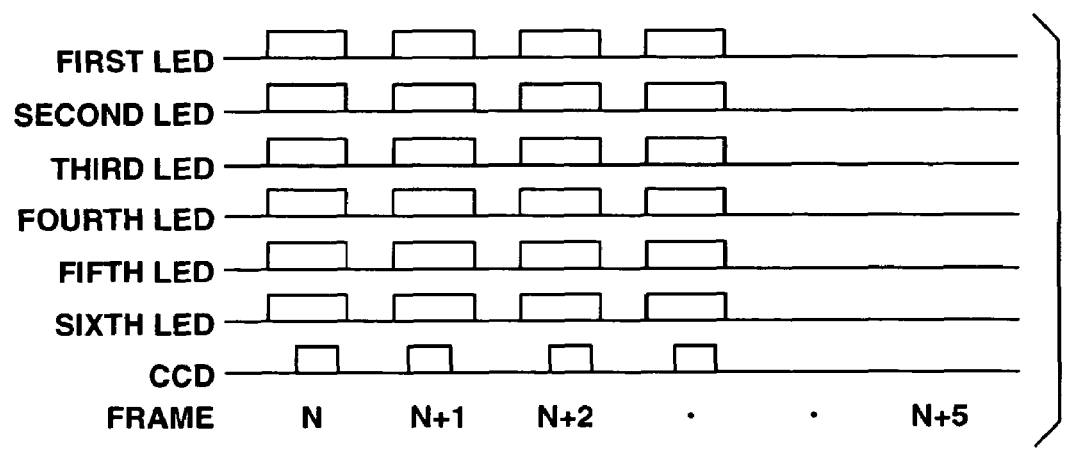
FIG. 29 is a timing chart showing an aspect of the operation of the light emission of each LED and image acquisition of an image pickup element in the monitor image acquisition of the third embodiment.

The operation of the monitor mode will be described next with reference to FIGS. 25, 28, and 29. FIG. 25 is a line diagram showing a spectroscopic characteristic of a spectroscopic image for each frame when a monitor image is generated. FIG. 28 is a flowchart showing the operation of the light emission of each LED and image acquisition of an image pickup element in the monitor image acquisition. FIG. 29 is a timing chart showing an aspect of the operation of the light emission of each LED and image acquisition of an image pickup element in the monitor image acquisition.

Further, so too in this embodiment, as per the embodiments above, general RGB image usage is assumed and the selection of the respective light-emission primary colors is performed so that the first LED 6a and second LED 6b correspond to a blue (B) category, the third LED 6c and fourth LED 6d correspond to a green (G) category, and the fifth LED 6e and sixth LED 6f correspond to a red (R) category.

When the monitor mode is restored as a result of the monitor mode being set by turning on the power supply switch or the spectroscopic image capture mode ending, the start of image pickup of the monitor image is standby (step S51).

Here, image pickup is started immediately and all of the LEDs 6a to 6f are lit (see FIG. 25) (step S52). After the lighting of all the LEDs 6a to 6f has started, image pickup by the CCD 8 is started (See FIG. 29) (step S53).

Once image pickup by the CCD 8 has finished, all the LEDs 6a to 6f are then turned off (step S54), and image data are read from the CCD 8, converted into digital data by the A/D converter 9, and then stored in predetermined storage areas (first, third, and fifth memories) in the memory 11 via the bus 10 (step S55).

While the monitor mode is set, a moving image is acquired by returning to the step S51 and repeating this operation.

The image obtained in this manner is converted into monitor image data and displayed on the LCD monitor 16 via the monitor I/F 15. Thereupon, the monitor image can also be displayed on the display 22 of the processing device 2 depending on the settings.

Further, in the timing chart shown in FIG. 29, although a reduction in the power consumed is sought by turning all the LEDs 6a to 6f on and off each time image pickup is performed by the CCD 8, the LEDs 6a to 6f may be turned on continuously while the monitor mode is set.

Furthermore, although not illustrated, the timing of the image acquisition by the light-emitting elements (LED) and image pickup elements (CCD) is not limited to that mentioned above. The same results are obtained even if the light-emitting elements are turned on following the start of the image acquisition by the image pickup elements and even if the image acquisition by the image pickup elements is ended after the light-emitting elements are switched off.

Further, with 6-band spectroscopic image capture mode of this embodiment being continued to constitute the monitor image acquisition method, a monitor image can also be generated by simultaneously performing memory addition of the first and second bands of the 6-band spectroscopic image, memory addition of the third and fourth bands, and memory addition of the fifth and sixth bands. In this case, the monitor image can be generated by performing memory addition without changing the photography section algorithm. This is effective as a monitor method during continuous spectroscopic image measurement.

Figure 30A:
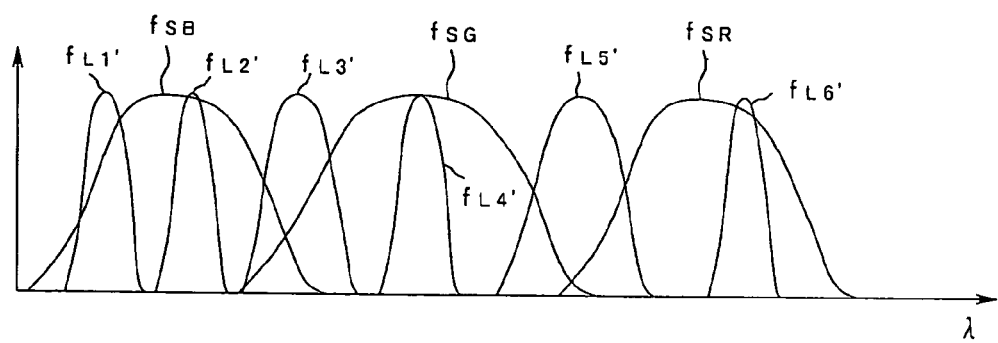
FIG. 30A and FIG. 30B are a line diagram showing an LED light emission spectral when an 8-band spectroscopic image is generated and a CCD spectroscopic sensitivity characteristic after being passed through a color filter array in the third embodiment.

Thereafter, FIGS. 30A to 36 show a modified example of the third embodiment. FIG. 30A and FIG. 30B are a line diagram showing an LED light emission spectral when an 8-band spectroscopic image is generated and a CCD spectroscopic sensitivity characteristic after being passed through a color filter array.

Although the LEDs only emit light of six primary colors (six bands), the modified example obtains an 8-band output as detection by providing LEDs of a light-emission spectroscopic characteristic that extends over the RGB detection bands of the CCD 8 via the color filter array 19.

That is, as shown in FIG. 30A, the light reception characteristics (indicated by each of the curves fL1' to fL6') of the light emitted by the respective LEDs 6a to 6f with respect to the curves fSB, fSG, fSR that show the total spectroscopic sensitivity characteristic obtained by the transmittance distribution of the color filter array 19 and the light reception sensitivity distribution of the CCD 8 are as follows.

First, two curves fL1' and fL2' are contained within the curve fSB that represents the spectroscopic bandwidth that corresponds to the blue color filter and a portion of curve fL3' is also contained within curve fSB.

Curve fL4' is contained within curve fSG that represents the spectroscopic bandwidth that corresponds to the green color filter and further a portion of curve fL3' and a portion of curve fL5' are contained within curve fSG.

Curve fL6' is contained within curve fSR that represents the spectroscopic bandwidth that corresponds to the red color filter and further a portion of curve fL5' is contained within curve fSR.

Thus, the constitution is such that the spectroscopic characteristic of the light emission by the third LED 6c (curve fL3') extends over the band of the blue color filter and the band of the green color filter and the spectroscopic characteristic of the light emission by the fifth LED 6e (curve fL5') extends over the band of the green color filter and the band of the red color filter.

Figure 30B:
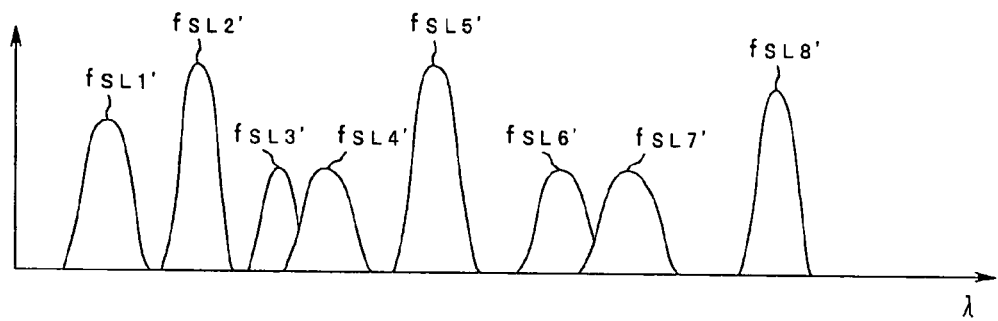

As a result of this constitution, the total spectroscopic sensitivity characteristic when light emitted by each of the LEDs 6a to 6f is received by the CCD 8 via the color filter array 19 has a total of 8 bands which are curve fSL1' (of curve fL1' and curve fSB), curve fSL2' (of curve fL2' and curve fSB), curve fSL3' (of curve fL3' and curve fSB), curve fSL4' (of curve fL3' and curve fSG), curve fSL5' (of curve fL4' and curve fSG), curve fSL6' (of curve fL5' and curve fSG), curve fSL7' (of curve fL5' and curve fSR), and curve fSL8' (of curve fL6' and curve fSR), as shown in FIG. 30B.

Figure 31A:
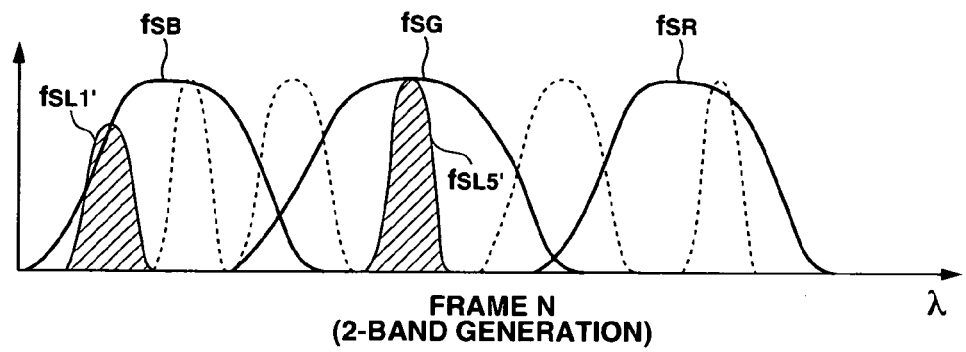
FIG. 31A to FIG. 31C are a line diagram showing a spectroscopic characteristic of a spectroscopic image for each frame when an 8-band spectroscopic image is generated in the third embodiment.
Figure 31B:
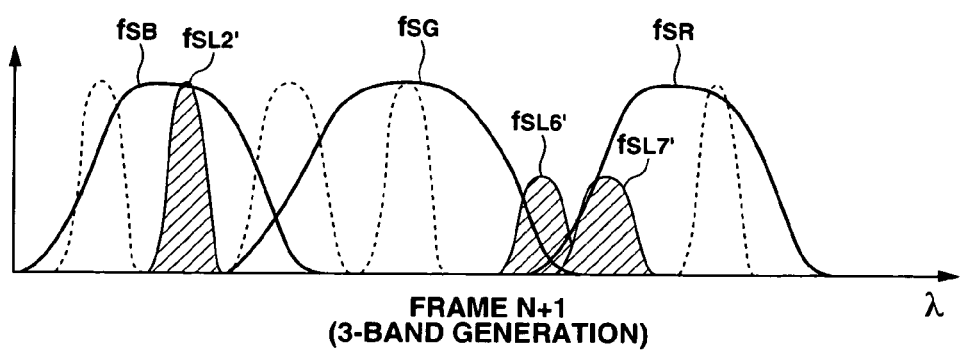
Figure 31C:
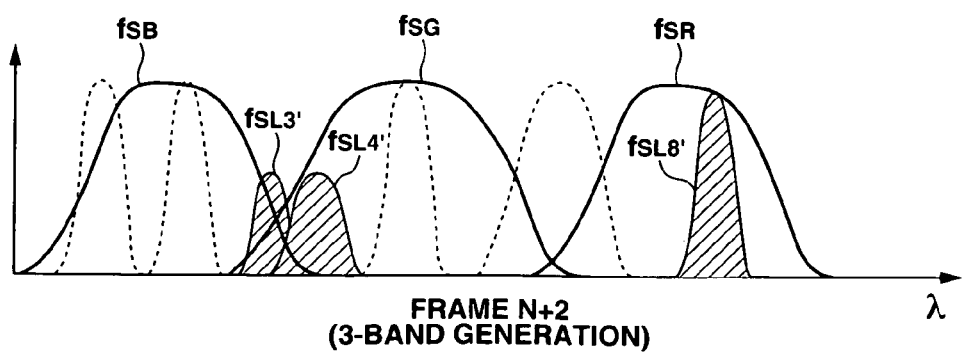
Figure 32:
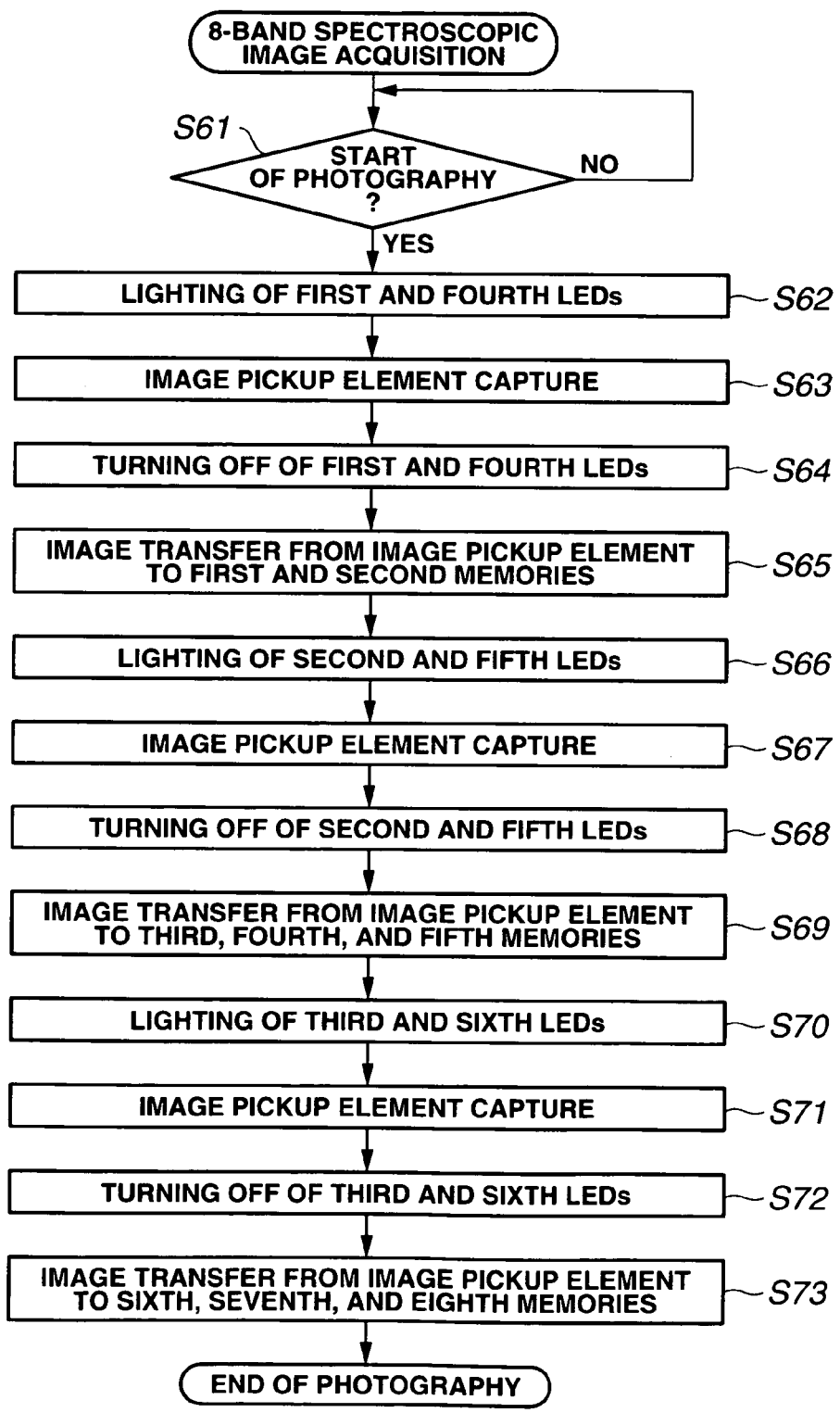
FIG. 32 is a flowchart showing the operation of the light emission of each LED and the image acquisition of the image pickup element in the 8-band spectroscopic image acquisition of the third embodiment.
Figure 33:
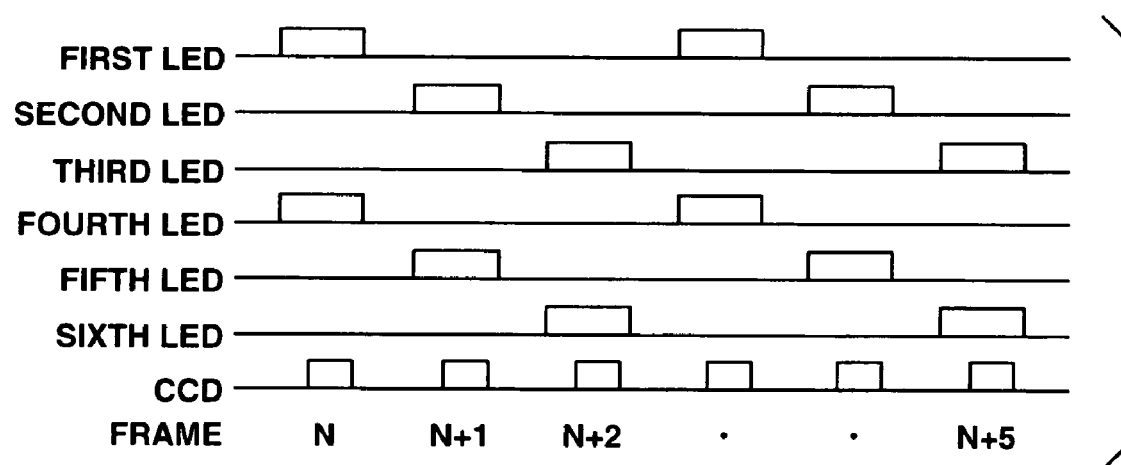
FIG. 33 is a timing chart showing an aspect of the operation of the light emission of each LED and the image acquisition of the image pickup element in the 8-band spectroscopic image acquisition of the third embodiment.

An operation that acquires an 8-band spectroscopic image will be described next with reference to FIGS. 31A to 33. FIG. 31A to FIG. 31C are a line diagram showing a spectroscopic characteristic of a spectroscopic image for each frame when an 8-band spectroscopic image is generated. FIG. 32 is a flowchart showing the operation of the light emission of each LED and the image acquisition of the image pickup element in the 8-band spectroscopic image acquisition. FIG. 33 is a timing chart showing an aspect of the operation of the light emission of each LED and the image acquisition of the image pickup element in the 8-band spectroscopic image acquisition.

Further, in the modified example, in order to pick up an 8-band spectroscopic image, the corresponding storage areas of the first to eighth memories are provided in the memory 11.

When a switch is made to the spectroscopic image capture mode by pressing the photography button 14a, a judgment to start the image pickup of the spectroscopic image is performed (step S61).

When the image pickup of the spectroscopic image is started, first a capture operation to capture the image of frame N as shown in FIG. 31A is started, the first LED 6a and fourth LED 6d are lit at the same time (step S62) and, after lighting has started, image pickup by the CCD 8 is started (See FIG. 33) (step S63).

Once image pickup by the CCD 8 has started, the LEDs 6a and 6d are then turned off (step S64), and image data are read from the CCD 8 and converted into digital data by the A/D converter 9 and then stored in predetermined storage areas (first and second memories) in memory 11 via the bus 10 (step S65). As a result, the image capture operation of frame N (acquisition of a 2-band object spectroscopic image) ends.

Thereafter, the capture operation to capture the image of frame N+1 as shown in FIG. 31B is started, the second LED 6b and fifth LED 6e are lit simultaneously (step S66) and, after lighting has started, image pickup by the CCD 8 is started (See FIG. 33 (step S67).

Once the image pickup by the CCD 8 has ended, the LEDs 6b and 6e are turned off (step S68), and image data are read from the CCD 8 and stored in predetermined storage areas (third, fourth, and fifth memories) in the memory 11 (step S69). As a result, the capture operation for the image of frame N+1 (acquisition of 3-band object spectroscopic image) ends.

In addition, the capture operation of the image of frame N+2 as shown in FIG. 31C is started and the third LED 6c and sixth LED 6f are lit at the same time (step S70) and, after the lighting is started, the image pickup by the CCD 8 is started (See FIG. 33) (step S71).

Once the image pickup by the CCD 8 has ended, the LEDs 6c and 6f are then turned off (step S72) and image data are read from the CCD 8 and then stored in predetermined areas (sixth, seventh, and eighth memories) within the memory 11 (step S73). As a result, the capture operation to capture the image of frame N+2 (the acquisition of a 3-band object spectroscopic image) ends.

When spectroscopic images are continuously captured as a moving image, the operation from frame N to frame N+2 is repeated.

Further, although not illustrated, the timing of the image acquisition by the light-emitting elements (LED) and image pickup element (CCD) is not limited to that mentioned above. The same results are obtained even if the light-emitting elements are turned on after the start of image acquisition by the image pickup element and even if image acquisition by the image pickup element is ended after the light-emitting elements are turned off, or similar.

Thus, the 6-band object spectroscopic image stored in the memory 11 is sent to the processing device 2 and color reproduction and image processing and so forth are performed by a processing program. The processing result is displayed on the display 22 by another processing program or transmitted to the photography device 1 and displayed on the LCD monitor 16.

Figure 34:
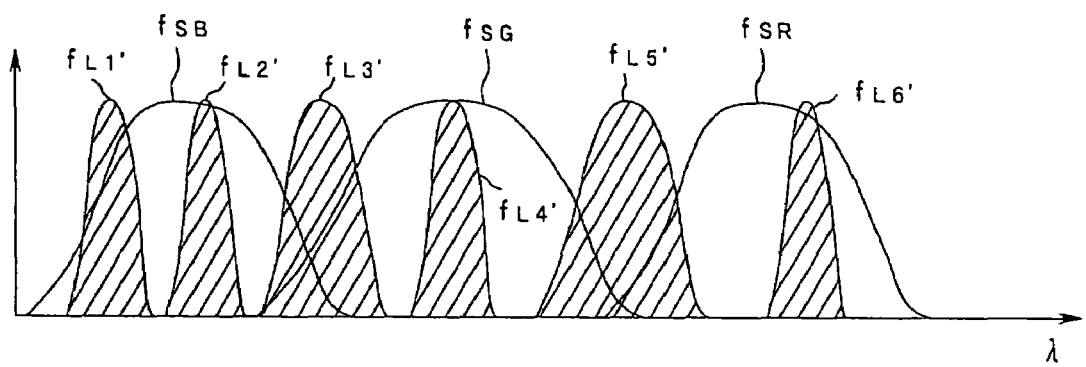
FIG. 34 is a line diagram showing a spectroscopic characteristic of a spectroscopic image for each frame when a monitor image is generated in the third embodiment.
Figure 35:
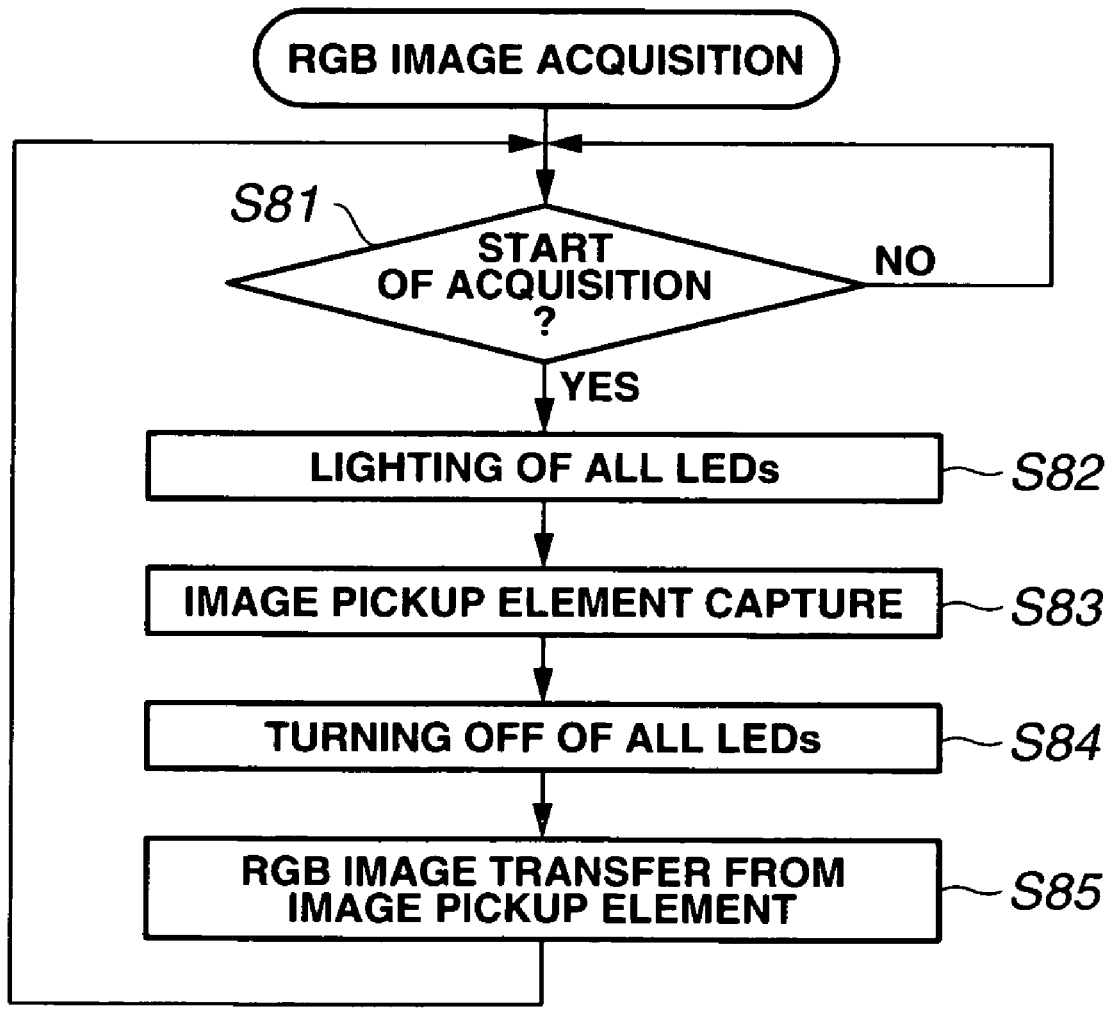
FIG. 35 is a flowchart showing the operation of the light emission of each LED and the image acquisition of the image pickup element in the monitor image acquisition of the third embodiment.
Figure 36:
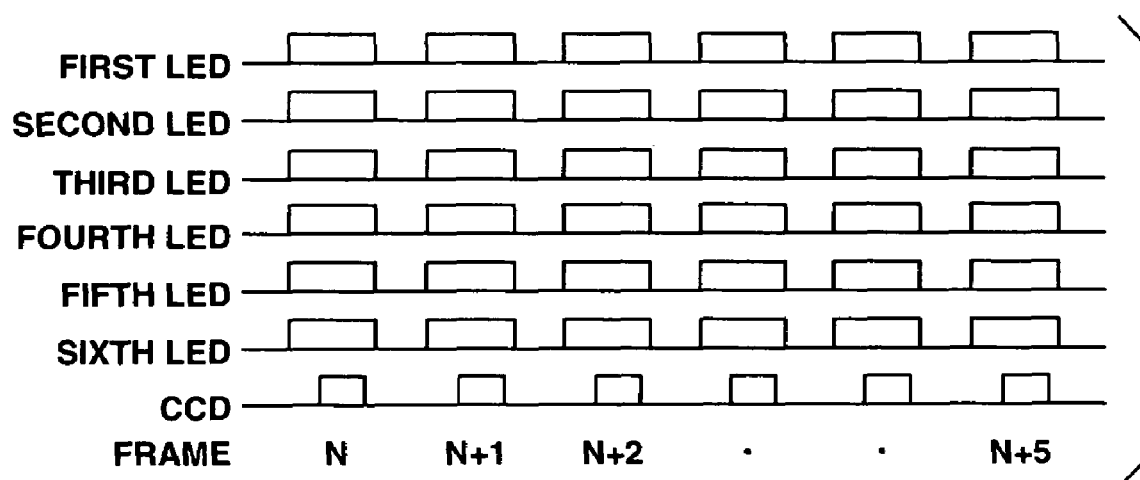
FIG. 36 is a timing chart showing an aspect of the operation of the light emission of each LED the image acquisition of the image pickup element in the monitor image acquisition and of the third embodiment.

An operation in which the monitor image is acquired will be described next with reference to FIGS. 34 to 36. FIG. 34 is a line diagram showing a spectroscopic characteristic of a spectroscopic image for each frame when a monitor image is generated. FIG. 35 is a flowchart showing the operation of the light emission of each LED and the image acquisition of the image pickup element in the monitor image acquisition. FIG. 36 is a timing chart showing an aspect of the operation of the light emission of each LED and the image acquisition of the image pickup element in the monitor image acquisition.

When the monitor mode is restored as a result of the monitor mode being set by turning on the power supply switch or the spectroscopic image capture mode ending, the start of image pickup of the monitor image is standby (step S81).

Here, image pickup is started immediately and all of the LEDs 6a to 6f are lit (see FIG. 34) (step S82). After the lighting of all the LEDs 6a to 6f has started, image pickup by the CCD 8 is started (See FIG. 36) (step S83).

Once image pickup by the CCD 8 has finished, all the LEDs 6a to 6f are then turned off (step S84), and image data are read from the CCD 8, converted into digital data by the A/D converter 9, and then stored in predetermined storage areas in the memory 11 via the bus 10 (step S85).

Here, although a reduction in the power consumed is sought by turning all the LEDs 6a to 6f on and off each time image pickup is performed by the CCD 8, the LEDs 6a to 6f may be turned on continuously while the monitor mode is set as described in FIG. 29 above.

Furthermore, although not illustrated, the timing of the image acquisition by the light-emitting elements (LED) and image pickup elements (CCD) is not limited to that mentioned above. The same results are obtained even if the light-emitting elements are turned on following the start of the image acquisition by the image pickup elements and even if the image acquisition by the image pickup elements is ended after the light-emitting elements are turned off.

Thereafter, until monitor mode is cancelled, the processing returns to step S81 and moving-image image data are continuously acquired by repeating the operation above.

The image obtained in this manner is converted into monitor image data and displayed on the LCD monitor 16 via the monitor I/F 15. Thereupon, the monitor image can also be displayed on the display 22 of the processing device 2 depending on the settings.

Further, although a single-panel image pickup element in combination with a 3-band color filter array is cited by way of example as the image pickup element in the above description, the image pickup element is not limited to such a combination and may be a three-panel type 3-band image pickup element constituted comprising a spectroscopic section such as a spectroscopic mirror or spectroscopic prism that separates the incident light into light of a plurality of wavelength bands, and a plurality of image pickup elements that perform image pickup on light of the plurality of wavelength bands that has undergone the spectroscopy of the spectroscopic section, or may be a two-panel-type image pickup element. In addition, the color filter is not limited to an RGB 3-band primary color filter and may naturally also be a complementary color filter.

Furthermore, although 8-band object spectroscopic image data is acquired from the LEDs of the 6-band light-emission spectrals above, the present invention is not limited to such LEDs. Optional object spectroscopic image data may be acquired by means of a combination. For example, even when only third and fifth LEDs are used, that is, only a 2-band light source is used, a 4-band object spectroscopic image can be obtained as indicated by fSL3', fSL4', fSL6', and fSL7' in FIG. 31B and FIG. 31C. In addition, various combinations are possible.

The third embodiment exhibits substantially the same effects as those of the first and second embodiments above. By using a color image pickup element, the number of image pickups required to acquire the object spectroscopic image can be reduced and a highly accurate color-reproduced moving image or the like can be more easily implemented.

In addition, because the constitution is such that the LED light emission spectrals extend over the spectroscopic sensitivity distribution of the light reception by the color image pickup element, 8-band object spectroscopic image data can be acquired while using the LEDs of the 6-band light emission spectrals.

Fourth Embodiment

Figure 37:
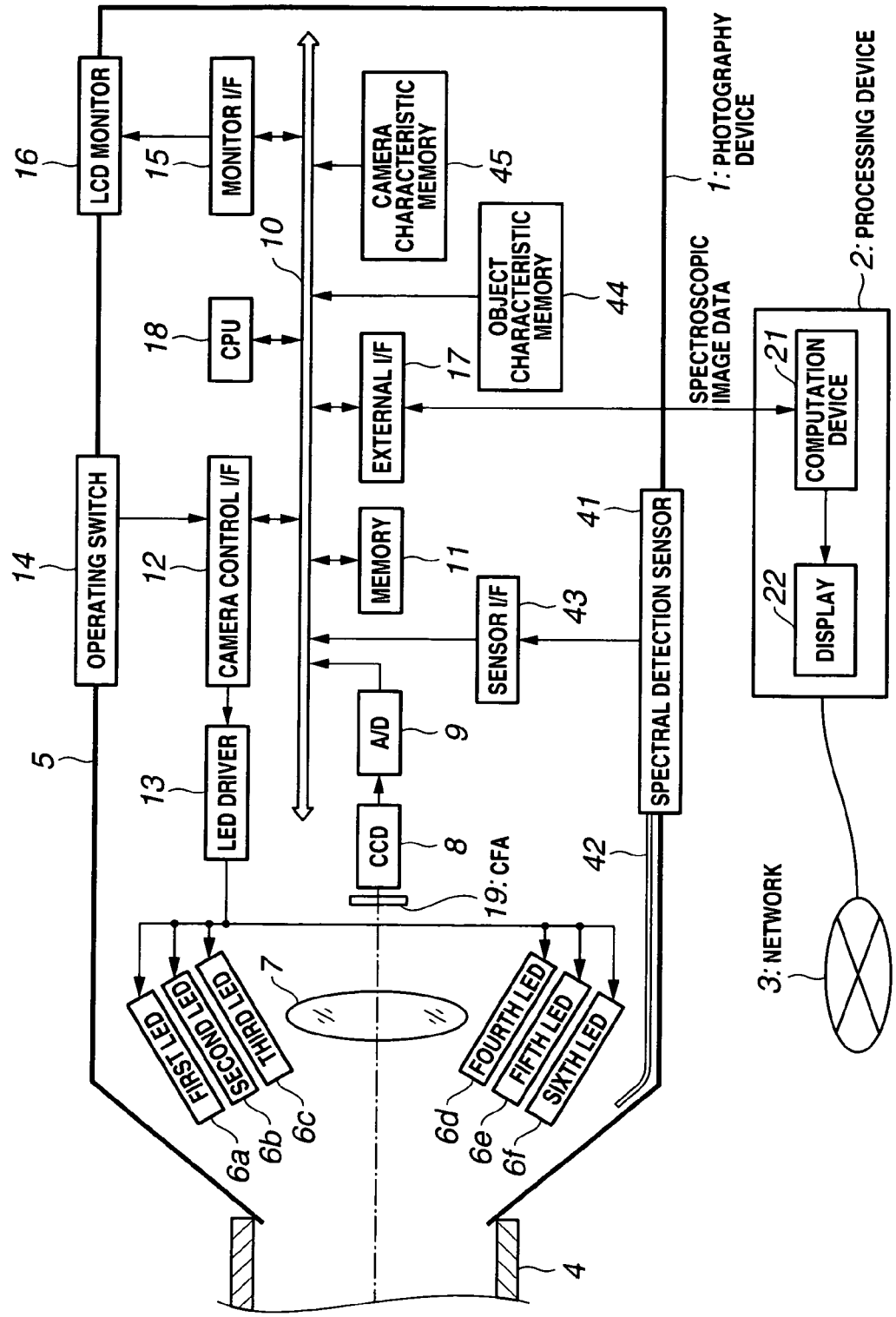
FIG. 37 is a block diagram showing the constitution of the image processing system of a fourth embodiment of the present invention.

FIGS. 37 to 42 and FIG. 89 show a fourth embodiment of the present invention. FIG. 37 is a block diagram showing the constitution of the image processing system. In the fourth embodiment, the same numerals are assigned to the same parts as those of the first to third embodiments and a description of such parts is omitted. Only the differences are mainly described.

The fourth embodiment has the basic constitution of the third embodiment above and is further constituted by adding a spectral detection sensor.

That is, as shown in FIG. 37, the photography device 1 of the image processing system is constituted further comprising: in addition to the constitution of the third embodiment shown in FIG. 21, a spectral detection sensor 41 that detects the spectral distribution of light; a probe 42 that introduces detected light to the spectral detection sensor 41; a sensor I/F 43 that converts the output from the spectral detection sensor 41 into a digital signal and processes and outputs the digital signal; an object characteristic memory 44 that stores the object characteristics, and a camera characteristic memory 45 that stores the camera characteristics.

Differing from a constitution in which a 6-band spectroscopic image is acquired by the CCD 8 by using the first LED 6a to sixth LED 6f, the spectral detection sensor 41 detects only spectrals rather than capturing light as an image.

The spectral detection sensor 41 has a light detection range that covers the full bandwidth of visible light (380 nm to 800 nm), performs detection by means of the grating system and has a resolution of 5 nm. Therefore, detailed spectral data can be acquired. Further, although a grating-system spectral detection sensor is cited by way of example here, other systems are acceptable.

The probe 42 uses flexible optical fiber (or an optical fiber bundle), for example, but is not limited to flexible optical fiber. Broad applications are possible as long as the probe 42 is capable of guiding the detected light.

While it is possible to detect the light spectral of the object when the light from the object is detected by using such a constitution, the spectral characteristic of the illumination light can also be measured by installing a standard white color plate in place of the object.

More precisely, the spectral characteristics of the respective LEDs 6a to 6f can be measured by blocking the external illumination light by using the attachment section 4 or the like and making the first LED 6a to sixth LED 6f emit light sequentially and detecting the light. As a result, deterioration in the light-emitting elements themselves and a variation in the spectral characteristic caused by a change in the environment such as the temperature can be detected. In addition, more accurate high color reproduction can be implemented because a profile of the illumination spectral that reflects the variation in the characteristic is obtained.

The spectral characteristic of the ambient illumination light can also be measured by detecting the external illumination light.

Figure 38:
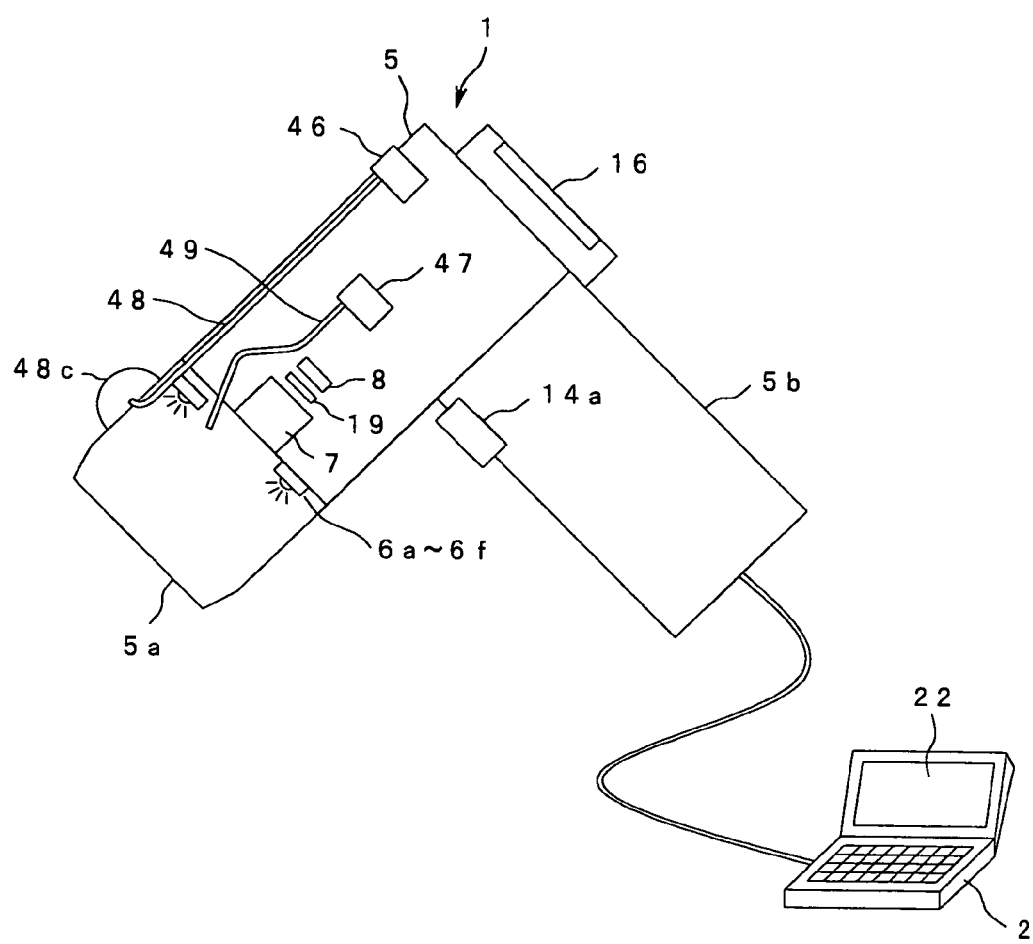
FIG. 38 shows an example of an aspect when an image processing system in which a plurality of spectral detection sensors are installed is used in the fourth embodiment.

Thereafter, FIG. 38 shows an example of an aspect when an image processing system in which a plurality of spectral detection sensors are installed is used.

FIG. 38 shows a more specific installation example of the spectral detection sensor. Here, two spectral detection sensors, that is, a first spectral detection sensor 47 and a second spectral detection sensor 46 are used.

The first spectral detection sensor 47 is installed to detect the spectroscopic spectral of the object part, wherein the tip of the optical fiber 49 constituting the probe is installed in a position that allows object light to enter via the projection opening 5a of the enclosure 5 in the vicinity of the first to sixth LEDs 6a to 6f.

As mentioned above, the first spectral detection sensor 47 can be used in order to detect the illumination spectral of the first to sixth LEDs 6a to 6f by installing a standard white color plate in place of the object and the spectroscopic reflection spectral of a spot (specified part) of the object can also be acquired directly by installing a lens or similar at the tip as will be described subsequently.

As a result, if spectral data for the paint color of an automobile, the paint color of a building, the spectroscopic characteristic of foodstuff, and the dye of clothing, and so forth are acquired directly by using the first spectral detection sensor 47, the data can be used as data for examining and confirming the aforementioned items.

Further, the second spectral detection sensor 46 is provided to make it possible to detect the illumination light spectral of an environment in which the object has been placed, wherein the tip of the optical fiber 48 constituting the probe is exposed at the outer surface of the enclosure 5, and a white, translucent integrating sphere 48c is attached to cover the tip of the optical fiber 48. An illumination spectral when the object in a position spaced apart from the photography device 1 is photographed with only solar light or indoor light can be acquired by using the second spectral detection sensor 46. As a result, because a profile of the illumination spectral according to the ambient illumination light can be created at the same time as the object image is photographed, real-time high-color reproduction can be automatically performed correspondingly even when the ambient illumination light changes.

In addition, by detecting the spectral of the peripheral ambient light of the photography device 1 and comparing the same with the spectrals of the LEDs contained in the photography device 1 itself, it is also possible to adaptively switch to performing image pickup by using either the peripheral ambient light or LED light. For example, because peripheral ambient light can be used when an RGB moving image is subjected to image pickup, in this case, a decrease in the power consumed or the like is also rendered possible by causing the built-in LEDs not to emit light.

Figure 39:
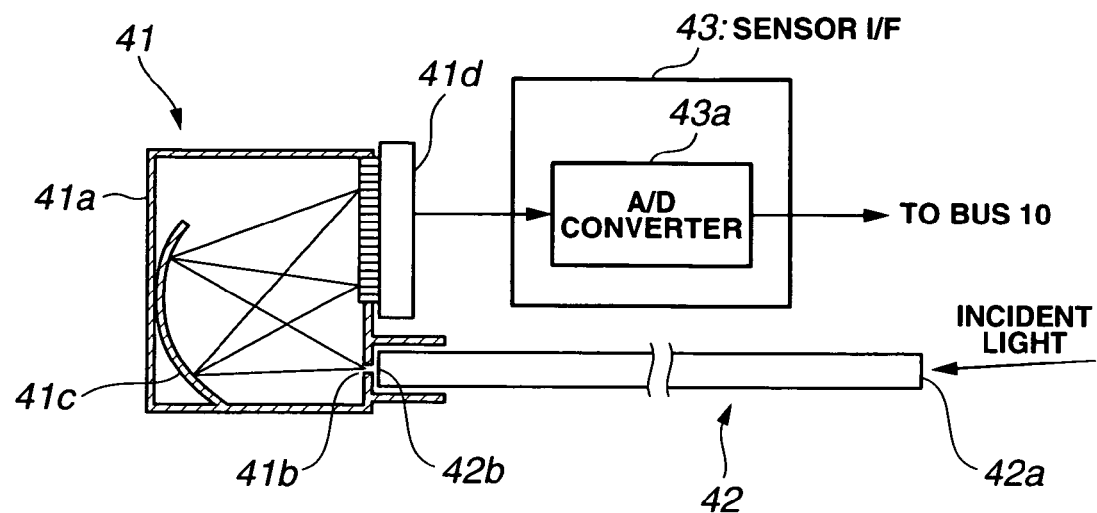
FIG. 39 is a sectional view of a constitutional example of a spectral detection sensor of the fourth embodiment.

FIG. 39 is a sectional view of a constitutional example of the spectral detection sensor 41.

The probe 42 has light that enters via an entrance end 42a and exits from an exit end 42b.

The spectral detection sensor 41 is constituted comprising a container box 41a, an incident light slit 41b that is provided open at one end of the container box 41a and which serves to allow light leaving the exit end 42b of the probe 42 to enter as slit light, a grating 41c installed in the container box 41a that subjects the slit light entering via the incident light slit 41b to spectroscopy in accordance with wavelength to cause the light to be reflected in different directions and condensed, and a photodiode array 41*d* that is attached to the container box 41*a* and which receives light that has been condensed in different positions in accordance with wavelength by the grating 41*c* and outputs a signal that corresponds with the intensity of the received light.

As a result, the photodiode array 41*d* O/E-converts different wavelengths in accordance with the light reception position and outputs a signal that corresponds with the intensity. The sensor I/F 43 is constituted comprising an A/D converter 43*a* for converting an analog signal that is output by the photodiode array 41*d* into a digital signal and outputs the converted digital signal to a CPU 18 or the like via the bus 10. The CPU 18 receives the digital signal as spectral information indicating the intensity of each wavelength and performs an analysis or the like.

Figure 40:
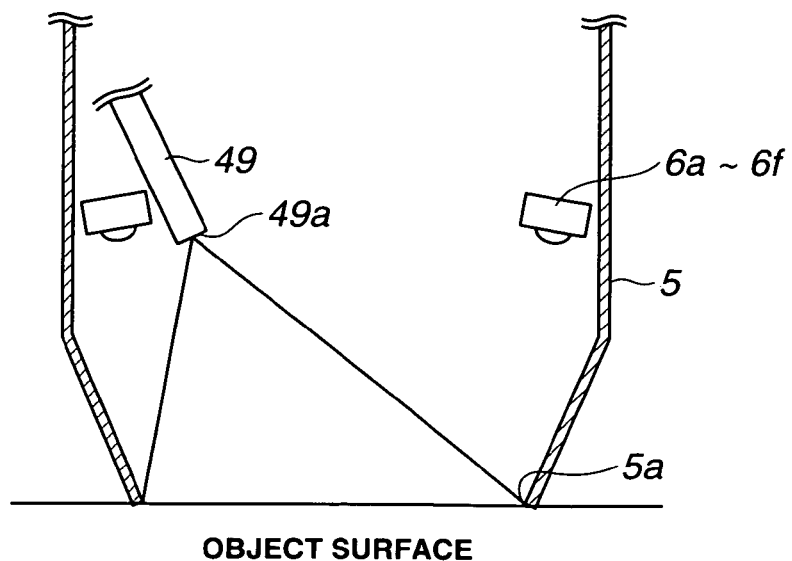
FIG. 40 is a sectional view of an aspect of the entrance end of an optical fiber that is connected to the spectral detection sensor of the fourth embodiment.

FIG. 40 is a sectional view of an aspect of an entrance end 49*a* of an optical fiber 49 that is connected to the spectral detection sensor 47. Further, an illustration of the photography optical system 7 and so forth has been omitted from FIG. 40.

Light from a certain angular range enters the entrance end 49*a* of the optical fiber 49. In the illustrated example, the optical fiber 49 is installed so that the reflected light reflected by the object surface constituting the photographic target that enters via the projection opening 5*a* of the enclosure 5 reaches the entrance end 49*a*.

The constitution shown in FIG. 40 employs a standard white color plate as the object as mentioned earlier and can be used in the acquisition of information on color changes over time by detecting LED illumination spectrals, and so forth.

Figure 41:
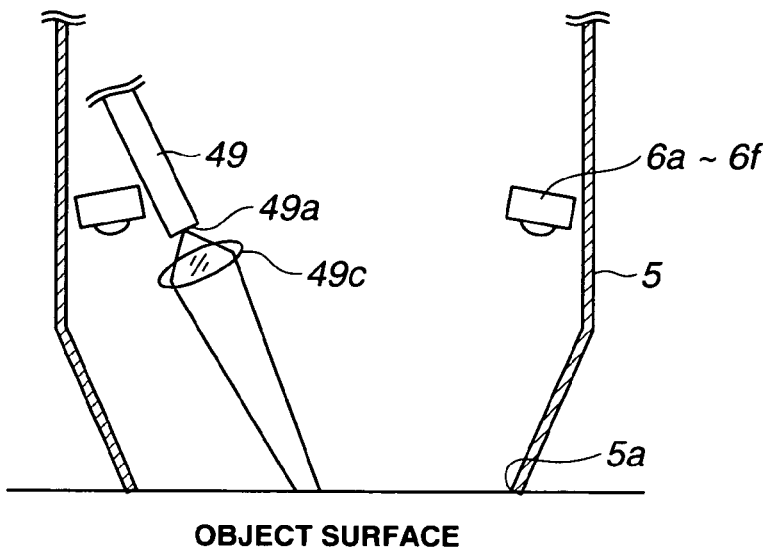
FIG. 41 is a sectional view of a constitutional example in which a sensor optical system is installed in the vicinity of the entrance end of the optical fiber that is connected to the spectral detection sensor of the fourth embodiment.

Further, FIG. 41 is a sectional view of a constitutional example in which a sensor optical system 49*c* is installed in the vicinity of the entrance end 49*a* of the optical fiber 49 that is connected to the spectral detection sensor 47. Further, an illustration of the photography optical system 7 and so forth has also been omitted from FIG. 41.

As shown in FIG. 41, by providing the sensor optical system 49*c* constituting a lens or similar at the entrance end 49*a* of the optical fiber 49 connected to the spectral detection sensor 47, the luminous flux entering the entrance end 49*a* can be limited to light from a certain range of the object. As a result, the spectral of a specific position of the object can be measured at a high wavelength resolution, as mentioned earlier.

Figure 42:
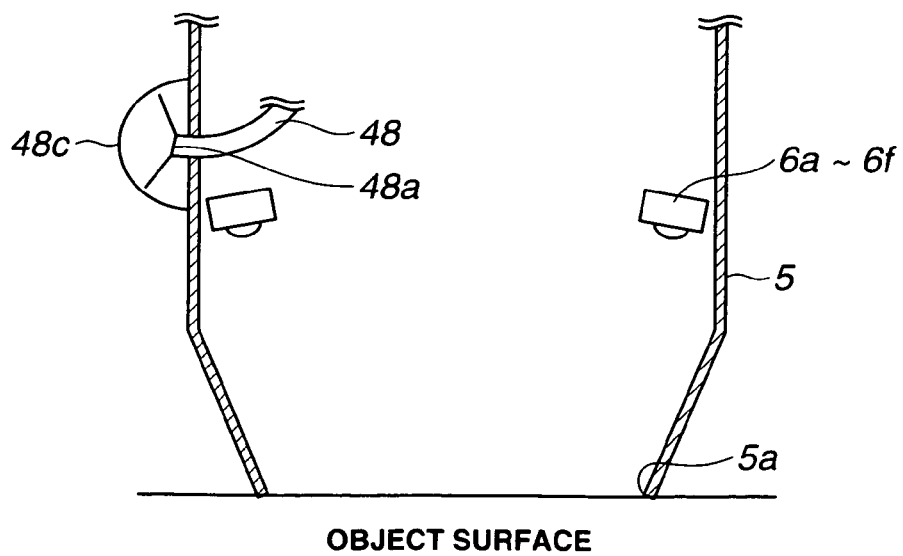
FIG. 42 is a sectional view of an aspect of the entrance end of the optical fiber that is connected to the spectral detection sensor that is provided for ambient light acquisition in the fourth embodiment.

FIG. 42 is a sectional view of an aspect of the entrance end 48*a* of the optical fiber 48 that is connected to the spectral detection sensor 46 that is provided for ambient light acquisition. Further, an illustration of the photography optical system 7 and so forth has also been omitted from FIG. 42.

As mentioned earlier, the entrance end 48*a* of the input optical fiber 48 is exposed at the outer surface of the enclosure 5 and the white and translucent integrating sphere 48*c* is attached to surround the entrance end 48*a*.

In such a constitution, when ambient illumination light is irradiated onto the integrating sphere 48*c*, the same is diffused and transmitted and enters from the entrance end 48*a* of the optical fiber 48. The incident light is transmitted by the optical fiber 48 and spectral measurement is performed by the spectral detection sensor 46.

The fourth embodiment affords substantially the same effects as those of the first to third embodiments. A spectral distribution of the object light can be obtained by providing the spectral detection sensor and more accurate color reproduction can also be performed in real time by acquiring the spectral distribution of the LEDs.

Further, the spectral distribution of a specified part of the object can also be acquired by using a sensor optical system. Because the sensor optical system has a 5 nm resolution, for example, as mentioned earlier, more detailed spectral data can be obtained for the specified part of the object, whereby a more accurate diagnosis and judgment can be performed.

In addition, because the spectral of ambient illumination light can be detected, a profile of the illumination spectral pertaining to the ambient illumination light can also be acquired in real time.

Figure 89:
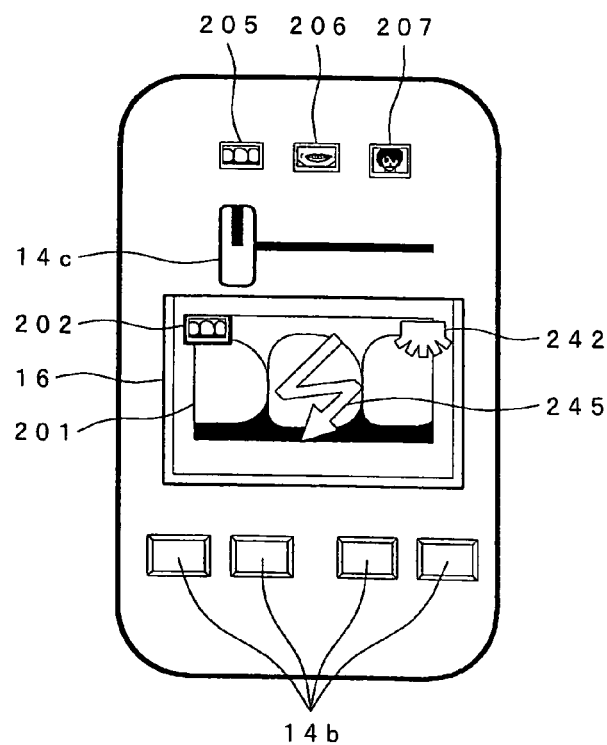
FIG. 89 shows an example of a light leakage alarm display in the fourth embodiment.

In addition, the existence of leaked light can also be detected by the spectral detection sensor 41 in macro-photography mode. Further, when the leaked light is detected, a warning to the photographer may be issued by means of a display and sound and so forth by using warning reporting means. The displayed warning may involve displaying a warning on the display means (setting state display means, for example) and a sound warning may involve the sounding of an alarm such as an alarm sound. FIG. 89 shows an example of an alarm display for leaked light. In this example, a warning to the effect that there is leaked light is issued by displaying a leaked light alarm 245 as a downward-facing zigzag arrow, for example, on a display monitor such as the LCD monitor 16.

Further, the warning reporting means is not limited to a warning notice when leaked light is detected. A warning notice in the event of a positional shift during photography or a warning notice when a shadow is produced in the photography optical system, or the like, may be issued.

Fifth Embodiment

The image processing system of a fifth embodiment of the present invention will be described next. In this fifth embodiment, the same numerals are assigned to the parts that are the same as those of the first to fourth embodiments above and a description thereof will be omitted. Only the differences are mainly described.

Figure 43:
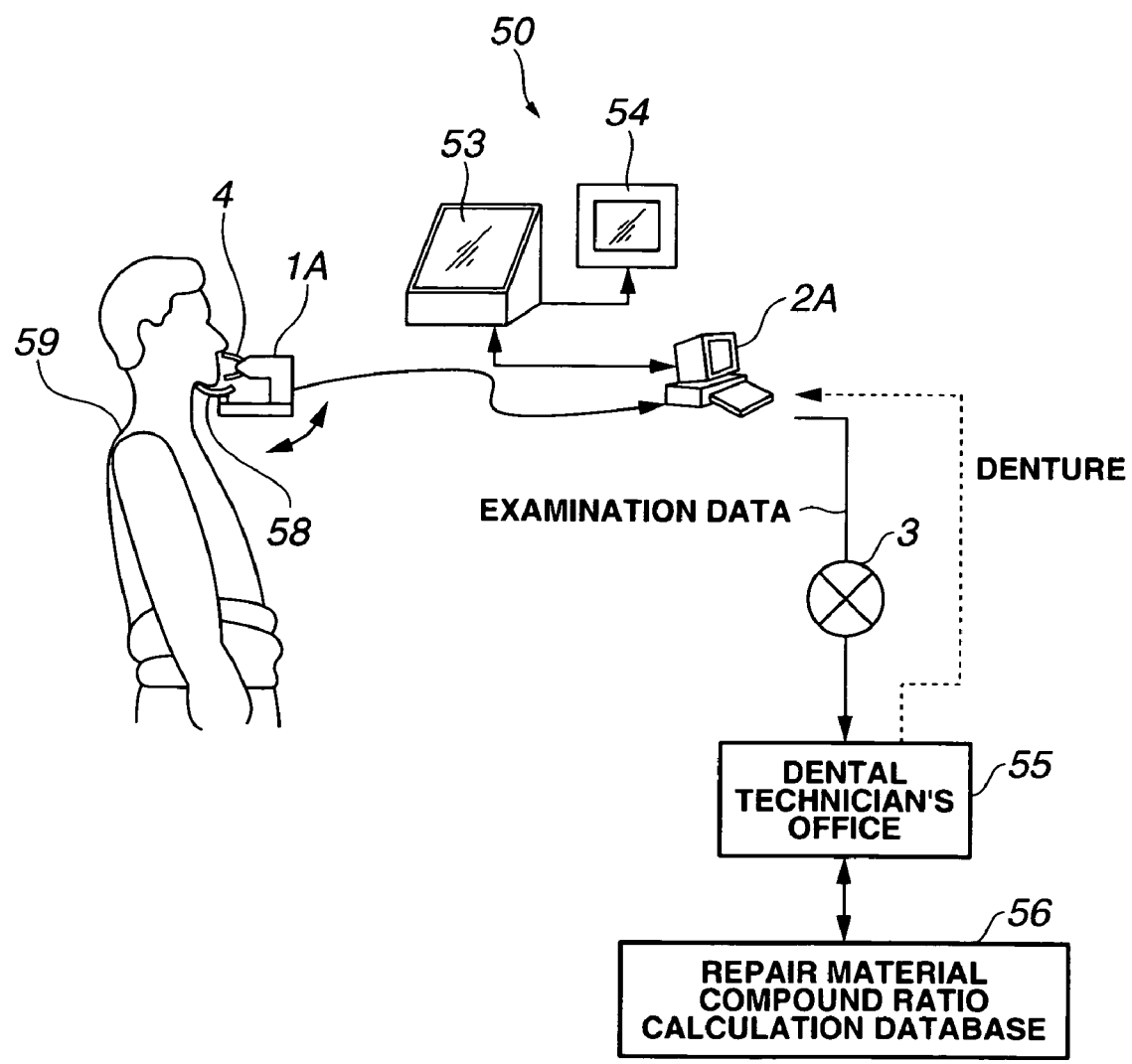
FIG. 43 is a system constitutional view of a dental image processing system of a fifth embodiment of the present invention.
Figure 44:
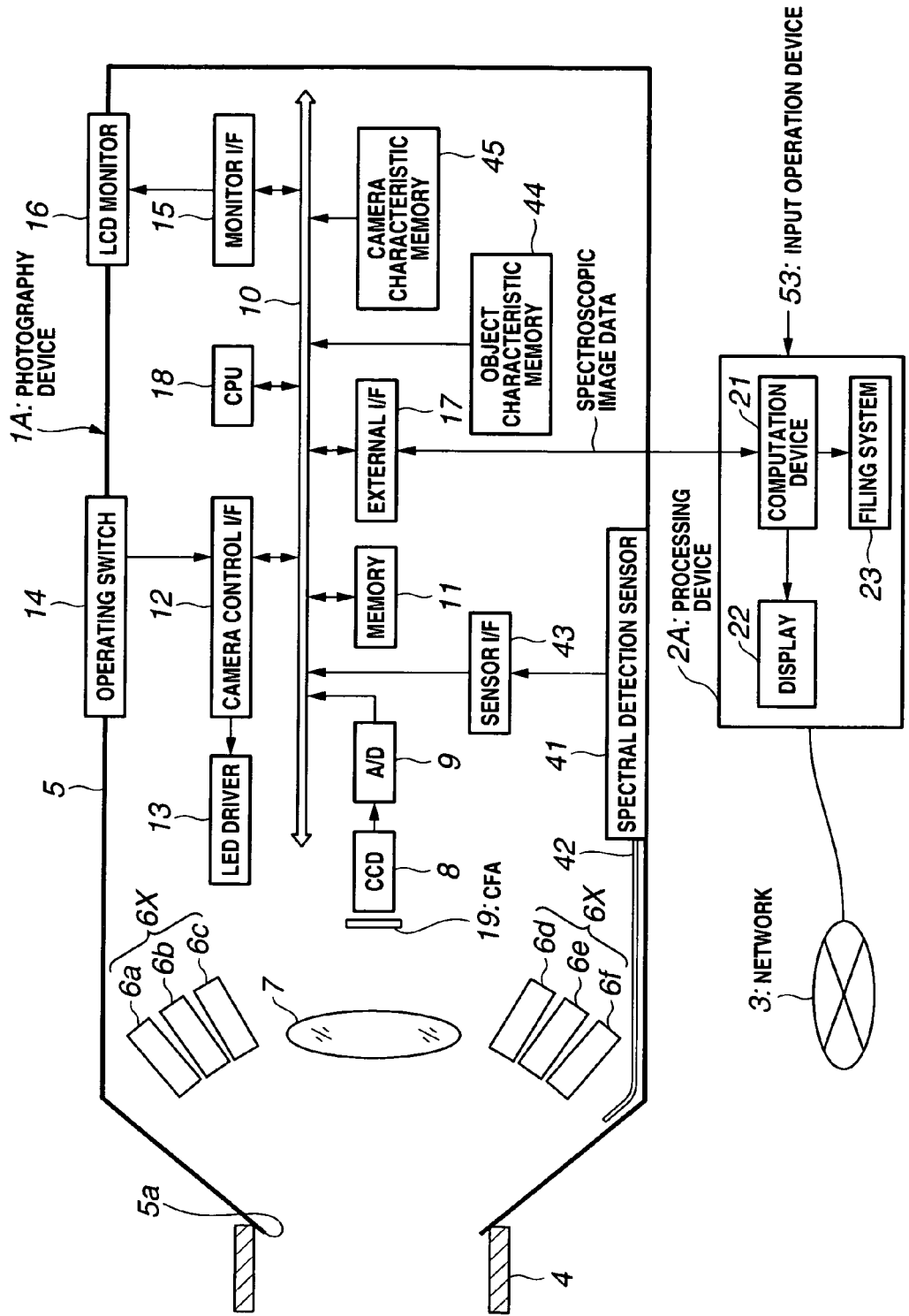
FIG. 44 is a block constitutional view of a photography device that is adopted as the dental image processing system in FIG. 43.

FIG. 43 is a system constitutional view of a dental image processing system constituting an image processing system of the fifth embodiment of the present invention. FIG. 44 is a block constitutional view of a photography device that is adopted as the dental image processing system in FIG. 43.

A dental image processing system 50 of the fifth embodiment is a system that acquires spectroscopic image information of the teeth of a patient 59 when dentures or false teeth are produced, performs highly accurate color reproduction and, by exchanging the spectroscopic image information with a dental technician's office 55 by means of the network 3, whereby the system is capable of supporting esthetic crown repair and whitening processing.

The dental image processing system 50 of this embodiment comprises a photography device (handheld multispectral camera, HMSC) 1A constituting an image photography section for acquiring image data of a spectroscopic image and monitor image of a patient's teeth as shown in FIG. 43, a processing device 2A constituting an image processing section that comprises an image memory and performs computing and managing image data obtained by the photography device 1A, a touch-panel-type input operation device 53 for performing a camera photography operation, a calibration monitor 54 for displaying a color reproduction state, a network 3 for linking the processing device 2A and the dental technician's office (communication device) 55, and a repair material compound ratio calculation database 56 that is provided in the dental technician's office 55.

Further, the repair material compound ratio calculation database 56 may be placed within or in parallel with a dental database that has functions useful to dentistry such as dental treatment information, a patient registration database, and a case database. Furthermore, the repair material compound ratio calculation database 56 or the dental database is not restricted to a dental technician's office 55 and may be placed on a specific website.

Further, although not illustrated, by providing the photography device 1A in a dental office, confirmation and evaluation of a created prosthesis or the like can also be implemented. In addition, by transmitting information such as images to the dentist via a network before sending a prosthesis to a dentist, the suitability of the prosthesis can be secured more reliably. That is, this system permits two-way data exchange and rapid and highly accurate prosthesis creation.

In addition, because information can be transmitted substantially in real time via the network, when treatment of the patient's teeth is difficult and so forth, information is exchanged with the dental technician's office during the time the patient stays at the dental office and, depending on the case, the information exchange can be performed once again to acquire additional information (images and so forth) desired by the dental technician, and the diagnosis of the patient and wishes of the patient can be collected without wasting time, which contributes to a rapid treatment and a contribution to an improvement in patient services.

In the photography device 1A, with an LED cluster 6X comprising a plurality of LEDs of different spectroscopic distribution characteristics serving as the light source, the object image illuminated by the light source (the image of the teeth of the patient 59 here) is captured via the photography optical system 7 whereupon the object image is converted into an image pickup signal by the CCD 8 that constitutes the image pickup means and stored as image data in the memory 11. The image data is transferred to the image memory of the processing device 2A via the external I/F 17. The constitution of the processing device 1A is substantially the same as that of the photography device 1 (FIGS. 1, 17, 21, and 37) applied to the image processing system of the first to fourth embodiments. FIG. 44 shows the same constituent elements with the same numerals assigned.

The processing device 2A is an image processing section as shown in FIG. 44 which is constituted further comprising a dental filing system 23 in addition to the same computation device 21 and display device 22 that are applied to the image processing section 2 of the image processing system of the first embodiment and so forth.

The computation device 21 performs color reproduction computation processing and image judgment computation processing (quantitative judgment) of the object on the basis of the spectroscopic image data and so forth captured by the photography device 1A. The image judgment computation processing is processing that performs a judgment of the grade of white of the patient's teeth, hue discrimination, correlation of skin grooves and hills and so forth of the skin surface, entropy analysis, and so forth, for example. The computation device 21 has the same constitution and function as the computation device 21 of the processing device 2A applied to the image processing system of the first embodiment.

The dental filing system 23 is a system for performing data filling of numerical management before and after bleaching of the patient's teeth, the bleaching frequency, and the results of compound calculations of denture and crown repair material. The dental filing system 23 contains image filling software. Further, image data photographed by means of the operation of the operating switch 14 by the photography device 1 are recorded and captured in a predetermined location of the image filling software in a predetermined memory section of the filing system 23.

The processing operation of the dental image processing system 50 of this embodiment with the above constitution will be described next.

When crown repair material or a denture matching the color of the teeth of the patient 59 is produced by applying the dental image processing system 50 in a dental office, first the whiteness and hue of the teeth of patient 59 are measured. The patient 59 places their jaw on a fixed base 58, thereby placing the head in a fixed state. A photography device 51 is attached to the fixed base 58. The disposable light-shielding attachment section 4 is placed at the patient 59's mouth and the periphery of the teeth to which the denture is to be introduced in the mouth is placed in a state in which the same can be photographed by the photography device 1. Further, a shift in the position of the object during photography can be prevented by fixing the photography device 51 as described above.

The light emission mode of the LED cluster 6X of the photography device 1 can be selected and designated by operating the touch-panel-type input operation device 53. Light emission modes include a mode that sequentially turns on the LED cluster 6X for each of the LEDs of a single primary color, a mode that selects and turns on the LEDs, and a mode that turns on all the LEDs at the same time, for example. The spectroscopic image capture mode or monitor mode is designated in accordance with the light emission mode or the number of spectroscopic bands of the spectroscopic image capture mode is designated.

Thereafter, the input operation device 53 is operated and the lighting of the LED cluster 6X is started. The operation can also be performed by the operating switch 14 of the photography device 1.

When the spectroscopic image capture mode is selected, an object image signal of the tooth of the patient 59 is captured via the CCD 8 with the lighting of the LED cluster 6X and stored in the memory 11 as spectroscopic image data. The spectroscopic image data is transferred to the processing device 2 and XYZ estimation computation is performed by the color reproduction computation section 33 (FIG. 12). A highly accurate color reproduction image of the teeth of the patient 59 produced from the computation results is then displayed on the display 22 or a calibration monitor 54.

Further, when the monitor mode is selected, a normal display image is displayed on the display 22. Further, the spectroscopic image capture mode and the monitor mode can be switched by the input operation device 53.

In addition, a judgment calculation is performed by the image discrimination computation section 34 (FIG. 13) of the processing device 2A on the basis of the spectroscopic image data and grade data relating to the shade of color of patient 59's teeth are determined. The grade data are the grades on the shade guide for comparing the shade of the teeth color and the values of the grade data are displayed on the calibration monitor 54. Further, the processing device 2A performs a compound calculation of the repair materials used on the basis of the grade data and determines repair material compound data.

Inspection data, which are grade data relating to the shade of tooth color and color reproduction image data relating to the teeth of patient 59, and repair material compound data are transferred to the computer section of the dental technician's office 55 via the network 3.

In the dental technician's office 55, a specific compound ratio is retrieved by means of the repair material compound ratio calculation database 56 on the basis of the inspection data and repair material compound data. Crown repairs and dentures are produced on the basis of this compound ratio. The dentures thus produced are distributed to the dental office and passed on to patient 59.

In the treatment process, data relating to tooth color and a color reproduction image are displayed on the calibration monitor 54 via the input operation device 53 for the patient 59 and the process of treating patient 59 can be shown and understood.

Further, the dental image processing system 50 can also be applied to teeth bleaching treatments in addition to the fabrication of crown repairs and dentures for the patient 59. That is, grade data relating to the shade of teeth, and color reproduction image data showing the bleaching results are determined by photographing the teeth of patient 59 in states before and after bleaching by means of the photography device 1A and then performing the abovementioned image computation processing. Numerical data before and after bleaching treatment are displayed on the calibration monitor 54 and are effective in obtaining the informed consent of patient 59. In addition, variations in the color reproduction image data and the grade data in the treatment process over time and due to the bleaching frequency can be confirmed visually. Further, data in the treatment process can also be accumulated.

When the dental image processing system 50 of the fifth embodiment is applied, because image data or grade data of favorable reproducibility that are not affected by normal indoor light are obtained, the highly accurate color reproduction image and the grade data determined by the processing device 2A are not subject to individual differences as is the case when the comparison data of a conventional shade guide are applied, are not affected by ambient light, and do not vary due to the camera or film and so forth used. Further, because the treatment process can be observed by the calibration monitor 54, the dental image processing system 50 is effective in obtaining the informed consent of patient 59.

Further, a touch-panel-type device can be applied as the input operation device 53 and a disposable light-shielding (attachment section 4) can be mounted at the tip of the photography section of the photography device 1A.

The dental image processing system 50 can also be applied to fields other than dentistry. For example, when applied to a dermatology system, the state of the skin being treated can be photographed, more accurate color reproduction image data can be obtained, and changes in the state of the skin in which there are no inconsistencies caused by illumination can be recorded. Further, the dental image processing system 50 can also be applied to a skin evaluation system, whereby accurate reproduction of the color of skin under normal reference illumination is made possible and the state of skin under special illumination can also be reproduced.

Sixth Embodiment

An image processing system constituting a sixth embodiment of the present invention will be described next with reference to FIGS. 45 to 48 and FIGS. 90A to 95. In the sixth embodiment, the same numerals are assigned to the parts that are the same as those of the first to fifth embodiments above and a description thereof will be omitted only the differences are mainly described.

Figure 45:
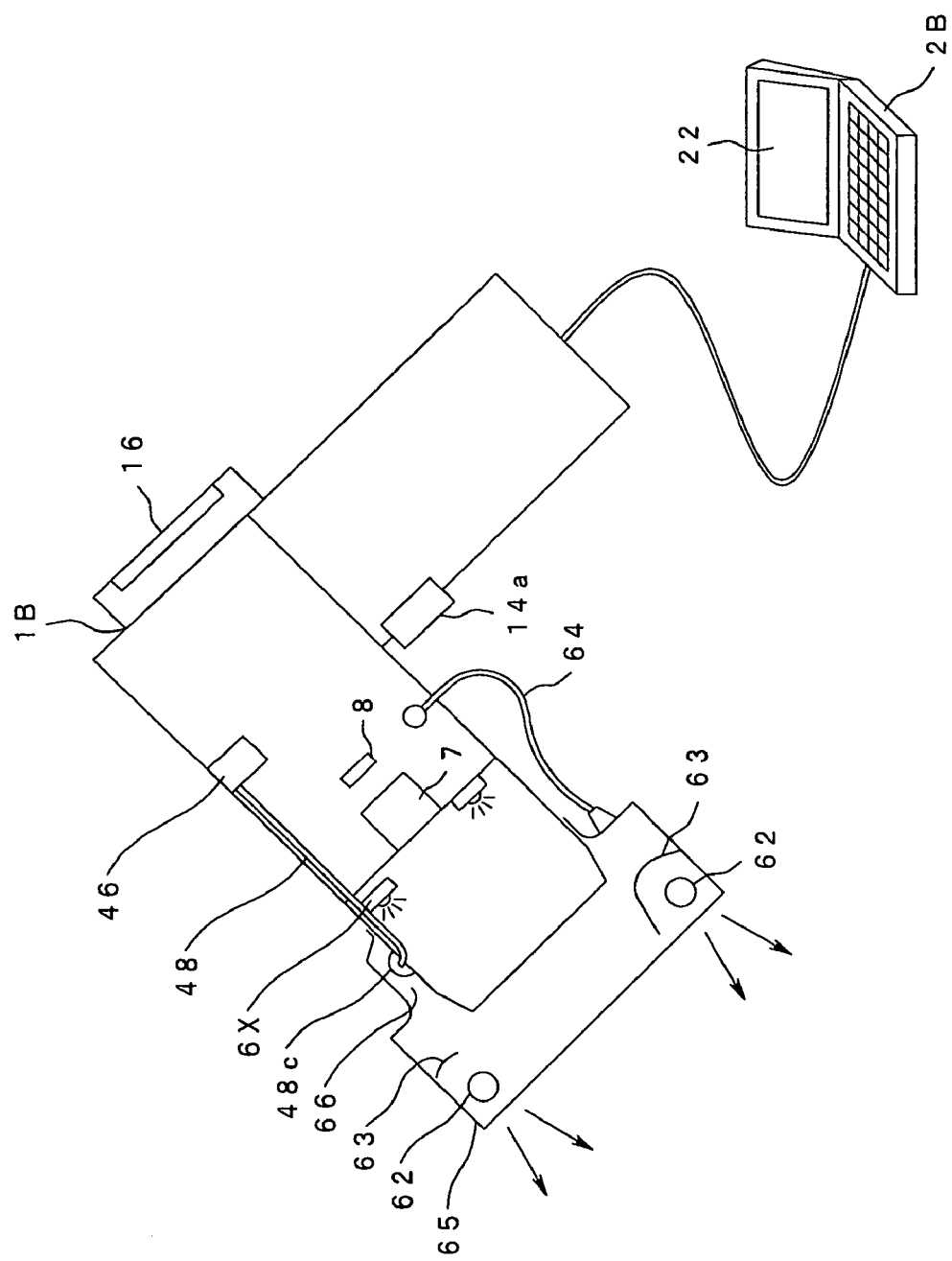
FIG. 45 shows the constitution of an image processing system of a sixth embodiment of the present invention.
Figure 46:
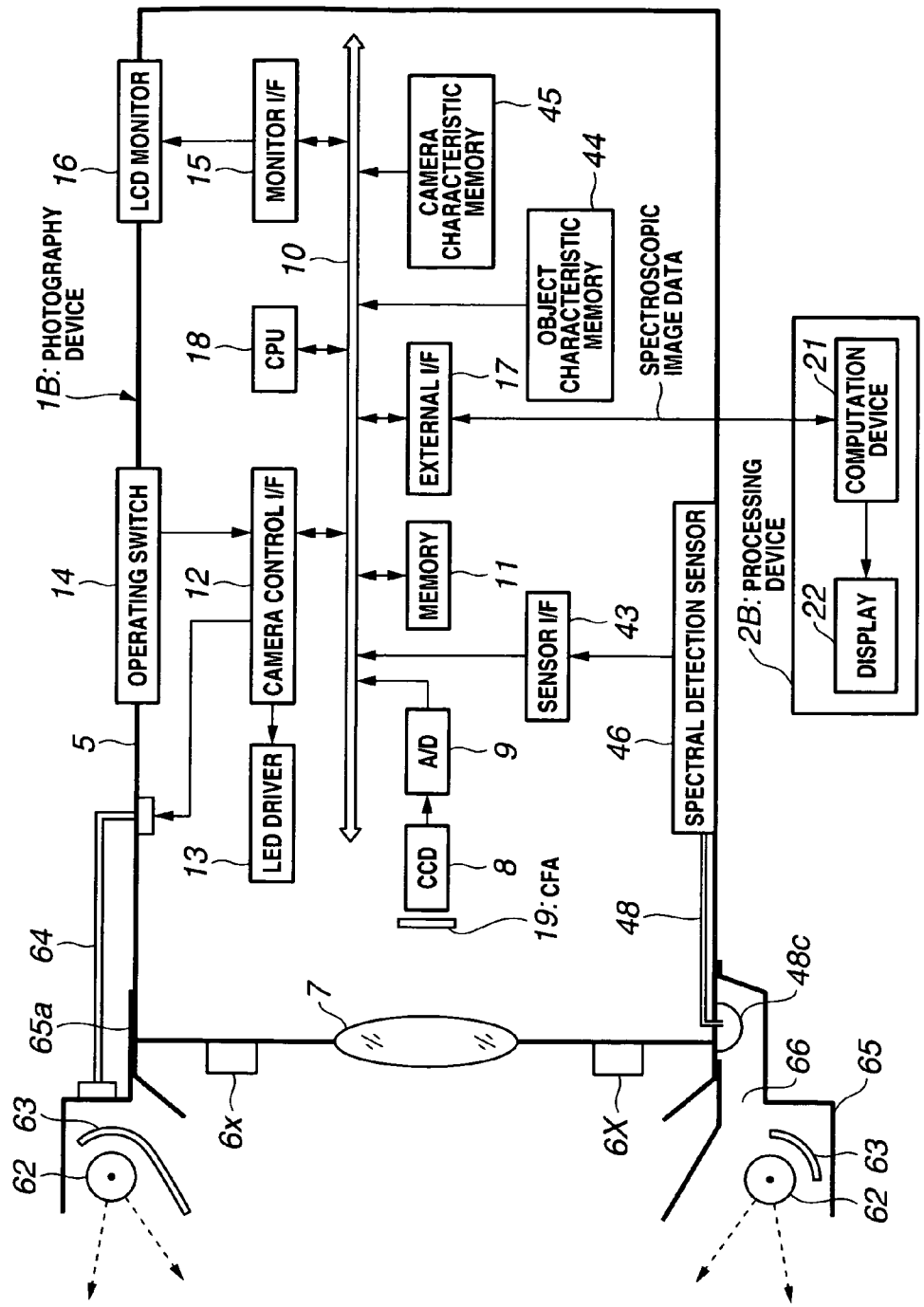
FIG. 46 is a block constitutional view of the image processing system in FIG. 45.
Figure 47:
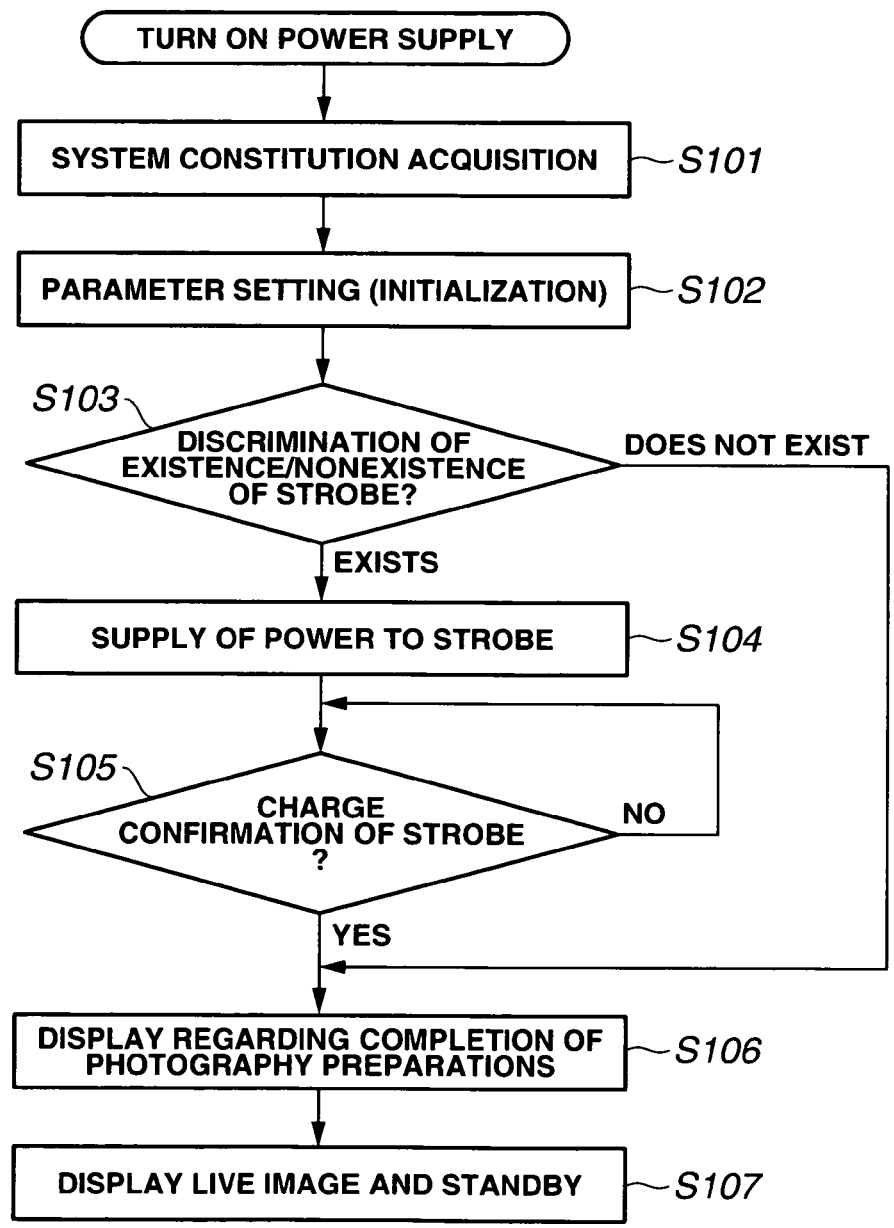
FIG. 47 is a flowchart of a photography standby processing routine in the photography processing of the photography device of the image processing system in FIG. 45.
Figure 48:
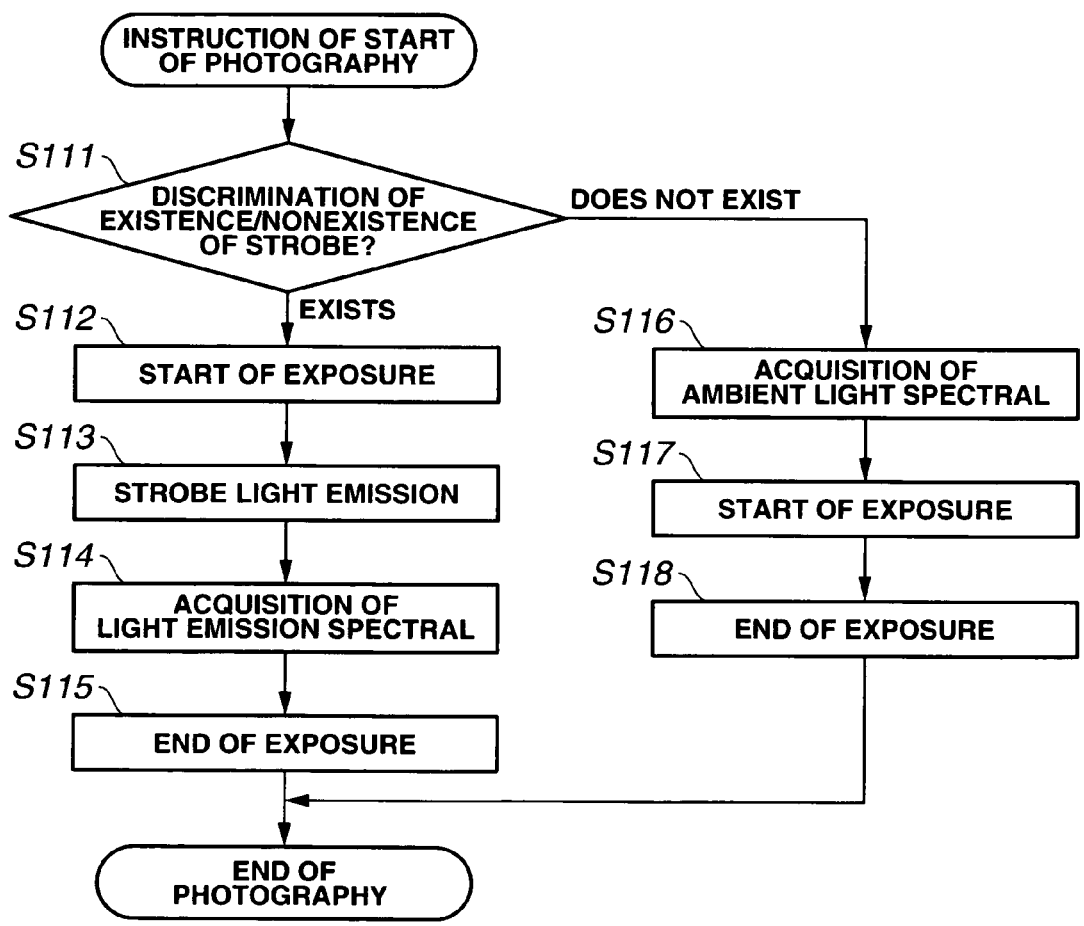
FIG. 48 is a flowchart of a photography routine in the photography processing of the photography device of the image processing system in FIG. 45.

Further, FIG. 45 shows the constitution of the image processing system of this embodiment. FIG. 46 is a block constitutional diagram of the image processing system. FIGS. 47 and 48 are flowcharts of the photography processing of the photography device of the image processing system, where FIG. 47 shows a flowchart of a photography standby processing routine and FIG. 48 shows a flowchart of a photography routine.

The image processing system of this embodiment comprises a photography device 1B that is the image photography section as shown in FIGS. 45 and 46 and which is capable of performing photography by means of LED illumination light or strobe illumination light, and a processing device 2B constituting an image processing section that comprises an image memory and is for determining highly accurate color reproduction image data from a spectroscopic image signal produced by the photography by the photography device 1B.

The photography device 1B has the same constitution and functions as the photography device 1 (FIG. 38) in which the color CCD and illumination light sensor applied to the image processing system of the fourth embodiment are integrated and a strobe light emission device 65 constituting an external strobe device is detachable. Further, in FIG. 46, constituent elements of the photography device 1B that are the same as those of the photography device 1 are indicated by means of the same numerals.

The processing device 2B comprises the same constitution and functions as the processing device 2 applied to the image processing system of the fourth embodiment.

The photography device 1B is capable of photographing a close-ranged object by means of built-in LED illumination, however, because the built-in LED illumination light does not reach the object when the distance to the object is on the order of a few centimeters to a few meters, photography can be performed by mounting the strobe light emission device 65 and causing a strobe light emission tube to emit light.

When an external light source such as the strobe light emission device 65 is mounted, the fact that the external light source is mounted can be displayed on the display means. FIG. 90A and FIG. 90B show an example of a display relating to the mounting of an illumination unit.

FIG. 90A is an example in which a mark 246 urging the mounting of an external illumination unit is displayed. Further, when the external illumination unit is mounted, the mark 247 shown in FIG. 90B is displayed.

Further, because the external light source can be selected from among different types of external light source, the optimum device can be used. Here, settings are made so that an operation that corresponds with the selected external light source is performed.

In addition, in order to acquire the optimum spectroscopic image, the illumination system and photography system and so forth can also be specialized for each object and for each of a variety of applications. In this case, the basic constitution of the photography device is not changed and, by making only the illumination system and photography system into the detachable type, greater cost reductions can be achieved than when a plurality of photography devices are prepared for each object.

FIGS. 91 to 95 show constitutional examples of a detachable unit.

Figure 91:
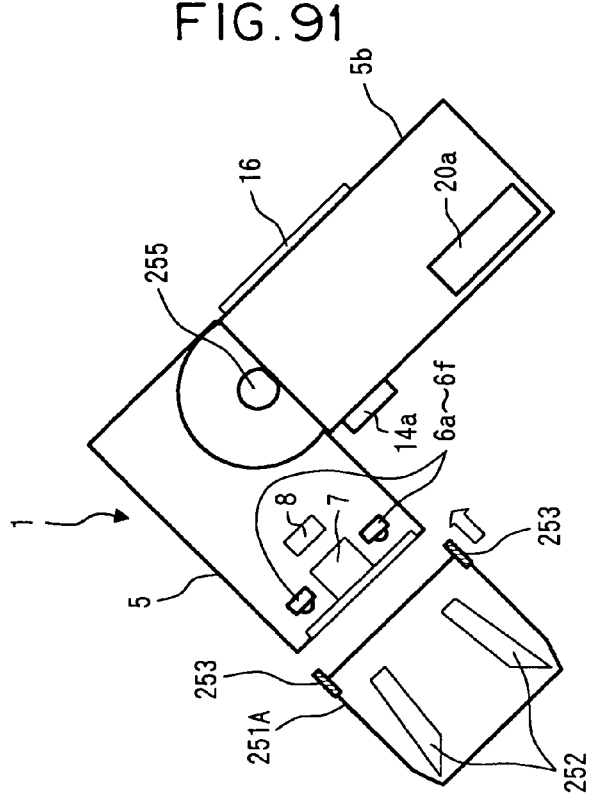
FIG. 91 shows an example in which only an 'illumination optical system' is a detachable unit in the sixth embodiment.

FIG. 91 shows an example in which only the 'illumination optical system' is a detachable unit 251A. This unit 251A is linked to the main body of the photography device 1 via a mechanical link 253. Further, the illumination optical system 252 is an optical system for irradiating light emitted by the LEDs 6a to 6f toward the object and is included in the illumination light source. Further, the enclosure 5 and grasp section 5b of the photography device 1 are constituted so that the same can be turned, for example, by a mechanism 255 (See FIG. 95 described subsequently).

Further, the system constitution of the illumination optical system is not limited to the illustrated system constitution and it is understood that low-cost, suitable applications are made possible through optimization of each object and each application in the fields such as coatings, dentistry, dermatology, and so forth.

Figure 92:
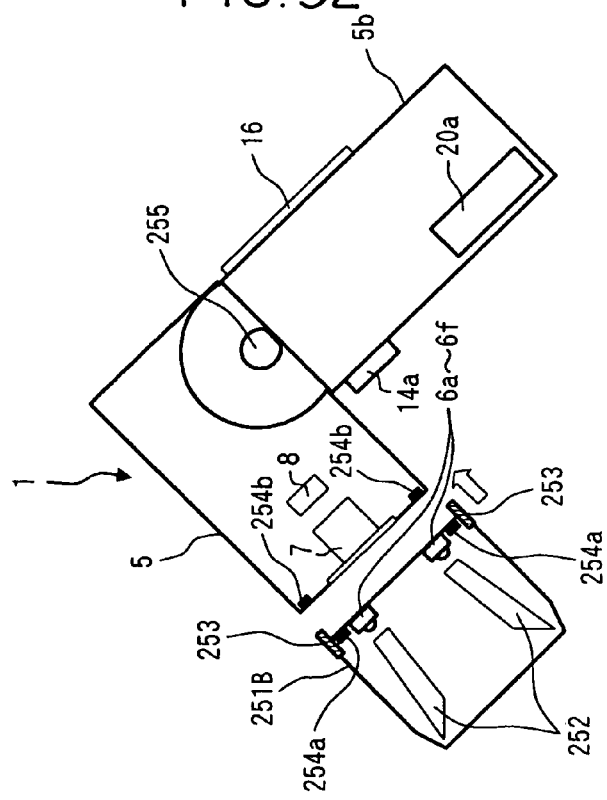
FIG. 92 shows an example in which a detachable unit is constituted by integrating an 'LED constituting a light source' and an 'illumination optical system' in the sixth embodiment.

FIG. 92 shows an example in which a detachable unit 251B is constituted by integrating a 'light source LED' and an 'illumination optical system'. The unit 251B is linked to the main body of the photography device via a mechanical link 253 and an electrical link. Here, the electrical link is constituted comprising an electrical connect 254a provided on the side of the unit 251B and an electrical connect 254b provided on the side of the main body of the photography device 1. Further, the electrical link is used for controlling the LEDs 6a to 6f and for the power supply and so forth. Further, the LEDs 6a to 6f that constitute the light source and the illumination optical system 252 are contained in the illumination light source.

Further, the system constitution of the LEDs constituting the light source and the illumination optical system are not limited to those illustrated and it is understood that low-cost, suitable applications are made possible through optimization of each object and each application in the fields such as coatings, dentistry, dermatology, and so forth.

Figure 93:
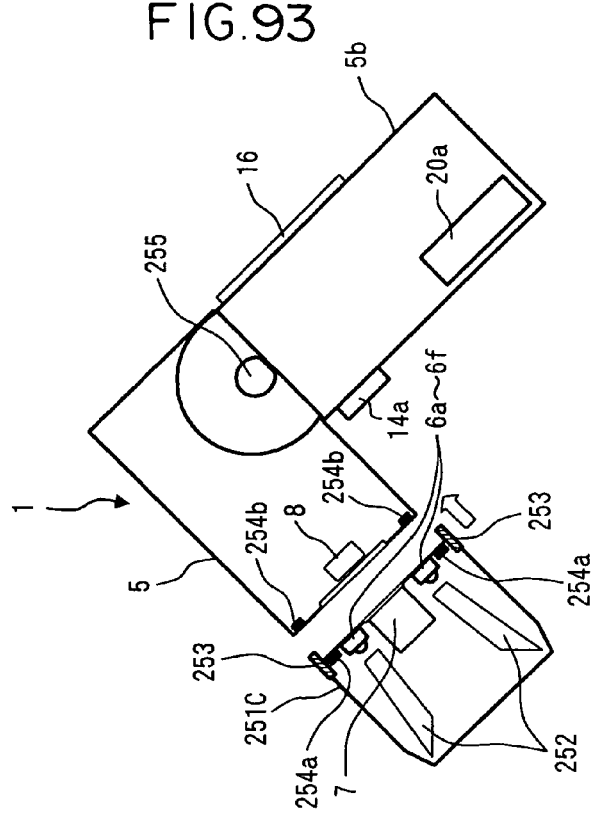
FIG. 93 shows an example in which a detachable unit is constituted by integrating an 'LED constituting a light source', an 'illumination optical system', and a 'photography optical system' in the sixth embodiment.

FIG. 93 shows an example in which a detachable unit 251C is constituted by integrating a 'light source LED', an 'illumination optical system', and a 'photography optical system'. The unit 251C is linked to the main body of the photography device 1 via the mechanical link 253 and electrical link mentioned earlier.

Further, the system constitution of the light source LED, illumination optical system, and photography optical system is not limited to the illustrated system constitution and it is understood that low-cost, suitable applications are made possible through optimization of each object and each application in the fields such as coatings, dentistry, dermatology, and so forth.

Figure 94:
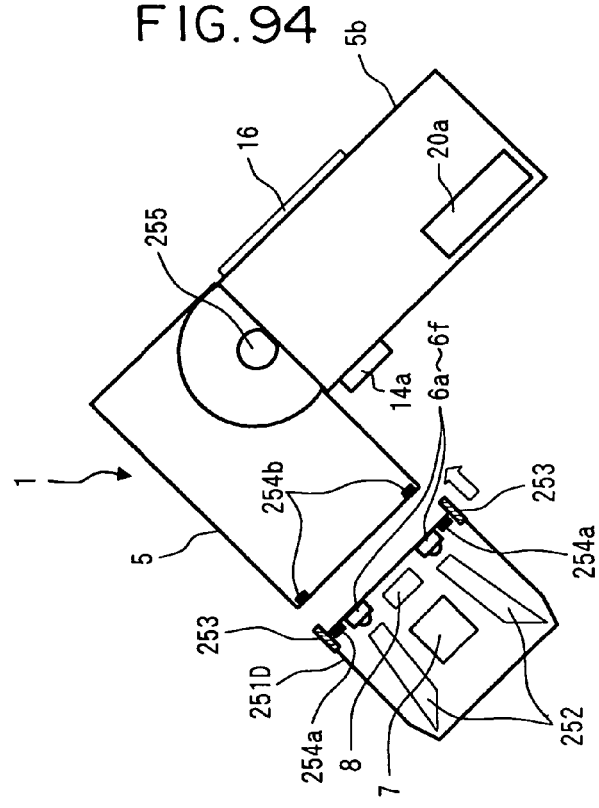
FIG. 94 shows an example in which a detachable unit is constituted by integrating an 'LED constituting a light source', an 'illumination optical system', a 'photography optical system', and an 'image pickup element' in the sixth embodiment.

FIG. 94 shows an example in which a detachable unit 251D is constituted by integrating a 'light source LED', an 'illumination optical system', a 'photography optical system', and an 'image pickup element'. The unit 251D is linked to the main body of the photography device 1 via the mechanical link 253 and electrical link mentioned earlier. Here, the electrical link constituted comprising electrical connects 254a and 254b is used in controlling the LEDs 6a to 6f and for the power supply and so forth and is used in driving the CCD 8 constituting the image pickup element and in the transmission of an image pickup signal from the CCD 8.

Further, the system constitution of the light source LED, illumination optical system, photography optical system, and image pickup element is not limited to the illustrated system constitution and it is understood that low-cost, suitable applications are made possible through optimization of each object each application in the fields such as coatings, dentistry, dermatology, and so forth.

Figure 95:
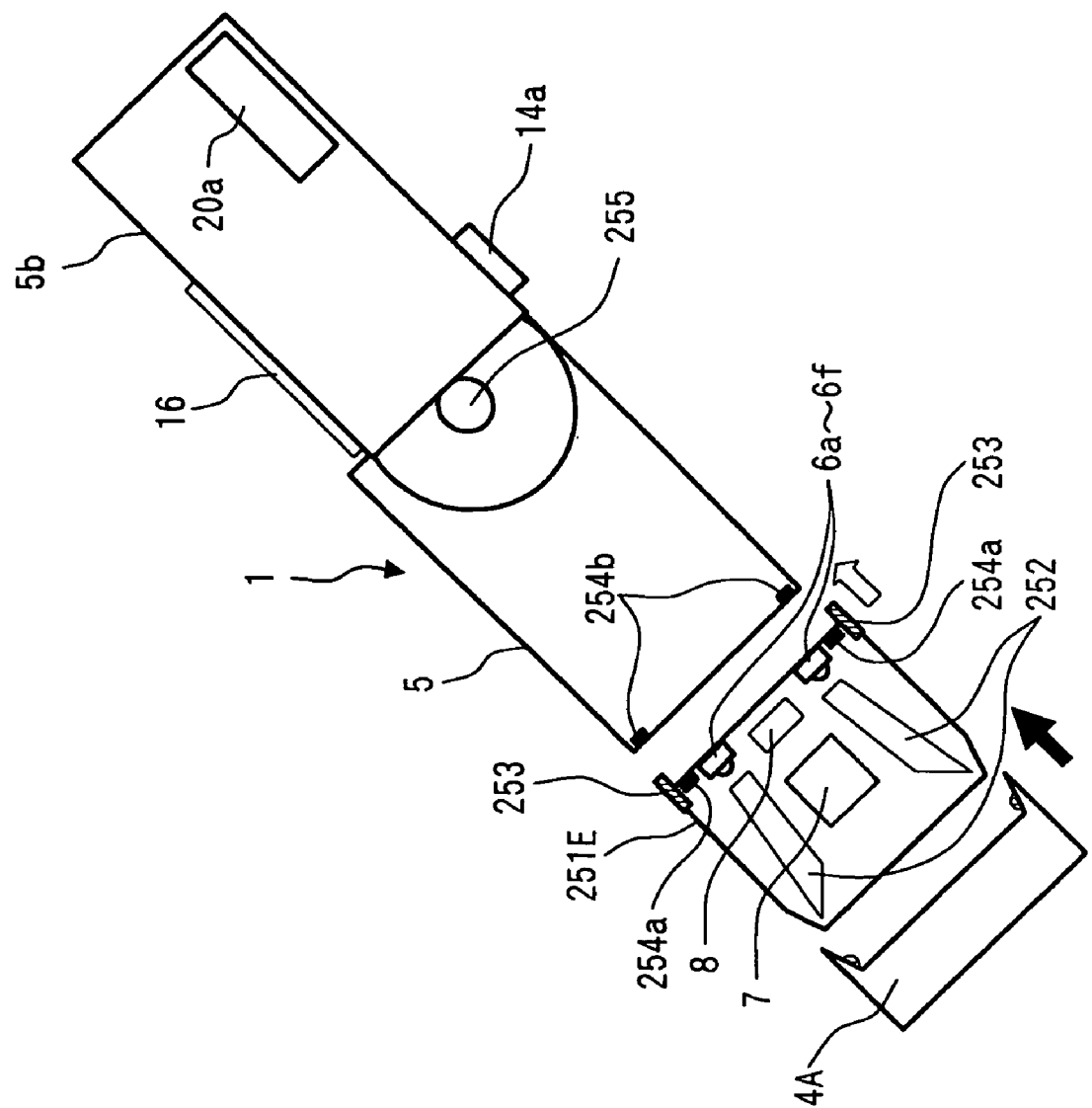
FIG. 95 shows an example in which it is possible to detachably couple a separate attachment adapter to the leading end of the unit as shown in FIG. 94, in the sixth embodiment.

FIG. 95 shows an example in which an additional attachment adapter 4A can be detachably linked to the tip of a unit 251E constituted in substantially the same way as unit 251D shown in FIG. 94. This attachment adapter 4A is used, in this example, when attaching the tip of photography device 1 to the object, and has a light-shielding function that prevents external light from being irradiated onto the object.

Thus, any one or more of the illumination light source, the photography optical system, the image pickup element section, and the photography operation section can be constituted as a detachable unit.

Further, because each detachable unit is a detachable-type unit, a plurality of types can be prepared beforehand and a more suitable detachable unit can be properly used in accordance with the applied application. Further, a storage element is integrated in the detachable unit and a variety of information, which include an ID number, type, usage time, initial information (light source output, wavelength, and electrical conditions (the current value, lighting pattern, forward voltage, and so forth that are required in order to emit light of the predetermined light amount), and degradation information, are pre-stored therein and read from the storage element during use, and conditions for performing the optimum image photography can be set on the basis of the information thus read. Further, a variety of information produced in the course of use can also be recorded in the storage element. Further, the type of the detachable unit that is mounted can also be displayed by using display means such as the LCD monitor 16 as mode display means and, in this case, the type can be more clearly confirmed.

The detachable unit is not limited to these examples and can be integrated by adopting another constitution. Here, providing a temperature detector serving as temperature detection means in the vicinity of the illumination light source, for example, measuring the temperature of the illumination light source, comparing the measurement result with the temperature characteristic of the illumination light source, and driving the light source to produce the optimum illumination characteristic may be considered. Because a temperature change attributable to variations in brightness can be detected and corrected by performing such control, the measurement accuracy can be improved. Further, spectroscopic detection means for performing spectroscopic detection on light from the object can also be provided in the detachable unit.

The strobe light emission device 65 can be mounted at the front of the enclosure 5 constituting the device main body of the photography device 1B but, in a state where the strobe light emission device 65 is not mounted, spectral detection of the ambient light can be performed by the spectral detection sensor 46 built into the photography device 1B because the integrating sphere 48c is exposed to the outside. Further, in a state where the strobe light emission device 65 is mounted, spectral detection of the strobe light is performed by the spectral detection sensor 46 because a portion of the strobe light is guided to the integrating sphere 48c.

The strobe light emission device 65 comprises, as shown in FIG. 46, a detachable mount section 65a at the front face section of the enclosure 5 of the photography device 1B, a reflective umbrella 63, a ring-shaped strobe light emission tube 62, a strobe light emission circuit (not illustrated) having a light-emitting charge condenser, and a connecting cable 64 for an electrical connection (supply/control signals) connecting the strobe light emission circuit with the photographic device 1B side.

Further, the electrical connection between the photography device 1B and the strobe light emission device 65 is made via a connector by means of the connecting cable 64 after mounting the strobe light emission device 65. However, a structure in which a connection electrode section is also disposed on the mount section of the strobe device such that the electrode section automatically enters a connected state when the strobe light emission device 65 is mounted in the enclosure 5 may also be adopted.

The electrically connected state afforded by the connecting cable 64 or the electrically connected state resulting from mounting the strobe light emission device 65 in the enclosure 5 is identified by the CPU18 on the photography device 1B side via the camera control I/F 12 and the identification code of the strobe is sensed. The system constitution of the photography device currently stored by the strobe identification code is updated by the identification code.

A portion toward the rear of the reflective umbrella is open and a waveguide 66 that guides the strobe light backward is formed. When strobe light is emitted, a portion of the strobe light passes through the waveguide 66 and enters the integrating sphere 48c constituting the detection section provided at the tip of the optical fiber 48 of the spectral detection sensor 46, and the spectral component of the strobe light is detected by the spectral detection sensor 46.

The photography processing operation by the photography device 1B of the image processing system of the sixth embodiment with the abovementioned constitution will be described next in accordance with the flowcharts of FIGS. 47 and 48.

When spectroscopic image data of the object is acquired by the photography device 1B, the supply switch of the photography device 1B is turned on first. As a resulting of turning on the supply switch, the photography preparation processing routine of FIG. 47 is started under the control by the CPU 18.

The CPU 18 captures system constitution data in step S101 and parameter settings (initialization) are made in step S102. A check is made to determine whether the strobe light emission device 65 is mounted in the photography device 1B in step S103. In cases where a strobe is not mounted, the processing jumps without further processing to step S106. However, when a strobe is mounted, the processing moves to step S104.

Power is supplied to the strobe light emission circuit in step S104 and charging of the light emission charge condenser is started. When charge completion is confirmed in step S105, the processing moves to step S106 and a display regarding the completion of photography preparations is displayed on the LCD monitor 16. In step S107, standby is implemented with the LCD monitor 16 in a monitor display state.

Thereafter, when the photography button 14a of the photography device 1B is operated as a result of being pressed by the photographer and a photography start indication signal is input, the photography processing routine of FIG. 48 is started under the control by the CPU 18.

The existence of a mounted strobe is checked in step S111 and, when a strobe is not mounted, the processing jumps to step S116. When a strobe is mounted, the processing moves to step S112.

Exposure of the CCD 8 is started in step S112 and the strobe light emission of the strobe light emission device 65 is started in step S113. Further, in step S114, a portion of the strobe emission light passes through the waveguide 66 and is captured from the integrating sphere 48c by the spectral detection sensor 46, and spectroscopic spectral data of the strobe emission light is acquired. After the required exposure time has elapsed, exposure is ended in step S115 and the photography processing ends.

On the other hand, when the processing jumps to step S116, because the strobe light emission device 65 is in an unmounted state, spectroscopic spectral data of the ambient light is acquired by the spectral detection sensor 46. In step S117, the LED cluster 6X is turned on in the abovementioned desired light emission mode and the exposure of the CCD 8 is started. This photography processing ends when the exposure ends in step S118.

Further, although not illustrated in FIG. 46, the spectral detection sensor 47 shown in FIG. 38 is built into the photography device 1B and the spectroscopic spectral data of the illumination light of the LED cluster 6X is also acquired at the same time by the spectral detection sensor 47.

After the photography processing has ended, the photographic image data and illumination light spectroscopic spectral data captured by the memory 11 of the photography device 1B is transmitted via the external I/F 17 to the processing device 2B where illumination light spectroscopic spectral data and camera characteristic data and object characteristic data are added to the photographic image data and spectroscopic image data are determined by means of computation.

The image processing system of the sixth embodiment described above allows an object to be photographed by mounting the strobe light emission device 65 in the photography device 1B even when the object distance is comparatively remote and there is a lack of brightness in the emission light of the LED cluster 6X. Moreover, because the spectroscopic image data are computed on the basis of the spectroscopic spectral data of the strobe light acquired for each strobe light emission, highly accurate color reproduction is possible by being performed based on spectroscopic image data in which variations in the spectral of each light emission and variations in the light emission spectral of the strobe light emission device 65 itself have been corrected.

Seventh Embodiment

The image processing system of the seventh embodiment of the present invention will be described next with reference to FIGS. 49 to 52. In the seventh embodiment, the same numerals are assigned to the parts that are the same as those of the first to sixth embodiments above and a description thereof will be omitted. Only the differences are mainly described.

Figure 49:
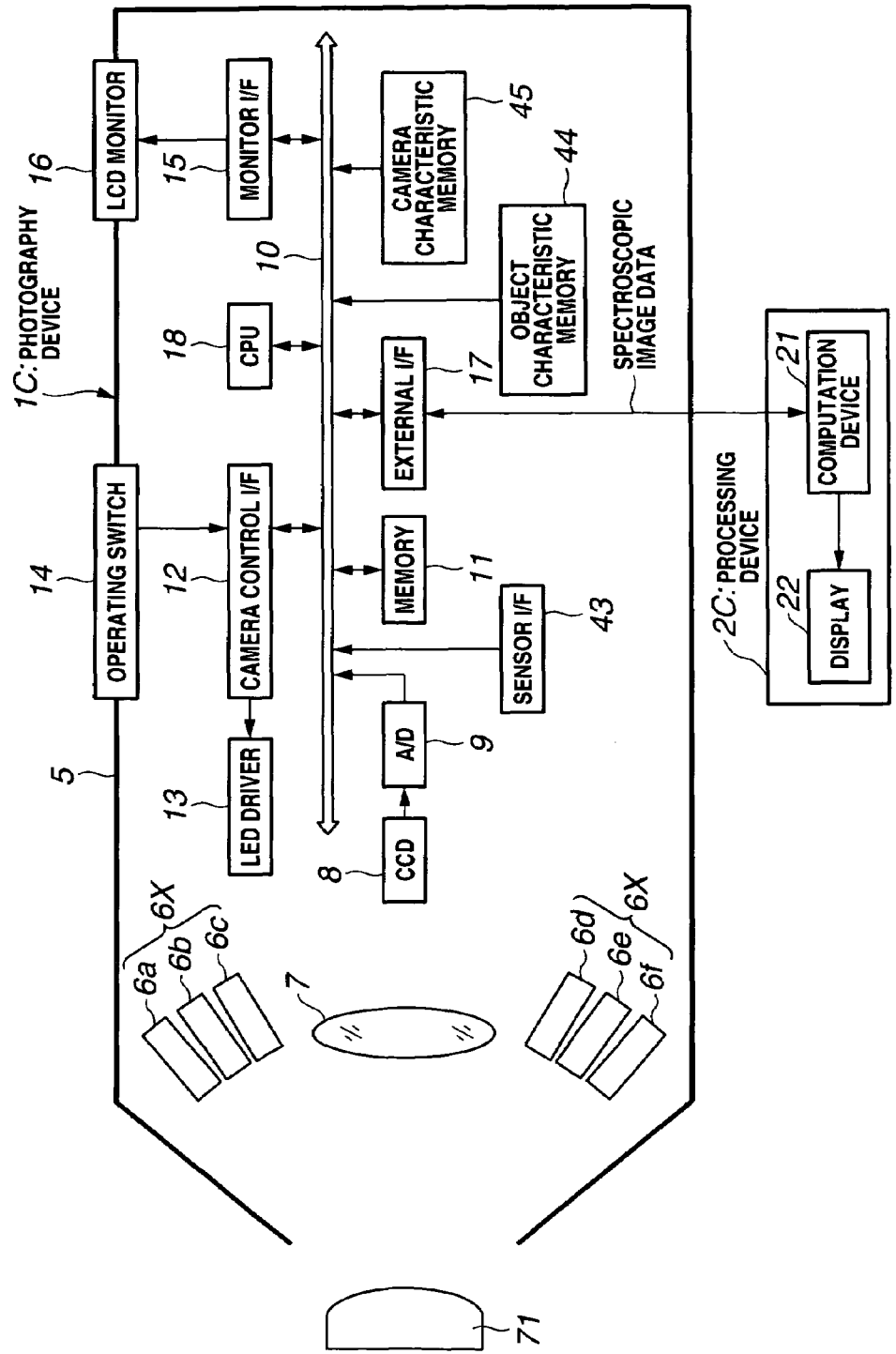
FIG. 49 is a block constitutional view of the image processing system of a seventh embodiment of the present invention.
Figure 50A:
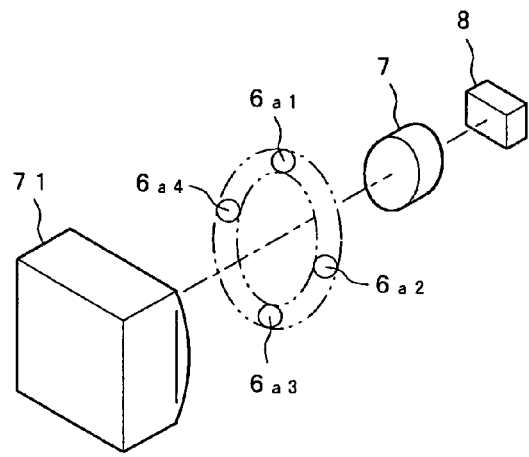
FIG. 50A and FIG. 50B show states when a regular reflection object is illuminated with LED light of each color by means of the photography device of the image processing system in FIG. 49, where
Figure 50B:
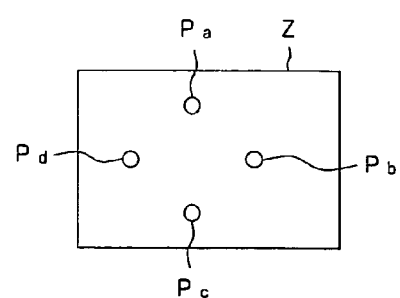
Figure 51:
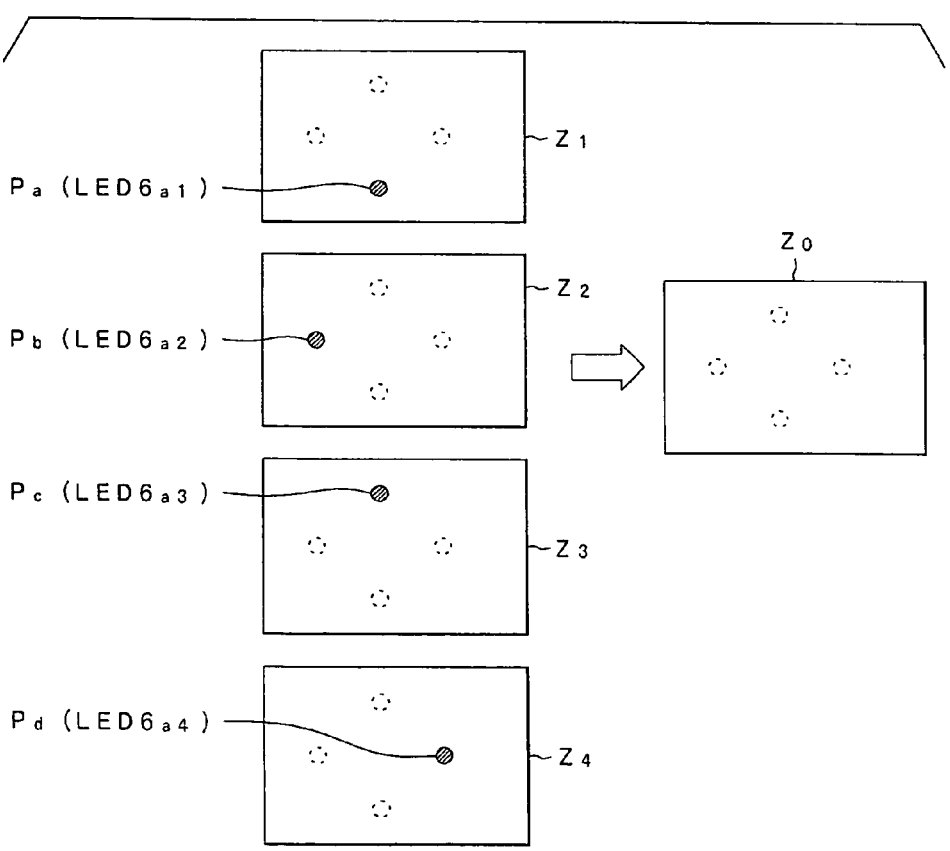
FIG. 51 shows an object image in which a regular reflection part exists being caused by illumination by LEDs of each color that is formed on the CCD when the regular reflection object is illuminated with LED light of each color by the photography device of the image processing system in FIG. 49 and an object image rendered by deleting the regular reflection part from the object image with the photography device of the image processing system.
Figure 52:
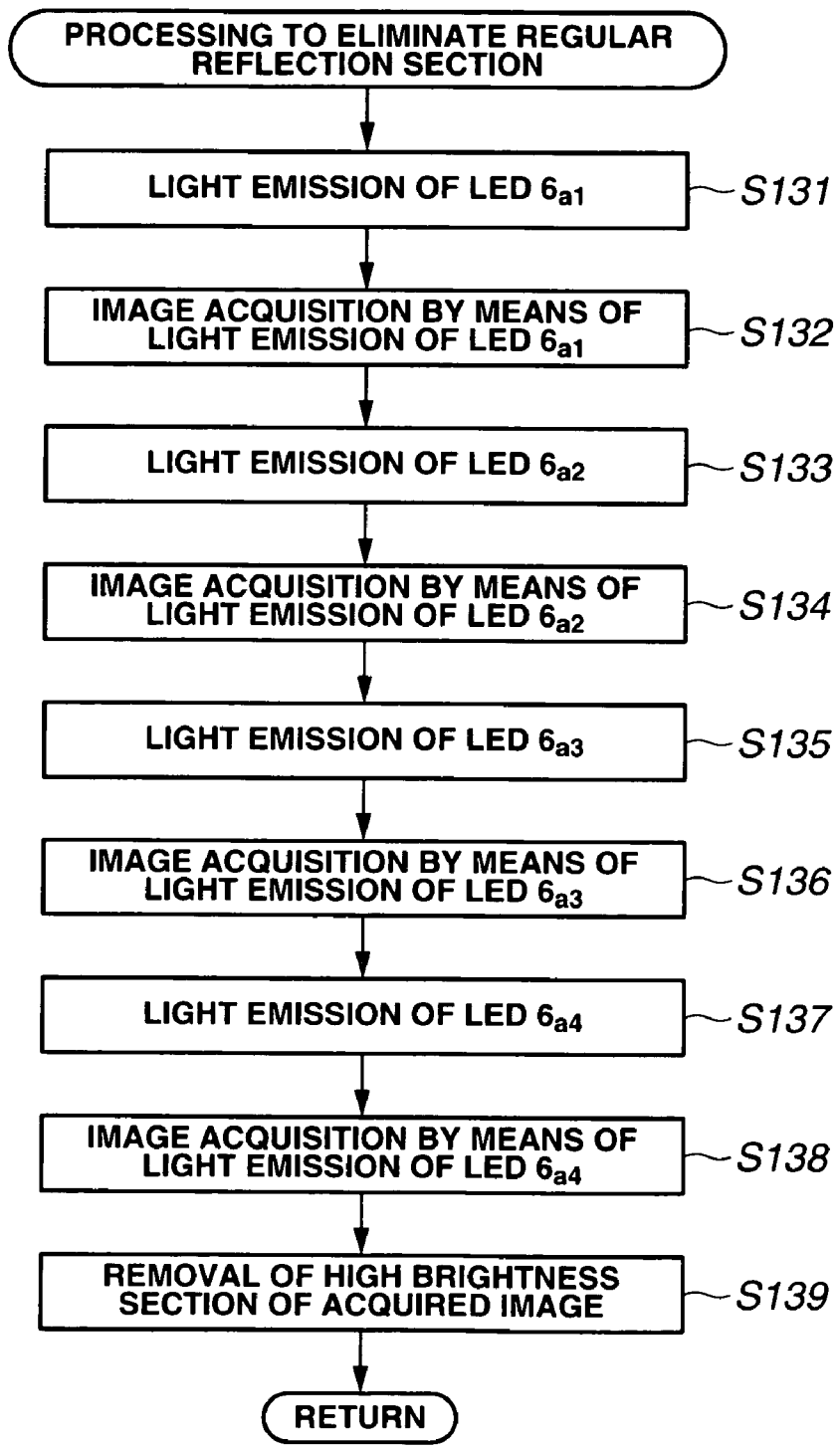
FIG. 52 is a flowchart of the regular reflection part deletion processing performed by the photography device of the image processing system in FIG. 49.

FIG. 49 is a block constitutional view of the image processing system of this embodiment. FIGS. 50A and 50B show states when a regular reflection object is illuminated with LED light of each color by means of the photography device of the image processing system in FIG. 49, where FIG. 50A shows the disposition of the regular reflection object, the LEDs of each color and the CCD during image formation and FIG. 50B shows an image with a regular reflection part formed on the CCD. FIG. 51 shows an object image in which a regular reflection part exists being caused by illumination by LEDs of each color on the image formation surface of the CCD and an object image rendered by deleting the regular reflection part from the object image by the photography device of the image processing system. FIG. 52 is a flowchart of the regular reflection part deletion processing of the photography device.

The image processing system of this embodiment comprises a photography device 1C that constitutes an image acquisition section that allows a spectroscopic image unaffected by regular reflection to be photographed as shown in FIG. 49 and a processing device 2C constituting an image processing section that comprises an image memory and is for determining highly accurate color reproduction image data from an object spectroscopic image signal produced by the photography by the photography device 1C.

The processing device 2C has the same constitution and functions as the processing device 2 applied to the image processing system of the first embodiment or the like and may use a personal computer.

The photography device 1C has substantially the same constitution as that of the photography device 1 (FIGS. 1, 17, 21, and 37) applied to the image processing system of the first to fourth embodiments as shown in FIG. 49. However, in the case of the photography device 1C in particular, a processing operation for regular reflection image data acquired as will be described subsequently is performed. Further, the constituent elements of the photography device 1C that are the same as those of the photography device 1 are described by assigning the same numerals to such elements.

The photography device 1C is able to determine image data without regular reflection parts by means of synthesis by deleting from the image data high brightness parts resulting from regular reflection of the illumination light from each of the LEDs of the LED cluster 6X even when object 71 is an object with a glossy curved surface that causes regular reflection. The image processing will be described hereinbelow.

For example, when the illumination light of LEDs 6a1, 6a2, 6a3, and 6a4 arranged in different ring-shape positions as an example is irradiated onto the abovementioned regular-reflection object 71, light of the same wavelength is emitted from each of the LEDs. When the light is subjected to regular reflection by the object 71, colored high brightness points are formed in different positions on the image formation surface of the CCD 8. That is, high brightness points Pa, Pb, Pc, and Pd that correspond to LEDs 6a1, 6a2, 6a3, and 6a4 are produced in different positions on image Z in FIG. 50B.

In the photography device 1C, the high brightness points Pa, Pb, Pc, and Pd resulting from the abovementioned regular reflection are removed by the regular reflection section deletion processing. When the deletion processing is described by means of FIG. 51, the regular reflection image of object 71 caused by the emission light of LED 6a1 is first shown by the high brightness point Pa on the CCD image formation plane Z1. Similarly, the regular reflection images of object 71 resulting from the emission light of each of the LEDs 6a2, 6a3, 6a4 are shown by the high brightness points Pb, Pc, and Pd on the CCD image formation planes Z2, Z3, and Z4 respectively. The remaining image data after removing the pixel data of the high brightness points Pa, Pb, Pc, and Pd are added or averaged to obtain spectroscopic image data (Z0 on CCD image formation plane) of object 71 that have been corrected to remove regular reflection high brightness parts.

The regular reflection section deletion processing will now be described by using the flowchart in FIG. 52. First, LED 6a1 is lit in step S131 and the image data at this time is acquired in step S132. Thereafter, LEDs 6a2, LED 6a3, and LED 6a4 are lit sequentially in steps S133 to S138 and the respective image data when each LED emits light are acquired. Spectroscopic image data from which regular reflection has been removed by generating image data excluding high brightness parts is obtained from each of the acquired image data in step S139. Further, the abovementioned example represents a case where there are four LED light sources but processing can also be performed in the same way in cases where there are other numbers of light sources.

The photography device 1C in the image processing system of the seventh embodiment is able to obtain spectroscopic image data without regular reflection parts by performing the regular reflection deletion processing mentioned above on the image data acquired even when object 71 is a regular reflection object.

Eighth Embodiment

The image processing system of an eighth embodiment of the present invention will be described next by using FIGS. 53, 54, and 96. In the eighth embodiment, the same numerals are assigned to the parts that are the same as those of the first to seventh embodiments above and a description thereof will be omitted only the differences are mainly described.

Figure 53:
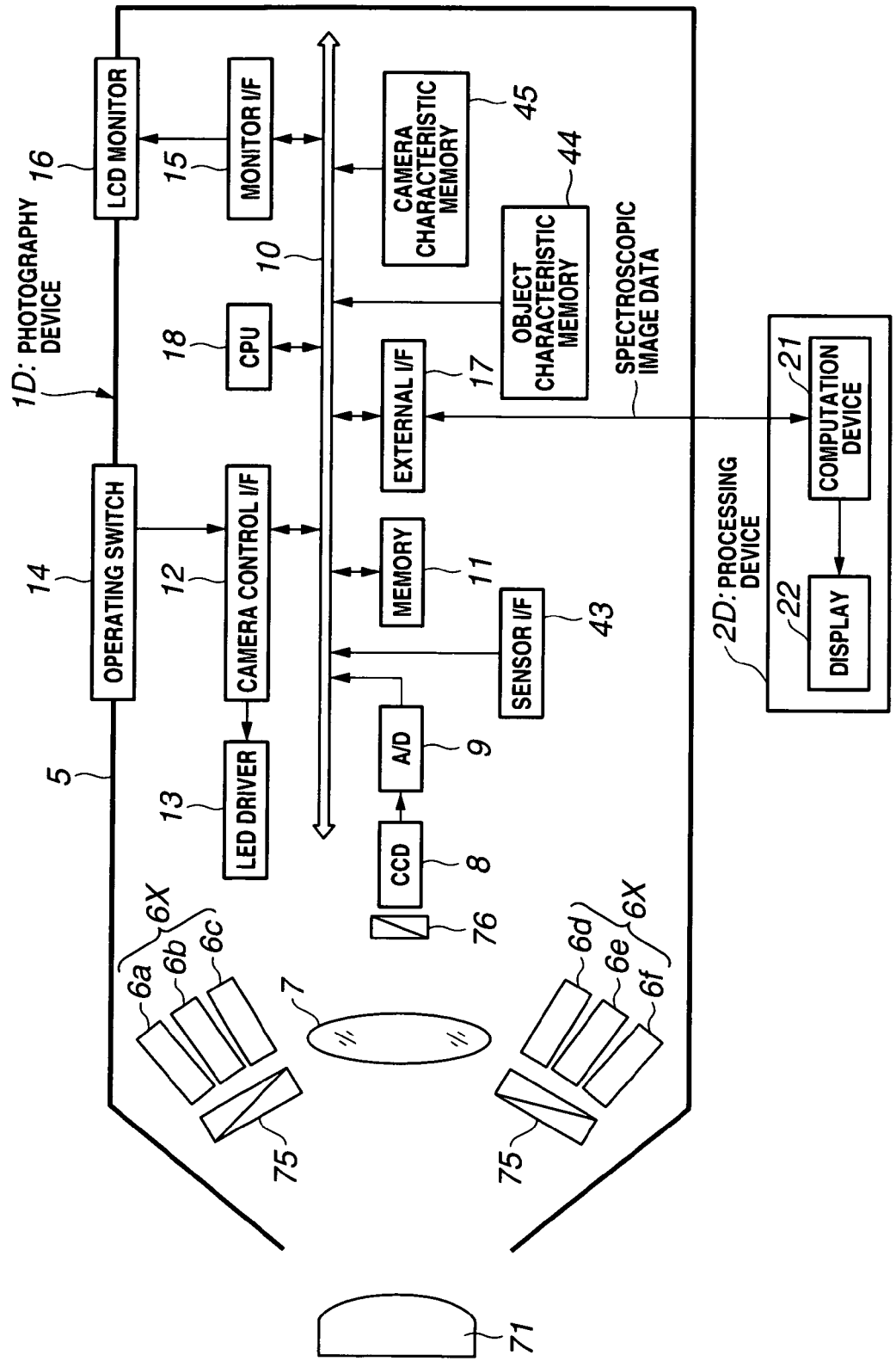
FIG. 53 is a block constitutional view of the image processing system of an eighth embodiment of the present invention.
Figure 54:
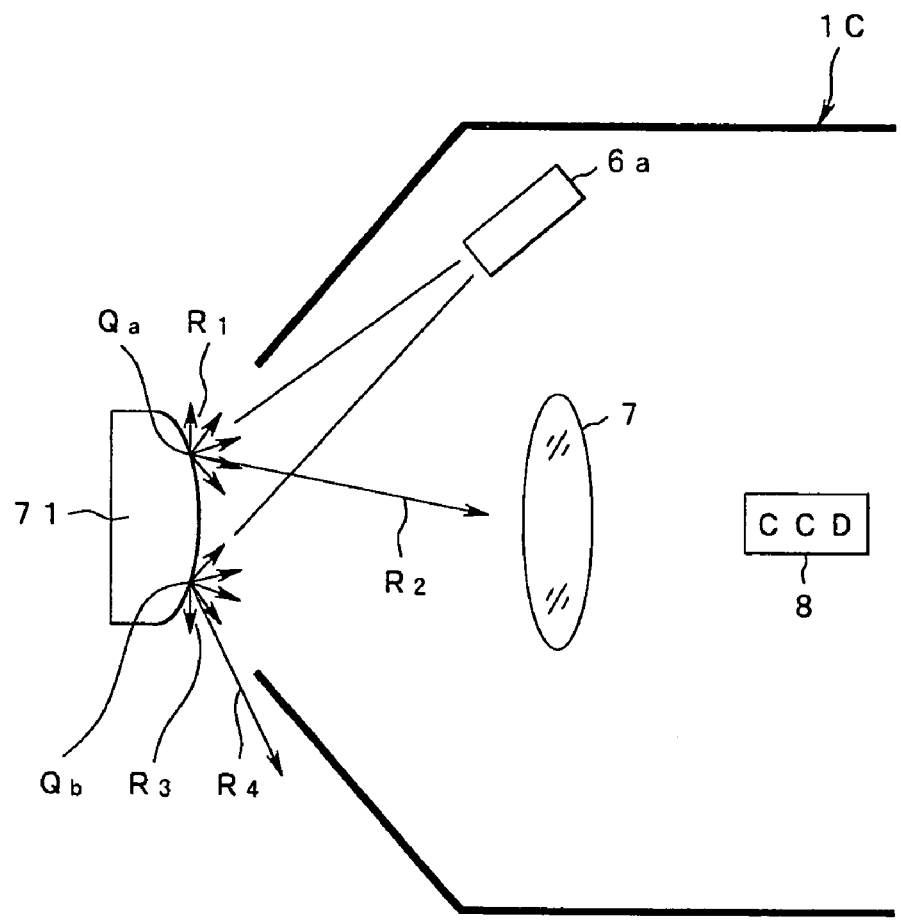
FIG. 54 shows a reflection state of light on the regular reflection object in a case where a regular reflection object is photographed by the photography device of the image processing system in FIG. 53.

Further, FIG. 53 is a block diagram of the image processing system of this embodiment and FIG. 54 shows a reflection state of light on the regular reflection object.

The image processing system of this embodiment comprises a photography device 1D constituting an image photography section capable of photographing a spectroscopic image of a regular reflection object, and a processing device 2D constituting an image processing section for determining highly accurate color reproduction image data from a spectroscopic image signal of the object that is photographed by the photography device 1D, as shown in FIG. 53.

The processing device 2D has the same constitution and functions as the processing device 2 applied to the image processing system of the first embodiment or the like and may use a personal computer.

The photography device 1D has substantially the same constitution as that of the photography device 1 (FIGS. 1, 17, 21, and 37) applied to the image processing system of the first to fourth embodiments as shown in FIG. 53. Additionally, a first polarizing plate 75 constituting rotatable reflected light removal means is disposed in front of the LED cluster 6X constituting the illumination light source and a second polarizing plate 76 constituting reflected light removal means is disposed in front of the CCD 8, in order to cut the regular reflection light.

Constituent elements of the photography device 1D that are the same as those of the photography device 1 are indicated by means of the same numerals.

When spectroscopic image data are acquired, spectroscopic image data are determined by detecting diffuse-reflected light on the basis of the spectroscopic reflectance of the object surface. However, when the surface of the object 71 is a surface similar to a mirror surface, the illumination light emitted toward the object 71 from the LED 6a as shown in FIG. 54 is reflected as diffuse-reflected light R1 and R3 (denoted by the short arrows in FIG. 54) at points Qa and Qb, for example, of the object surface but a portion of the illumination light is reflected as regular reflection light R2 and R4 (denoted by the long arrows in FIG. 54). The regular reflection light R2 and R4 is reflected in a direction symmetrical to the incident angle of the illumination light and has substantially the same spectral as the spectral of the illumination light. Further, the components of the regular reflection light R2 and R4 are larger than the components of the regular reflection light R1 and R3 and are an obstacle to the measurement of the spectroscopic reflectance of the object. The regular reflection light R4 does not influence because the reflection direction is not toward the CCD 8 but the other regular reflection light R2 is transmitted by the photography optical system 7 and captured by the CCD 8 such that point Qa in the photographic image is photographed as a high brightness point. Therefore, if the regular reflection light component produced by the state of the surface of object 71 is not removed, suitable spectroscopic image data cannot be acquired.

Therefore, in the case of the photography device 1D of this embodiment, the regular reflection light component is cut so as not to enter the CCD 8 by disposing the first polarizing plate 75 in front of the LED cluster 6X and the second polarizing plate 76 in front of the CCD 8 as mentioned earlier. That is, illumination light from the LED cluster 6X is polarized by the first polarizing plate 75. The light diffuse-reflected by the surface of the object 71 has various polarization directions but the regular reflection light enters the photography optical system 7 while retaining a unidirectional polarized state. The first polarizing plate 75 is disposed following rotational adjustment with respect to the second polarizing plate 76 and the polarized regular reflection light is removed by the second polarizing plate 76. Then, only the diffuse-reflected light enters the CCD 8 and an object image without high brightness parts caused by regular reflection is photographed.

Figure 96:
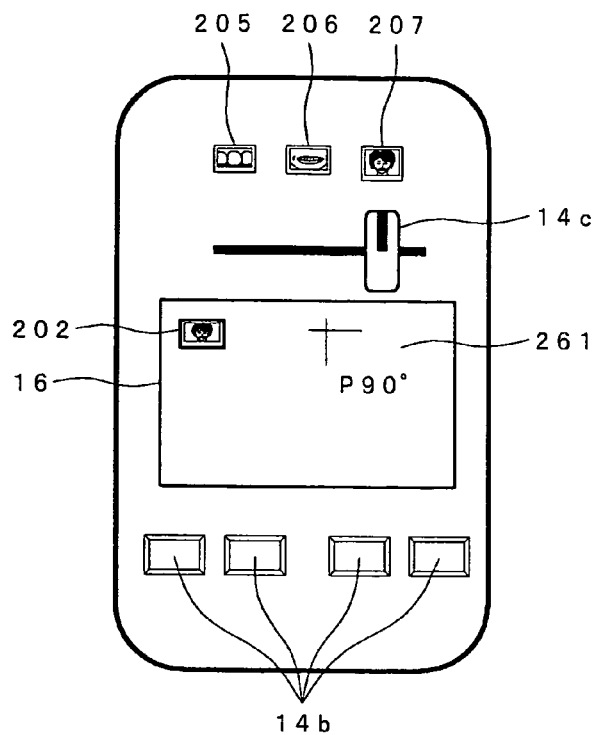
FIG. 96 shows an example in which the inserted state of a polarizing plate is displayed on the display means in the eighth embodiment.

FIG. 96 shows an example in which the inserted state of a polarizing plate is displayed on the display means.

In this example, a text-containing mark 261 is displayed to make it possible to confirm whether both the first polarizing plate 75 and second polarizing plate 76 are inserted in the light path and to make it possible to confirm at what kind of relative rotation angle the polarizing plates 75 and 76 are inserted. This example shows that the polarizing plates 75 and 76 are inserted in the light path at a relative 90-degree angle. Further, the display of the insertion state of polarizing plates 75 and 76 is not limited to the example shown in FIG. 96.

When the photography device 1D of the image processing system of the eighth embodiment is applied as above, a high brightness section caused by regular reflection light is not produced in the photographic image even when the object 71 has a glossy surface, whereby suitable spectroscopic image data are acquired and high brightness color reproduction is possible.

Further, although the second polarizing plate 76 is disposed between the photography optical system 7 and the CCD 8 in the photography device 1D, the same effect is also obtained by adopting a constitution in which the second polarizing plate 76 is disposed on the side of the object 71 in front of the photography optical system 7.

Ninth Embodiment

The image processing system constituting a ninth embodiment of the present invention will be described next by using FIGS. 55 and 56. In the ninth embodiment, the same numerals are assigned to the parts that are the same as those of the first to eighth embodiments above and a description thereof will be omitted only the differences are mainly described.

Figure 55:
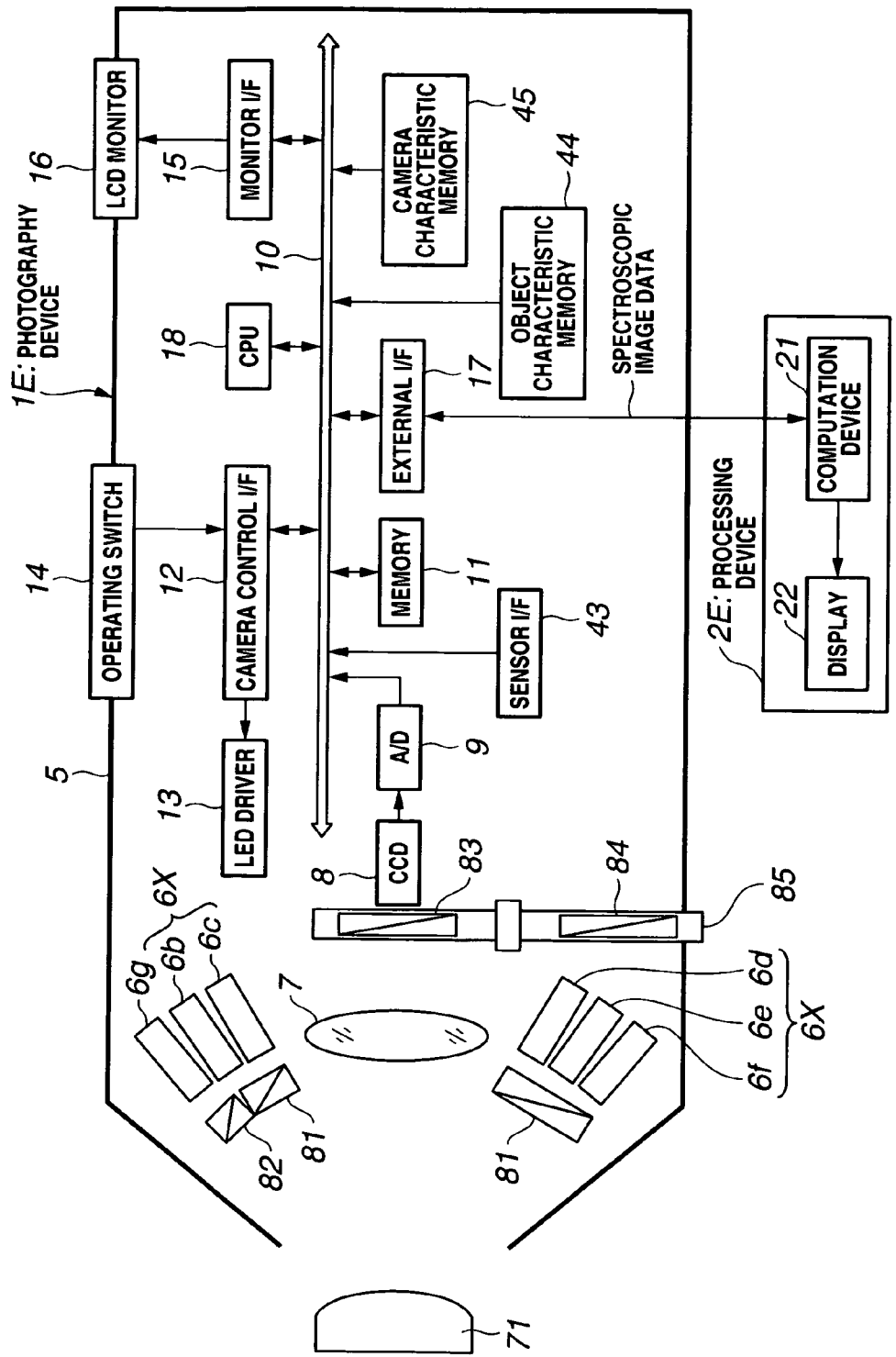
FIG. 55 is a block constitutional diagram of the image processing system of a ninth embodiment of the present invention.
Figure 56:
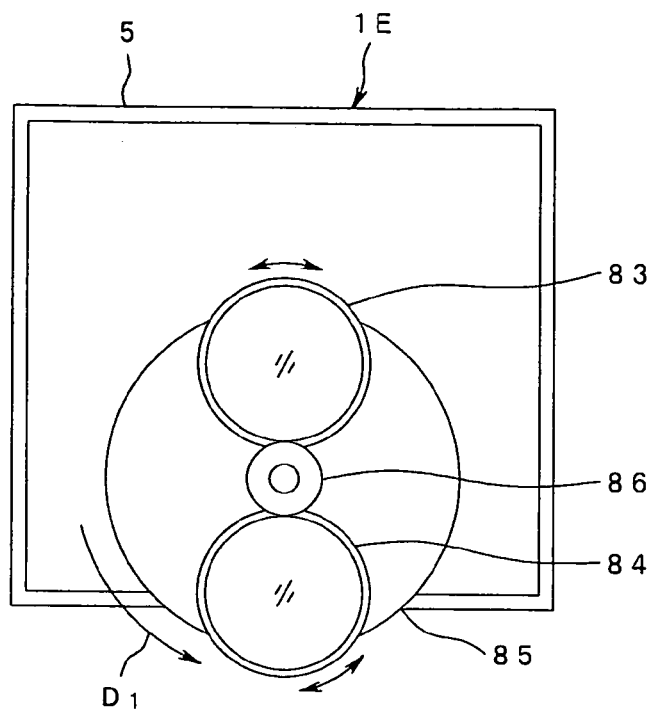
FIG. 56 is a front view of a second polarizing plate that is disposed in front of the CCD in the photography device of the image processing system in FIG. 55.

Further, FIG. 55 is a block constitutional diagram of the image processing system of this embodiment and FIG. 56 is a front view of a second polarizing plate that is disposed in front of the CCD in the photography device of the image processing system in FIG. 55.

The image processing system of this embodiment comprises a photography device 1E constituting an image photography section capable of photographing a spectroscopic image rendered by visible light and near infrared light of a regular reflection object, and a processing device 2E constituting an image processing section for determining highly accurate color reproduction image data from a spectroscopic image signal of the object that is photographed by the photography device 1E, as shown in FIG. 55.

The processing device 2E has the same constitution and functions as the processing device 2 applied to the image processing system of the first embodiment or the like and may use a personal computer.

The photography device 1E has substantially the same constitution as that of the photography device 1 (FIGS. 1, 17, 21, and 37) applied to the image processing system of the first to fourth embodiments as shown in FIG. 55. Additionally, in the photography device 1E, an LED 6g constituting a near infrared light source is disposed in the periphery of the photography optical system 7 in addition to the LED cluster 6X constituting a visible light source as the illumination light source. Further, a first polarizing plate 81 constituting reflected light removal means is disposed in front of the LED cluster 6X and a first polarizing plate 82 is disposed in front of the LED 6g, in order to cut the regular reflection light. Further, a rotatable polarizing plate dial 85 (FIG. 56) on which second polarizing plates 83 and 84 constituting reflected light removal means are mounted is disposed in front of the CCD 8.

The same numerals are assigned to the constituent elements of the photography device 1E that are the same as those of the photography device 1 and a description of such elements is suitably omitted. Only the different processing parts are mainly described hereinbelow.

The photography device 1E is capable of acquiring spectroscopic image data rendered by visible light by turning on the LED cluster 6X and is able to acquire spectroscopic image data rendered by near infrared light by turning on the LED 6g.

Here, when the object is glossy object 71, regular reflection light is captured and a high brightness section is produced in the image data. However, the photography device 1E is able to remove regular reflection light not only from object images rendered by visible light but also from an object image rendered by near infrared light. Hence, the photography device 1E is able to capture suitable spectroscopic image data without a high brightness section in either case.

In the photography device 1E, the second polarizing plate 83 for visible light and the second polarizing plate 84 for near infrared light are mounted on the polarizing plate dial 85.

When photography using visible light is performed by the photography device 1E, the polarizing plate dial 85 is rotated manually in the direction of the arrow D1, for example, to switch the visible-light second polarizing plate 83 to face the CCD 8. Following the switch, the visible-light first polarizing plate 81 is adjusted by rotating the visible-light second polarizing plate 83 via a central rotating roller 86 by rotatively operating the near-infrared second polarizing plate 84 that protrudes outside the photography device enclosure.

Therefore, when the visible light LED cluster 6X is lit in accordance with a predetermined light emission mode, light transmitted by the first polarizing plate 81 is reflected by the object 71 and enters the photography optical system 7. The diffused light component of the reflected light is transmitted by the second polarizing plate 83 but the regular reflection light component is removed by the second polarizing plate 83. Therefore, the object image rendered by visible light without a high brightness section caused by regular reflection is converted into an image pickup signal by the CCD 8 and captured as spectroscopic image data.

On the other hand, when photography rendered by near infrared light is performed, the polarizing plate dial 85 is rotated manually to cause the near infrared second polarizing plate 84 to face the CCD 8. Further, the near infrared first polarizing plate 82 is adjusted by rotating the near infrared second polarizing plate 84 via the central rotating roller 86 by rotatively operating the visible-light second polarizing plate 83 that protrudes outside the photography device enclosure.

Then, when the near infrared light LED 6g is lit in accordance with a predetermined light emission mode, the near infrared light transmitted by the first polarizing plate 82 is reflected by the object 71 and enters the photography optical system 7. The diffused light component of the near infrared light is transmitted by the second polarizing plate 84 but the regular reflection light component is removed by the second polarizing plate 84. Therefore, the object image rendered by the near infrared light without a high brightness section caused by regular reflection is converted into an image pickup signal by the CCD 8 and captured as spectroscopic image data.

The photography device 1E of the image processing system of the ninth embodiment is capable of performing photography by means of a near infrared light source in addition to photography by means of a visible light source and is capable of acquiring spectroscopic image data by capturing an object image without a high brightness section in which the effect of regular reflection is suppressed by means of both light sources even for a regular reflection glossy object, whereby highly accurate color reproduction is possible.

In particular, the polarizing plate applied to the photography device 1E need not employ such a costly polarizing plate as having the polarization characteristic with respect to all wavelengths covering visible light and near infrared light. The low-cost visible-light first polarizing plate 81 and second polarizing plate 83 are applied to the visible light source and the near infrared first polarizing plate 82 and second polarizing plate 84 are applied to the near infrared light source and, therefore, product costs can be suppressed.

Tenth Embodiment

An image processing system which is a tenth embodiment of the present invention will be described next with reference to FIGS. 57 to 59B. In the tenth embodiment, the same numerals are assigned to the parts that are the same as those of the first to ninth embodiments above and a description thereof will be omitted. Only the differences are mainly described.

Figure 57:
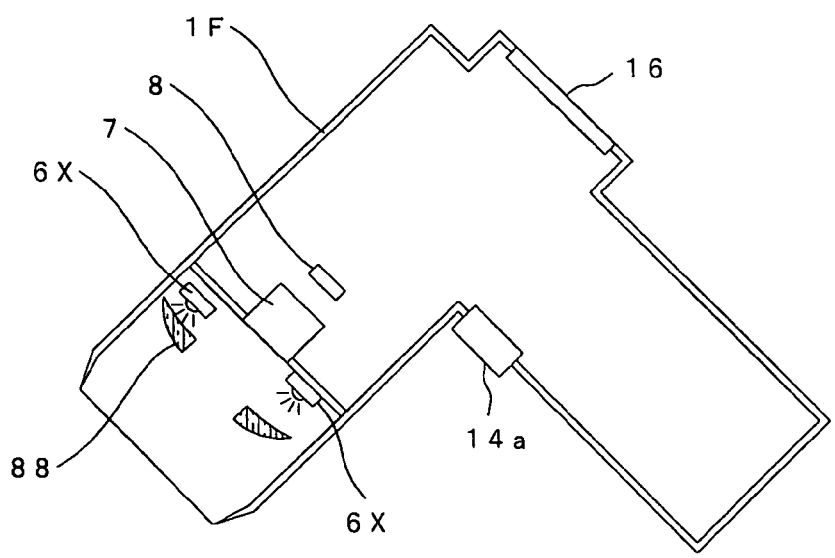
FIG. 57 is a block constitutional view of the image processing system of a tenth embodiment of the present invention.
Figure 58A:
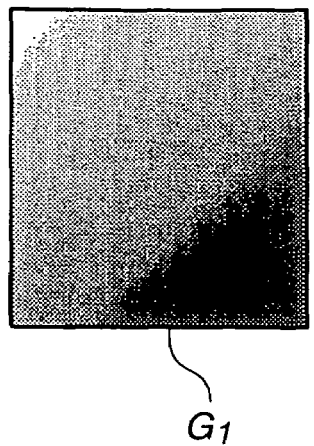
Figure 58B:
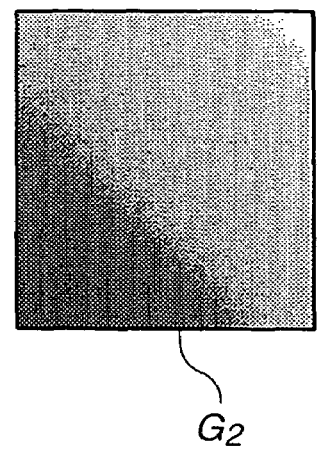
Figure 59A:
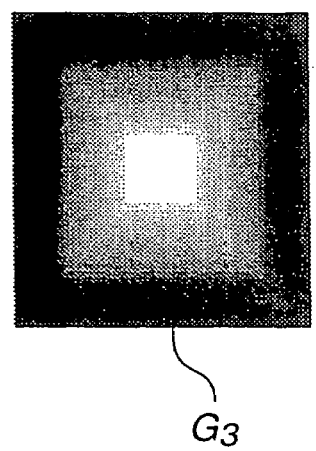
Figure 59B:
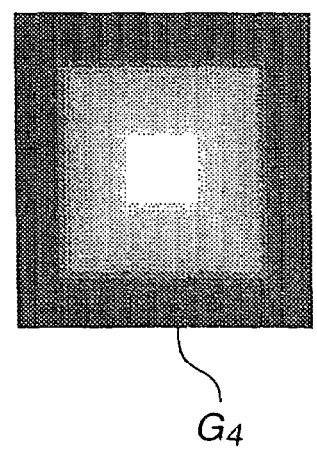

Further, FIG. 57 is a block constitutional view of the image processing system of this embodiment. FIGS. 58A and 58B show an aspect before correction of the state of a shading performed by an LED light source of the photography device of the image processing system, and FIGS. 59A and 59B show an aspect following correction of the state of a shading performed by an LED light source of the photography device of the image processing system.

The image processing system of this embodiment comprises a photography device 1F constituting an image photography section and a photography device (not illustrated) constituting an image processing section for determining highly accurate color reproduction image data from the spectroscopic image signal of the object photographed by the photography device 1F.

The photography device 1F has substantially the same constitution as that of the photography device 1 (FIGS. 1, 17, 21, and 37) applied to the image processing system of the first to fourth embodiments as shown in FIG. 57. Additionally, in the photography device 1F, a shading corrective lens 88 constituting an optical member that alleviates the illumination mirror is mounted in front of the LED cluster 6X constituting the illumination light source.

Further, the constituent elements of the photography device 1F that are the same as those of the photography device 1 are described by assigning the same numerals to these elements.

When LED 6a and LED 6d in the LED cluster 6X disposed in mutually different positions are lit separately, for example, in a state where the shading corrective lens 88 is not mounted in the photography device 1F, the state of illumination of the object is such that different parts such as the top left of screen G1 and the top right of screen G2 are more brightly irradiated than other parts as shown in FIGS. 58A and 58B. When this phenomenon is not corrected, there is the problem that correct measurement is not possible because the intensity distribution of the observed spectrals is different depending on positions on the screen.

Therefore, the shading corrective lens 88 is mounted in front of the LED cluster 6X, as mentioned earlier, in the photography device 1F. Illumination light from LED 6a or LED 6d is adjusted by mounting the shading corrective lens 88 and the correction is such that respective clear parts are concentrated in the center of the screen as shown in screens G3 and G4 of FIGS. 59A and 59B respectively. The effect of the light source position is alleviated with the illumination light corrected, meaning that there are no errors in the spectral intensity distribution caused by the position on the screen and correct measurement is implemented. The highly accurate spectroscopic image data can be acquired.

Further, there are sometimes cases where shading affected by the illumination position still remains even when the constitution of the photography device 1F of this embodiment is adopted. In this case, photography is performed with a white sheet or the like serving as the object and shading correction data with respect to screen position of each LED of the LED cluster 6X is calculated on the basis of the image data obtained. Further, more accurate correction is possible if electrical shading correction is performed for each LED.

Although usage of optical shading correction and image processing shading correction are combined in the earlier example, the same correction results can also be obtained by executing shading correction by means of image processing alone without using the shading correction optical system 88.

Further, shading correction can also be performed by using a diffuser instead of the shading correction optical system (lens) 88.

Eleventh Embodiment

The image processing system constituting an eleventh embodiment of the present invention will be described next by using FIGS. 60 and 61. In the eleventh embodiment, the same numerals are assigned to the parts that are the same as those of the first to tenth embodiments above and a description thereof will be omitted. Only the differences are mainly described.

Figure 60:
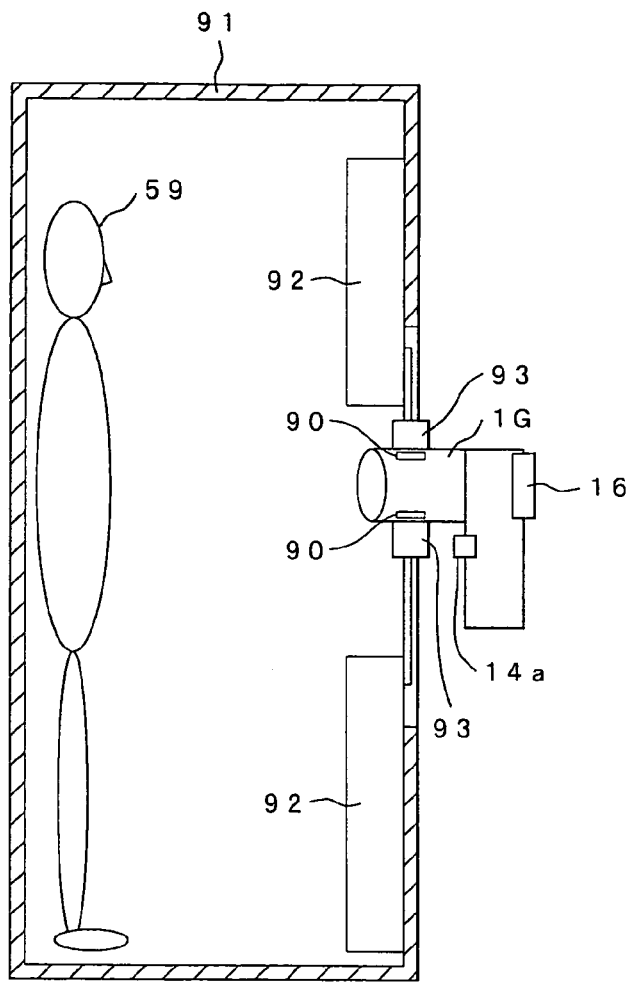
FIG. 60 is a block constitutional view of the image processing system of an eleventh embodiment of the present invention.

FIG. 60 is a block constitutional view of the image processing system of this embodiment. FIG. 61 shows the disposition of LED light source sections of the photography device in the image processing system.

The image processing system of this embodiment comprises a photography device 1G constituting an image photography section, a dark room 91 constituting a photography room, and a photography device (not illustrated) constituting an image processing section for determining highly accurate color reproduction image data from the spectroscopic image signal of the object photographed by the photography device 1G.

The photography device 1G has substantially the same constitution as that of the photography device 1 (FIGS. 1, 17, 21, and 37) applied to the image processing system of the first to fourth embodiments as shown in FIG. 60. Additionally, a connection terminal section (connect section) 90 for a connection with the illumination light source in the dark room 91 is installed in the photography device 1G. Further, the constituent elements of the photography device 1G that are the same as those of the photography device 1 are described by assigning the same numerals to such elements.

Furthermore, the photography device has the same constitution as the processing device 2 applied to the image processing system of the first embodiment or the like and may use a personal computer.

The dark room 91 has a space into which the patient 59 is introduced, for example, and has a structure that blocks light from the outside, for example. A plurality of illumination devices 92 which are external illumination devices are disposed in the dark room 91.

Figure 61:
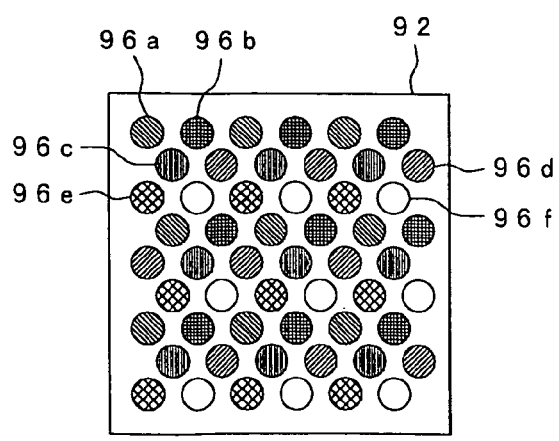
FIG. 61 shows the disposition of LED light source sections of the photography device in the image processing system in FIG. 60.

A plurality of sets of LEDs 96a to 96f of the same light emission wavelength as those of the first LED 6a to the sixth LED 6f respectively constituting the LED cluster 6X built into the photography device 1G as shown in FIG. 61 are arranged in the illumination device 92. In FIG. 61, the circle symbols represent each of the LEDs. The same pattern design of the circle symbols represents an LED with the same light emission wavelength. As shown in FIG. 61, the pluralities of sets of LEDs 96a to 96f are distributed within the illumination device 92 equally without bias, which generally enables a surface-light emission. The power supply to the LEDs 96a to LED 96f is supplied via a connection connector 93. When the photography device 1G is mounted in the dark room 91, the connection connector 93 is connected to a connection terminal section 90 on the side of the photography device 1G.

When photography is performed by the photography device 1G with the abovementioned constitution, the photography device 1G is first installed in the dark room 91 and each LED of the illumination device 92 is set in a lit state. The patient 59, who is the object, is then introduced to the dark room 91.

Then, the required part of the patient 59 is photographed by lighting each LED of the illumination device 92 and the desired spectroscopic image data are obtained, wherein the order of lighting the respective LEDs of the illumination device 92 at such time is the lighting timing of the LED cluster 6X in the photography device 1G that is lit in accordance with the light emission mode of the photography device 1G.

According to the image processing system of the abovementioned eleventh embodiment, accurate color measurement is possible in a state where ambient light has no effect even when the object size is large, whereby highly accurate color reproduction is possible. Further, the dark room 91 may be a simple device in which only a mount section having the connector section 93 of the photography device 1 and the illumination device 92 are provided, whereby an inexpensive image processing system that allows large objects to be photographed is obtained.

If a wide-angle photography optical system is applied to the photography optical system 7 of the photography device 1G, the photographic range widens, whereby photography of a larger object, for example, a large article such as an automobile body is permitted.

Twelfth Embodiment

An image processing system constituting a twelfth embodiment of the present invention will be described next by using the block constitutional view of FIG. 62. In this twelfth embodiment, the same numerals are assigned to the parts that are the same as those of the first to eleventh embodiments above and a description thereof will be omitted. Only the differences are mainly described.

The image processing system of this embodiment comprises a photography device 1H constituting an image photography section, and a processing device 2H constituting an image processing section for determining highly accurate color reproduction image data from a spectroscopic image signal of the object photographed by the photography device 1H and judging the state of the object in accordance with the image data.

Figure 62:
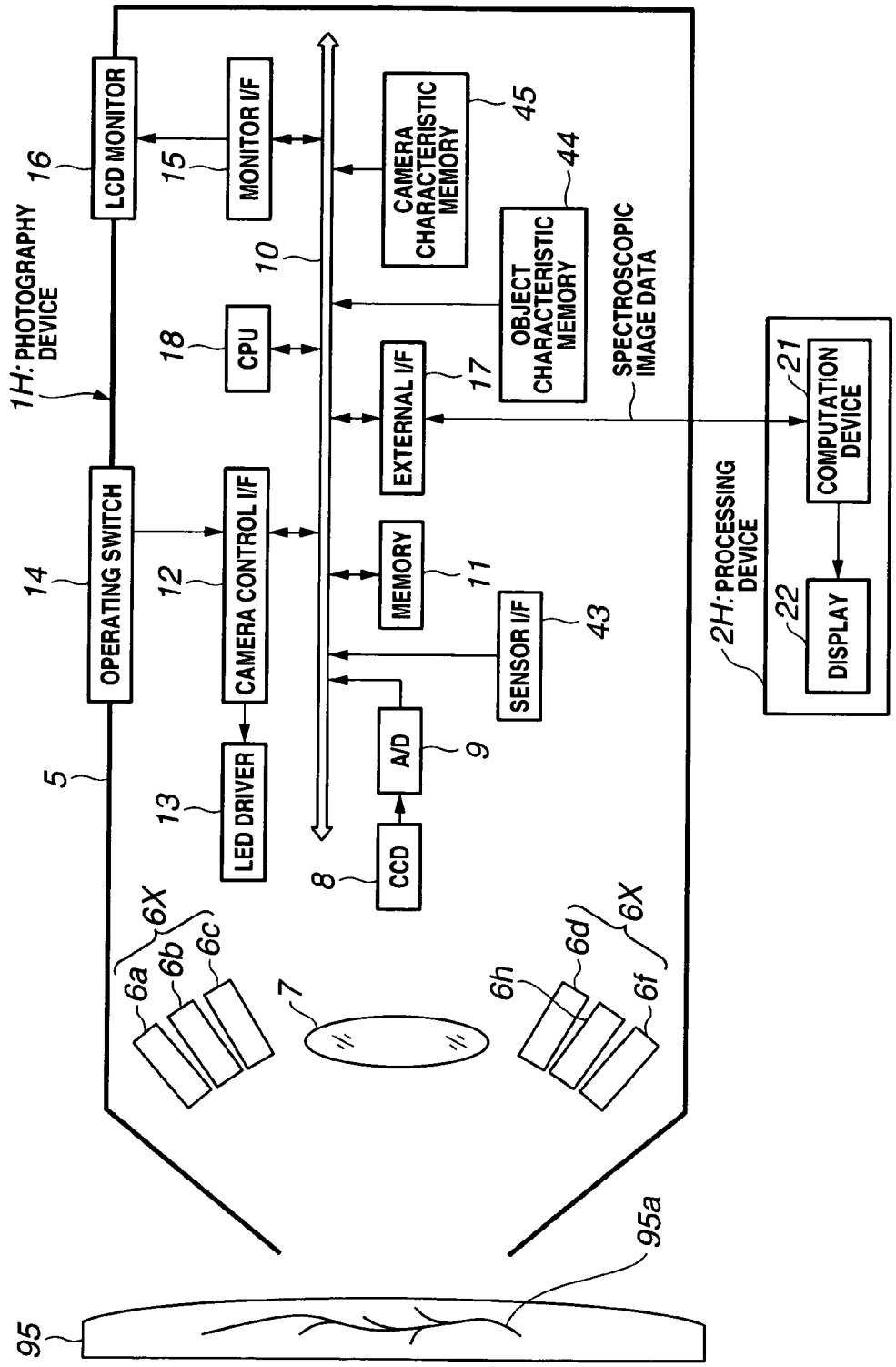
FIG. 62 is a block constitutional view of an image processing system which is a twelfth embodiment of the present invention.

The photography device 1H has substantially the same constitution as that of the photography device 1 (FIGS. 1, 17, 21, and 37) applied to the image processing system of the first to fourth embodiments as shown in FIG. 62. Further, in the photography device 1H, a plurality of LEDs 6h constituting a near infrared light source with a center wavelength of 780 nm to 900 nm are disposed in the periphery of the photography optical system 7 in addition to the plurality of LED clusters 6X constituting visible light sources as illumination light sources. Further, the constituent elements of the photography device 1H that are the same as those of the photography device 1 are described by assigning the same numerals to such elements.

Furthermore, the processing device 2H is the same as the processing device 2 applied to the image processing system of the first embodiment or the like and may use a personal computer.

In the photography device 1H, when an LED cluster 6X constituting the visible light source is lit by means of a predetermined light emission mode, visible spectroscopic image data is acquired. Further, when the body surface of patient 95 constituting the object is irradiated by turning on the LED 6h constituting a near infrared light source, near infrared spectroscopic image data are obtained.

During photography by means of near infrared light, the LED 6h is continuously lit with the photography device 1H in near infrared light photography mode. Image data of thirty frames per second of the surface of the body of the patient 95 are captured in this state and then displayed. The acquired image is displayed as a monochrome image on the LCD monitor 16 and the display 22 of the processing device 2H.

The near infrared light of a center wavelength of 780 nm to 900 nm of LED 6h above reaches a deep part of the body surface in comparison with visible light and, hence, the state of a subcutaneous blood vessel 95a below the skin can be photographed. For example, when the photography device 1H is set in a blood flow observation mode, for example, the blood flow state of the subcutaneous blood vessel 95a can be observed on the display 22 by means of the thirty-frames per second moving image data. Further, the blood flow state can also be directly observed by means of a monochrome image on the LCD monitor 16 of the photography device.

In the case of the image processing system of the twelfth embodiment, the judgment processing of the blood flow state can also be automatically performed, the LED 6h can be lit for a predetermined time as a result of the photographer operating the operating switch 14 of the photography device 1H by pressing the operating switch 14, and moving image data rendered by means of the photographed near infrared light is transferred to the processing device 2H. The processing device 2H discriminates a blood flow state by computing the moving image data.

Further, the image processing system of the twelfth embodiment is also capable of finding the pulse rate or heart rate by processing the moving image data of the blood flow state in addition to the discrimination processing of the blood flow state.

Thirteenth Embodiment

The image processing system constituting a thirteenth embodiment of the present invention will be described next by using the block constitutional view of FIG. 63. In this thirteenth embodiment, the same numerals are assigned to the parts that are the same as those of the first to twelfth embodiments above and a description thereof will be omitted. Only the differences are mainly described.

The image processing system of this embodiment comprises a photography device 1J constituting an image photography section, and a processing device 2J constituting an image processing section for determining highly accurate color reproduction image data from a spectroscopic image signal of the object photographed by the photography device 1J and judging the surface state of the object on the basis of the image data.

Figure 63:
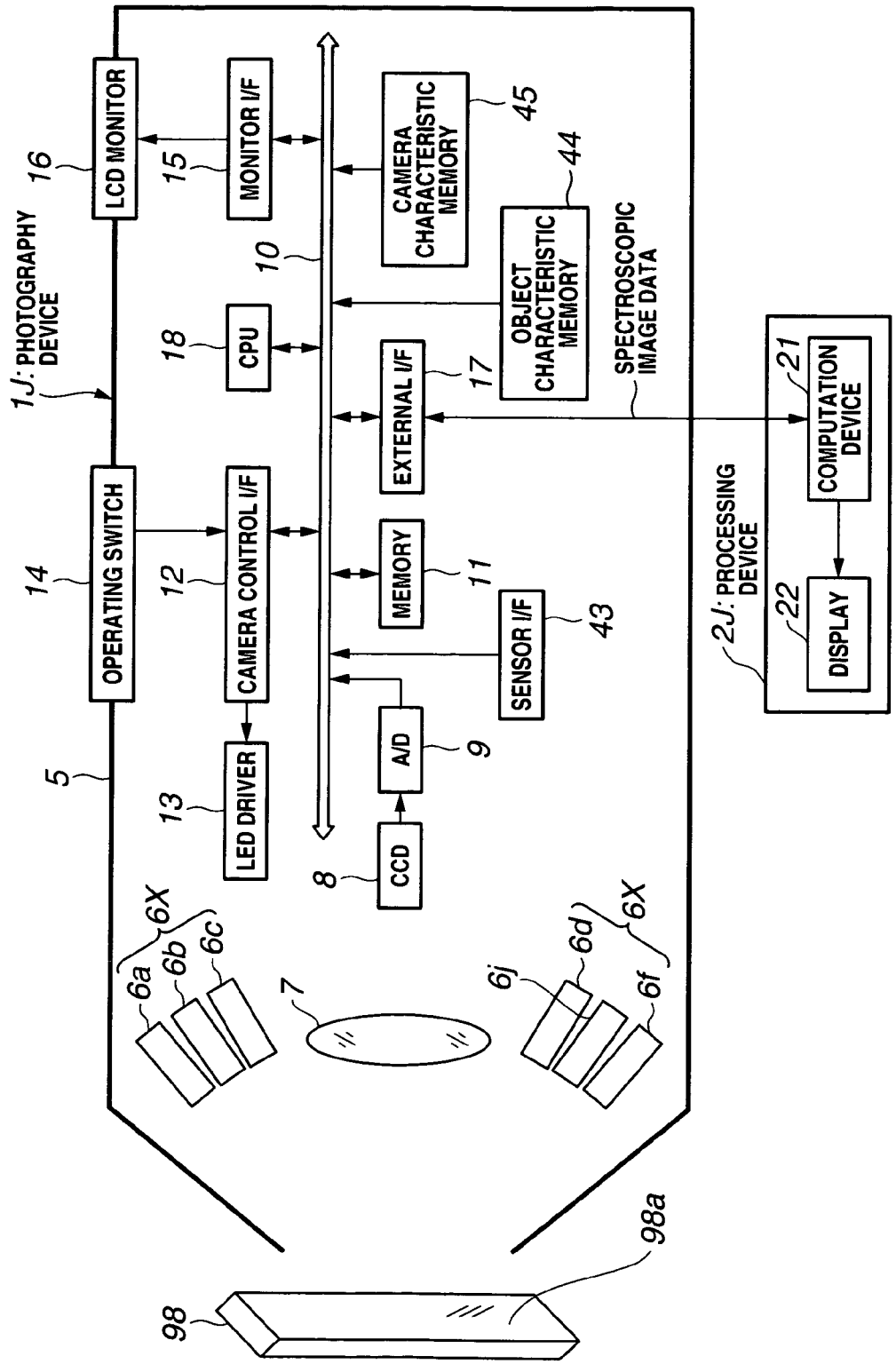
FIG. 63 is a block constitutional view of an image processing system which is a thirteenth embodiment of the present invention.

The photography device 1J has substantially the same constitution as that of the photography device 1 (FIGS. 1, 17, 21, and 37) applied to the image processing system of the first to fourth embodiments as shown in FIG. 63. Further, in the photography device 1J, a plurality of LEDs 6j constituting an ultraviolet light source with a center wavelength of 300 nm to 380 nm are disposed in the periphery of the photography optical system 7, in addition to the plurality of LED clusters 6X constituting visible light sources as illumination light sources. The constituent elements of the photography device 1J that are the same as those of the photography device 1 are described hereinbelow by assigning the same numerals to such elements.

Furthermore, the processing device 2J is the same as the processing device 2 applied to the image processing system of the first embodiment or the like.

In the photography device 1J, when an LED cluster 6X constituting the visible light source is lit by means of a predetermined light emission mode, visible spectroscopic image data is acquired. Further, when the surface 98a of an examined member 98 constituting the object is irradiated by turning on the LED 6j constituting an ultraviolet light source, ultraviolet spectroscopic image data are obtained.

When photography by means of ultraviolet light is performed, the LED 6j is lit with the photography device 1J in ultraviolet light photography mode. Image data of the surface 98a of the examined member 98 are captured in this state and then displayed. The acquired image is displayed as a monochrome image on the LCD monitor 16 and the display 22 of the processing device 2J.

The ultraviolet light of a center wavelength of 300 nm to 380 nm of LED 6j above undergoes scatter reflection at a more shallow point from the surface of the object in comparison with that of visible light and, therefore, the state of the object surface such as a fine surface flaw can be observed by means of the photographic image.

Further, a photography device of a modified example, which combines the photography devices 1H and 1J applied to the twelfth and thirteenth embodiments respectively, can be proposed. In the photography device of the modified example, the LED 6h, which constitutes a near infrared light source, and the LED 6j, which constitutes an ultraviolet light source, are disposed in the periphery of the photography optical system 7 in addition to the visible light LED cluster 6X as light sources.

According to the photography device of the modified example, because spectroscopic image data of objects of a wide range of types can be obtained, patient blood flow observation and surface flaw of the examined member and so forth of the detected member can be performed by means of the same photography device.

Figure 97:
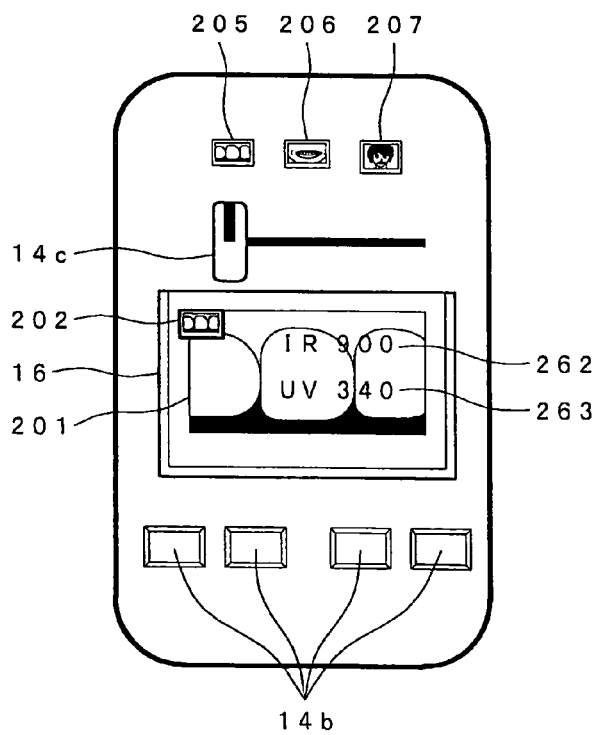
FIG. 97 shows an example in which the light emission of infrared rays and ultraviolet rays that is applied to the twelfth and thirteenth embodiments respectively is displayed.

Here, FIG. 97 shows an example in which light emission of infrared light and ultraviolet light emission, which are applied to the twelfth and thirteenth embodiments, are displayed.

Selectable LED light emission modes include an infrared mode that causes infrared light to be emitted and an ultraviolet mode that causes ultraviolet light to be emitted. Further, the type of LED light emission mode in which light emission is performed and wavelength information for each type of LED light emission mode are displayed.

More specifically, in this example, it is explicitly displaying the fact that near infrared light of wavelength 900 nm is being emitted by means of text 262 such as 'IR 900' and by displaying the fact that ultraviolet light of wavelength 340 nm is being emitted by means of text 263 such as 'UV 340'. Naturally, the display for the light emission of near infrared light and ultraviolet light or the like is not limited to the example shown in FIG. 97.

Fourteenth Embodiment

The image processing system constituting a fourteenth embodiment of the present invention will be described next by using the block constitutional view of FIG. 64. In this fourteenth embodiment, the same numerals are assigned to the parts that are the same as those of the first to thirteenth embodiments above and a description thereof will be omitted. Only the differences are mainly described.

The image processing system of this embodiment comprises a photography device 1K constituting an image photography section, and a processing device 2K constituting an image processing section for determining highly accurate color reproduction image data from a spectroscopic image signal of the object photographed by the photography device 1K.

Figure 64:
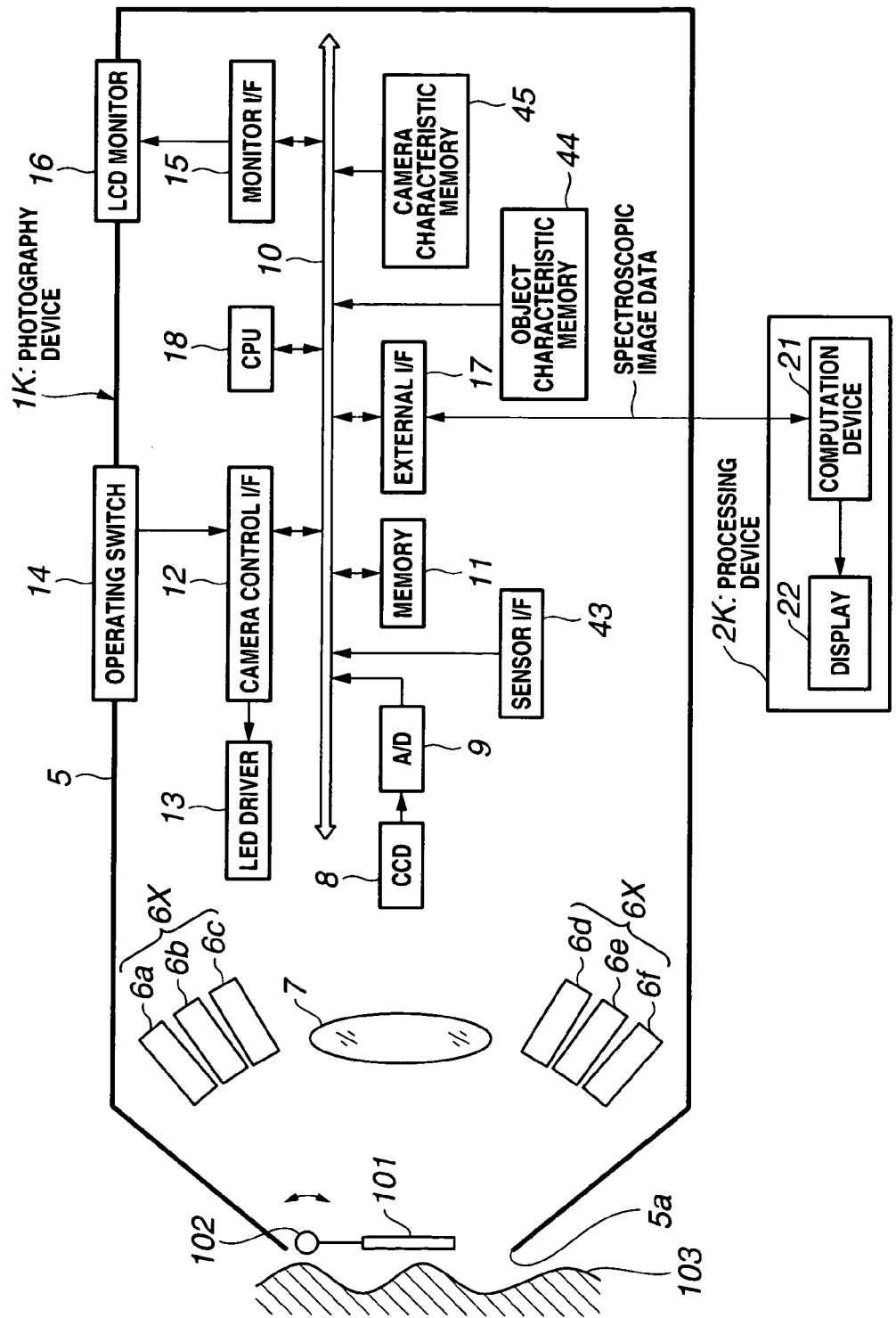
FIG. 64 is a block constitutional view of an image processing system which is a fourteenth embodiment of the present invention.

The photography device 1K has substantially the same constitution as that of the photography device 1 (FIGS. 1, 17, 21, and 37) applied to the image processing system of the first to fourth embodiments as shown in FIG. 64. However, also disposed in the photography device 1K is a color chart 101 that is freely turnably supported by a support spindle 102 in the opening 5a of the enclosure 5 and on which reference colors used for calibration are disposed.

Further, the constituent elements of the photography device 1K that are the same as those of the photography device 1 are described by assigning the same numerals to such elements.

The processing device 2K is the same as the processing device 2 applied to the image processing system of the first embodiment or the like.

The photography device 1K of this embodiment contains the abovementioned color chart 101 in the enclosure 5 so that the color chart storage management that is conventionally difficult is no longer required and degradation caused by dirt of color chart and external light can be prevented and, when the color chart 101 is not employed, the same is withdrawn from the projection opening 5a of the photography optical system 7 within the enclosure 5 and stored. In the stored state, the color chart 101 is withdrawn outside the illumination light path of the LED cluster 6X and the illumination light illuminating the object 103 is not obstructed. Further, the color chart 101 is turned toward the projection opening 5a of the photography optical system 7 as shown in FIG. 64 only during calibration. The image data of the color chart 101 is captured via the CCD 8 in this state and spectroscopic image data for color calibration is acquired.

According to the photography device 1K of the fourteenth embodiment, storage management of the color chart 101 is not required, dirt does not readily stick because the color chart 101 is not handled by hand, and colors are not degraded even if exposed to external light, whereby calibration of colors that are always accurate is possible.

Further, although the color chart 101 is turnably supported in the enclosure 5 in the photography device 1K of this embodiment, a constitution in which the color chart is stuck to the inside surface of a lens cap (not shown) that is detachable from the projection opening 5a of the enclosure 5 can also be adopted instead. In this case, the calibration is performed in a state where the lens cap is mounted.

Fifteenth Embodiment

An image processing system constituting a fifteenth embodiment of the present invention will be described next by using the system constitutional view of FIG. 65. In this fifteenth embodiment, the same numerals are assigned to the parts that are the same as those of the first to fourteenth embodiments above and a description thereof will be omitted. Only the differences are mainly described.

The image processing system of this embodiment comprises a photography device 1L constituting an image photography section, a cellular phone 110 that is connected via a cable 112 to the photography device 1L, and an in-house processing system 119 that is capable of communicating with the cellular phone 110.

The in-house processing system 119 comprises an in-house communication device 115, a processing device 116, a database 117, and a monitor 118.

Figure 65:
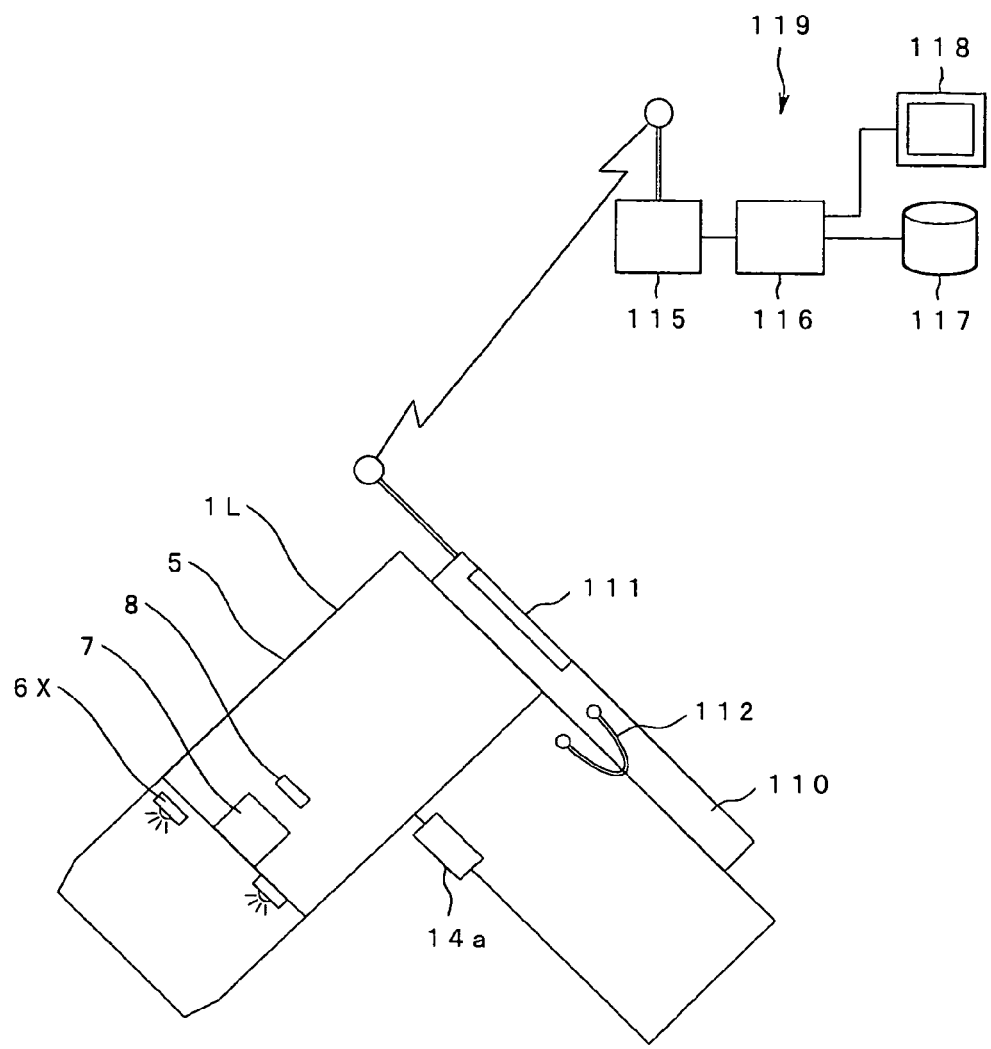
FIG. 65 is a system constitutional view of an image processing system which is a fifteenth embodiment of the present invention.

The photography device 1K has substantially the same constitution as that of the photography device 1 (FIGS. 1, 17, 21, and 37) applied to the image processing system of the first to fourth embodiments as shown in FIG. 65. Further, the same constituent elements of the photography device 1K are described by assigning the same numerals to such elements.

The cellular phone 110 transmits spectroscopic image data rendered by photographing the affected part of the patient acquired by the photography device 1L to the in-house communication device 115 of the in-house processing system 119 by means of a public switched network. Further, an LCD monitor 111 is provided in the cellular phone 110.

The processing device 116 of the in-house processing system 119 is an image processing section for determining highly accurate color reproduction data based on the spectroscopic image signal of the affected part received via the in-house communication device 115 and has the same constitution as that of the processing device 2 applied to the first embodiment or the like.

The spectroscopic image data processing operation of the image processing system of the fifteenth embodiment with the above constitution will be described hereinbelow by dividing the respective processing into steps of the processing of the cellular phone 110, the processing of the in-house processing system 119, and the processing of the photography device 1L.

When this is described based on the processing step of the cellular phone 110, the ID of the photography device 1L is first confirmed when the cellular phone 110 is connected to the photography device 1L. If the ID is invalid, an error message is output. If the cellular phone 110 and photography device 1L are matched, the cellular phone 110 is set to photography mode, and the settings are such that the monitor 111 of the cellular phone functions as the monitor of the photography device 1L, and the operating button of the cellular phone functions as the operating switch of the photography device 1L.

A connection request is output via a public switched network to the preset in-house processing system 119. A connection is established when authentication by the in-house processing system 119 has ended.

Thereafter, the monitor image from the photography device 1L is displayed on the monitor 111 of the cellular phone 110 and photography preparations are complete.

When the photography button 14a of the photography device 1L is operated by the user by being pressed, the output of photographic image data from the photography device 1L is awaited When photographic image data are output, the image data are displayed on the monitor 111. The image data are transmitted to the side of the in-house processing system 119 and a user operation is awaited.

When an image database search request of the in-house processing system 119 is effected as a result of a user operation, the database 117 of the in-house processing system 119 is accessed, and information of the database 117 is acquired and displayed on the monitor 118.

In addition, a search request is output to the database 117 as a result of the user operation. The search result from the database is received and displayed on the monitor 111.

Thereafter, when the processing step on the side of the in-house processing system 119 is described, a connection request from the cellular phone 110 is first received and the ID of the cellular phone is confirmed. If the ID is invalid, an error message is output and the connection is disconnected. The ID of the photography device 1D is further confirmed. If the ID of the photography device 1D is invalid, an error message is output and the connection is disconnected.

Thereafter, authentication information is requested and authentication information input by the user is confirmed. If the authentication information is invalid, an error message is output and the connection is disconnected. If the authentication information is not invalid, a connection is established and a transmission from the cellular phone 110 is awaited.

When photography is performed by the photography device 1L, image data from the cellular phone 110 is received.

The received image data are recorded in the database 117 together with the ID of the cellular phone, the ID of the photography device, and the user authentication information, and a transmission from the cellular phone 110 is awaited.

When a search request from the cellular phone 110 to the database 117 is received, a search of the database 117 is performed, the search results are transmitted to the cellular phone 110, and a transmission from the cellular phone 110 is awaited.

Thereafter, when the processing step of the photography device 1L is described, the ID of the cellular phone 110 is confirmed when the cellular phone 110 is connected.

A photography-enable state in which image data from the photography device 1L is transmitted to the cellular phone 110 as monitor image data is assumed and the operation of the photography button 14a or a photography request from the cellular phone 110 are awaited.

When a photography execution operation by the user is performed, the LED cluster 6X of the light source section of the photography device 1L is turned on by means of a predetermined sequence, photography is executed, and the acquired photography image data are transmitted to the side of the cellular phone 110.

As a result of the constitution of the image processing system of the fifteenth embodiment above, there is no need to dispose a liquid-crystal monitor in the photography device 1L and the photography device 1L can be constituted inexpensively. Further, because there is no need to use a cable when connecting to the in-house processing system 119, there is greater handling freedom during photography. Further, because a public switched network can be used as the communication line, there is a wide range of locations that can be used. Because the operating buttons of the cellular phone 110 can be used, more complex text information such as names and symptoms can be input.

In addition, speech data may be input together with image data by using the microphone of the cellular phone 110. In this case, in addition to it being possible to input information such as comments by means of speech, operations can also be performed by means of speech and user-friendliness improves.

Further, a PHS that is used in-house may be adopted as the cellular phone 110 and a LAN terminal device or PDA device may be used.

Sixteenth Embodiment

An image processing system constituting a sixteenth embodiment of the present invention will be described next by using a drawing that shows the constitution of the image photography section applied to the image processing system of FIG. 66. In the sixteenth embodiment, the same numerals are assigned to the parts that are the same as those of the first to fifteenth embodiments above and a description thereof will be omitted. Only the differences are mainly described.

Figure 66:
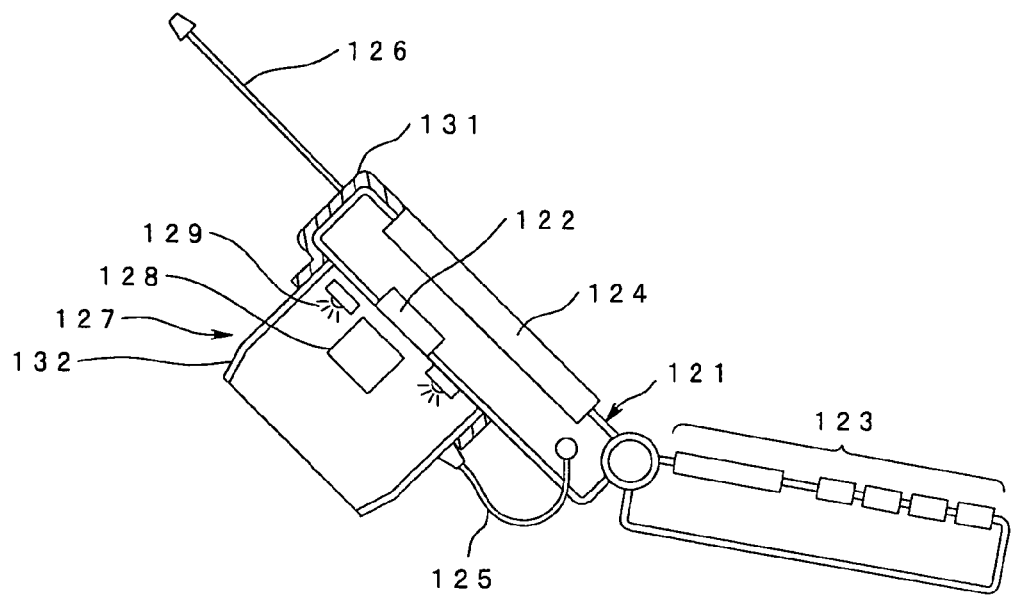
FIG. 66 is a block constitutional view of an image photography section that is applied to an image processing system which is a sixteenth embodiment of the present invention.

In the image processing system of this embodiment, an illumination unit, in which the image pickup section of the system is the unit, is the detachable type and, therefore, the LED illumination unit 127 constituting the image photography section comprises, as shown in FIG. 66, a cellular phone 121 with an attached camera mounted detachably, and an in-house processing system 119 that can communicate with the cellular phone 110.

Further, because the illumination unit is the detachable type, a plurality of types can be prepared beforehand and a more suitable illumination unit can be properly used in accordance with the applied application. Further, a storage element is integrated in the illumination unit and a variety of information such as an ID number, type, usage time, initial information (light source output, wavelength, and electrical conditions (the current value, lighting pattern, forward voltage, and so forth that are required in order to emit light of the predetermined light amount), and degradation information are pre-stored and read from the storage element during use, and conditions for performing the optimum image photography can be set on the basis of the information thus read. Further, a variety of information produced in the course of use can also be recorded in the storage element. Further, the type of the illumination unit that is mounted can also be displayed by using display means such as the LCD monitor 16 as mode display means and, in this case, the type can be more clearly confirmed.

The in-house processing system 119 is the same as the system applied to the fifteenth embodiment shown in FIG. 65 and comprises the in-house communication device 115, processing device 116, database 117, and monitor 118.

The camera-equipped cellular phone 121 has the same photography processing function as the photography processing section of the photography device 1 (FIG. 1) applied to the image processing system of the first embodiment, in a state where the LED illumination unit 127 is mounted. That is, the camera-equipped cellular phone 121 comprises a camera lens 122 constituting a photography optical system, an LCD monitor 124, an operating switch 123, an antenna 126, and a connection connector, and built into the cellular phone 121 are a CCD, an A/D conversion circuit, an image data memory, a camera control I/F, a data transceiver circuit, a monitor I/F, an external I/F, and a CPU or the like that governs the control of the cellular phone, and so forth.

Furthermore, the LED illumination unit 127 that can be mounted on the camera-equipped cellular phone 121 comprises a close-up lens 128 that is fixed to the main body of the cellular phone 121 by means of a unit fixing tool 131 and is located opposite the camera lens 122 of the cellular phone in the mounted state, an LED cluster 129 disposed along the outer circumference of the close-up lens 128, a light-shielding tube 132 provided outside the LED cluster 129, and a connecting cable 125 that is connected to the connector section of the cellular phone 121.

The LED cluster 129 is an LED cluster of respectively having different spectroscopic distribution characteristics similarity to those of the LED cluster 6X provided in the photography device 1 of the first embodiment and is an LED cluster of plural sets of LEDs of six types that are equivalent to the blue light source LEDs 6a and 6b of different wavelengths, green light source LEDs 6a and 6b of different wavelengths, and red light source LEDs 6a and 6b of different wavelengths.

The photography operation of the image processing system of the sixteenth embodiment with the abovementioned constitution will be described next.

The operating switch 123 is operated in a state where the LED illumination unit 127 mounted on the camera-equipped cellular phone 121 faces the body surface of the patient constituting the object, the LED cluster 129 is lit in accordance with a predetermined light emission order according to the selected light emission mode and the corresponding photographic image data of the body surface of the patient are captured during the light emission by the respective LEDs by a CCD (not shown) provided in the cellular phone 121. The image data are temporarily stored in memory in the cellular phone 121.

Thereafter, spectroscopic image data are transmitted from the antenna 126 to the in-house processing system 119 via a public switched network by operating the operating switch 123. The in-house processing system 119 performs image processing that is based on the spectroscopic image data and performs high-color reproduction processing.

Further, the exchange of data between the cellular phone 121 and in-house processing system 119 is the same as that of the eleventh embodiment.

According to the image processing system of the twelfth embodiment, a dedicated photography device is not required and the photography device of the image processing system can be used simply by mounting the LED illumination unit 127 on a conventional camera-equipped cellular phone, whereby an inexpensive system that employs a public switched network can be provided.

Further, another camera-equipped terminal device can also be adopted in place of the cellular phone 121 and examples of such terminal devices include a LAN terminal device, PDA device, or the like, for example.

Seventeenth Embodiment

Figure 67:
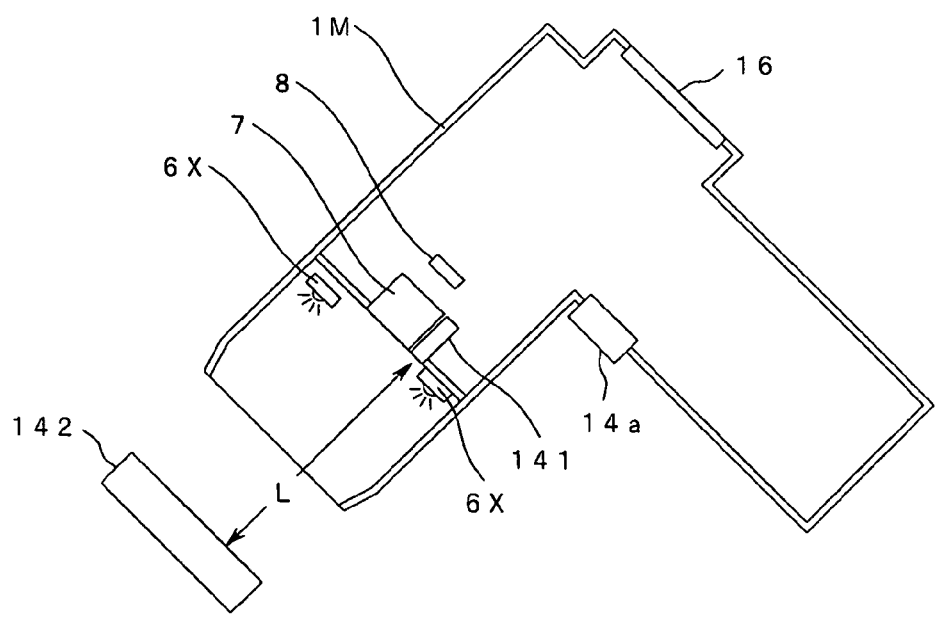
FIG. 67 is a block constitutional view of a photography device that is applied to an image processing system which is a seventeenth embodiment of the present invention.

The image processing system constituting a seventeenth embodiment will be described next with reference to FIGS. 67 and 98. FIG. 67 is a block constitutional view of a photography device that is applied to the image processing system. In the seventeenth embodiment, the same numerals are assigned to the parts that are the same as those of the first to sixteenth embodiments above and a description thereof will be omitted. Only the differences are mainly described.

The image processing system of this embodiment comprises a photography device 1M constituting an image photography section, and a processing device (not illustrated) constituting an image processing section for determining highly accurate color reproduction image data from a spectroscopic image signal of the object that is photographed by the photography device 1M.

The photography device 1M has substantially the same constitution as that of the photography device 1 (FIGS. 1, 17, 21, and 37) applied to the image processing system of the first to fourth embodiments as shown in FIG. 67. In addition, the photography device 1M is provided with a range sensor 141 constituting range means for measuring the photographic range L which is the spacing distance between the photography device 1M and the object 142. Further, the constituent elements among the constituent elements of the photography device 1M that are the same as those of the photography device 1 are described by assigning the same numerals to such elements.

The applied processing device is the same as the processing device 2 applied to the image processing system of the first embodiment or the like.

The photography operation of the image processing system of this embodiment is performed in accordance with the following processing steps.

First, the user places the photography device 1M with respect to the object 142 constituting the body of the patient, measures the photography distance by means of the range sensor 141, and registers the measurement result. The differential from the target photography distance is displayed signed on the monitor 16. The user moves the photography device 1M while viewing the display of the monitor 16. When the photography distance matches the target photography distance, there is a display to that effect on the monitor 16 and the photography device 1M waits in a photography-capable state. Photography starts when the user operates the photography button 14a.

In the case of the image processing system of the seventeenth embodiment, when the same part as the object 142 of the patient's body is photographed by determining the object distance by using the above mentioned object distance measurement function of the photography device 1M, the size of the image is the same in a comparison with the previously photographed image data and a comparative study then becomes extremely easy to perform.

A modified example of the photography device of the image processing system of the seventeenth embodiment will be described next hereinbelow.

The photography device 1M of the modified example performs photography by means of the following processing steps. That is, previously photographed image data that the user wishes to compare are designated and the desired photography distance information is acquired from the designated image data and displayed on the monitor 16.

Actual photography distance information obtained when photography is performed by the user determining an overall distance through visual measurement is acquired by the photography device 1M, and the scaling factor correction coefficient is calculated from the actual photography distance and the desired photography distance. An image of the same size in a state where the scaling factor of the image that is actually photographed is corrected based on the scaling factor correction coefficient is displayed.

If the user roughly sets the distance to the object 142 by using the function of the photography device 1M of the modified example, the user is able to observe image data of the same scaling factor as the previous image.

Further, a display of the measurement mode above may be implemented. FIG. 98 shows a display example of the measurement mode. In this example, the determination of whether the respective measurement modes for temperature detection, auscultation, pulse detection, and range are valid is displayed on the LCD monitor 16 constituting the display means by means of each of the icons 265, 266, 267, and 268.

Figure 98:
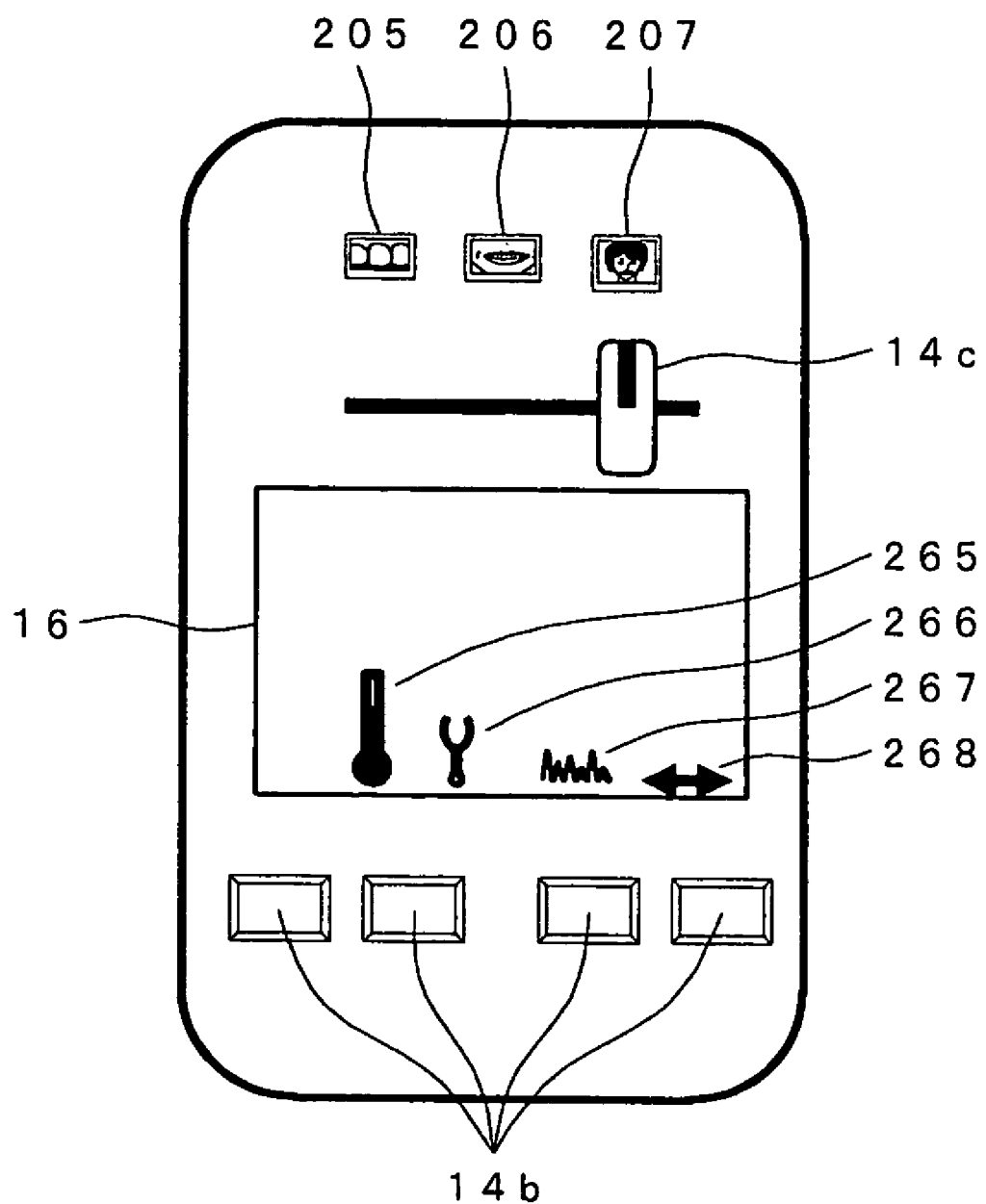
FIG. 98 shows a display example of a measurement mode in a seventeenth embodiment.

Naturally, the display of the measurement modes is not limited to the example shown in FIG. 98.

Eighteenth Embodiment

The image processing system constituting an eighteenth embodiment of the present invention will be described next by using the illustration of the state of the examination by the system in FIG. 68. In the eighteenth embodiment, the same numerals are assigned to the parts that are the same as those of the first to seventeenth embodiments above and a description thereof will be omitted only the differences are mainly described.

The image processing system of this embodiment comprises a photography device 1N constituting an image photography section, a digitizer-equipped examination table 153, and a processing device (not illustrated) constituting an image processing section for determining highly accurate color reproduction image data from a spectroscopic image signal of the object that is photographed by the photography device 1N.

Figure 68:
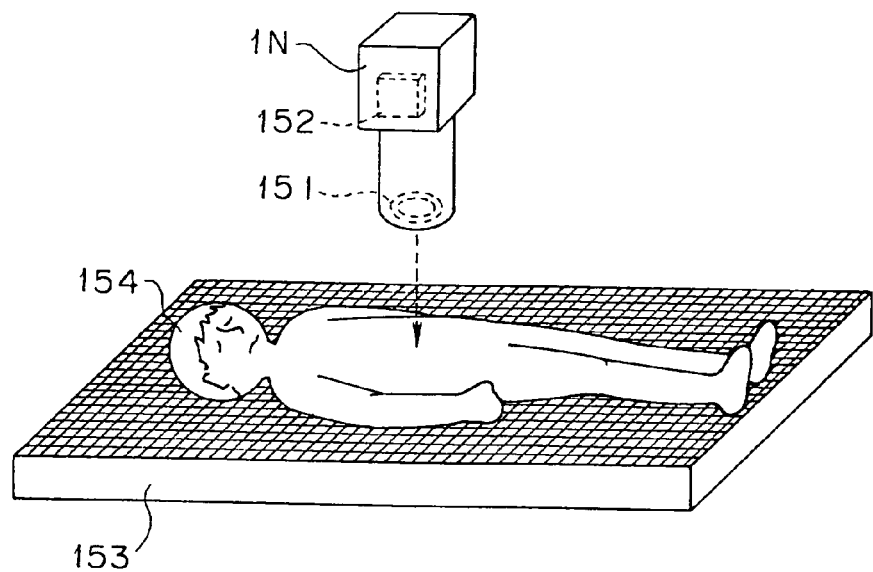
FIG. 68 shows a state of a medical examination by an image processing system which is an eighteenth embodiment of the present invention.

The photography device 1N has substantially the same constitution as that of the photography device 1 (FIGS. 1, 17, 21, and 37) applied to the image processing system of the first to fourth embodiments as shown in FIG. 68. In addition, the photography device 1N has a position detection coil 151 constituting object part detection means for detecting the coordinates of the photography device 1N that is built into the tip of the lens barrel of the photography device 1N and has an integrated angle detection sensor 152 that uses gravity or the like to detect the attitude of the photography device 1N.

Further, the constituent elements among the constituent elements of the photography device 1N that are the same as those of the photography device 1 are described by assigning the same numerals to such elements.

Furthermore, the processing device is the same as the processing device 2 applied to the image processing system of the first embodiment or the like.

It is assumed that the photography device 1N of this embodiment is used during an examination at a medical clinic or the like. A digitizer device that produces a magnetic field from a plurality of points is attached to the digitizer-equipped examination table 153 such that the position of the detection coil 151 of the photography device 1N can be detected and the position of the photography device 1N can be sensed. In addition, the direction of orientation of the photography device 1N to the horizontality can be sensed by means of the angle detection sensor 152 of the photography device 1N.

When photography is performed by means of the photography device 1N, a patient 154 constituting the object undergoing an examination is stretched out in a predetermined position on the digitizer-equipped examination table 153. Photography is performed by the photography device 1N in this state and the relative positional coordinates of the photography device 1N and the patient 154 during photography, as well as the tilt of the photography device 1N, which is the orientation of the photography device 1N during photography, are detected. The detection data are recorded together with the image data. The particular part of the patient that is photographed is automatically recorded based on the detection data. Therefore, the position of the photographed affected part and the photography direction when image data are acquired can be confirmed and displacement of the photographed part and variations in the photography direction and so forth can be prevented, whereby correct image acquisition is executed.

Nineteenth Embodiment

The image processing system of a nineteenth embodiment of the present invention will be described next by using the illustration showing the state of photography by the system of FIG. 69. In the nineteenth embodiment, the same numerals are assigned to the parts that are the same as those of the first to eighteenth embodiments above and a description thereof will be omitted only the differences are mainly described.

The image processing system of this embodiment comprises a photography device 1P constituting an image photography section, a processing device (not illustrated) constituting an image processing section for determining highly accurate color reproduction image data from a spectroscopic image signal of the object that is photographed by the photography device 1P, and an examination chair 161.

The photography device 1P has substantially the same constitution as that of the photography device 1 (FIGS. 1, 17, 21, and 37) applied to the image processing system of the first to fourth embodiments. In addition, the photography device 1P has a built-in light pattern projection device (not shown) constituting object part detection means that projects a special light pattern onto the object. However, the light pattern projection device may be disposed fixed to the photography device 1P instead of being built into the photography device 1P.

Further, the constituent elements of the photography device 1P that are the same as those of the photography device 1 are described by assigning the same numerals to such elements.

Furthermore, the processing device is the same as the processing device 2 applied to the image processing system of the first embodiment or the like.

A digitizer is applied in order to specify the photography position in the eighteenth embodiment. However, in the nineteenth embodiment, the photography part of the spectroscopic image data is specified by referencing an image that is photographed in a state where a special light pattern is projected onto the patient.

Figure 69:
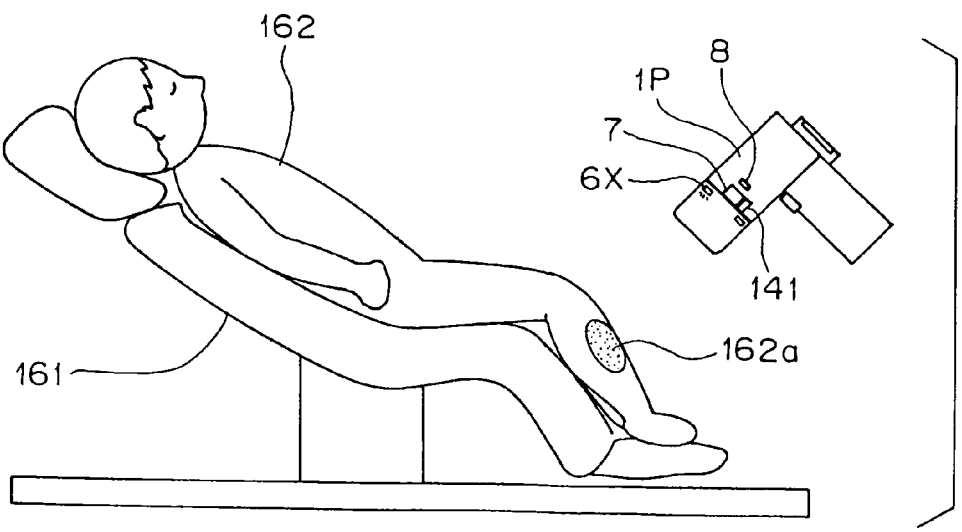
FIG. 69 shows a state of a medical examination by an image processing system which is a nineteenth embodiment of the present invention.

That is, when photography is performed by the photography device 1P of the image processing system of this embodiment, a patient 162 constituting the object is made to sit on the examination table 161 as shown in FIG. 69. Then, the photography device 1P is placed in a position that allows an affected part 162*a* of the patient 162 to be photographed. Hence, light pattern having a certain characteristic is projected onto the patient 162 by the light pattern projection device and the area around the affected part 162*a* in the light pattern projection state is photographed temporarily in monitor mode. Spectroscopic image data are acquired by performing photography with the illumination light of the LED cluster 6X in spectroscopic image capture mode continuously without moving the photography device 1P.

The image processing system of this embodiment as described above is capable of reliably specifying the photography position in which the spectroscopic image data are acquired by means of the projection image of the light pattern.

Further, the photography device of the following modified example can be proposed as a modified example of the photography device of the image processing system of the nineteenth embodiment.

That is, the photography device of the modified example comprises a temperature sensor used for body temperature measurement at the tip of the device main body, a pulse sensor for detecting the pulse, and a microphone (sensor) for detecting Korotkov's sounds during blood pressure measurement, respiratory sounds and the heartbeat in the chest, and intestinal murmurs of the abdomen, and has an auscultation function. In addition to object spectroscopic image data, data for the body temperature, pulse and heartbeat and so forth can be acquired by these sensors. The data for the body temperature, pulse, and heartbeat, and so forth during photography of the affected part of the patient are simultaneously saved to memory in association with the spectroscopic image data. As a result, measurement data for the body temperature, pulse, and heartbeat and so forth measured by the sensor of the photography device on a daily basis can be transmitted to an affiliated medical facility via a public switched network and, therefore elaborate health management at home can be implemented.

Further, a photography device constituting an image photography section and a processing device constituting an image processing section are provided separately in the image processing system of each of the embodiments above but a constitution that integrates and combines both the photography device and the processing device in a single portable device is naturally possible. In this case, an image processing system results that allows image processing operations to be performed at the same time while performing photography, and so forth, and, depending on the intended usage, is extremely easy to handle.

It is understood that the present invention is not limited to the embodiments above and that a variety of modifications and applications are possible within a scope not departing from the spirit of the invention.

What is claimed is:

1. A photography device comprising:
    an illumination light source which illuminates an object, and which comprises a plurality of light-emitting elements that perform light emission of a plurality of different spectroscopic distribution characteristics that are mutually independent in at least a range of visible light;
    a photography optical system which forms an object image;
    an image pickup element section which outputs an image signal by picking up the object image formed by the photography optical system;
    a mode selection section which selects one of a spectroscopic image capture mode for capturing sequential multiband spectroscopic still images of the object so as to perform multiband illumination with at least four primary colors, and an RGB capture mode for capturing an RGB image of the object; and
    a mode display section which is configured to display mode-related information corresponding to each of the spectroscopic image capture mode and the RGB capture mode,
    wherein when the spectroscopic image capture mode is selected by the mode selection section, the plurality of light-emitting elements sequentially emit light in accordance with the spectroscopic distribution characteristics to perform the multiband illumination, and wherein the image pickup element section picks up an image of the object at each sequential light emission to capture sequential multiband spectroscopic still images of the object, and the mode display section displays the mode-related information that corresponds to the spectroscopic image capture mode, and
    wherein when the RGB capture mode is selected by the mode selection section: (i) light-emitting elements of three colors of red, green and blue selected from the plurality of light-emitting elements one of simultaneously and sequentially emit light, wherein the image pickup element section captures the RGB image of the object while the light-emitting elements of red, green and blue are emitting light, and the mode display section displays the mode-related information that corresponds to the RGB capture mode; or (ii) a plurality of clusters of light-emitting elements of the plurality of light-emitting elements including a cluster of light-emitting elements belonging to blue, a cluster of light-emitting elements belonging to green, and a cluster of light-emitting elements belonging to red, sequentially emit light cluster by cluster, and wherein the image pickup element section captures the RGB image of the object while the plurality of clusters of light-emitting elements are sequentially emitting light, and the mode display section displays the mode-related information that corresponds to the RGB capture mode.

2. The photography device according to claim 1, wherein the mode selection selects one of a plurality of light emission modes including an illumination light lit mode that illuminates the object by turning on the illumination light source and an illumination light unlit mode in which the illumination light source is not lit.

3. The photography device according to claim 1, wherein in the spectroscopic image capture mode, a spectroscopic image is read more rapidly than normal reading.

4. The photography device according to claim 1, wherein the mode selection section further selects one of a plurality of capture modes including a full capture mode that captures an entirety of the object and a partial capture mode that captures a portion of the object.

5. The photography device according to claim 1, wherein an illumination unit is adapted to be attached to and detached from the photography device, and wherein the mode display section is further configured to display an attached/detached state of the illumination unit.

6. The photography device according to claim 1, wherein an illumination unit is adapted to be attached to and detached from the photography device, and wherein the mode display section is further configured to display a type of the illumination unit when the illumination unit is mounted.

7. The photography device according to claim 1, wherein an external operation section is adapted to be connected to the photography device, and is arranged to allow an operation related to the photography device to be performed from outside the photography device, and
wherein the mode display section is further configured to display a state to indicate whether the external operation section is connected and operable.

8. The photography device according to claim 7, wherein the external operation section is a foot switch which is operable by foot.

9. The photography device according to claim 7, wherein the external operation section is connected to the photography device via a network.

10. The photography device according to claim 1, wherein the mode selection section selects one of a plurality of capture modes including a measurement mode that performs temperature detection, a measurement mode that performs pulse detection, a measurement mode that performs auscultation, and a measurement mode that performs ranging; and
wherein the mode display section is further configured to display, by means of icons that correspond to the respective measurement modes, whether the respective measurement modes for temperature detection, pulse detection, auscultation, and ranging are effective.

11. The photography device according to claim 1, wherein the mode display section is further configured to display plural light emission modes and wavelength information for each of the light emission modes.

12. The photography device according to claim 11, wherein the light emission modes include at least one of an infrared mode in which infrared light is emitted and an ultraviolet mode in which ultraviolet light is emitted.

13. The photography device according to claim 1, further comprising:
a first polarizing plate insertable in a light path from the illumination light source to the object; and
a second polarizing plate insertable in a light path from the object to the image pickup element section,
wherein the mode display section is further configured to display whether the first polarizing plate and second polarizing plate are inserted in the respective light paths.

14. The photography device according to claim 13, wherein the first polarizing plate and second polarizing plate are rotatable relative to each other; and
wherein the mode display section is further configured to display a relative rotation angle between the first polarizing plate and the second polarizing plate.

15. The photography device according to claim 1, wherein the mode display section is further configured to display a next operating procedure of a serial operation of the photography device.

16. The photography device according to claim 1, further comprising an operation instruction section which instructs a next operating procedure of a serial operation of the photography device.

17. The photography device according to claim 16, wherein the operation instruction section instructs the next operating procedure by controlling the mode display section to display the next operating procedure.

18. The photography device according to claim 16, wherein the operation instruction section comprises a progress status display section for displaying which operation of which stage in the serial operation of the photography device is being performed.

19. The photography device according to claim 1, wherein the mode display section is further configured to display a progress status with respect to which operation of which stage in a serial operation of the photography device is being performed.

20. The photography device according to claim 1, further comprising a set state display section which displays a set state of the photography device.

21. The photography device according to claim 20, wherein the mode display section serves as the set state display section.

22. The photography device according to claim 20, wherein at least a portion of the information displayed on the mode display section and information displayed on the set state display section are transferrable to an external device as image-data additional data.

23. The photography device according to claim 21, wherein at least a portion of information displayed on the set state display section is transferrable to an external device as image-data additional data.

24. The photography device according to claim 1, further comprising a warning reporting section for issuing a warning with respect to the photography device.

25. The photography device according to claim 20, further comprising a warning reporting section for issuing a warning with respect to the photography device.

26. The photography device according to claim 24, wherein the warning reporting section issues a warning report at least one of when leaked light is detected, when a positional shift occurs during photography, and when the photography optical system is dim.

27. The photography device according to claim 15, wherein the warning reporting section issues a warning report at least one of when leaked light is detected, when a positional shift occurs during photography, and when the photography optical system is dim.

28. The photography device according to claim 24, wherein the warning reporting section issues a warning report by displaying the warning on the mode display section.

29. The photography device according to claim 25, wherein the warning reporting section issues a warning report by displaying the warning on the mode display section.

30. The photography device according to claim 24, wherein the warning reporting section issues a warning report by displaying the warning on a set state display section.

31. The photography device according to claim 25, wherein the warning reporting section issues a warning report by displaying the warning on the set state display section.

32. The photography device according to claim 1, wherein the mode display section displays the mode-related information with icons.

33. A photography device comprising:
   an illumination light source which illuminates an object, and which comprises a plurality of light-emitting elements that perform light emission of a plurality of different spectroscopic distribution characteristics that are mutually independent in at least the range of visible light;
   a photography optical system which forms an object image;
   an image pickup element section which outputs an image signal by picking up the object image formed by the photography optical system;
   a mode selection section which selects one of a first light emission mode in which the plurality of light-emitting elements sequentially emit light in accordance with the spectroscopic distribution characteristics so as to perform multiband illumination with at least four primary colors, and a second light emission mode in which light-emitting elements of the plurality of the light-emitting elements perform light emission in red, green and blue selected from among the plurality of spectroscopic distribution characteristics; and
   a mode display section which is configured to display mode-related information corresponding to each of the first and second light emission modes,
   wherein when the first light emission mode is selected by the mode selection section, the plurality of light-emitting elements sequentially emit light in accordance with the spectroscopic distribution characteristics to perform the multiband illumination, wherein the image pickup element section picks up an image of the object at each sequential light emission to capture sequential multi-band spectroscopic still images of the object, and the mode display section displays the mode-related information that corresponds to the first light emission mode, and
   wherein when the second light emission mode is selected by the mode selection section: (i) the light-emitting elements of three colors of red, green and blue selected from the plurality of light-emitting elements one of simultaneously and sequentially emit light, and wherein the image pickup element section captures an RGB image of the object while the light-emitting elements of red, green and blue are emitting light, and the mode display section displays the mode-related information that corresponds to the second light emission mode; or (ii) a plurality of clusters of light-emitting elements of the plurality of light-emitting elements including a cluster of light-emitting elements belonging to blue, a cluster of light-emitting elements belonging to green, and a cluster of light-emitting elements belonging to red, sequentially emit light cluster by cluster, and wherein the image pickup element section captures an RGB image of the object while the plurality of clusters of light-emitting elements are sequentially emitting light, and the mode display section displays the mode-related information that corresponds to the second light emission mode.

34. An image processing system comprising: a photography device comprising:
   an illumination light source which illuminates an object, and which comprises a plurality of light-emitting elements that perform light emission of a plurality of different spectroscopic distribution characteristics that are mutually independent in at least a range of visible light;
   a photography optical system which forms an object image;
   an image pickup element section which outputs an image signal by picking up the object image formed by the photography optical system;
   a mode selection section which selects one of a spectroscopic image capture mode for capturing sequential multiband spectroscopic still images of the object so as to perform multiband illumination with at least four primary colors, and an RGB capture mode for capturing an RGB image of the object; and
   a mode display section which is configured to display mode-related information corresponding to each of the spectroscopic image capture mode and the RGB capture mode,
   wherein when the spectroscopic image capture mode is selected by the mode selection section, the plurality of light-emitting elements sequentially emit light in accordance with the spectroscopic distribution characteristics to perform the multiband illumination, and wherein the image pickup element section picks up an image of the object at each sequential light emission to capture sequential multiband spectroscopic still images of the object, and the mode display section displays the mode-related information that corresponds to the spectroscopic image capture mode, and
   wherein when the RGB capture mode is selected by the mode selection section: (i) light-emitting elements of three colors of red, green and blue selected from the plurality of light-emitting elements one of simultaneously and sequentially emit light, wherein the image pickup element section captures the RGB image of the object while the light-emitting elements of red, green and blue are emitting light, and the mode display section displays the mode-related information that corresponds to the RGB capture mode; or (ii) a plurality of clusters of light-emitting elements of the plurality of light-emitting elements including a cluster of light-emitting elements belonging to blue, a cluster of light-emitting elements belonging to green, and a cluster of light-emitting elements belonging to red, sequentially emit light cluster by cluster, and wherein the image pickup element section captures the RGB image of the object while the plurality of clusters of light-emitting elements are sequentially emitting light, and the mode display section displays the mode-related information that corresponds to the RGB capture mode; and a processing device comprising a computation section which performs a desired image processing based on the image signal.

35. An image processing system comprising:

a photography device comprising:

- an illumination light source which illuminates an object, and which comprises a plurality of light-emitting elements that perform light emission of a plurality of different spectroscopic distribution characteristics that are mutually independent in at least the range of visible light;
- a photography optical system which forms an object image;
- an image pickup element section which outputs an image signal by picking up the object image formed by the photography optical system;
- a mode selection section which selects one of a first light emission mode in which the plurality of light-emitting elements sequentially emit light in accordance with the spectroscopic distribution characteristics so as to perform multiband illumination with at least four primary colors, and a second light emission mode in which light-emitting elements of the plurality of the light-emitting elements perform light emission in red, green and blue selected from among the plurality of spectroscopic distribution characteristics; and
- a mode display section which is configured to display mode-related information corresponding to each of the first and second light emission modes, wherein when the first light emission mode is selected by the mode selection section, the plurality of light-emitting elements sequentially emit light in accordance with the spectroscopic distribution characteristics to perform the multiband illumination, wherein the image pickup element section picks up an image of the object at each sequential light emission to capture sequential multiband spectroscopic still images of the object, and the mode display section displays the mode-related information that corresponds to the first light emission mode, and wherein when the second light emission mode is selected by the mode selection section: (i) the light-emitting elements of three colors of red, green and blue selected from the plurality of light-emitting elements one of simultaneously and sequentially emit light, and wherein the image pickup element section captures an RGB image of the object while the light-emitting elements of red, green and blue are emitting light, and the mode display section displays the mode-related information that corresponds to the second light emission mode; or (ii) a plurality of clusters of light-emitting elements of the plurality of light-emitting elements including a cluster of light-emitting elements belonging to blue, a cluster of light-emitting elements belonging to green, and a cluster of light-emitting elements belonging to red, sequentially emit light cluster by cluster, and wherein the image pickup element section captures an RGB image of the object while the plurality of clusters of light-emitting elements are sequentially emitting light, and the mode display section displays the mode-related information that corresponds to the second light emission mode; and a processing device comprising a computation section which performs a desired image processing based on the image signal.

* * * * *

UNITED STATES PATENT AND TRADEMARK OFFICE
CERTIFICATE OF CORRECTION

| | | |
|---|---|---|
| PATENT NO. | : 7,826,728 B2 | Page 1 of 1 |
| APPLICATION NO. | : 11/486455 | |
| DATED | : November 2, 2010 | |
| INVENTOR(S) | : Osamu Konno | |

It is certified that error appears in the above-identified patent and that said Letters Patent is hereby corrected as shown below:

In the Claims:

Column 73, Line 4,(Claim 27, Line 1);

After "claim" change "15" to --25--.

Signed and Sealed this

Twenty-second Day of February, 2011

David J. Kappos
*Director of the United States Patent and Trademark Office*